US012398397B2

(12) United States Patent
Carrillo Rincón et al.

(10) Patent No.: US 12,398,397 B2
(45) Date of Patent: Aug. 26, 2025

(54) INDUCIBLE PROMOTERS

(71) Applicant: Worcester Polytechnic Institute, Worcester, MA (US)

(72) Inventors: Andrés Felipe Carrillo Rincón, Worcester, MA (US); Natalie G. Farny, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 18/136,660

(22) Filed: Apr. 19, 2023

(65) Prior Publication Data

US 2024/0018529 A1 Jan. 18, 2024

Related U.S. Application Data

(60) Provisional application No. 63/332,507, filed on Apr. 19, 2022.

(51) Int. Cl.
*C12N 15/63* (2006.01)
*C12N 15/11* (2006.01)

(52) U.S. Cl.
CPC .......... *C12N 15/635* (2013.01); *C12N 15/111* (2013.01); *C12N 2830/36* (2013.01); *C12N 2840/002* (2013.01)

(58) Field of Classification Search
CPC .............................. C12N 15/635; C12P 23/00
USPC ............................................ 435/320.1, 91.1
See application file for complete search history.

(56) References Cited

U.S. PATENT DOCUMENTS 4,551,433 A * 11/1985 DeBoer .................. C12P 21/02 435/69.3
6,117,651 A 9/2000 Schultz et al.
7,495,092 B2 * 2/2009 Barrangou ........... C12N 15/746 435/243
8,846,374 B2 * 9/2014 Sharpe .................. C12P 7/6432 435/254.2
2014/0140959 A1 5/2014 Szalay et al.

FOREIGN PATENT DOCUMENTS

WO 2019123324 A1 6/2019

OTHER PUBLICATIONS

Aoyama, T. et al. “Essential structure of *E.coli* promoter: effect of spacer length between the two consensus sequences on promoLer function” pp. 5855-5864. Nucleic Acids Research. vol. 11, No. 17. 1983; Abstract; DOI: 10.1093/nar/11.17.5855.
Spencer, J. et al.. “A TATA Binding Protein Mutant with Increased Affinity for DNA Directs Transcription from a Reversed TATA Sequence In Vivo” pp. 8744-8755. Molecular and Cellular Biology. vol. 22, No. 24. Dec. 2002; Abstract; p. 8748; DOI: 10.1128/MCB. 22.24.87 44-8755.2002.
International Search Report and Written Opinion in International Application No. PCT/US2023/065954 mailed Jan. 31, 2024.
Harley, C. et al., “Analysis of E. colt promoter sequences,” Nucleic Acids Research, Jan. 1987, vol. 15, No. 5., pp. 2343-2361.
Lanzer, M. et al., “Promoters largely determine the efficiency of repressor action,” Proceedings of the National Academy of Sciences, Dec. 1988, vol. 85., pp. 8973-8977.
Rincón, A. et al., “Unlocking the strength of inducible promoters in Gram-negative bacteria,” Microbial Biotechnology, May 2023, vol. 16., pp. 961-976.

* cited by examiner

*Primary Examiner* — Allison M Fox
*Assistant Examiner* — Hanan Isam Abuzeineh
(74) *Attorney, Agent, or Firm* — Greenberg Traurig, LLP; Roman Fayerberg; Leslie A. Serunian

(57) ABSTRACT

Provided herein are nucleic acid constructs that comprise an inducible promoter. Dual expression systems are provided comprising two nucleic acid constructs or a single nucleic acid construct with two inducible promoters. Also provided are methods of expressing transcripts by transforming a nucleic acid construct described herein into a prokaryotic cell and contacting the prokaryotic cell with an inducer. Methods of producing a carotenoid are also disclosed herein.

16 Claims, 34 Drawing Sheets

Specification includes a Sequence Listing.

| | | | | | | | | | | | | | | | | |
|---|---|---|---|---|---|---|---|---|---|---|---|---|---|---|---|---|
| | | | | | aTc | | | aTc | | aTc | | | aTc | | | aTc |
| hours | WT | lacI | V1Tc | V1Tc tetR | V1Tc tetR | V2Tc | V2Tc tetR | V2Tc tetR | V2Tc tetR 19 | V2Tc tetR 19 | V3Tc | V3Tc tetR | V3Tc tetR | V4Tc | V4Tc tetR | V4Tc tetR |
| 4 | 0% | 100% | 20% | 0% | 0% | 15% | 0% | 2% | 0% | 2% | 0% | 0% | 0% | 25% | 0% | 0% |
| 8 | 0% | 100% | 29% | 0% | 15% | 32% | 0% | 90% | 1% | 73% | 0% | 0% | 1% | 43% | 0% | 3% |
| 12 | 0% | 100% | 47% | 0% | 21% | 55% | 0% | 95% | 0% | 123% | 0% | 0% | 1% | 63% | 0% | 4% |
| 16 | 0% | 100% | 80% | 0% | 31% | 99% | 0% | 100% | 1% | 152% | 1% | 0% | 1% | 95% | 0% | 5% |

| | | | | | | | | | | | | | | | | |
|---|---|---|---|---|---|---|---|---|---|---|---|---|---|---|---|---|
| | | | IPTG | | | IPTG | | IPTG | | | IPTG | | | IPTG | | IPTG |
| hours | V1Lac | V1Lac lacI | V1Lac lacI | V2Lac CloDF13 | V2Lac lacI CloDF13 | V2Lac lacI CloDF13 | V2Lac lacI | V2Lac lacI | V3Lac | V3Lac lacI | V3Lac lacI | V4Lac | V4Lac lacI | V4Lac lacI | pET21 BL21 | pET21 BL21 |
| 4 | 2% | 0% | 0% | 54% | 2% | 2% | 15% | 17% | 15% | 0% | 0% | 3% | 0% | 0% | 4% | 4% |
| 8 | 2% | 0% | 0% | 72% | 7% | 16% | 44% | 90% | 33% | 0% | 4% | 8% | 0% | 0% | 19% | 103% |
| 12 | 4% | 0% | 2% | 99% | 12% | 29% | 88% | 182% | 56% | 1% | 11% | 13% | 0% | 0% | 31% | 138% |
| 16 | 9% | 0% | 5% | 140% | 16% | 41% | 135% | 262% | 91% | 1% | 22% | 21% | 0% | 1% | 35% | 143% |

FIG. 4C

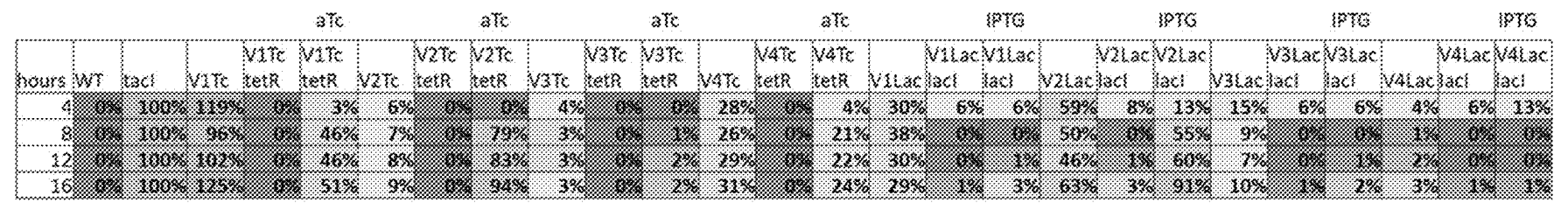

| | | | | | aTc | | | aTc | | | aTc | | | aTc | | | IPTG | | | IPTG | | | IPTG | | | IPTG |
|---|---|---|---|---|---|---|---|---|---|---|---|---|---|---|---|---|---|---|---|---|---|---|---|---|---|---|
| hours | WT | tacI | V1Tc | V1Tc tetR | V1Tc tetR | V2Tc | V2Tc tetR | V2Tc tetR | V3Tc | V3Tc tetR | V3Tc tetR | V4Tc | V4Tc tetR | V4Tc tetR | V1Lac | V1Lac lacI | V1Lac lacI | V2Lac | V2Lac lacI | V2Lac lacI | V3Lac | V3Lac lacI | V3Lac lacI | V4Lac | V4Lac lacI | V4Lac lacI |
| 4 | 0% | 100% | 119% | 0% | 3% | 6% | 0% | 0% | 4% | 0% | 0% | 28% | 0% | 4% | 30% | 6% | 6% | 59% | 8% | 13% | 15% | 6% | 6% | 4% | 6% | 13% |
| 8 | 0% | 100% | 96% | 0% | 46% | 7% | 0% | 79% | 3% | 0% | 1% | 26% | 0% | 21% | 38% | 0% | 0% | 50% | 0% | 55% | 9% | 0% | 0% | 1% | 0% | 0% |
| 12 | 0% | 100% | 102% | 0% | 46% | 8% | 0% | 83% | 3% | 0% | 2% | 29% | 0% | 22% | 30% | 0% | 1% | 46% | 1% | 60% | 7% | 0% | 1% | 2% | 0% | 0% |
| 16 | 0% | 100% | 125% | 0% | 51% | 9% | 0% | 94% | 3% | 0% | 2% | 31% | 0% | 24% | 29% | 1% | 3% | 63% | 3% | 91% | 10% | 1% | 2% | 3% | 1% | 1% |

*FIG. 6C*

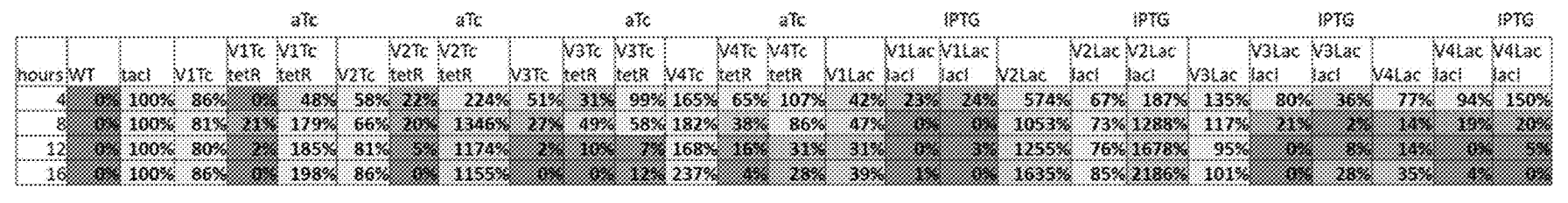

| | | | | | aTc | | | aTc | | | aTc | | | aTc |
|---|---|---|---|---|---|---|---|---|---|---|---|---|---|---|
| hours | WT | tacI | V1Tc | V1Tc tetR | V1Tc tetR | V2Tc | V2Tc tetR | V2Tc tetR | V3Tc | V3Tc tetR | V3Tc tetR | V4Tc | V4Tc tetR | V4Tc tetR |
| 4 | 0% | 100% | 86% | 0% | 48% | 58% | 22% | 224% | 51% | 31% | 99% | 165% | 65% | 107% |
| 8 | 0% | 100% | 81% | 21% | 179% | 66% | 20% | 1346% | 27% | 49% | 58% | 182% | 38% | 86% |
| 12 | 0% | 100% | 80% | 2% | 185% | 81% | 5% | 1174% | 2% | 10% | 7% | 168% | 16% | 31% |
| 16 | 0% | 100% | 86% | 0% | 198% | 86% | 0% | 1155% | 0% | 0% | 12% | 237% | 4% | 28% |

| | | | IPTG | | | IPTG | | | IPTG | | | IPTG |
|---|---|---|---|---|---|---|---|---|---|---|---|---|
| hours | V1Lac | V1Lac lacI | V1Lac lacI | V2Lac | V2Lac lacI | V2Lac lacI | V3Lac | V3Lac lacI | V3Lac lacI | V4Lac | V4Lac lacI | V4Lac lacI |
| 4 | 42% | 23% | 24% | 574% | 67% | 187% | 135% | 80% | 36% | 77% | 94% | 150% |
| 8 | 47% | 0% | 0% | 1053% | 73% | 1288% | 117% | 21% | 2% | 14% | 19% | 20% |
| 12 | 31% | 0% | 3% | 1255% | 76% | 1678% | 95% | 0% | 8% | 14% | 0% | 5% |
| 16 | 39% | 1% | 0% | 1635% | 85% | 2186% | 101% | 0% | 28% | 35% | 4% | 0% |

*FIG. 7C*

SEQUENCE LISTING

```
Sequence total quantity: 79
SEQ ID NO: 1           moltype =   length =
SEQUENCE: 1
000

SEQ ID NO: 2           moltype =   length =
SEQUENCE: 2
000

SEQ ID NO: 3           moltype = DNA  length = 81
FEATURE                Location/Qualifiers
source                 1..81
                       mol_type = other DNA
                       organism = synthetic construct
SEQUENCE: 3
aggctttaca ctttatgctt ccggctcgta tgttgtgtgg aattgtgagc ggataacaat  60
ttcacacagg aaacagctat g                                            81

SEQ ID NO: 4           moltype = DNA  length = 81
FEATURE                Location/Qualifiers
source                 1..81
                       mol_type = other DNA
                       organism = synthetic construct
SEQUENCE: 4
aggctttaca ctttatgctt ccggctcgta taatgtgtgg aattgtgagc ggataacaat  60
ttcacacagg aaacagctat g                                            81

SEQ ID NO: 5           moltype = DNA  length = 85
FEATURE                Location/Qualifiers
source                 1..85
                       mol_type = other DNA
                       organism = synthetic construct
SEQUENCE: 5
gagctgttga caattaatca tcggctcgta taatgtgtgg aattgtgagc ggataacaat  60
ttcacacagg aaacagaatc atatg                                        85

SEQ ID NO: 6           moltype = DNA  length = 85
FEATURE                Location/Qualifiers
source                 1..85
                       mol_type = other DNA
                       organism = synthetic construct
SEQUENCE: 6
aggctttaca ctttatgctt ccggctcgta tgttgtgtgg aattgtgagc ggataacaac  60
gcagtaagag aggaatgtac atatg                                        85

SEQ ID NO: 7           moltype = DNA  length = 89
FEATURE                Location/Qualifiers
source                 1..89
                       mol_type = other DNA
                       organism = synthetic construct
```

-continued

```
SEQUENCE: 7
gagctgttga cactttatgc ttccggctcg tataatgtgt gtggaattgt gagcggataa  60
caacgcagta agagaggaat gtacatatg                                     89

SEQ ID NO: 8           moltype = DNA  length = 112
FEATURE                Location/Qualifiers
source                 1..112
                       mol_type = other DNA
                       organism = synthetic construct
SEQUENCE: 8
gagctgttga cactttatgc ttccggctcg tataatgtgt gtggaattgt gagcggataa  60
caagtggaat tgtgagcgga taacaatttc acacaggaaa cagaatcata tg          112

SEQ ID NO: 9           moltype = DNA  length = 106
FEATURE                Location/Qualifiers
source                 1..106
                       mol_type = other DNA
                       organism = synthetic construct
SEQUENCE: 9
ctttatgctt ccggctcgtt gacagtgtgg aattgtgagc ggataacaat ataatgtgtg  60
gaattgtgag cggataacaa tttcacacag gaaacagaat catatg                 106

SEQ ID NO: 10          moltype = DNA  length = 71
FEATURE                Location/Qualifiers
source                 1..71
                       mol_type = other DNA
                       organism = synthetic construct
SEQUENCE: 10
ggatccttga cactctatca ttgatagagt tattttacca ctccctatca gtgatagaga  60
aaagtgaaat g                                                        71

SEQ ID NO: 11          moltype = DNA  length = 86
FEATURE                Location/Qualifiers
source                 1..86
                       mol_type = other DNA
                       organism = synthetic construct
SEQUENCE: 11
ggatccttga cactctatca ttgatagagt tattttacca ctccctatca gtgatagaga  60
cgcagtaaga gaggaatgta catatg                                        86

SEQ ID NO: 12          moltype = DNA  length = 84
FEATURE                Location/Qualifiers
source                 1..84
                       mol_type = other DNA
                       organism = synthetic construct
SEQUENCE: 12
gagctgttga caactctatc attgatagag ttataatgtt ccctatcagt gatagagacg  60
cagtaagaga ggaatgtaca tatg                                          84

SEQ ID NO: 13          moltype = DNA  length = 107
FEATURE                Location/Qualifiers
source                 1..107
                       mol_type = other DNA
                       organism = synthetic construct
SEQUENCE: 13
gagctgttga caactctatc attgatagag ttataatgtt ccctatcagt gatagagagt  60
ggaattgtga gcggataaca atttcacaca ggaaacagaa tcatatg                107

SEQ ID NO: 14          moltype = DNA  length = 106
FEATURE                Location/Qualifiers
source                 1..106
                       mol_type = other DNA
                       organism = synthetic construct
SEQUENCE: 14
ttgacactct atcattgata gagtttgaca tccctatcag tgatagagat ataatgtgtg  60
gaattgtgag cggataacaa tttcacacag gaaacagaat catatg                 106

SEQ ID NO: 15          moltype = DNA  length = 81
FEATURE                Location/Qualifiers
source                 1..81
                       mol_type = other DNA
                       organism = synthetic construct
SEQUENCE: 15
attgcctcga gactgatttt taaggcgact gatgagtcgc cttttttttg tctagctaac  60
tcacattaat tgcgttgcgc t                                             81

SEQ ID NO: 16          moltype = DNA  length = 72
FEATURE                Location/Qualifiers
source                 1..72
```

```
                         mol_type = other DNA
                         organism = synthetic construct
SEQUENCE: 16
gcaatggatc cagtcaaaag cctccgaccg gaggcttttg actagtacaa tctgctctga  60
tgccgcatag tt                                                       72

SEQ ID NO: 17            moltype = DNA  length = 33
FEATURE                  Location/Qualifiers
source                   1..33
                         mol_type = other DNA
                         organism = synthetic construct
SEQUENCE: 17
ggcgcgtact ccaaaaggat ctaggtgaag atc                                33

SEQ ID NO: 18            moltype = DNA  length = 32
FEATURE                  Location/Qualifiers
source                   1..32
                         mol_type = other DNA
                         organism = synthetic construct
SEQUENCE: 18
gagttcttct gattagacaa aaaaaaggcg ac                                 32

SEQ ID NO: 19            moltype = DNA  length = 35
FEATURE                  Location/Qualifiers
source                   1..35
                         mol_type = other DNA
                         organism = synthetic construct
SEQUENCE: 19
tttttttgtc taatcagaag aactcgtcaa gaagg                              35

SEQ ID NO: 20            moltype = DNA  length = 32
FEATURE                  Location/Qualifiers
source                   1..32
                         mol_type = other DNA
                         organism = synthetic construct
SEQUENCE: 20
gcccgacggc gaggatctcg tcgtgacgca tg                                 32

SEQ ID NO: 21            moltype = DNA  length = 31
FEATURE                  Location/Qualifiers
source                   1..31
                         mol_type = other DNA
                         organism = synthetic construct
SEQUENCE: 21
cacgacgaga tcctcgccgt cgggcatccg c                                  31

SEQ ID NO: 22            moltype = DNA  length = 51
FEATURE                  Location/Qualifiers
source                   1..51
                         mol_type = other DNA
                         organism = synthetic construct
SEQUENCE: 22
gtctagactg caggaattca agcttcatat gggatccgga ccaaaacgaa a            51

SEQ ID NO: 23            moltype = DNA  length = 51
FEATURE                  Location/Qualifiers
source                   1..51
                         mol_type = other DNA
                         organism = synthetic construct
SEQUENCE: 23
aagcttgaat tcctgcagtc tagaccatgg ctcgaggacg aacaataagg c            51

SEQ ID NO: 24            moltype = DNA  length = 31
FEATURE                  Location/Qualifiers
source                   1..31
                         mol_type = other DNA
                         organism = synthetic construct
SEQUENCE: 24
cctagatcct tttggagtac gcgcccgggg a                                  31

SEQ ID NO: 25            moltype = DNA  length = 21
FEATURE                  Location/Qualifiers
source                   1..21
                         mol_type = other DNA
                         organism = synthetic construct
SEQUENCE: 25
tactggtttc acattcacca c                                             21

SEQ ID NO: 26            moltype = DNA  length = 22
```

-continued

```
FEATURE                Location/Qualifiers
source                 1..22
                       mol_type = other DNA
                       organism = synthetic construct
SEQUENCE: 26
gtggtgaatg tgaaaccagt aa                                          22

SEQ ID NO: 27          moltype = DNA  length = 18
FEATURE                Location/Qualifiers
source                 1..18
                       mol_type = other DNA
                       organism = synthetic construct
SEQUENCE: 27
tttccagtcg ggaaacct                                               18

SEQ ID NO: 28          moltype = DNA  length = 18
FEATURE                Location/Qualifiers
source                 1..18
                       mol_type = other DNA
                       organism = synthetic construct
SEQUENCE: 28
aggtttcccg actggaaa                                               18

SEQ ID NO: 29          moltype = DNA  length = 20
FEATURE                Location/Qualifiers
source                 1..20
                       mol_type = other DNA
                       organism = synthetic construct
SEQUENCE: 29
ccaatacaac gtgggttgct                                             20

SEQ ID NO: 30          moltype = DNA  length = 24
FEATURE                Location/Qualifiers
source                 1..24
                       mol_type = other DNA
                       organism = synthetic construct
SEQUENCE: 30
aaccggaatt cccccgtggc cggg                                        24

SEQ ID NO: 31          moltype = DNA  length = 27
FEATURE                Location/Qualifiers
source                 1..27
                       mol_type = other DNA
                       organism = synthetic construct
SEQUENCE: 31
aaccgctcga gtcactgccc gctttcc                                     27

SEQ ID NO: 32          moltype = DNA  length = 32
FEATURE                Location/Qualifiers
source                 1..32
                       mol_type = other DNA
                       organism = synthetic construct
SEQUENCE: 32
attgcctgca gtcactgccc gctttccagt cg                               32

SEQ ID NO: 33          moltype = DNA  length = 62
FEATURE                Location/Qualifiers
source                 1..62
                       mol_type = other DNA
                       organism = synthetic construct
SEQUENCE: 33
gcaattctag aagtcaaaag cctccgaccg gaggcttttg actccccgtg gccgggggac  60
tg                                                                62

SEQ ID NO: 34          moltype = DNA  length = 49
FEATURE                Location/Qualifiers
source                 1..49
                       mol_type = other DNA
                       organism = synthetic construct
SEQUENCE: 34
gcctccggtc ggaggctttt gacttctaga gagctgttga cactttatg             49

SEQ ID NO: 35          moltype = DNA  length = 50
FEATURE                Location/Qualifiers
source                 1..50
                       mol_type = other DNA
                       organism = synthetic construct
SEQUENCE: 35
taatgagctc ctcaccctta ctcaccatgg gtacattcct ctcttactgc            50
```

```
SEQ ID NO: 36          moltype = DNA  length = 25
FEATURE                Location/Qualifiers
source                 1..25
                       mol_type = other DNA
                       organism = synthetic construct
SEQUENCE: 36
taatgagctc ctcaccctta ctcac                                         25

SEQ ID NO: 37          moltype = DNA  length = 23
FEATURE                Location/Qualifiers
source                 1..23
                       mol_type = other DNA
                       organism = synthetic construct
SEQUENCE: 37
catgggattc tgtttcctgt gtg                                           23

SEQ ID NO: 38          moltype = DNA  length = 34
FEATURE                Location/Qualifiers
source                 1..34
                       mol_type = other DNA
                       organism = synthetic construct
SEQUENCE: 38
tcagtctcga gttacttgtc gtcatcatcc ttat                               34

SEQ ID NO: 39          moltype = DNA  length = 759
FEATURE                Location/Qualifiers
source                 1..759
                       mol_type = other DNA
                       organism = synthetic construct
SEQUENCE: 39
atggtgagta agggtgagga gctcattaag gagaacatgc acatgaagct gtatatggag  60
ggcaccgtaa acaaccacca cttcaagtgt accaccgagg gtgaaggtaa accctacgag  120
gggacgcaga cccaacgcat caaggtcgtg gagggcggcc cgctgccttt cgcattcgac  180
attctggcga cctgttttat gtacggctcg aagaccttca tcaaccacac ccaaggcatc  240
ccggacttct tcaagcagag cttccctgag ggcttcacct gggagcgcgt caccacgtat  300
gaagacggtg gggtgctcac cgtgacccag gacacgagct tgcaggatgg ctgcttgatt  360
tacaacgtca agctgcgcgg ggtgaacttc cctagcaacg ggccagtgat gcagaaaaag  420
acgctgggtt gggaggccac caccgagacc ctgtacccgg ccgacggggg gctggaaggg  480
cggtgcgata tggccctgaa attggtcggc ggcggtcatt tgcactgcaa tctcaagacc  540
acgtaccgct ccaagaaacc cgccaaaaac ctgaagatgc ctggtgttta ttttgtcgac  600
cggcgcctgg agcgcatcaa ggaagcggac aatgagacgt acgtggaaca gcacgaagtg  660
gccgtggctc gttattgcga tctgccgtcg aagctgggtc acaaactgaa cggcatggat  720
gagctgtaca aagattataa ggatgatgac gacaagtaa                          759

SEQ ID NO: 40          moltype = DNA  length = 742
FEATURE                Location/Qualifiers
source                 1..742
                       mol_type = other DNA
                       organism = synthetic construct
SEQUENCE: 40
atgtccaaag gtgaagagct gtttaccggc gtcgtgccca ttctggtgga gctggatggc  60
gacgtcaacg ggcacaagtt tagcgtccgt ggcgaaggtg agggcgacgc cacgaacggt  120
aagctgacgc tgaaattcat ttgcaccacc ggcaaattgc ctgtaccctg gcccaccctg  180
gtgaccacgc tcacctacgg cgtacagtgc ttcagccgtt acccggacca catgaagcgt  240
cacgacttct tcaaaagcgc catgccggag ggttacgtgc aggagcgtac gattagtttc  300
aaggacgacg gcacctataa gacccgtgcc gaagtgaagt tcgaaggcga tacgttggtg  360
aaccgtatcg agttgaaggg tatcgacttt aaggaagacg gcaacatcct gggccataag  420
ctggagtaca atttcaacag ccataacgtt tacatcaccg ccgataaaca gaagaacggc  480
attaaagcca actttaagat ccgccacaac gtcgaagacg gctcggtgca gctggccgac  540
cattatcagc aaaacacccc catcggtgat gggcccgtgc tgctgccgga taaccattat  600
ctgagcacgc agtcggtgct cagcaaggac cctaacgaaa agcgcgatca catggtgctg  660
ctggagttcg tcacggcggc ggggatcacc catgggatgg acgagctcta caaagactat  720
aaagatgacg atgacaagta aa                                            742

SEQ ID NO: 41          moltype = DNA  length = 624
FEATURE                Location/Qualifiers
source                 1..624
                       mol_type = other DNA
                       organism = synthetic construct
SEQUENCE: 41
atgtcccgcc tggataaatc gaaagtgatt aactcggccc tcgaattgct gaatgaagtc  60
ggtatcgagg ggctgacgac ccgtaaattg gcacaaaagt tgggggtgga gcaacccacg  120
ttgtattggc acgtcaaaaa taagcgggca ttgctggatg ccctcgctat tgaaatgttg  180
gatcgccacc atacccattt ctgtccactg gagggcgagt cctggcagga ctttctccgc  240
aacaacgcga aatcctttcg ctgtgcactc ttgtcccatc gggacggtgc taaggtgcac  300
ttgggcaccc gtcccaccga aaaacaatac gaaaccttgg aaaatcaatt ggcgtttttg  360
tgccagcaag ggtttagctt ggagaatgct ctctatgcgc tctcggctgt cgggcacttt  420
acgttggggt gcgtgttgga ggaccaggag catcaagtcg caaaagagga gcgtgaaacc  480
```

-continued

```
ccaaccacgg actcgatgcc acctctgctc cgccaagcta tcgaactctt cgatcatcag  540
ggcgcggagc cagccttcct ctttgggctg gagctgatta tctgcggttt ggaaaaacaa  600
ctcaagtgtg aaagcgggtc ctaa                                         624

SEQ ID NO: 42          moltype = DNA  length = 1758
FEATURE                Location/Qualifiers
source                 1..1758
                       mol_type = other DNA
                       organism = synthetic construct
SEQUENCE: 42
catatggtgg acggtaatta ttcggtagcg tccaacgtta tggtgccgat gcgcgacggg  60
gtgcgcttgg ctgtagatct gtaccgcccg gacgcagatg gccctgtacc ggtcctgctg  120
gtccgcaacc cctacgacaa attcgacgtg ttcgcttgga gtacgcagag cacgaactgg  180
ctggaatttg tgcgcgatgg gtacgccgtc gtcatccaag acacccgggg cctctttgca  240
tccgaaggtg agttcgttcc acatgttgat gacgaggcgg atgcggaaga cacgctgagc  300
tggatcttgg aacaagcatg gtgcgacggc aatgtgggta tgttcggtgt aagctacctg  360
ggcgttacgc agtggcaagc tgctgttagc ggtgtgggtg gtttgaaggc aatcgccccg  420
agcatggcga gcgcggatct gtaccgtgcc ccctggtacg gtcctggcgg cgccctgagc  480
gtggaagcac tcctgggctg gagcgcattg atcggtacgg gcctgattac cagccgtagc  540
gatgcccgcc cggaagacgc agccgacttc gtacagctgg cagccatcct gaacgatgtg  600
gccggtgccg caagcgtgac ccctctggcc gaacagccct tgttgggccg cctgatccct  660
tgggtgatcg accaggtggt ggaccatcca gacaacgacg agtcgtggca gagcatctcg  720
ctctttgaac gtttgggtgg gctcgctacc ccggccttga ttaccgccgg gtggtacgat  780
ggcttcgtgg gcgagagcct ccgtaccttc gtagctgtga aggacaacgc ggatgcgcgt  840
ctggtggtgg ggccgtggag ccacagcaat ctgaccggcc gtaatgccga ccgtaagttt  900
gggatcgccg cgacctaccc catccaggag gcgacgacca tgcacaaggc ttttttcgac  960
cggcacctcc gtggcgagac cgatgccctg gcaggggtgc ccaaggtgcg cctcttcgta  1020
atgggtatcg atgagtggcg cgacgagacc gactggccat tgccagatac cgcttacacg  1080
ccttttttacc tcgggggctc cggtgcggcc aacacgagca cgggtggtgg gaccctgtcg  1140
acctcgatca gcggcacgga gtcggcggac acctacctgt atgatcctgc cgaccccgtg  1200
ccaagtctgg gcggcaccct cctcttccat aatggggaca acggtccagc tgaccagcgc  1260
ccgattcacg atcgcgacga cgtgctgtgc tactccaccg aggtgttgac cgaccccgtg  1320
gaagtaacgg ggacggtttc ggctcgcctg ttcgtgtcct cgtcggccgt ggataccgat  1380
tttaccgcca agttggtcga cgtgttcccc gatggtcggg caatcgctct ctgcgacggc  1440
atcgtgcgta tgcgctaccg ggagaccttg gtaaatccta cgctcattga ggccggtgag  1500
atttacgagg tggctattga tatgctggcc accagcaacg tgtttttgcc gggccaccgc  1560
atcatggtgc aagttagcag ctcgaacttc ccgaagtacg accgcaactc caacaccggc  1620
ggcgtcatcg ctcgcgagca actggaggaa atgtgcaccg ccgtaaaccg cattcaccgc  1680
ggccccgaac acccgtccca tatcgtgctg ccgatcatta agcgcgacta taaggacgac  1740
gacgataagt gaaagctt                                                1758

SEQ ID NO: 43          moltype = DNA  length = 58
FEATURE                Location/Qualifiers
source                 1..58
                       mol_type = other DNA
                       organism = synthetic construct
SEQUENCE: 43
ttgacagcta gctcagtcct aggtataatg ctagccgcag taagagagga atgtacac    58

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
000

SEQ ID NO: 51          moltype =   length =
SEQUENCE: 51
```

```
000

SEQ ID NO: 52          moltype =   length =
SEQUENCE: 52
000

SEQ ID NO: 53          moltype =   length =
SEQUENCE: 53
000

SEQ ID NO: 54          moltype = DNA  length = 2334
FEATURE                Location/Qualifiers
source                 1..2334
                       mol_type = other DNA
                       organism = synthetic construct
SEQUENCE: 54
gagctgttga caactctatc attgatagag ttataatgtt ccctatcagt gatagagacg  60
cagtaagaga ggaatgtaca tatgaagctt ctcggtacca aattccagaa aagaggcctc  120
ccgaaagggg ggcctttttt cgttttggtc cgaattcttg acagctagct cagtcctagg  180
tataatgcta gccgcagtaa gagaggaatg tacacatgtc ccgcctggat aaatcgaaag  240
tgattaactc ggccctcgaa ttgctgaatg aagtcggtat cgaggggctg acgacccgta  300
aattggcaca aaagttgggg gtggagcaac ccacgttgta ttggcacgtc aaaaataagc  360
gggcattgct ggatgccctc gctattgaaa tgttggatcg ccaccatacc catttctgtc  420
cactggaggg cgagtcctgg caggactttc tccgcaacaa cgcgaaatcc tttcgctgtg  480
cactcttgtc ccatcgggac ggtgctaagg tgcacttggg cacccgtccc accgaaaaac  540
aatacgaaac cttggaaaat caattggcgt ttttgtgcca gcaagggttt agcttggaga  600
atgctctcta tgcgctctcg gctgtcgggc actttacgtt ggggtgcgtg ttggaggacc  660
aggagcatca agtcgcaaaa gaggagcgtg aaaccccaac cacggactcg atgccacctc  720
tgctccgcca agctatcgaa ctcttcgatc atcagggcgc ggagccagcc ttcctctttg  780
ggctggagct gattatctgc ggtttggaaa aacaactcaa gtgtgaaagc gggtcctaac  840
tgcagtcact gcccgctttc cagtcgggaa acctgtcgtg ccagctgcat taatgaatcg  900
gccaacgcgc ggggagaggc ggtttgcgta ttgggcgcca gggtggtttt tcttttcacc  960
agtgagacgg gcaacagctg attgcccttc accgcctggc cctgagagag ttgcagcaag  1020
cggtccacgc tggtttgccc cagcaggcga aaatcctgtt tgatggtggt taacggcggg  1080
atataacatg agctgtcttc ggtatcgtcg tatcccacta ccgagatatc cgcaccaacg  1140
cgcagcccgg actcggtaat ggcgcgcatt gcgcccagcg ccatctgatc gttggcaacc  1200
agcatcgcag tgggaacgat gccctcattc agcatttgca tggtttgttg aaaaccggac  1260
atggcactcc agtcgccttc ccgttccgct atcggctgaa tttgattgcg agtgagatat  1320
ttatgccagc cagccagacg cagacgcgcc gagacagaac ttaatgggcc cgctaacagc  1380
gcgatttgct ggtgacccaa tgcgaccaga tgctccacgc ccagtcgcgt accgtcttca  1440
tgggagaaaa taatactgtt gatgggtgtc tggtcagaga catcaagaaa taacgccgga  1500
acattagtgc aggcagcttc cacagcaatg gcatcctggt catccagcgg atagttaatg  1560
atcagcccac tgacgcgttg cgcgagaaga ttgtgcaccg ccgctttaca ggcttcgacg  1620
ccgcttcgtt ctaccatcga caccaccacg ctggcaccca gttgatcggc gcgagattta  1680
atcgccgcga caatttgcga cggcgcgtgc agggccagac tggaggtggc aacgccaatc  1740
agcaacgact gtttgcccgc cagttgttgt gccacgcggt tgggaatgta attcagctcc  1800
gccatcgccg cttccacttt ttcccgcgtt ttcgcagaaa cgtggctggc ctggttcacc  1860
acgcgggaaa cggtctgata agagacaccg gcatactctg cgacatcgta taacgttact  1920
ggtttcacat tcaccaccct gaattgactc tcttccgggc gctatcatgc cataccgcga  1980
aaggttttgc gccattcgat ggtgtccggg atctcgacgc tctcccttat gcgactcctg  2040
cattaggaag cagcccagta gtaggttgag gccgttgagc accgccgccg caaggaatgg  2100
tgcatgcaag gagatggcgc ccaacagtcc cccggccacg gggagtcaaa agcctccggt  2160
cggaggcttt tgacttctag agagctgttg acactttatg cttccggctc gtataatgtg  2220
tgtggaattg tgagcggata acaacgcagt aagagaggaa tgtacccatg gccatggctc  2280
gaggacgaac aataaggcct ccctaacggg gggccttttt tattgataac aaaa        2334

SEQ ID NO: 55          moltype = DNA  length = 2351
FEATURE                Location/Qualifiers
source                 1..2351
                       mol_type = other DNA
                       organism = synthetic construct
SEQUENCE: 55
gagctgttga caactctatc attgatagag ttataatgtt ccctatcagt gatagagacg  60
cagtaagaga ggaatgtaca tatgaagctt ctcggtacca aattccagaa aagaggcctc  120
ccgaaagggg ggcctttttt cgttttggtc cgaattcttg acagctagct cagtcctagg  180
tataatgcta gccgcagtaa gagaggaatg tacacatgtc ccgcctggat aaatcgaaag  240
tgattaactc ggccctcgaa ttgctgaatg aagtcggtat cgaggggctg acgacccgta  300
aattggcaca aaagttgggg gtggagcaac ccacgttgta ttggcacgtc aaaaataagc  360
gggcattgct ggatgccctc gctattgaaa tgttggatcg ccaccatacc catttctgtc  420
cactggaggg cgagtcctgg caggactttc tccgcaacaa cgcgaaatcc tttcgctgtg  480
cactcttgtc ccatcgggac ggtgctaagg tgcacttggg cacccgtccc accgaaaaac  540
aatacgaaac cttggaaaat caattggcgt ttttgtgcca gcaagggttt agcttggaga  600
atgctctcta tgcgctctcg gctgtcgggc actttacgtt ggggtgcgtg ttggaggacc  660
aggagcatca agtcgcaaaa gaggagcgtg aaaccccaac cacggactcg atgccacctc  720
tgctccgcca agctatcgaa ctcttcgatc atcagggcgc ggagccagcc ttcctctttg  780
ggctggagct gattatctgc ggtttggaaa aacaactcaa gtgtgaaagc gggtcctaac  840
tgcagtcact gcccgctttc cagtcgggaa acctgtcgtg ccagctgcat taatgaatcg  900
gccaacgcgc ggggagaggc ggtttgcgta ttgggcgcca gggtggtttt tcttttcacc  960
agtgagacgg gcaacagctg attgcccttc accgcctggc cctgagagag ttgcagcaag  1020
```

```
cggtccacgc tggtttgccc cagcaggcga aaatcctgtt tgatggtggt taacggcggg  1080
atataacatg agctgtcttc ggtatcgtcg tatcccacta ccgagatatc cgcaccaacg  1140
cgcagcccgg actcggtaat ggcgcgcatt gcgcccagcg ccatctgatc gttggcaacc  1200
agcatcgcag tgggaacgat gccctcattc agcatttgca tggtttgttg aaaaccggac  1260
atggcactcc agtcgccttc ccgttccgct atcggctgaa tttgattgcg agtgagatat  1320
ttatgccagc cagccagacg cagacgcgcc gagacagaac ttaatgggcc cgctaacagc  1380
gcgatttgct ggtgacccaa tgcgaccaga tgctccacgc ccagtcgcgt accgtcttca  1440
tgggagaaaa taatactgtt gatgggtgtc tggtcagaga catcaagaaa taacgccgga  1500
acattagtgc aggcagcttc cacagcaatg gcatcctggt catccagcgg atagttaatg  1560
atcagcccac tgacgcgttg cgcgagaaga ttgtgcaccg ccgctttaca ggcttcgacg  1620
ccgcttcgtt ctaccatcga caccaccacg ctggcaccca gttgatcggc gcgagattta  1680
atcgccgcga caatttgcga cggcgcgtgc agggccagac tggaggtggc aacgccaatc  1740
agcaacgact gtttgcccgc cagttgttgt gccacgcggt tgggaatgta attcagctcc  1800
gccatcgccg cttccacttt ttcccgcgtt ttcgcagaaa cgtggctggc ctggttcacc  1860
acgcgggaaa cggtctgata agagacaccg gcatactctg cgacatcgta taacgttact  1920
ggtttcacat tcaccaccct gaattgactc tcttccgggc gctatcatgc cataccgcga  1980
aaggttttgc gccattcgat ggtgtccggg atctcgacgc tctcccttat gcgactcctg  2040
cattaggaag cagcccagta gtaggttgag gccgttgagc accgccgccg caaggaatgg  2100
tgcatgcaag gagatggcgc ccaacagtcc cccggccacg gggagtcaaa agcctccggt  2160
cggaggcttt tgacttctag agagctgttg acactttatg cttccggctc gtataatgtg  2220
tgtggaattg tgagcggata acaagtggaa ttgtgagcgg ataacaattt cacacaggaa  2280
acagaatccc atggctcgag gacgaacaat aaggcctccc taacgggggg cctttttat   2340
tgataacaaa a                                                       2351
```

```
SEQ ID NO: 56          moltype = DNA  length = 1625
FEATURE                Location/Qualifiers
source                 1..1625
                       mol_type = other DNA
                       organism = synthetic construct
SEQUENCE: 56
ggatccgagc tgttgacaac tctatcattg atagagttat aatgttccct atcagtgata  60
gagacgcagt aagagaggaa tgtacatatg gtgagtaagg gtgaggagct cattaaggag  120
aacatgcaca tgaagctgta tatggagggc accgtaaaca accaccactt caagtgtacc  180
accgagggtg aaggtaaacc ctacgagggg acgcagaccc aacgcatcaa ggtcgtggag  240
ggcggcccgc tgcctttcgc attcgacatt ctggcgacct gttttatgta cggctcgaag  300
accttcatca accacaccca aggcatcccg gacttcttca agcagagctt ccctgagggc  360
ttcacctggg agcgcgtcac cacgtatgaa gacggtgggg tgctcaccgt gacccaggac  420
acgagcttgc aggatggctg cttgatttac aacgtcaagc tgcgcggggt gaacttccct  480
agcaacgggc cagtgatgca gaaaaagacg ctgggttggg aggccaccac cgagaccctg  540
tacccggccg acgggggcgt ggaagggcgg tgcgatatgg ccctgaaatt ggtcggcggc  600
ggtcatttgc actgcaatct caagaccacg taccgctcca agaaacccgc caaaaacctg  660
aagatgcctg gtgtttattt tgtcgaccgg cgcctggagc gcatcaagga agcggacaat  720
gagacgtacg tggaacagca cgaagtggcc gtggctcgtt attgcgatct gccgtcgaag  780
ctgggtcaca aactgaacgg catggatgag ctgtacaaag attataagga tgatgacgac  840
aagtaaaagc ttctcggtac caaattccag aaaagaggcc tcccgaaagg ggggcctttt  900
ttcgttttgg tccgaattct tgacagctag ctcagtccta ggtataatgc tagccgcagt  960
aagagaggaa tgtacacatg tcccgcctgg ataaatcgaa agtgattaac tcggccctcg  1020
aattgctgaa tgaagtcggt atcgaggggc tgacgacccg taaattggca caaaagttgg  1080
gggtggagca acccacgttg tattggcacg tcaaaaataa gcgggcattg ctggatgccc  1140
tcgctattga aatgttggat cgccaccata cccatttctg tccactggag ggcgagtcct  1200
ggcaggactt tctccgcaac aacgcgaaat cctttcgctg tgcactcttg tcccatcggg  1260
acggtgctaa ggtgcacttg ggcacccgtc ccaccgaaaa acaatacgaa accttggaaa  1320
atcaattggc gtttttgtgc cagcaagggt ttagcttgga gaatgctctc tatgcgctct  1380
cggctgtcgg gcactttacg ttggggtgcg tgttggagga ccaggagcat caagtcgcaa  1440
aagaggagcg tgaaacccca accacggact cgatgccacc tctgctccgc caagctatcg  1500
aactcttcga tcatcagggc gcggagccag ccttcctctt tggctggag  ctgattatct  1560
gcggtttgga aaaacaactc aagtgtgaaa gcgggtccta actgcagtct agaccatggc  1620
tcgag                                                              1625
```

```
SEQ ID NO: 57          moltype = DNA  length = 2234
FEATURE                Location/Qualifiers
source                 1..2234
                       mol_type = other DNA
                       organism = synthetic construct
SEQUENCE: 57
ggatccgagc tgttgacact ttatgcttcc ggctcgtata atgtgtgtgg aattgtgagc  60
ggataacaac gcagtaagag aggaatgtac atatggtgag taagggtgag gagctcatta  120
aggagaacat gcacatgaag ctgtatatgg agggcaccgt aaacaaccac cacttcaagt  180
gtaccaccga gggtgaaggt aaaccctacg aggggacgca gacccaacgc atcaaggtcg  240
tggagggcgg cccgctgcct ttcgcattcg acattctggc gacctgtttt atgtacggct  300
cgaagacctt catcaaccac acccaaggca tcccggactt cttcaagcag agcttccctg  360
agggcttcac ctgggagcgc gtcaccacgt atgaagacgg tggggtgctc accgtgaccc  420
aggacacgag cttgcaggat ggctgcttga tttacaacgt caagctgcgc ggggtgaact  480
tccctagcaa cgggccagtg atgcagaaaa agacgctggg ttgggaggcc accaccgaga  540
ccctgtaccc ggccgacggg ggcgtggaag ggcggtgcga tatggccctg aaattggtcg  600
gcggcggtca tttgcactgc aatctcaaga ccacgtaccg ctccaagaaa cccgccaaaa  660
acctgaagat gcctggtgtt tattttgtcg accggcgcct ggagcgcatc aaggaagcgg  720
acaatgagac gtacgtggaa cagcacgaag tggccgtggc tcgttattgc gatctgccgt  780
cgaagctggg tcacaaactg aacggcatgg atgagctgta caaagattat aaggatgatg  840
```

```
acgacaagta aaagcttctc ggtaccaaat tccagaaaag aggcctcccg aaaggggggc  900
ctttttttcgt tttggtccga attcccccgt ggccggggga ctgttgggcg ccatctcctt  960
gcatgcacca ttccttgcgg cggcggtgct caacggcctc aacctactac tgggctgctt  1020
cctaatgcag gagtcgcata agggagagcg tcgagatccc ggacaccatc gaatggcgca  1080
aaacctttcg cggtatggca tgatagcgcc cggaagagag tcaattcagg gtggtgaatg  1140
tgaaaccagt aacgttatac gatgtcgcag agtatgccgg tgtctcttat cagaccgttt  1200
cccgcgtggt gaaccaggcc agccacgttt ctgcgaaaac gcgggaaaaa gtggaagcgg  1260
cgatggcgga gctgaattac attcccaacc gcgtggcaca acaactggcg ggcaaacagt  1320
cgttgctgat tggcgttgcc acctccagtc tggccctgca cgcgccgtcg caaattgtcg  1380
cggcgattaa atctcgcgcc gatcaactgg gtgccagcgt ggtggtgtcg atggtagaac  1440
gaagcggcgt cgaagcctgt aaagcggcgg tgcacaatct tctcgcgcaa cgcgtcagtg  1500
ggctgatcat taactatccg ctggatgacc aggatgccat tgctgtggaa gctgcctgca  1560
ctaatgttcc ggcgttattt cttgatgtct ctgaccagac acccatcaac agtattattt  1620
tctcccatga agacggtacg cgactgggcg tggagcatct ggtcgcattg ggtcaccagc  1680
aaatcgcgct gttagcgggc ccattaagtt ctgtctcggc gcgtctgcgt ctggctggct  1740
ggcataaata tctcactcgc aatcaaattc agccgatagc ggaacgggaa ggcgactgga  1800
gtgccatgtc cggttttcaa caaaccatgc aaatgctgaa tgagggcatc gttcccactg  1860
cgatgctggt tgccaacgat cagatggcgc tgggcgcaat gcgcgccatt accgagtccg  1920
ggctgcgcgt tggtgcggat atctcggtag tgggatacga cgataccgaa gacagctcat  1980
gttatatccc gccgttaacc accatcaaac aggattttcg cctgctgggg caaaccagcg  2040
tggaccgctt gctgcaactc tctcagggcc aggcggtgaa gggcaatcag ctgttgcccg  2100
tctcactggt gaaaagaaaa accaccctgg cgcccaatac gcaaaccgcc tctccccgcg  2160
cgttggccga ttcattaatg cagctggcac gacaggtttc ccgactggaa agcgggcagt  2220
gactgcagct cgag                                                     2234

SEQ ID NO: 58          moltype =   length =
SEQUENCE: 58
000

SEQ ID NO: 59          moltype =   length =
SEQUENCE: 59
000

SEQ ID NO: 60          moltype = DNA  length = 2257
FEATURE                Location/Qualifiers
source                 1..2257
                       mol_type = other DNA
                       organism = synthetic construct
SEQUENCE: 60
ggatccgagc tgttgacact ttatgcttcc ggctcgtata atgtgtgtgg aattgtgagc  60
ggataacaag tggaattgtg agcggataac aatttcacac aggaaacaga atcatatggt  120
gagtaagggt gaggagctca ttaaggagaa catgcacatg aagctgtata tggagggcac  180
cgtaaacaac caccacttca agtgtaccac cgagggtgaa ggtaaaccct acgaggggac  240
gcagacccaa cgcatcaagg tcgtggaggg cggcccgctg cctttcgcat tcgacattct  300
ggcgacctgt tttatgtacg gctcgaagac cttcatcaac cacacccaag gcatcccgga  360
cttcttcaag cagagcttcc ctgagggctt cacctgggag cgcgtcacca cgtatgaaga  420
cggtggggtg ctcaccgtga cccaggacac gagcttgcag gatggctgct tgatttacaa  480
cgtcaagctg cgcggggtga acttccctag caacgggcca gtgatgcaga aaaagacgct  540
gggttgggag gccaccaccg agaccctgta cccggccgac ggggggctgg aagggcggtg  600
cgatatggcc ctgaaattgg tcggcggcgg tcatttgcac tgcaatctca agaccacgta  660
ccgctccaag aaacccgcca aaaacctgaa gatgcctggt gtttattttg tcgaccggcg  720
cctggagcgc atcaaggaag cggacaatga gacgtacgtg gaacagcacg aagtggccgt  780
ggctcgttat tgcgatctgc cgtcgaagct gggtcacaaa ctgaacggca tggatgagct  840
gtacaaagat tataaggatg atgacgacaa gtaaaagctt ctcggtacca aattccagaa  900
aagaggcctc ccgaaagggg ggcctttttt cgttttggtc cgaattcccc cgtggccggg  960
ggactgttgg gcgccatctc cttgcatgca ccattccttg cggcggcggt gctcaacggc  1020
ctcaacctac tactgggctg cttcctaatg caggagtcgc ataagggaga gcgtcgagat  1080
cccggacacc atcgaatggc gcaaaacctt tcgcggtatg gcatgatagc gcccggaaga  1140
gagtcaattc agggtggtga atgtgaaacc agtaacgtta tacgatgtcg cagagtatgc  1200
cggtgtctct tatcagaccg tttcccgcgt ggtgaaccag gccagccacg tttctgcgaa  1260
aacgcgggaa aaagtggaag cggcgatggc ggagctgaat tacattccca accgcgtggc  1320
acaacaactg gcgggcaaac agtcgttgct gattggcgtt gccacctcca gtctggccct  1380
gcacgcgccg tcgcaaattg tcgcggcgat taaatctcgc gccgatcaac tgggtgccag  1440
cgtggtggtg tcgatggtag aacgaagcgg cgtcgaagcc tgtaaagcgg cggtgcacaa  1500
tcttctcgcg caacgcgtca gtgggctgat cattaactat ccgctggatg accaggatgc  1560
cattgctgtg gaagctgcct gcactaatgt tccggcgtta tttcttgatg tctctgacca  1620
gacacccatc aacagtatta ttttctccca tgaagacggt acgcgactgg gcgtggagca  1680
tctggtcgca ttgggtcacc agcaaatcgc gctgttagcg ggcccattaa gttctgtctc  1740
ggcgcgtctg cgtctggctg gctggcataa atatctcact cgcaatcaaa ttcagccgat  1800
agcggaacgg gaaggcgact ggagtgccat gtccggtttt caacaaacca tgcaaatgct  1860
gaatgagggc atcgttccca ctgcgatgct ggttgccaac gatcagatgg cgctgggcgc  1920
aatgcgcgcc attaccgagt ccgggctgcg cgttggtgcg gatatctcgg tagtgggata  1980
cgacgatacc gaagacagct catgttatat cccgccgtta accaccatca aacaggattt  2040
tcgcctgctg gggcaaacca gcgtggaccg cttgctgcaa ctctctcagg gccaggcggt  2100
gaagggcaat cagctgttgc ccgtctcact ggtgaaaaga aaaaccaccc tggcgcccaa  2160
tacgcaaacc gcctctcccc gcgcgttggc cgattcatta atgcagctgg cacgacaggt  2220
ttcccgactg gaaagcgggc agtgactgca gctcgag                            2257

SEQ ID NO: 61          moltype = DNA  length = 1595
```

```
FEATURE                  Location/Qualifiers
source                   1..1595
                         mol_type = other DNA
                         organism = synthetic construct
SEQUENCE: 61
ggatccgagc tgttgacaac tctatcattg atagagttat aatgttccct atcagtgata  60
gagacgcagt aagagaggaa tgtacatatg tccaaaggtg aagagctgtt taccggcgtc  120
gtgcccattc tggtggagct ggatggcgac gtcaacgggc acaagtttag cgtccgtggc  180
gaaggtgagg gcgacgccac gaacggtaag ctgacgctga aattcatttg caccaccggc  240
aaattgcctg taccctggcc caccctggtg accacgctca cctacggcgt acagtgcttc  300
agccgttacc cggaccacat gaagcgtcac gacttcttca aaagcgccat gccggagggt  360
tacgtgcagg agcgtacgat tagtttcaag gacgacggca cctataagac ccgtgccgaa  420
gtgaagttcg aaggcgatac gttggtgaac cgtatcgagt tgaagggtat cgactttaag  480
gaagacggca acatcctggg ccataagctg gagtacaatt tcaacagcca taacgtttac  540
atcaccgccg ataaacagaa gaacggcatt aaagccaact ttaagatccg ccacaacgtc  600
gaagacggct cggtgcagct ggccgaccat tatcagcaaa acacccccat cggtgatggg  660
cccgtgctgc tgccggataa ccattatctg agcacgcagt cggtgctcag caaggaccct  720
aacgaaaagc gcgatcacat ggtgctgctg gagttcgtca cggcggcggg gatcacccat  780
gggatggacg agctctacaa agactataaa gatgacgatg acaagtaaaa gcttctcggt  840
accaaattcc agaaaagagg cctcccgaaa ggggggcctt ttttcgtttt ggtccgaatt  900
cttgacagct agctcagtcc taggtataat gctagccgca gtaagagagg aatgtacaca  960
tgtcccgcct ggataaatcg aaagtgatta actcggccct cgaattgctg aatgaagtcg  1020
gtatcgaggg gctgacgacc cgtaaattgg cacaaaagtt gggggtggag caacccacgt  1080
tgtattggca cgtcaaaaat aagcgggcat tgctggatgc cctcgctatt gaaatgttgg  1140
atcgccacca tacccatttc tgtccactgg agggcgagtc ctggcaggac tttctccgca  1200
acaacgcgaa atcctttcgc tgtgcactct tgtcccatcg ggacggtgct aaggtgcact  1260
tgggcacccg tcccaccgaa aaacaatacg aaaccttgga aaatcaattg gcgtttttgt  1320
gccagcaagg gtttagcttg gagaatgctc tctatgcgct ctcggctgtc gggcacttta  1380
cgttggggtg cgtgttggag gaccaggagc atcaagtcgc aaaagaggag cgtgaaaccc  1440
caaccacgga ctcgatgcca cctctgctcc gccaagctat cgaactcttc gatcatcagg  1500
gcgcggagcc agccttcctc tttgggctgg agctgattat ctgcggtttg gaaaaacaac  1560
tcaagtgtga aagcgggtcc taactgcagc tcgag                             1595

SEQ ID NO: 62            moltype = DNA  length = 2216
FEATURE                  Location/Qualifiers
source                   1..2216
                         mol_type = other DNA
                         organism = synthetic construct
SEQUENCE: 62
ggatccgagc tgttgacact ttatgcttcc ggctcgtata atgtgtgtgg aattgtgagc  60
ggataacaac gcagtaagag aggaatgtac atatgtccaa aggtgaagag ctgtttaccg  120
gcgtcgtgcc cattctggtg gagctggatg gcgacgtcaa cgggcacaag tttagcgtcc  180
gtggcgaagg tgagggcgac gccacgaacg gtaagctgac gctgaaattc atttgcacca  240
ccggcaaatt gcctgtaccc tggcccaccc tggtgaccac gctcacctac ggcgtacagt  300
gcttcagccg ttacccggac cacatgaagc gtcacgactt cttcaaaagc gccatgccgg  360
agggttacgt gcaggagcgt acgattagtt tcaaggacga cggcacctat aagacccgtg  420
ccgaagtgaa gttcgaaggc gatacgttgg tgaaccgtat cgagttgaag ggtatcgact  480
ttaaggaaga cggcaacatc ctgggccata agctggagta caatttcaac agccataacg  540
tttacatcac cgccgataaa cagaagaacg gcattaaagc caactttaag atccgccaca  600
acgtcgaaga cggctcggtg cagctggccg accattatca gcaaaacacc cccatcggtg  660
atgggcccgt gctgctgccg gataaccatt atctgagcac gcagtcggtg ctcagcaagg  720
accctaacga aaagcgcgat cacatggtgc tgctggagtt cgtcacggcg gcggggatca  780
cccatgggat ggacgagctc tacaaagact ataaagatga cgatgacaag taaaagcttc  840
tcggtaccaa attccagaaa agaggcctcc cgaaaggggg gcctttttc gttttggtcc  900
gaattccccc gtggccgggg gactgttggg cgccatctcc ttgcatgcac cattccttgc  960
ggcggcggtg ctcaacggcc tcaacctact actgggctgc ttcctaatgc aggagtcgca  1020
taagggagag cgtcgagatc ccggacacca tcgaatggcg caaaaccttt cgcggtatgg  1080
catgatagcg cccggaagag agtcaattca gggtggtgaa tgtgaaacca gtaacgttat  1140
acgatgtcgc agagtatgcc ggtgtctctt atcagaccgt ttcccgcgtg gtgaaccagg  1200
ccagccacgt ttctgcgaaa acgcgggaaa aagtggaagc ggcgatggcg gagctgaatt  1260
acattcccaa ccgcgtggca caacaactgg cgggcaaaca gtcgttgctg attggcgttg  1320
ccacctccag tctggccctg cacgcgccgt cgcaaattgt cgcggcgatt aaatctcgcg  1380
ccgatcaact gggtgccagc gtggtggtgt cgatggtaga acgaagcggc gtcgaagcct  1440
gtaaagcggc ggtgcacaat cttctcgcgc aacgcgtcag tgggctgatc attaactatc  1500
cgctggatga ccaggatgcc attgctgtgg aagctgcctg cactaatgtt ccggcgttat  1560
ttcttgatgt ctctgaccag acacccatca acagtattat tttctcccat gaagacggta  1620
cgcgactggg cgtggagcat ctggtcgcat tgggtcacca gcaaatcgcg ctgttagcgg  1680
gcccattaag ttctgtctcg gcgcgtctgc gtctggctgg ctggcataaa tatctcactc  1740
gcaatcaaat tcagccgata gcggaacggg aaggcgactg gagtgccatg tccggttttc  1800
aacaaaccat gcaaatgctg aatgagggca tcgttcccac tgcgatgctg gttgccaacg  1860
atcagatggc gctgggcgca atgcgcgcca ttaccgagtc cgggctgcgc gttggtgcgg  1920
atatctcggt agtgggatac gacgataccg aagacagctc atgttatatc ccgccgttaa  1980
ccaccatcaa acaggatttt cgcctgctgg ggcaaaccag cgtggaccgc ttgctgcaac  2040
tctctcaggg ccaggcggtg aagggcaatc agctgttgcc cgtctcactg gtgaaaagaa  2100
aaaccaccct ggcgcccaat acgcaaaccg cctctccccg cgcgttggcc gattcattaa  2160
tgcagctggc acgacaggtt tcccgactgg aaagcgggca gtgactgcag ctcgag      2216

SEQ ID NO: 63            moltype = DNA  length = 2239
FEATURE                  Location/Qualifiers
```

```
source                  1..2239
                        mol_type = other DNA
                        organism = synthetic construct
SEQUENCE: 63
ggatccgagc tgttgacact ttatgcttcc ggctcgtata atgtgtgtgg aattgtgagc  60
ggataacaag tggaattgtg agcggataac aatttcacac aggaaacaga atcatatgtc  120
caaaggtgaa gagctgttta ccggcgtcgt gcccattctg gtggagctgg atggcgacgt  180
caacgggcac aagtttagcg tccgtggcga aggtgagggc gacgccacga acggtaagct  240
gacgctgaaa ttcatttgca ccaccggcaa attgcctgta ccctggccca ccctggtgac  300
cacgctcacc tacggcgtac agtgcttcag ccgttacccg gaccacatga agcgtcacga  360
cttcttcaaa agcgccatgc cggagggtta cgtgcaggag cgtacgatta gtttcaagga  420
cgacggcacc tataagaccc gtgccgaagt gaagttcgaa ggcgatacgt tggtgaaccg  480
tatcgagttg aagggtatcg actttaagga agacggcaac atcctgggcc ataagctgga  540
gtacaatttc aacagccata acgtttacat caccgccgat aaacagaaga acggcattaa  600
agccaacttt aagatccgcc acaacgtcga agacggctcg gtgcagctgg ccgaccatta  660
tcagcaaaac accccccatcg gtgatgggcc cgtgctgctg ccggataacc attatctgag  720
cacgcagtcg gtgctcagca aggaccctaa cgaaaagcgc gatcacatgg tgctgctgga  780
gttcgtcacg gcggcgggga tcacccatgg gatggacgag ctctacaaag actataaaga  840
tgacgatgac aagtaaaagc ttctcggtac caaattccag aaaagaggcc tcccgaaagg  900
ggggcctttt ttcgttttgg tccgaattcc cccgtggccg gggggactgtt gggcgccatc  960
tccttgcatg caccattcct tgcggcggcg gtgctcaacg gcctcaacct actactgggc  1020
tgcttcctaa tgcaggagtc gcataaggga gagcgtcgag atcccggaca ccatcgaatg  1080
gcgcaaaacc tttcgcggta tggcatgata gcgcccggaa gagagtcaat tcagggtggt  1140
gaatgtgaaa ccagtaacgt tatacgatgt cgcagagtat gccggtgtct cttatcagac  1200
cgtttcccgc gtggtgaacc aggccagcca cgtttctgcg aaaacgcggg aaaaagtgga  1260
agcggcgatg gcggagctga attacattcc caaccgcgtg gcacaacaac tggcgggcaa  1320
acagtcgttg ctgattggcg ttgccacctc cagtctggcc ctgcacgcgc cgtcgcaaat  1380
tgtcgcggcg attaaatctc gcgccgatca actgggtgcc agcgtggtgg tgtcgatggt  1440
agaacgaagc ggcgtcgaag cctgtaaagc ggcggtgcac aatcttctcg cgcaacgcgt  1500
cagtgggctg atcattaact atccgctgga tgaccaggat gccattgctg tggaagctgc  1560
ctgcactaat gttccggcgt tatttcttga tgtctctgac cagacaccca tcaacagtat  1620
tattttctcc catgaagacg gtacgcgact gggcgtggag catctggtcg cattgggtca  1680
ccagcaaatc gcgctgttag cgggcccatt aagttctgtc tcggcgcgtc tgcgtctggc  1740
tggctggcat aaatatctca ctcgcaatca aattcagccg atagcggaac gggaaggcga  1800
ctggagtgcc atgtccggtt ttcaacaaac catgcaaatg ctgaatgagg gcatcgttcc  1860
cactgcgatg ctggttgcca acgatcagat ggcgctgggc gcaatgcgcg ccattaccga  1920
gtccgggctg cgcgttggtg cggatatctc ggtagtggga tacgacgata ccgaagacag  1980
ctcatgttat atcccgccgt taaccaccat caaacaggat tttcgcctgc tggggcaaac  2040
cagcgtggac cgcttgctgc aactctctca gggccaggcg gtgaagggca atcagctgtt  2100
gcccgtctca ctggtgaaaa gaaaaaccac cctggcgccc aatacgcaaa ccgcctctcc  2160
ccgcgcgttg gccgattcat taatgcagct ggcacgacag gtttcccgac tggaaagcgg  2220
gcagtgactg cagctcgag                                              2239

SEQ ID NO: 64           moltype = DNA  length = 2543
FEATURE                 Location/Qualifiers
source                  1..2543
                        mol_type = other DNA
                        organism = synthetic construct
SEQUENCE: 64
aaaaggatct aggtgaagat cctttttgat aatctcatga ccaaaatccc ttaacgtgag  60
ttttcgttcc actgagcgtc agaccccgta gaaaagatca aaggatcttc ttgagatcct  120
ttttttctgc gcgtaatctg ctgcttgcaa acaaaaaaac caccgctacc agcggtggtt  180
tgtttgccgg atcaagagct accaactctt tttccgaagg taactggctt cagcagagcg  240
cagataccaa atactgttct tctagtgtag ccgtagttag gccaccactt caagaactct  300
gtagcaccgc ctacatacct cgctctgcta atcctgttac cagtggctgc tgccagtggc  360
gataagtcgt gtcttaccgg gttggactca agacgatagt taccggataa ggcgcagcgg  420
tcgggctgaa cggggggttc gtgcacacag cccagcttgg agcgaacgac ctacaccgaa  480
ctgagatacc tacagcgtga gctatgagaa agcgccacgc ttcccgaagg gagaaaggcg  540
gacaggtatc cggtaagcgg cagggtcgga acaggagagc gcacgaggga gcttccaggg  600
ggaaacgcct ggtatcttta tagtcctgtc gggtttcgcc acctctgact tgagcgtcga  660
tttttgtgat gctcgtcagg ggggcggagc ctatggaaaa acgccagcaa cgcggccttt  720
ttacggttcc tggccttttg ctggcctttt gctcacatgt tctttcctgc gttatcccct  780
gattctgtgg ataaccgtat taccgccttt gagtgagctg ataccgctcg ccgcagccga  840
acgaccgagc gcagcgagtc agtgagcgag gaagcggaag agcgcccaat acgcaaaccg  900
cctctgggag accagaaaca aaaaaaggcc gcgttagcgg ccttcaataa ttggacctgg  960
ctcctaactg atttttaagg cgactgatga gtcgcctttt ttttgtctaa tcagaagaac  1020
tcgtcaagaa ggcgatagaa ggcgatgcgc tgcgaatcgg gagcggcgat accgtaaagc  1080
acgaggaagc ggtcagccca ttcgccgcca agctcttcag caatatcacg ggtagccaac  1140
gctatgtcct gatagcggtc cgccacaccc agccggccac agtcgatgaa tccagaaaag  1200
cggccatttt ccaccatgat attcggcaag caggcatcgc catgcgtcac gacgagatcc  1260
tcgccgtcgg gcatccgcgc cttgagcctg gcgaacagtt cggctggcgc gagcccctga  1320
tgctcttcgt ccagatcatc ctgatcgaca agaccggctt ccatccgagt acgtgctcgc  1380
tcgatgcgat gtttcgcttg gtggtcgaat gggcaggtag ccggatcaag cgtatgcagc  1440
cgccgcattg catcagccat gatggatact ttctcggcag gagcaaggtg agatgacagg  1500
agatcctgcc ccggcacttc gcccaatagc agccagtccc ttcccgcttc agtgacaacg  1560
tcgagcacag ctgcgcaagg aacgcccgtc gtggccagcc acgatagccg cgctgcctcg  1620
tcttggagtt cattcagggc accggacagg tcggtcttga caaaaagaac cgggcgcccc  1680
tgcgctgaca gccggaacac ggcggcatca gagcagccga ttgtctgttg tgcccagtca  1740
tagccgaata gcctctccac ccaagcggcc ggagaacctg cgtgcaatcc atcttgttca  1800
```

-continued

```
atcatgcgaa acgatcctca tcctgtctct tgatcagatc ttgatcccct gcgccatcag  1860
atccttggcg gcaagaaagc catccagttt actttgcagg gcttcccaac cttaccagag  1920
ggcgccccag ctggcaattc cggttcgctt gctgtccata aaaccgccca gtctagctat  1980
cgccatgtaa gcccactgca agctacctgc tttctctttg cgcttgcgtt ttcccttgtc  2040
cagatagccc agtagctgac attcatccgg gacgtcgtgc ccaactgggg gtaacctttg  2100
agttctctca gttgggggat cgatagtcaa aagcctccgg tcggaggctt ttgactagca  2160
cctcggtacc aaattccaga aaagaggcct cccgaaaggg gggccttttt tcgttttggt  2220
ccggatccca tatgaagctt gaattcctgc agtctagacc atggctcgag gacgaacaat  2280
aaggcctccc taacgggggg cctttttttat tgataacaaa aatccacaag gaaaaattaa  2340
aggggagata aaatcccccc tttttggtta actgcggccg cgtcgtggtt tgtctggtca  2400
accaccgcgg tctcagtggt gtacggtaca aaccccgacg ctagcaacgc atgagaaagc  2460
ccccggaaga tcaccttccg ggggcttttt tattgcgctg cgggtgccag ggcgtgccct  2520
tgggctcccc gggcgcgtac tcc                                          2543

SEQ ID NO: 65          moltype = DNA  length = 3794
FEATURE                Location/Qualifiers
source                 1..3794
                       mol_type = other DNA
                       organism = synthetic construct
SEQUENCE: 65
ggatccgagc tgttgacaac tctatcattg atagagttat aatgttccct atcagtgata  60
gagacgcagt aagagaggaa tgtacatatg gtgagtaagg gtgaggagct cattaaggag  120
aacatgcaca tgaagctgta tatggagggc accgtaaaca accaccactt caagtgtacc  180
accgagggtg aaggtaaacc ctacgagggg acgcagaccc aacgcatcaa ggtcgtggag  240
ggcggcccgc tgcctttcgc attcgacatt ctggcgacct gttttatgta cggctcgaag  300
accttcatca accacaccca aggcatcccg gacttcttca agcagagctt ccctgagggc  360
ttcacctggg agcgcgtcac cacgtatgaa gacggtgggg tgctcaccgt gacccaggac  420
acgagcttgc aggatggctg cttgatttac aacgtcaagc tgcgcggggt gaacttccct  480
agcaacggcc cagtgatgca gaaaaagacg ctgggttggg aggccaccac cgagaccctg  540
tacccggccg acgggggct ggaagggcgg tgcgatatgg ccctgaaatt ggtcggcggc  600
ggtcatttgc actgcaatct caagaccacg taccgctcca agaaacccgc caaaaacctg  660
aagatgcctg gtgtttattt tgtcgaccgg cgcctggagc gcatcaagga agcggacaat  720
gagacgtacg tggaacagca cgaagtggcc gtggctcgtt attgcgatct gccgtcgaag  780
ctgggtcaca aactgaacgg catggatgag ctgtacaaag attataagga tgatgacgac  840
aagtaaaagc ttctcggtac caaattccag aaaagaggcc tcccgaaagg ggggcctttt  900
ttcgttttgg tccgaattct tgacagctag ctcagtccta ggtataatgc tagccgcagt  960
aagagaggaa tgtacacatg tcccgcctgg ataaatcgaa agtgattaac tcggccctcg  1020
aattgctgaa tgaagtcggt atcgaggggc tgacgacccg taaattggca caaaagttgg  1080
gggtggagca acccacgttg tattggcacg tcaaaaataa gcgggcattg ctggatgccc  1140
tcgctattga aatgttggat cgccaccata cccatttctg tccactggag ggcgagtcct  1200
ggcaggactt tctccgcaac aacgcgaaat cctttcgctg tgcactcttg tcccatcggg  1260
acggtgctaa ggtgcacttg ggcacccgtc ccaccgaaaa acaatacgaa accttggaaa  1320
atcaattggc gtttttgtgc cagcaagggt ttagcttgga gaatgctctc tatgcgctct  1380
cggctgtcgg gcactttacg ttggggtgcg tgttggagga ccaggagcat caagtcgcaa  1440
aagaggagcg tgaaacccca accacggact cgatgccacc tctgctccgc caagctatcg  1500
aactcttcga tcatcagggc gcggagccag ccttcctctt tgggctggag ctgattatct  1560
gcggtttgga aaaacaactc aagtgtgaaa gcgggtccta actgcagtca ctgcccgctt  1620
tccagtcggg aaacctgtcg tgccagctgc attaatgaat cggccaacgc gcggggagag  1680
gcggtttgcg tattgggcgc cagggtggtt tttcttttca ccagtgagac gggcaacagc  1740
tgattgccct tcaccgcctg gccctgagag agttgcagca agcggtccac gctggtttgc  1800
cccagcaggc gaaaatcctg tttgatggtg gttaacggcg ggatataaca tgagctgtct  1860
tcggtatcgt cgtatcccac taccgagata tccgcaccaa cgcgcagccc ggactcggta  1920
atggcgcgca ttgcgcccag cgccatctga tcgttggcaa ccagcatcgc agtgggaacg  1980
atgccctcat tcagcatttg catggtttgt tgaaaaccgg acatggcact ccagtcgcct  2040
tcccgttccg ctatcggctg aatttgattg cgagtgagat atttatgcca gccagccaga  2100
cgcagacgcg ccgagacaga acttaatggg cccgctaaca gcgcgatttg ctggtgaccc  2160
aatgcgacca gatgctccac gcccagtcgc gtaccgtctt catgggagaa aataatactg  2220
ttgatgggtg tctggtcaga gacatcaaga aataacgccg gaacattagt gcaggcagct  2280
tccacagcaa tggcatcctg gtcatccagc ggatagttaa tgatcagccc actgacgcgt  2340
tgcgcgagaa gattgtgcac cgccgcttta caggcttcga cgccgcttcg ttctaccatc  2400
gacaccacca cgctggcacc cagttgatcg gcgcgagatt taatcgccgc gacaatttgc  2460
gacggcgcgt gcagggccag actggaggtg gcaacgccaa tcagcaacga ctgtttgccc  2520
gccagttgtt gtgccacgcg gttgggaatg taattcagct ccgccatcgc cgcttccact  2580
ttttcccgcg ttttcgcaga aacgtggctg gcctggttca ccacgcggga aacggtctga  2640
taagagacac cggcatactc tgcgacatcg tataacgtta ctggtttcac attcaccacc  2700
ctgaattgac tctcttccgg gcgctatcat gccataccgc gaaaggtttt gcgccattcg  2760
atggtgtccg ggatctcgac gctctccctt atgcgactcc tgcattagga agcagcccag  2820
tagtaggttg aggccgttga gcaccgccgc cgcaaggaat ggtgcatgca aggagatggc  2880
gcccaacagt cccccggcca cggggagtca aaagcctccg gtcggaggct tttgacttct  2940
agagagctgt tgacacttta tgcttccggc tcgtataatg tgtgtggaat tgtgagcgga  3000
taacaacgca gtaagagagg aatgtaccca tggtgagtaa gggtgaggag ctcattaagg  3060
agaacatgca catgaagctg tatatggagg gcaccgtaaa caaccaccac ttcaagtgta  3120
ccaccgaggg tgaaggtaaa ccctacgagg ggacgcagac ccaacgcatc aaggtcgtgg  3180
agggcggccc gctgcctttc gcattcgaca ttctggcgac ctgttttatg tacggctcga  3240
agaccttcat caaccacacc caaggcatcc cggacttctt caagcagagc ttccctgagg  3300
gcttcacctg ggagcgcgtc accacgtatg aagacggtgg ggtgctcacc gtgacccagg  3360
acacgagctt gcaggatggc tgcttgattt acaacgtcaa gctgcgcggg gtgaacttcc  3420
ctagcaacgg gccagtgatg cagaaaaaga cgctgggttg ggaggccacc accgagaccc  3480
tgtacccggc cgacgggggg ctggaagggc ggtgcgatat ggccctgaaa ttggtcggcg  3540
```

-continued

```
gcggtcattt gcactgcaat ctcaagacca cgtaccgctc caagaaaccc gccaaaaacc  3600
tgaagatgcc tggtgtttat tttgtcgacc ggcgcctgga gcgcatcaag gaagcggaca  3660
atgagacgta cgtggaacag cacgaagtgg ccgtggctcg ttattgcgat ctgccgtcga  3720
agctgggtca caaactgaac ggcatggatg agctgtacaa agattataag gatgatgacg  3780
acaagtaact cgag                                                    3794

SEQ ID NO: 66          moltype = DNA  length = 3817
FEATURE                Location/Qualifiers
source                 1..3817
                       mol_type = other DNA
                       organism = synthetic construct
SEQUENCE: 66
ggatccgagc tgttgacaac tctatcattg atagagttat aatgttccct atcagtgata  60
gagacgcagt aagagaggaa tgtacatatg gtgagtaagg gtgaggagct cattaaggag  120
aacatgcaca tgaagctgta tatggagggc accgtaaaca accaccactt caagtgtacc  180
accgagggtg aaggtaaacc ctacgagggg acgcagaccc aacgcatcaa ggtcgtggag  240
ggcggcccgc tgcctttcgc attcgacatt ctggcgacct gttttatgta cggctcgaag  300
accttcatca accacaccca aggcatcccg gacttcttca agcagagctt ccctgagggc  360
ttcacctggg agcgcgtcac cacgtatgaa gacggtgggg tgctcaccgt gacccaggac  420
acgagcttgc aggatggctg cttgatttac aacgtcaagc tgcgcggggt gaacttccct  480
agcaacgggc cagtgatgca gaaaaagacg ctgggttggg aggccaccac cgagaccctg  540
tacccggccg acgggggct ggaagggcgg tgcgatatgg ccctgaaatt ggtcggcggc  600
ggtcatttgc actgcaatct caagaccacg taccgctcca agaaacccgc caaaaacctg  660
aagatgcctg gtgtttattt tgtcgaccgg cgcctggagc gcatcaagga agcggacaat  720
gagacgtacg tggaacagca cgaagtggcc gtggctcgtt attgcgatct gccgtcgaag  780
ctgggtcaca aactgaacgg catggatgag ctgtacaaag attataagga tgatgacgac  840
aagtaaaagc ttctcggtac caaattccag aaaagaggcc tcccgaaagg ggggcctttt  900
ttcgttttgg tccgaattct tgacagctag ctcagtccta ggtataatgc tagccgcagt  960
aagagaggaa tgtacacatg tcccgcctgg ataaatcgaa agtgattaac tcggccctcg  1020
aattgctgaa tgaagtcggt atcgagggc tgacgacccg taaattggca caaaagttgg  1080
gggtggagca acccacgttg tattggcacg tcaaaaataa gcgggcattg ctggatgccc  1140
tcgctattga aatgttggat cgccaccata cccatttctg tccactggag ggcgagtcct  1200
ggcaggactt tctccgcaac aacgcgaaat cctttcgctg tgcactcttg tcccatcggg  1260
acggtgctaa ggtgcacttg ggcacccgtc ccaccgaaaa acaatacgaa accttggaaa  1320
atcaattggc gtttttgtgc cagcaagggt ttagcttgga gaatgctctc tatgcgctct  1380
cggctgtcgg gcactttacg ttggggtgcg tgttggagga ccaggagcat caagtcgcaa  1440
aagaggagcg tgaaacccca accacggact cgatgccacc tctgctccgc caagctatcg  1500
aactcttcga tcatcagggc gcggagccag ccttcctctt tgggctggag ctgattatct  1560
gcggtttgga aaaacaactc aagtgtgaaa gcgggtccta actgcagtca ctgcccgctt  1620
tccagtcggg aaacctgtcg tgccagctgc attaatgaat cggccaacgc gcggggagag  1680
gcggtttgcg tattgggcgc cagggtggtt tttcttttca ccagtgagac gggcaacagc  1740
tgattgccct tcaccgcctg gccctgagag agttgcagca agcggtccac gctggtttgc  1800
cccagcaggc gaaaatcctg tttgatggtg gttaacggcg ggatataaca tgagctgtct  1860
tcggtatcgt cgtatcccac taccgagata tccgcaccaa cgcgcagccc ggactcggta  1920
atggcgcgca ttgcgcccag cgccatctga tcgttggcaa ccagcatcgc agtgggaacg  1980
atgccctcat tcagcatttg catggtttgt tgaaaaccgg acatggcact ccagtcgcct  2040
tcccgttccg ctatcggctg aatttgattg cgagtgagat atttatgcca gccagccaga  2100
cgcagacgcg ccgagacaga acttaatggg cccgctaaca gcgcgatttg ctggtgaccc  2160
aatgcgacca gatgctccac gcccagtcgc gtaccgtctt catgggagaa aataatactg  2220
ttgatgggtg tctggtcaga gacatcaaga aataacgccg gaacattagt gcaggcagct  2280
tccacagcaa tggcatcctg gtcatccagc ggatagttaa tgatcagccc actgacgcgt  2340
tgcgcgagaa gattgtgcac cgccgcttta caggcttcga cgccgcttcg ttctaccatc  2400
gacaccacca cgctggcacc cagttgatcg gcgcgagatt taatcgccgc gacaatttgc  2460
gacggcgcgt gcagggccag actggaggtg gcaacgccaa tcagcaacga ctgtttgccc  2520
gccagttgtt gtgccacgcg gttgggaatg taattcagct ccgccatcgc cgcttccact  2580
ttttcccgcg ttttcgcaga aacgtggctg gcctggttca ccacgcggga aacggtctga  2640
taagagacac cggcatactc tgcgacatcg tataacgtta ctggtttcac attcaccacc  2700
ctgaattgac tctcttccgg gcgctatcat gccataccgc gaaaggtttt gcgccattcg  2760
atggtgtccg ggatctcgac gctctccctt atgcgactcc tgcattagga agcagcccag  2820
tagtaggttg aggccgttga gcaccgccgc cgcaaggaat ggtgcatgca aggagatggc  2880
gcccaacagt cccccggcca cggggagtca aaagcctccg gtcggaggct tttgacttct  2940
agagagctgt tgacacttta tgcttccggc tcgtataatg tgtgtggaat tgtgagcgga  3000
taacaagtgg aattgtgagc ggataacaat ttcacacagg aaacagaatc ccatggtgag  3060
taagggtgag gagctcatta aggagaacat gcacatgaag ctgtatatgg agggcaccgt  3120
aaacaaccac cacttcaagt gtaccaccga gggtgaaggt aaaccctacg aggggacgca  3180
gacccaacgc atcaaggtcg tggagggcgg cccgctgcct ttcgcattcg acattctggc  3240
gacctgtttt atgtacggct cgaagacctt catcaaccac acccaaggca tcccggactt  3300
cttcaagcag agcttccctg agggcttcac ctgggagcgc gtcaccacgt atgaagacgg  3360
tggggtgctc accgtgaccc aggacacgag cttgcaggat ggctgcttga tttacaacgt  3420
caagctgcgc ggggtgaact tccctagcaa cgggccagtg atgcagaaaa agacgctggg  3480
ttgggaggcc accaccgaga ccctgtaccc ggccgacggg gggctggaag ggcggtgcga  3540
tatggccctg aaattggtcg gcggcggtca tttgcactgc aatctcaaga ccacgtaccg  3600
ctccaagaaa cccgccaaaa acctgaagat gcctggtgtt tattttgtcg accggcgcct  3660
ggagcgcatc aaggaagcgg acaatgagac gtacgtggaa cagcacgaag tggccgtggc  3720
tcgttattgc gatctgccgt cgaagctggg tcacaaactg aacggcatgg atgagctgta  3780
caaagattat aaggatgatg acgacaagta actcgag                           3817

SEQ ID NO: 67          moltype = DNA  length = 3776
FEATURE                Location/Qualifiers
```

```
source                  1..3776
                        mol_type = other DNA
                        organism = synthetic construct
SEQUENCE: 67
ggatccgagc tgttgacaac tctatcattg atagagttat aatgttccct atcagtgata  60
gagacgcagt aagagaggaa tgtacatatg tccaaaggtg aagagctgtt taccggcgtc  120
gtgcccattc tggtggagct ggatggcgac gtcaacgggc acaagtttag cgtccgtggc  180
gaaggtgagg gcgacgccac gaacggtaag ctgacgctga aattcatttg caccaccggc  240
aaattgcctg taccctggcc caccctggtg accacgctca cctacggcgt acagtgcttc  300
agccgttacc cggaccacat gaagcgtcac gacttcttca aaagcgccat gccggagggt  360
tacgtgcagg agcgtacgat tagtttcaag gacgacggca cctataagac ccgtgccgaa  420
gtgaagttcg aaggcgatac gttggtgaac cgtatcgagt tgaagggtat cgactttaag  480
gaagacggca acatcctggg ccataagctg gagtacaatt tcaacagcca taacgtttac  540
atcaccgccg ataaacagaa gaacggcatt aaagccaact ttaagatccg ccacaacgtc  600
gaagacggct cggtgcagct ggccgaccat tatcagcaaa acacccccat cggtgatggg  660
cccgtgctgc tgccggataa ccattatctg agcacgcagt cggtgctcag caaggaccct  720
aacgaaaagc gcgatcacat ggtgctgctg gagttcgtca cggcggcggg gatcacccat  780
gggatggacg agctctacaa agactataaa gatgacgatg acaagtaaaa gcttctcggt  840
accaaattcc agaaaagagg cctcccgaaa gggggccttt tttcgttttt ggtccgaatt  900
cttgacagct agctcagtcc taggtataat gctagccgca gtaagagagg aatgtacaca  960
tgtcccgcct ggataaatcg aaagtgatta actcggccct cgaattgctg aatgaagtcg  1020
gtatcgaggg gctgacgacc cgtaaattgg cacaaaagtt ggggggtggag caacccacgt  1080
tgtattggca cgtcaaaaat aagcgggcat tgctggatgc cctcgctatt gaaatgttgg  1140
atcgccacca tacccatttc tgtccactgg agggcgagtc ctggcaggac tttctccgca  1200
acaacgcgaa atcctttcgc tgtgcactct tgtcccatcg ggacggtgct aaggtgcact  1260
tgggcacccg tcccaccgaa aaacaatacg aaaccttgga aaatcaattg gcgtttttgt  1320
gccagcaagg gtttagcttg gagaatgctc tctatgcgct ctcggctgtc gggcacttta  1380
cgttggggtg cgtgttggag gaccaggagc atcaagtcgc aaaagaggag cgtgaaaccc  1440
caaccacgga ctcgatgcca cctctgctcc gccaagctat cgaactcttc gatcatcagg  1500
gcgcggagcc agccttcctc tttgggctgg agctgattat ctgcggtttg gaaaaacaac  1560
tcaagtgtga aagcgggtcc taactgcagt cactgcccgc tttccagtcg ggaaacctgt  1620
cgtgccagct gcattaatga atcggccaac gcgcggggag aggcggtttg cgtattgggc  1680
gccagggtgg tttttctttt caccagtgag acgggcaaca gctgattgcc cttcaccgcc  1740
tggccctgag agagttgcag caagcggtcc acgctggttt gccccagcag gcgaaaatcc  1800
tgtttgatgg tggttaacgg cgggatataa catgagctgt cttcggtatc gtcgtatccc  1860
actaccgaga tatccgcacc aacgcgcagc ccggactcgg taatggcgcg cattgcgccc  1920
agcgccatct gatcgttggc aaccagcatc gcagtgggaa cgatgccctc attcagcatt  1980
tgcatggttt gttgaaaacc ggacatggca ctccagtcgc cttcccgttc cgctatcggc  2040
tgaatttgat tgcgagtgag atatttatgc cagccagcca gacgcagacg cgccgagaca  2100
gaacttaatg ggcccgctaa cagcgcgatt tgctggtgac ccaatgcgac cagatgctcc  2160
acgcccagtc gcgtaccgtc ttcatgggag aaaataatac tgttgatggg tgtctggtca  2220
gagacatcaa gaaataacgc cggaacatta gtgcaggcag cttccacagc aatggcatcc  2280
tggtcatcca gcggatagtt aatgatcagc ccactgacgc gttgcgcgag aagattgtgc  2340
accgccgctt tacaggcttc gacgccgctt cgttctacca tcgacaccac cacgctggca  2400
cccagttgat cggcgcgaga tttaatcgcc gcgacaattt gcgacggcgc gtgcagggcc  2460
agactggagg tggcaacgcc aatcagcaac gactgtttgc ccgccagttg ttgtgccacg  2520
cggttgggaa tgtaattcag ctccgccatc gccgcttcca ctttttcccg cgttttcgca  2580
gaaacgtggc tggcctggtt caccacgcgg gaaacggtct gataagagac accggcatac  2640
tctgcgacat cgtataacgt tactggtttc acattcacca ccctgaattg actctcttcc  2700
gggcgctatc atgccatacc gcgaaaggtt ttgcgccatt cgatggtgtc cgggatctcg  2760
acgctctccc ttatgcgact cctgcattag gaagcagccc agtagtaggt tgaggccgtt  2820
gagcaccgcc gccgcaagga atggtgcatg caaggagatg gcgcccaaca gtcccccggc  2880
cacggggagt caaaagcctc cggtcggagg cttttgactt ctagagagct gttgacactt  2940
tatgcttccg gctcgtataa tgtgtgtgga attgtgagcg gataacaacg cagtaagaga  3000
ggaatgtacc catggtgagt aagggtgagg agctcattaa ggagaacatg cacatgaagc  3060
tgtatatgga gggcaccgta aacaaccacc acttcaagtg taccaccgag ggtgaaggta  3120
aaccctacga ggggacgcag acccaacgca tcaaggtcgt ggagggcggc ccgctgcctt  3180
tcgcattcga cattctggcg acctgtttta tgtacggctc gaagaccttc atcaaccaca  3240
cccaaggcat cccggacttc ttcaagcaga gcttccctga gggcttcacc tgggagcgcg  3300
tcaccacgta tgaagacggt ggggtgctca ccgtgaccca ggacacgagc ttgcaggatg  3360
gctgcttgat ttacaacgtc aagctgcgcg gggtgaactt ccctagcaac gggccagtga  3420
tgcagaaaaa gacgctgggt tgggaggcca ccaccgagac cctgtacccg gccgacgggg  3480
ggctggaagg gcggtgcgat atggccctga aattggtcgg cggcggtcat ttgcactgca  3540
atctcaagac cacgtaccgc tccaagaaac ccgccaaaaa cctgaagatg cctggtgttt  3600
attttgtcga ccggcgcctg gagcgcatca aggaagcgga caatgagacg tacgtggaac  3660
agcacgaagt ggccgtggct cgttattgcg atctgccgtc gaagctgggt cacaaactga  3720
acggcatgga tgagctgtac aaagattata aggatgatga cgacaagtaa ctcgag      3776

SEQ ID NO: 68           moltype = DNA  length = 3799
FEATURE                 Location/Qualifiers
source                  1..3799
                        mol_type = other DNA
                        organism = synthetic construct
SEQUENCE: 68
ggatccgagc tgttgacaac tctatcattg atagagttat aatgttccct atcagtgata  60
gagacgcagt aagagaggaa tgtacatatg tccaaaggtg aagagctgtt taccggcgtc  120
gtgcccattc tggtggagct ggatggcgac gtcaacgggc acaagtttag cgtccgtggc  180
gaaggtgagg gcgacgccac gaacggtaag ctgacgctga aattcatttg caccaccggc  240
aaattgcctg taccctggcc caccctggtg accacgctca cctacggcgt acagtgcttc  300
```

-continued

```
agccgttacc cggaccacat gaagcgtcac gacttcttca aaagcgccat gccggagggt  360
tacgtgcagg agcgtacgat tagtttcaag gacgacggca cctataagac ccgtgccgaa  420
gtgaagttcg aaggcgatac gttggtgaac cgtatcgagt tgaagggtat cgactttaag  480
gaagacggca acatcctggg ccataagctg gagtacaatt tcaacagcca taacgtttac  540
atcaccgccg ataaacagaa gaacggcatt aaagccaact ttaagatccg ccacaacgtc  600
gaagacggct cggtgcagct ggccgaccat tatcagcaaa acacccccat cggtgatggg  660
cccgtgctgc tgccggataa ccattatctg agcacgcagt cggtgctcag caaggaccct  720
aacgaaaagc gcgatcacat ggtgctgctg gagttcgtca cggcggcggg gatcacccat  780
gggatggacg agctctacaa agactataaa gatgacgatg acaagtaaaa gcttctcggt  840
accaaattcc agaaaagagg cctcccgaaa ggggggcctt ttttcgtttt ggtccgaatt  900
cttgacagct agctcagtcc taggtataat gctagccgca gtaagagagg aatgtacaca  960
tgtcccgcct ggataaatcg aaagtgatta actcggccct cgaattgctg aatgaagtcg  1020
gtatcgaggg gctgacgacc cgtaaattgg cacaaaagtt gggggtggag caacccacgt  1080
tgtattggca cgtcaaaaat aagcgggcat tgctggatgc cctcgctatt gaaatgttgg  1140
atcgccacca tacccatttc tgtccactgg agggcgagtc ctggcaggac tttctccgca  1200
acaacgcgaa atcctttcgc tgtgcactct tgtcccatcg ggacggtgct aaggtgcact  1260
tgggcacccg tcccaccgaa aaacaatacg aaaccttgga aaatcaattg gcgtttttgt  1320
gccagcaagg gtttagcttg gagaatgctc tctatgcgct ctcggctgtc gggcacttta  1380
cgttggggtg cgtgttggag gaccaggagc atcaagtcgc aaaagaggag cgtgaaaccc  1440
caaccacgga ctcgatgcca cctctgctcc gccaagctat cgaactcttc gatcatcagg  1500
gcgcggagcc agccttcctc tttgggctgg agctgattat ctgcggtttg gaaaaacaac  1560
tcaagtgtga aagcgggtcc taactgcagt cactgcccgc tttccagtcg ggaaacctgt  1620
cgtgccagct gcattaatga atcggccaac gcgcggggag aggcggtttg cgtattgggc  1680
gccagggtgg tttttctttt caccagtgag acgggcaaca gctgattgcc cttcaccgcc  1740
tggccctgag agagttgcag caagcggtcc acgctggttt gccccagcag gcgaaaatcc  1800
tgtttgatgg tggttaacgg cgggatataa catgagctgt cttcggtatc gtcgtatccc  1860
actaccgaga tatccgcacc aacgcgcagc ccggactcgg taatggcgcg cattgcgccc  1920
agcgccatct gatcgttggc aaccagcatc gcagtgggaa cgatgccctc attcagcatt  1980
tgcatggttt gttgaaaacc ggacatggca ctccagtcgc cttcccgttc cgctatcggc  2040
tgaatttgat tgcgagtgag atatttatgc cagccagcca gacgcagacg cgccgagaca  2100
gaacttaatg ggcccgctaa cagcgcgatt tgctggtgac ccaatgcgac cagatgctcc  2160
acgcccagtc gcgtaccgtc ttcatgggag aaaataatac tgttgatggg tgtctggtca  2220
gagacatcaa gaaataacgc cggaacatta gtgcaggcag cttccacagc aatggcatcc  2280
tggtcatcca gcggatagtt aatgatcagc ccactgacgc gttgcgcgag aagattgtgc  2340
accgccgctt tacaggcttc gacgccgctt cgttctacca tcgacaccac cacgctggca  2400
cccagttgat cggcgcgaga tttaatcgcc gcgacaattt gcgacggcgc gtgcagggcc  2460
agactggagg tggcaacgcc aatcagcaac gactgtttgc ccgccagttg ttgtgccacg  2520
cggttgggaa tgtaattcag ctccgccatc gccgcttcca ctttttcccg cgttttcgca  2580
gaaacgtggc tggcctggtt caccacgcgg gaaacggtct gataagagac accggcatac  2640
tctgcgacat cgtataacgt tactggtttc acattcacca ccctgaattg actctcttcc  2700
gggcgctatc atgccatacc gcgaaaggtt ttgcgccatt cgatggtgtc cgggatctcg  2760
acgctctccc ttatgcgact cctgcattag gaagcagccc agtagtaggt tgaggccgtt  2820
gagcaccgcc gccgcaagga atggtgcatg caaggagatg gcgcccaaca gtcccccggc  2880
cacggggagt caaaagcctc cggtcggagg cttttgactt ctagagagct gttgacactt  2940
tatgcttccg gctcgtataa tgtgtgtgga attgtgagcg gataacaagt ggaattgtga  3000
gcggataaca atttcacaca ggaaacagaa tcccatggtg agtaagggtg aggagctcat  3060
taaggagaac atgcacatga agctgtatat ggagggcacc gtaaacaacc accacttcaa  3120
gtgtaccacc gagggtgaag gtaaacccta cgaggggacg cagacccaac gcatcaaggt  3180
cgtggagggc ggcccgctgc ctttcgcatt cgacattctg gcgacctgtt ttatgtacgg  3240
ctcgaagacc ttcatcaacc acacccaagg catcccggac ttcttcaagc agagcttccc  3300
tgagggcttc acctgggagc gcgtcaccac gtatgaagac ggtggggtgc tcaccgtgac  3360
ccaggacacg agcttgcagg atggctgctt gatttacaac gtcaagctgc gcggggtgaa  3420
cttccctagc aacgggccag tgatgcagaa aaagacgctg ggttgggagg ccaccaccga  3480
gaccctgtac ccggccgacg gggggctgga agggcggtgc gatatggccc tgaaattggt  3540
cggcggcggt catttgcact gcaatctcaa gaccacgtac cgctccaaga aacccgccaa  3600
aaacctgaag atgcctggtg tttattttgt cgaccggcgc ctggagcgca tcaaggaagc  3660
ggacaatgag acgtacgtgg aacagcacga agtggccgtg gctcgttatt gcgatctgcc  3720
gtcgaagctg ggtcacaaac tgaacggcat ggatgagctg tacaaagatt ataaggatga  3780
tgacgacaag taactcgag                                              3799

SEQ ID NO: 69          moltype = DNA  length = 3404
FEATURE                Location/Qualifiers
source                 1..3404
                       mol_type = other DNA
                       organism = synthetic construct
SEQUENCE: 69
catatgtatc cgtttataag gacagcccga atgacggtct gcgcaaaaaa acacgttcat  60
ctcactcgcg atgctgcgga gcagttactg gctgatattg atcgacgcct tgatcagtta  120
ttgcccgtgg agggagaacg ggatgttgtg ggtgccgcga tgcgtgaagg tgcgctggca  180
ccgggaaaac gtattcgccc catgttgctg ttgctgaccg cccgcgatct gggttgcgct  240
gtcagccatg acggattact ggatttggcc tgtgcggtgg aaatggtcca cgcggcttcg  300
ctgatccttg acgatatgcc ctgcatggac gatgcgaagc tgcggcgcgg acgccctacc  360
attcattctc attacggaga gcatgtggca atactggcgg cggttgcctt gctgagtaaa  420
gcctttggcg taattgccga tgcagatggc ctcacgccgc tggcaaaaaa tcgggcggtt  480
tctgaactgt caaacgccat cggcatgcaa ggattggttc agggtcagtt caaggatctg  540
tctgaagggg ataagccgcg cagcgctgaa gctattttga tgacgaatca ctttaaaacc  600
agcacgctgt tttgtgcctc catgcagatg gcctcgattg ttgcgaatgc ctccagcgaa  660
gcgcgtgatt gcctgcatcg tttttcactt gatcttggtc aggcatttca actgctggac  720
gatttgaccg atggcatgac cgacaccggt aaggatagca atcaggacgc cggtaaatcg  780
```

-continued

```
acgctggtca atctgttagg cccgagggcg gttgaagaac gtctgagaca acatcttcag  840
cttgccagtg agcatctctc tgcggcctgc caacacgggc acgccactca acattttatt  900
caggcctggt ttgacaaaaa actcgctgcc gtcagttaac gcagtaagag aggaatgtag  960
atatgaataa tccgtcgtta ctcaatcatg cggtcgaaac gatggcagtt ggctcgaaaa  1020
gttttgcgac agcctcaaag ttatttgatg caaaaacccg gcgcagcgta ctgatgctct  1080
acgcctggtg ccgccattgt gacgatgtta ttgacgatca gacgctgggc tttcaggccc  1140
ggcagcctgc cttacaaacg cccgaacaac gtctgatgca acttgagatg aaaacgcgcc  1200
aggcctatgc aggatcgcag atgcacgaac cggcgtttgc ggcttttcag gaagtggcta  1260
tggctcatga tatcgccccg gcttacgcgt ttgatcatct ggaaggcttc gccatggatg  1320
tacgcgaagc gcaatacagc caactggatg atacgctgcg ctattgctat cacgttgcag  1380
gcgttgtcgg cttgatgatg gcgcaaatca tgggcgtgcg ggataacgcc acgctggacc  1440
gcgcctgtga ccttgggctg gcatttcagt tgaccaatat tgctcgcgat attgtggacg  1500
atgcgcatgc gggccgctgt tatctgccgg caagctggct ggagcatgaa ggtctgaaca  1560
aagagaatta tgcggcacct gaaaaccgtc aggcgctgag ccgtatcgcc cgtcgtttgg  1620
tgcaggaagc agaaccttac tatttgtctg ccacagccgg cctggcaggg ttgcccctgc  1680
gttccgcctg ggcaatcgct acggcgaagc aggtttaccg gaaaataggt gtcaaagttg  1740
aacaggccgg tcagcaagcc tgggatcagc ggcagtcaac gaccacgccc gaaaaattaa  1800
cgctgctgct ggccgcctct ggtcaggccc ttacttcccg gatgcgggct catcctcccc  1860
gccctgcgca tctctggcag cgcccgctct gaaataattt tgtttaactt taagaaggag  1920
atataatgaa accaactacg gtaattggtg caggcttcgg tggcctggca ctggcaattc  1980
gtctacaagc tgcggggatt cccgtcttac tgcttgaaca acgtgataaa cccggcggtc  2040
gggcttatgt ctacgaggat caggggttta ccttttgatgc aggcccgacg gttatcaccg  2100
atcccagtgc cattgaagaa ctgtttgcac tggcaggaaa acagttaaaa gagtatgtcg  2160
aactgctgcc ggttacgccg ttttaccgcc tgtgttggga gtcagggaag gtctttaatt  2220
acgataacga tcaaacccgg ctcgaagcgc agattcagca gtttaatccc cgcgatgtcg  2280
aaggttatcg tcagtttctg gactattcac gcgcggtgtt taaagaaggc tatctaaagc  2340
tcggtactgt cccttttttta tcgttcagag acatgcttcg cgccgcacct caactggcga  2400
aactgcaggc atggagaagc gtttacagta aggttgccag ttacatcgaa gatgaacatc  2460
tgcgccaggc gttttctttc cactcgctgt tggtgggcgg caatcccttc gccacctcat  2520
ccatttatac gttgatacac gcgctggagc gtgagtgggg cgtctggttt ccgcgtggcg  2580
gcaccggcgc attagttcag gggatgataa agctgtttca ggatctgggt ggcgaagtcg  2640
tgttaaacgc cagagtcagc cacatggaaa cgacaggaaa caagattgaa gccgtgcatt  2700
tagaggacgg tcgcaggttc ctgacgcaag ccgtcgcgtc aaatgcagat gtggttcata  2760
cctatcgcga cctgttaagc cagcaccctg ccgcggttaa gcagtccaac aaactgcaga  2820
ctaagcgcat gagtaactct ctgtttgtgc tctattttgg tttgaatcac catcatgatc  2880
agctcgcgca tcacacggtt tgtttcggcc cgcgttaccg cgagctgatt gacgaaattt  2940
ttaatcatga tggcctcgca gaggacttct cactttatct gcacgcgccc tgtgtcacgg  3000
attcgtcact ggcgcctgaa ggttgcggca gttactatgt gttggcgccg gtgccgcatt  3060
taggcaccgc gaacctcgac tggacggttg aggggccaaa actacgcgac cgtatttttg  3120
cgtaccttga gcagcattac atgcctggct tacggagtca gctggtcacg caccggatgt  3180
ttacgccgtt tgattttcgc gaccagctta atgcctatca tggctcagcc ttttctgtgg  3240
agcccgttct tacccagagc gcctggtttc ggccgcataa ccgcgataaa accattacta  3300
atctctacct ggtcggcgca ggcacgcatc ccggcgcagg cattcctggc gtcatcggct  3360
cggcaaaagc gacagcaggt ttgatgctgg aggatctgat ttga                  3404
```

```
SEQ ID NO: 70           moltype = DNA  length = 4255
FEATURE                 Location/Qualifiers
source                  1..4255
                        mol_type = other DNA
                        organism = synthetic construct
SEQUENCE: 70
ggatccgagc tgttgacaac tctatcattg atagagttat aatgttccct atcagtgata  60
gagacgcagt aagagaggaa tgtacatatg tatccgttta taaggacagc ccgaatgacg  120
gtctgcgcaa aaaaacacgt tcatctcact cgcgatgctg cggagcagtt actggctgat  180
attgatcgac gccttgatca gttattgccc gtggagggag aacgggatgt tgtgggtgcc  240
gcgatgcgtg aaggtgcgct ggcaccggga aaacgtattc gccccatgtt gctgttgctg  300
accgcccgcg atctgggttg cgctgtcagc catgacggat tactggattt ggcctgtgcg  360
gtggaaatgg tccacgcggc ttcgctgatc cttgacgata tgccctgcat ggacgatgcg  420
aagctgcggc gcggacgccc taccattcat tctcattacg gagagcatgt ggcaatactg  480
gcggcggttg ccttgctgag taaagccttt ggcgtaattg ccgatgcaga tggcctcacg  540
ccgctggcaa aaaatcgggc ggtttctgaa ctgtcaaacg ccatcggcat gcaaggattg  600
gttcagggtc agttcaagga tctgtctgaa ggggataagc cgcgcagcgc tgaagctatt  660
ttgatgacga atcactttaa aaccagcacg ctgttttgtg cctccatgca gatggcctcg  720
attgttgcga atgcctccag cgaagcgcgt gattgcctgc atcgtttttc acttgatctt  780
ggtcaggcat ttcaactgct ggacgatttg accgatggca tgaccgacac cggtaaggat  840
agcaatcagg acgccggtaa atcgacgctg gtcaatctgt taggcccgag ggcggttgaa  900
gaacgtctga gacaacatct tcagcttgcc agtgagcatc tctctgcggc ctgccaacac  960
gggcacgcca ctcaacattt tattcaggcc tggtttgaca aaaaactcgc tgccgtcagt  1020
taacgcagta agagaggaat gtagatatga ataatccgtc gttactcaat catgcggtcg  1080
aaacgatggc agttggctcg aaaagttttg cgacagcctc aaagttattt gatgcaaaaa  1140
cccggcgcag cgtactgatg ctctacgcct ggtgccgcca ttgtgacgat gttattgacg  1200
atcagacgct gggctttcag gcccggcagc ctgccttaca aacgcccgaa caacgtctga  1260
tgcaacttga gatgaaaacg cgccaggcct atgcaggatc gcagatgcac gaaccggcgt  1320
ttgcggcttt tcaggaagtg gctatggctc atgatatcgc cccggcttac gcgtttgatc  1380
atctggaagg cttcgccatg gatgtacgcg aagcgcaata cagccaactg gatgatacgc  1440
tgcgctattg ctatcacgtt gcaggcgttg tcggcttgat gatggcgcaa atcatgggcg  1500
tgcgggataa cgccacgctg gaccgcgcct gtgaccttgg gctggcattt cagttgacca  1560
atattgctcg cgatattgtg gacgatgcgc atgcgggccg ctgttatctg ccggcaagct  1620
ggctggagca tgaaggtctg aacaaagaga attatgcggc acctgaaaac cgtcaggcgc  1680
```

-continued

```
tgagccgtat cgcccgtcgt ttggtgcagg aagcagaacc ttactatttg tctgccacag  1740
ccggcctggc agggttgccc ctgcgttccg cctgggcaat cgctacggcg aagcaggttt  1800
accggaaaat aggtgtcaaa gttgaacagg ccggtcagca agcctgggat cagcggcagt  1860
caacgaccac gcccgaaaaa ttaacgctgc tgctggccgc ctctggtcag gcccttactt  1920
cccggatgcg ggctcatcct ccccgccctg cgcatctctg gcagcgcccg ctctgaaata  1980
attttgttta actttaagaa ggagatataa tgaaaccaac tacggtaatt ggtgcaggct  2040
tcggtggcct ggcactggca attcgtctac aagctgcggg gattcccgtc ttactgcttg  2100
aacaacgtga taaacccggc ggtcgggctt atgtctacga ggatcagggg tttacctttg  2160
atgcaggccc gacggttatc accgatccca gtgccattga agaactgttt gcactggcag  2220
gaaaacagtt aaaagagtat gtcgaactgc tgccggttac gccgttttac cgcctgtgtt  2280
gggagtcagg gaaggtcttt aattacgata acgatcaaac ccggctcgaa gcgcagattc  2340
agcagtttaa tccccgcgat gtcgaaggtt atcgtcagtt tctggactat tcacgcgcgg  2400
tgtttaaaga aggctatcta aagctcggta ctgtcccttt tttatcgttc agagacatgc  2460
ttcgcgccgc acctcaactg gcgaaactgc aggcatggag aagcgtttac agtaaggttg  2520
ccagttacat cgaagatgaa catctgcgcc aggcgttttc tttccactcg ctgttggtgg  2580
gcggcaatcc cttcgccacc tcatccattt atacgttgat acacgcgctg gagcgtgagt  2640
ggggcgtctg gtttccgcgt ggcggcaccg gcgcattagt tcaggggatg ataaagctgt  2700
ttcaggatct gggtggcgaa gtcgtgttaa acgccagagt cagccacatg gaaacgacag  2760
gaaacaagat tgaagccgtg catttagagg acggtcgcag gttcctgacg caagccgtcg  2820
cgtcaaatgc agatgtggtt catacctatc gcgacctgtt aagccagcac cctgccgcgg  2880
ttaagcagtc caacaaactg cagactaagc gcatgagtaa ctctctgttt gtgctctatt  2940
ttggtttgaa tcaccatcat gatcagctcg cgcatcacac ggtttgtttc ggcccgcgtt  3000
accgcgagct gattgacgaa atttttaatc atgatggcct cgcagaggac ttctcacttt  3060
atctgcacgc gccctgtgtc acggattcgt cactggcgcc tgaaggttgc ggcagttact  3120
atgtgttggc gccggtgccg catttaggca ccgcgaacct cgactggacg gttgaggggc  3180
caaaactacg cgaccgtatt tttgcgtacc ttgagcagca ttacatgcct ggcttacgga  3240
gtcagctggt cacgcaccgg atgtttacgc cgtttgattt tcgcgaccag cttaatgcct  3300
atcatggctc agccttttct gtggagcccg ttcttaccca gagcgcctgg tttcggccgc  3360
ataaccgcga taaaaccatt actaatctct acctggtcgg cgcaggcacg catcccggcg  3420
caggcattcc tggcgtcatc ggctcggcaa aagcgacagc aggtttgatg ctggaggatc  3480
tgatttgaaa gcttctcggt accaaattcc agaaaagagg cctcccgaaa ggggggcctt  3540
ttttcgtttt ggtccgaatt cttgacagct agctcagtcc taggtataat gctagccgca  3600
gtaagagagg aatgtacaca tgtcccgcct ggataaatcg aaagtgatta actcggccct  3660
cgaattgctg aatgaagtcg gtatcgaggg gctgacgacc cgtaaattgg cacaaaagtt  3720
gggggtggag caacccacgt tgtattggca cgtcaaaaat aagcgggcat tgctggatgc  3780
cctcgctatt gaaatgttgg atcgccacca tacccatttc tgtccactgg agggcgagtc  3840
ctggcaggac tttctccgca acaacgcgaa atcctttcgc tgtgcactct tgtcccatcg  3900
ggacggtgct aaggtgcact tgggcacccg tcccaccgaa aaacaatacg aaaccttgga  3960
aaatcaattg gcgtttttgt gccagcaagg gtttagcttg gagaatgctc tctatgcgct  4020
ctcggctgtc gggcacttta cgttggggtg cgtgttggag gaccaggagc atcaagtcgc  4080
aaaagaggag cgtgaaaccc caaccacgga ctcgatgcca cctctgctcc gccaagctat  4140
cgaactcttc gatcatcagg gcgcggagcc agccttcctc tttgggctgg agctgattat  4200
ctgcggtttg gaaaaacaac tcaagtgtga aagcgggtcc taactgcagc tcgag       4255

SEQ ID NO: 71           moltype = DNA  length = 5439
FEATURE                 Location/Qualifiers
source                  1..5439
                        mol_type = other DNA
                        organism = synthetic construct
SEQUENCE: 71
ggatccgagc tgttgacaac tctatcattg atagagttat aatgttccct atcagtgata  60
gagacgcagt aagagaggaa tgtacatatg tatccgttta taaggacagc ccgaatgacg  120
gtctgcgcaa aaaaacacgt tcatctcact cgcgatgctg cggagcagtt actggctgat  180
attgatcgac gccttgatca gttattgccc gtggagggag aacgggatgt tgtgggtgcc  240
gcgatgcgtg aaggtgcgct ggcaccggga aaacgtattc gccccatgtt gctgttgctg  300
accgcccgcg atctgggttg cgctgtcagc catgacggat tactggattt ggcctgtgcg  360
gtggaaatgg tccacgcggc ttcgctgatc cttgacgata tgccctgcat ggacgatgcg  420
aagctgcggc gcggacgccc taccattcat tctcattacg gagagcatgt ggcaatactg  480
gcggcggttg ccttgctgag taaagccttt ggcgtaattg ccgatgcaga tggcctcacg  540
ccgctggcaa aaaatcgggc ggtttctgaa ctgtcaaacg ccatcggcat gcaaggattg  600
gttcagggtc agttcaagga tctgtctgaa ggggataagc cgcgcagcgc tgaagctatt  660
ttgatgacga atcactttaa aaccagcacg ctgttttgtg cctccatgca gatggcctcg  720
attgttgcga atgcctccag cgaagcgcgt gattgcctgc atcgtttttc acttgatctt  780
ggtcaggcat ttcaactgct ggacgatttg accgatggca tgaccgacac cggtaaggat  840
agcaatcagg acgccggtaa atcgacgctg gtcaatctgt taggcccgag ggcggttgaa  900
gaacgtctga gacaacatct tcagcttgcc agtgagcatc tctctgcggc ctgccaacac  960
gggcacgcca ctcaacattt tattcaggcc tggtttgaca aaaaactcgc tgccgtcagt  1020
taacgcagta agagaggaat gtagatatga ataatccgtc gttactcaat catgcggtcg  1080
aaacgatggc agttggctcg aaaagttttg cgacagcctc aaagttattt gatgcaaaaa  1140
cccggcgcag cgtactgatg ctctacgcct ggtgccgcca ttgtgacgat gttattgacg  1200
atcagacgct gggctttcag gcccggcagc ctgccttaca aacgcccgaa caacgtctga  1260
tgcaacttga gatgaaaacg cgccaggcct atgcaggatc gcagatgcac gaaccggcgt  1320
ttgcggcttt tcaggaagtg gctatggctc atgatatcgc cccggcttac gcgtttgatc  1380
atctggaagg cttcgccatg gatgtacgcg aagcgcaata cagccaactg gatgatacgc  1440
tgcgctattg ctatcacgtt gcaggcgttg tcggcttgat gatggcgcaa atcatgggcg  1500
tgcgggataa cgccacgctg gaccgcgcct gtgaccttgg gctggcattt cagttgacca  1560
atattgctcg cgatattgtg gacgatgcgc atgcgggccg ctgttatctg ccggcaagct  1620
ggctggagca tgaaggtctg aacaaagaga attatgcggc acctgaaaac cgtcaggcgc  1680
tgagccgtat cgcccgtcgt ttggtgcagg aagcagaacc ttactatttg tctgccacag  1740
```

```
ccggcctggc agggttgccc ctgcgttccg cctgggcaat cgctacggcg aagcaggttt  1800
accggaaaat aggtgtcaaa gttgaacagg ccggtcagca agcctgggat cagcggcagt  1860
caacgaccac gcccgaaaaa ttaacgctgc tgctggccgc ctctggtcag gcccttactt  1920
cccggatgcg ggctcatcct ccccgccctg cgcatctctg gcagcgcccg ctctgaaata  1980
attttgttta actttaagaa ggagatataa tgaaaccaac tacggtaatt ggtgcaggct  2040
tcggtggcct ggcactggca attcgtctac aagctgcggg gattcccgtc ttactgcttg  2100
aacaacgtga taaacccggc ggtcgggctt atgtctacga ggatcagggg tttacctttg  2160
atgcaggccc gacggttatc accgatccca gtgccattga agaactgttt gcactggcag  2220
gaaaacagtt aaaagagtat gtcgaactgc tgccggttac gccgttttac cgcctgtgtt  2280
gggagtcagg gaaggtcttt aattacgata acgatcaaac ccggctcgaa gcgcagattc  2340
agcagtttaa tccccgcgat gtcgaaggtt atcgtcagtt tctggactat tcacgcgcgg  2400
tgtttaaaga aggctatcta aagctcggta ctgtcccttt tttatcgttc agagacatgc  2460
ttcgcgccgc acctcaactg gcgaaactgc aggcatggag aagcgtttac agtaaggttg  2520
ccagttacat cgaagatgaa catctgcgcc aggcgttttc tttccactcg ctgttggtgg  2580
gcggcaatcc cttcgccacc tcatccattt atacgttgat acacgcgctg gagcgtgagt  2640
ggggcgtctg gtttccgcgt ggcggcaccg gcgcattagt tcaggggatg ataaagctgt  2700
ttcaggatct gggtggcgaa gtcgtgttaa acgccagagt cagccacatg gaaacgacag  2760
gaaacaagat tgaagccgtg catttagagg acggtcgcag gttcctgacg caagccgtcg  2820
cgtcaaatgc agatgtggtt catacctatc gcgacctgtt aagccagcac cctgccgcgg  2880
ttaagcagtc caacaaactg cagactaagc gcatgagtaa ctctctgttt gtgctctatt  2940
ttggtttgaa tcaccatcat gatcagctcg cgcatcacac ggtttgtttc ggcccgcgtt  3000
accgcgagct gattgacgaa atttttaatc atgatggcct cgcagaggac ttctcacttt  3060
atctgcacgc gccctgtgtc acggattcgt cactggcgcc tgaaggttgc ggcagttact  3120
atgtgttggc gccggtgccg catttaggca ccgcgaacct cgactggacg gttgaggggc  3180
caaaactacg cgaccgtatt tttgcgtacc ttgagcagca ttacatgcct ggcttacgga  3240
gtcagctggt cacgcaccgg atgtttacgc cgtttgattt tcgcgaccag cttaatgcct  3300
atcatggctc agccttttct gtggagcccg ttcttaccca gagcgcctgg tttcggccgc  3360
ataaccgcga taaaaccatt actaatctct acctggtcgg cgcaggcacg catcccggcg  3420
caggcattcc tggcgtcatc ggctcggcaa aagcgacagc aggtttgatg ctggaggatc  3480
tgatttgacg cagtaagaga ggaatgtaga tatgggagcg gctatgcaac cgcattatga  3540
tctgattctc gtgggggctg gactcgcgaa tggccttatc gccctgcgtc tccagcagca  3600
gcaacctgat atgcgtattt tgcttatcga cgccgcaccc caggcgggcg ggaatcatac  3660
gtggtcattt caccacgatg atttgactga gagccaacat cgttggatag ctccgctggt  3720
ggttcatcac tggcccgact atcaggtacg ctttcccaca cgccgtcgta agctgaacag  3780
cggctacttt tgtattactt ctcagcgttt cgctgaggtt ttacagcgac agtttggccc  3840
gcacttgtgg atggataccg cggtcgcaga ggttaatgcg gaatctgttc ggttgaaaaa  3900
gggtcaggtt atcggtgccc gcgcggtgat tgacgggcgg ggttatgcgg caaattcagc  3960
actgagcgtg ggcttccagg cgtttattgg ccaggaatgg cgattgagcc acccgcatgg  4020
tttatcgtct cccattatca tggatgccac ggtcgatcag caaaatggtt atcgcttcgt  4080
gtacagcctg ccgctctcgc cgaccagatt gttaattgaa gatacgcact atattgataa  4140
tgcgacatta gatcctgaat gcgcgcggca aaatatttgc gactatgccg cgcaacaggg  4200
ttggcagctt cagacactgc tgcgagaaga acagggcgcc ttacccatta ctctgtcggg  4260
caatgccgac gcattctggc agcagcgccc cctggcctgt agtggattac gtgccggtct  4320
gttccatcct accaccggct attcactgcc gctggcggtt gccgtggccg accgcctgag  4380
tgcacttgat gtctttacgt cggcctcaat tcaccatgcc attacgcatt ttgcccgcga  4440
gcgctggcag cagcagggct ttttccgcat gctgaatcgc atgctgtttt tagccggacc  4500
cgccgattca cgctggcggg ttatgcagcg tttttatggt ttacctgaag atttaattgc  4560
ccgtttttat gcgggaaaac tcacgctgac cgatcggcta cgtattctga gcggcaagcc  4620
gcctgttccg gtattagcag cattgcaagc cattatgacg actcatcgtt gaaagcttct  4680
cggtaccaaa ttccagaaaa gaggcctccc gaaagggggg ccttttttcg ttttggtccg  4740
aattcttgac agctagctca gtcctaggta taatgctagc cgcagtaaga gaggaatgta  4800
cacatgtccc gcctggataa atcgaaagtg attaactcgg ccctcgaatt gctgaatgaa  4860
gtcggtatcg aggggctgac gacccgtaaa ttggcacaaa agttgggggt ggagcaaccc  4920
acgttgtatt ggcacgtcaa aaataagcgg gcattgctgg atgccctcgc tattgaaatg  4980
ttggatcgcc accataccca tttctgtcca ctggagggcg agtcctggca ggactttctc  5040
cgcaacaacg cgaaatcctt tcgctgtgca ctcttgtccc atcgggacgg tgctaaggtg  5100
cacttgggca cccgtcccac cgaaaaacaa tacgaaacct tggaaaatca attggcgttt  5160
ttgtgccagc aagggtttag cttggagaat gctctctatg cgctctcggc tgtcgggcac  5220
tttacgttgg ggtgcgtgtt ggaggaccag gagcatcaag tcgcaaaaga ggagcgtgaa  5280
accccaacca cggactcgat gccacctctg ctccgccaag ctatcgaact cttcgatcat  5340
cagggcgcgg agccagcctt cctctttggg ctggagctga ttatctgcgg tttggaaaaa  5400
caactcaagt gtgaaagcgg gtcctaactg cagctcgag                         5439
```

```
SEQ ID NO: 72          moltype = DNA  length = 6837
FEATURE                Location/Qualifiers
source                 1..6837
                       mol_type = other DNA
                       organism = synthetic construct
SEQUENCE: 72
ggatccgagc tgttgacaac tctatcattg atagagttat aatgttccct atcagtgata  60
gagacgcagt aagagaggaa tgtacatatg tatccgttta taaggacagc ccgaatgacg  120
gtctgcgcaa aaaaacacgt tcatctcact cgcgatgctg cggagcagtt actggctgat  180
attgatcgac gccttgatca gttattgccc gtggagggag aacgggatgt tgtgggtgcc  240
gcgatgcgtg aaggtgcgct ggcaccggga aaacgtattc gccccatgtt gctgttgctg  300
accgcccgcg atctgggttg cgctgtcagc catgacggat tactggattt ggcctgtgcg  360
gtggaaatgg tccacgcggc ttcgctgatc cttgacgata tgccctgcat ggacgatgcg  420
aagctgcggc gcggacgccc taccattcat tctcattacg gagagcatgt ggcaatactg  480
gcggcggttg ccttgctgag taaagccttt ggcgtaattg ccgatgcaga tggcctcacg  540
ccgctggcaa aaaatcgggc ggtttctgaa ctgtcaaacg ccatcggcat gcaaggattg  600
```

-continued

```
gttcagggtc agttcaagga tctgtctgaa ggggataagc cgcgcagcgc tgaagctatt  660
ttgatgacga atcactttaa aaccagcacg ctgttttgtg cctccatgca gatggcctcg  720
attgttgcga atgcctccag cgaagcgcgt gattgcctgc atcgtttttc acttgatctt  780
ggtcaggcat ttcaactgct ggacgatttg accgatggca tgaccgacac cggtaaggat  840
agcaatcagg acgccggtaa atcgacgctg gtcaatctgt taggcccgag ggcggttgaa  900
gaacgtctga gacaacatct tcagcttgcc agtgagcatc tctctgcggc ctgccaacac  960
gggcacgcca ctcaacattt tattcaggcc tggtttgaca aaaaactcgc tgccgtcagt  1020
taacgcagta agagaggaat gtagatatga ataatccgtc gttactcaat catgcggtcg  1080
aaacgatggc agttggctcg aaaagttttg cgacagcctc aaagttattt gatgcaaaaa  1140
cccggcgcag cgtactgatg ctctacgcct ggtgccgcca ttgtgacgat gttattgacg  1200
atcagacgct gggctttcag gcccggcagc ctgccttaca aacgcccgaa caacgtctga  1260
tgcaacttga gatgaaaacg cgccaggcct atgcaggatc gcagatgcac gaaccggcgt  1320
ttgcggcttt tcaggaagtg gctatggctc atgatatcgc cccggcttac gcgtttgatc  1380
atctggaagg cttcgccatg gatgtacgcg aagcgcaata cagccaactg gatgatacgc  1440
tgcgctattg ctatcacgtt gcaggcgttg tcggcttgat gatggcgcaa atcatgggcg  1500
tgcgggataa cgccacgctg gaccgcgcct gtgaccttgg gctggcattt cagttgacca  1560
atattgctcg cgatattgtg gacgatgcgc atgcgggccg ctgttatctg ccggcaagct  1620
ggctggagca tgaaggtctg aacaaagaga attatgcggc acctgaaaac cgtcaggcgc  1680
tgagccgtat cgcccgtcgt ttggtgcagg aagcagaacc ttactatttg tctgccacag  1740
ccggcctggc agggttgccc ctgcgttccg cctgggcaat cgctacggcg aagcaggttt  1800
accggaaaat aggtgtcaaa gttgaacagg ccggtcagca agcctgggat cagcggcagt  1860
caacgaccac gcccgaaaaa ttaacgctgc tgctggccgc ctctggtcag gcccttactt  1920
cccggatgcg ggctcatcct ccccgccctg cgcatctctg gcagcgcccg ctctgaaata  1980
attttgttta actttaagaa ggagatataa tgaaaccaac tacggtaatt ggtgcaggct  2040
tcggtggcct ggcactggca attcgtctac aagctgcggg gattcccgtc ttactgcttg  2100
aacaacgtga taaacccggc ggtcgggctt atgtctacga ggatcagggg tttacctttg  2160
atgcaggccc gacggttatc accgatccca gtgccattga agaactgttt gcactggcag  2220
gaaaacagtt aaaagagtat gtcgaactgc tgccggttac gccgttttac cgcctgtgtt  2280
gggagtcagg gaaggtcttt aattacgata acgatcaaac ccggctcgaa gcgcagattc  2340
agcagtttaa tccccgcgat gtcgaaggtt atcgtcagtt tctggactat tcacgcgcgg  2400
tgtttaaaga aggctatcta aagctcggta ctgtcccttt tttatcgttc agagacatgc  2460
ttcgcgccgc acctcaactg gcgaaactgc aggcatggag aagcgtttac agtaaggttg  2520
ccagttacat cgaagatgaa catctgcgcc aggcgttttc tttccactcg ctgttggtgg  2580
gcggcaatcc cttcgccacc tcatccattt atacgttgat acacgcgctg gagcgtgagt  2640
ggggcgtctg gtttccgcgt ggcggcaccg gcgcattagt tcaggggatg ataaagctgt  2700
ttcaggatct gggtggcgaa gtcgtgttaa acgccagagt cagccacatg gaaacgacag  2760
gaaacaagat tgaagccgtg catttagagg acggtcgcag gttcctgacg caagccgtcg  2820
cgtcaaatgc agatgtggtt catacctatc gcgacctgtt aagccagcac cctgccgcgg  2880
ttaagcagtc caacaaactg cagactaagc gcatgagtaa ctctctgttt gtgctctatt  2940
ttggtttgaa tcaccatcat gatcagctcg cgcatcacac ggtttgtttc ggcccgcgtt  3000
accgcgagct gattgacgaa atttttaatc atgatggcct cgcagaggac ttctcacttt  3060
atctgcacgc gccctgtgtc acggattcgt cactggcgcc tgaaggttgc ggcagttact  3120
atgtgttggc gccggtgccg catttaggca ccgcgaacct cgactggacg gttgaggggc  3180
caaaactacg cgaccgtatt tttgcgtacc ttgagcagca ttacatgcct ggcttacgga  3240
gtcagctggt cacgcaccgg atgtttacgc cgtttgattt tcgcgaccag cttaatgcct  3300
atcatggctc agccttttct gtggagcccg ttcttaccca gagcgcctgg tttcggccgc  3360
ataaccgcga taaaaccatt actaatctct acctggtcgg cgcaggcacg catcccggcg  3420
caggcattcc tggcgtcatc ggctcggcaa aagcgacagc aggtttgatg ctggaggatc  3480
tgatttgaaa gcttctcggt accaaattcc agaaaagagg cctcccgaaa ggggggcctt  3540
ttttcgtttt ggtccgaatt cttgacagct agctcagtcc taggtataat gctagccgca  3600
gtaagagagg aatgtacaca tgtcccgcct ggataaatcg aaagtgatta actcggccct  3660
cgaattgctg aatgaagtcg gtatcgaggg gctgacgacc cgtaaattgg cacaaaagtt  3720
gggggtggag caacccacgt tgtattggca cgtcaaaaat aagcgggcat tgctggatgc  3780
cctcgctatt gaaatgttgg atcgccacca tacccatttc tgtccactgg agggcgagtc  3840
ctggcaggac tttctccgca acaacgcgaa atcctttcgc tgtgcactct tgtcccatcg  3900
ggacggtgct aaggtgcact tgggcacccg tcccaccgaa aaacaatacg aaaccttgga  3960
aaatcaattg gcgtttttgt gccagcaagg gtttagcttg gagaatgctc tctatgcgct  4020
ctcggctgtc gggcacttta cgttggggtg cgtgttggag gaccaggagc atcaagtcgc  4080
aaaagaggag cgtgaaaccc caaccacgga ctcgatgcca cctctgctcc gccaagctat  4140
cgaactcttc gatcatcagg gcgcggagcc agccttcctc tttgggctgg agctgattat  4200
ctgcggtttg gaaaaacaac tcaagtgtga aagcgggtcc taactgcagt cactgcccgc  4260
tttccagtcg ggaaacctgt cgtgccagct gcattaatga atcggccaac gcgcggggag  4320
aggcggtttg cgtattgggc gccagggtgg tttttctttt caccagtgag acgggcaaca  4380
gctgattgcc cttcaccgcc tggccctgag agagttgcag caagcggtcc acgctggttt  4440
gccccagcag gcgaaaatcc tgtttgatgg tggttaacgg cgggatataa catgagctgt  4500
cttcggtatc gtcgtatccc actaccgaga tatccgcacc aacgcgcagc ccggactcgg  4560
taatggcgcg cattgcgccc agcgccatct gatcgttggc aaccagcatc gcagtgggaa  4620
cgatgccctc attcagcatt tgcatggttt gttgaaaacc ggacatggca ctccagtcgc  4680
cttcccgttc cgctatcggc tgaatttgat tgcgagtgag atatttatgc cagccagcca  4740
gacgcagacg cgccgagaca gaacttaatg ggcccgctaa cagcgcgatt tgctggtgac  4800
ccaatgcgac cagatgctcc acgcccagtc gcgtaccgtc ttcatgggag aaaataatac  4860
tgttgatggg tgtctggtca gagacatcaa gaaataacgc cggaacatta gtgcaggcag  4920
cttccacagc aatggcatcc tggtcatcca gcggatagtt aatgatcagc ccactgacgc  4980
gttgcgcgag aagattgtgc accgccgctt tacaggcttc gacgccgctt cgttctacca  5040
tcgacaccac cacgctggca cccagttgat cggcgcgaga tttaatcgcc gcgacaattt  5100
gcgacggcgc gtgcagggcc agactggagg tggcaacgcc aatcagcaac gactgtttgc  5160
ccgccagttg ttgtgccacg cggttgggaa tgtaattcag ctccgccatc gccgcttcca  5220
ctttttcccg cgttttcgca gaaacgtggc tggcctggtt caccacgcgg gaaacggtct  5280
gataagagac accggcatac tctgcgacat cgtataacgt tactggtttc acattcacca  5340
```

```
ccctgaattg actctcttcc gggcgctatc atgccatacc gcgaaaggtt ttgcgccatt  5400
cgatggtgtc cgggatctcg acgctctccc ttatgcgact cctgcattag gaagcagccc  5460
agtagtaggt tgaggccgtt gagcaccgcc gccgcaagga atggtgcatg caaggagatg  5520
gcgcccaaca gtcccccggc cacggggagt caaaagcctc cggtcggagg cttttgactt  5580
ctagagagct gttgacactt tatgcttccg gctcgtataa tgtgtgtgga attgtgagcg  5640
gataacaacg cagtaagaga ggaatgtacc catggagcgg ctatgcaacc gcattatgat  5700
ctgattctcg tgggggctgg actcgcgaat ggccttatcg ccctgcgtct ccagcagcag  5760
caacctgata tgcgtatttt gcttatcgac gccgcacccc aggcgggcgg gaatcatacg  5820
tggtcatttc accacgatga tttgactgag agccaacatc gttggatagc tccgctggtg  5880
gttcatcact ggcccgacta tcaggtacgc tttcccacac gccgtcgtaa gctgaacagc  5940
ggctactttt gtattacttc tcagcgtttc gctgaggttt tacagcgaca gtttggcccg  6000
cacttgtgga tggataccgc ggtcgcagag gttaatgcgg aatctgttcg gttgaaaaag  6060
ggtcaggtta tcggtgcccg cgcggtgatt gacgggcggg gttatgcggc aaattcagca  6120
ctgagcgtgg gcttccaggc gtttattggc caggaatggc gattgagcca cccgcatggt  6180
ttatcgtctc ccattatcat ggatgccacg gtcgatcagc aaaatggtta tcgcttcgtg  6240
tacagcctgc cgctctcgcc gaccagattg ttaattgaag atacgcacta tattgataat  6300
gcgacattag atcctgaatg cgcgcggcaa aatatttgcg actatgccgc gcaacagggt  6360
tggcagcttc agacactgct gcgagaagaa cagggcgcct tacccattac tctgtcgggc  6420
aatgccgacg cattctggca gcagcgcccc ctggcctgta gtggattacg tgccggtctg  6480
ttccatccta ccaccggcta ttcactgccg ctggcggttg ccgtggccga ccgcctgagt  6540
gcacttgatg tctttacgtc ggcctcaatt caccatgcca ttacgcattt tgcccgcgag  6600
cgctggcagc agcagggctt tttccgcatg ctgaatcgca tgctgttttt agccggaccc  6660
gccgattcac gctggcgggt tatgcagcgt ttttatggtt tacctgaaga tttaattgcc  6720
cgtttttatg cgggaaaact cacgctgacc gatcggctac gtattctgag cggcaagccg  6780
cctgttccgg tattagcagc attgcaagcc attatgacga ctcatcgttg actcgag     6837

SEQ ID NO: 73          moltype = DNA  length = 6860
FEATURE                Location/Qualifiers
source                 1..6860
                       mol_type = other DNA
                       organism = synthetic construct
SEQUENCE: 73
ggatccgagc tgttgacaac tctatcattg atagagttat aatgttccct atcagtgata  60
gagacgcagt aagagaggaa tgtacatatg tatccgttta taaggacagc ccgaatgacg  120
gtctgcgcaa aaaaacacgt tcatctcact cgcgatgctg cggagcagtt actggctgat  180
attgatcgac gccttgatca gttattgccc gtggagggag aacgggatgt tgtgggtgcc  240
gcgatgcgtg aaggtgcgct ggcaccggga aaacgtattc gccccatgtt gctgttgctg  300
accgcccgcg atctgggttg cgctgtcagc catgacggat tactggattt ggcctgtgcg  360
gtggaaatgg tccacgcggc ttcgctgatc cttgacgata tgccctgcat ggacgatgcg  420
aagctgcggc gcggacgccc taccattcat tctcattacg gagagcatgt ggcaatactg  480
gcggcggttg ccttgctgag taaagccttt ggcgtaattg ccgatgcaga tggcctcacg  540
ccgctggcaa aaaatcgggc ggtttctgaa ctgtcaaacg ccatcggcat gcaaggattg  600
gttcagggtc agttcaagga tctgtctgaa ggggataagc cgcgcagcgc tgaagctatt  660
ttgatgacga atcactttaa aaccagcacg ctgttttgtg cctccatgca gatggcctcg  720
attgttgcga atgcctccag cgaagcgcgt gattgcctgc atcgtttttc acttgatctt  780
ggtcaggcat ttcaactgct ggacgatttg accgatggca tgaccgacac cggtaaggat  840
agcaatcagg acgccggtaa atcgacgctg gtcaatctgt taggcccgag ggcggttgaa  900
gaacgtctga gacaacatct tcagcttgcc agtgagcatc tctctgcggc ctgccaacac  960
gggcacgcca ctcaacattt tattcaggcc tggtttgaca aaaaactcgc tgccgtcagt  1020
taacgcagta agagaggaat gtagatatga ataatccgtc gttactcaat catgcggtcg  1080
aaacgatggc agttggctcg aaaagttttg cgacagcctc aaagttattt gatgcaaaaa  1140
cccggcgcag cgtactgatg ctctacgcct ggtgccgcca ttgtgacgat gttattgacg  1200
atcagacgct gggctttcag gcccggcagc ctgccttaca aacgcccgaa caacgtctga  1260
tgcaacttga gatgaaaacg cgccaggcct atgcaggatc gcagatgcac gaaccggcgt  1320
ttgcggcttt tcaggaagtg gctatggctc atgatatcgc cccggcttac gcgtttgatc  1380
atctggaagg cttcgccatg gatgtacgcg aagcgcaata cagccaactg gatgatacgc  1440
tgcgctattg ctatcacgtt gcaggcgttg tcggcttgat gatggcgcaa atcatgggcg  1500
tgcgggataa cgccacgctg gaccgcgcct gtgaccttgg gctggcattt cagttgacca  1560
atattgctcg cgatattgtg gacgatgcgc atgcgggccg ctgttatctg ccggcaagct  1620
ggctggagca tgaaggtctg aacaaagaga attatgcggc acctgaaaac cgtcaggcgc  1680
tgagccgtat cgcccgtcgt ttggtgcagg aagcagaacc ttactatttg tctgccacag  1740
ccggcctggc agggttgccc ctgcgttccg cctgggcaat cgctacggcg aagcaggttt  1800
accggaaaat aggtgtcaaa gttgaacagg ccggtcagca agcctgggat cagcggcagt  1860
caacgaccac gcccgaaaaa ttaacgctgc tgctggccgc ctctggtcag gcccttactt  1920
cccggatgcg ggctcatcct ccccgccctg cgcatctctg gcagcgcccg ctctgaaata  1980
attttgttta actttaagaa ggagatataa tgaaaccaac tacggtaatt ggtgcaggct  2040
tcggtggcct ggcactggca attcgtctac aagctgcggg gattcccgtc ttactgcttg  2100
aacaacgtga taaacccggc ggtcgggctt atgtctacga ggatcagggg tttacctttg  2160
atgcaggccc gacggttatc accgatccca gtgccattga agaactgttt gcactggcag  2220
gaaaacagtt aaaagagtat gtcgaactgc tgccggttac gccgttttac cgcctgtgtt  2280
gggagtcagg gaaggtcttt aattacgata acgatcaaac ccggctcgaa gcgcagattc  2340
agcagtttaa tccccgcgat gtcgaaggtt atcgtcagtt tctggactat tcacgcgcgg  2400
tgtttaaaga aggctatcta aagctcggta ctgtcccttt tttatcgttc agagacatgc  2460
ttcgcgccgc acctcaactg gcgaaactgc aggcatggag aagcgtttac agtaaggttg  2520
ccagttacat cgaagatgaa catctgcgcc aggcgttttc tttccactcg ctgttggtgg  2580
gcggcaatcc cttcgccacc tcatccattt atacgttgat acacgcgctg gagcgtgagt  2640
ggggcgtctg gtttccgcgt ggcggcaccg gcgcattagt tcaggggatg ataaagctgt  2700
ttcaggatct gggtggcgaa gtcgtgttaa acgccagagt cagccacatg gaaacgacag  2760
gaaacaagat tgaagccgtg catttagagg acggtcgcag gttcctgacg caagccgtcg  2820
```

-continued

```
cgtcaaatgc agatgtggtt catacctatc gcgacctgtt aagccagcac cctgccgcgg  2880
ttaagcagtc caacaaactg cagactaagc gcatgagtaa ctctctgttt gtgctctatt  2940
ttggtttgaa tcaccatcat gatcagctcg cgcatcacac ggtttgtttc ggcccgcgtt  3000
accgcgagct gattgacgaa atttttaatc atgatggcct cgcagaggac ttctcacttt  3060
atctgcacgc gccctgtgtc acggattcgt cactggcgcc tgaaggttgc ggcagttact  3120
atgtgttggc gccggtgccg catttaggca ccgcgaacct cgactggacg gttgaggggc  3180
caaaactacg cgaccgtatt tttgcgtacc ttgagcagca ttacatgcct ggcttacgga  3240
gtcagctggt cacgcaccgg atgtttacgc cgtttgattt tcgcgaccag cttaatgcct  3300
atcatggctc agccttttct gtggagcccg ttcttaccca gagcgcctgg tttcggccgc  3360
ataaccgcga taaaaccatt actaatctct acctggtcgg cgcaggcacg catcccggcg  3420
caggcattcc tggcgtcatc ggctcggcaa aagcgacagc aggtttgatg ctggaggatc  3480
tgatttgaaa gcttctcggt accaaattcc agaaaagagg cctcccgaaa ggggggcctt  3540
ttttcgtttt ggtccgaatt cttgacagct agctcagtcc taggtataat gctagccgca  3600
gtaagagagg aatgtacaca tgtcccgcct ggataaatcg aaagtgatta actcggccct  3660
cgaattgctg aatgaagtcg gtatcgaggg gctgacgacc cgtaaattgg cacaaaagtt  3720
gggggtggag caacccacgt tgtattggca cgtcaaaaat aagcgggcat tgctggatgc  3780
cctcgctatt gaaatgttgg atcgccacca tacccatttc tgtccactgg agggcgagtc  3840
ctggcaggac tttctccgca acaacgcgaa atcctttcgc tgtgcactct tgtcccatcg  3900
ggacggtgct aaggtgcact tgggcacccg tcccaccgaa aaacaatacg aaaccttgga  3960
aaatcaattg gcgtttttgt gccagcaagg gtttagcttg gagaatgctc tctatgcgct  4020
ctcggctgtc gggcacttta cgttggggtg cgtgttggag gaccaggagc atcaagtcgc  4080
aaaagaggag cgtgaaaccc caaccacgga ctcgatgcca cctctgctcc gccaagctat  4140
cgaactcttc gatcatcagg gcgcggagcc agccttcctc tttgggctgg agctgattat  4200
ctgcggtttg gaaaaacaac tcaagtgtga aagcgggtcc taactgcagt cactgcccgc  4260
tttccagtcg ggaaacctgt cgtgccagct gcattaatga atcggccaac gcgcggggag  4320
aggcggtttg cgtattgggc gccagggtgg tttttctttt caccagtgag acgggcaaca  4380
gctgattgcc cttcaccgcc tggccctgag agagttgcag caagcggtcc acgctggttt  4440
gccccagcag gcgaaaatcc tgtttgatgg tggttaacgg cgggatataa catgagctgt  4500
cttcggtatc gtcgtatccc actaccgaga tatccgcacc aacgcgcagc ccggactcgg  4560
taatggcgcg cattgcgccc agcgccatct gatcgttggc aaccagcatc gcagtgggaa  4620
cgatgccctc attcagcatt tgcatggttt gttgaaaacc ggacatggca ctccagtcgc  4680
cttcccgttc cgctatcggc tgaatttgat tgcgagtgag atatttatgc cagccagcca  4740
gacgcagacg cgccgagaca gaacttaatg ggcccgctaa cagcgcgatt tgctggtgac  4800
ccaatgcgac cagatgctcc acgcccagtc gcgtaccgtc ttcatgggag aaaataatac  4860
tgttgatggg tgtctggtca gagacatcaa gaaataacgc cggaacatta gtgcaggcag  4920
cttccacagc aatggcatcc tggtcatcca gcggatagtt aatgatcagc ccactgacgc  4980
gttgcgcgag aagattgtgc accgccgctt tacaggcttc gacgccgctt cgttctacca  5040
tcgacaccac cacgctggca cccagttgat cggcgcgaga tttaatcgcc gcgacaattt  5100
gcgacggcgc gtgcagggcc agactggagg tggcaacgcc aatcagcaac gactgtttgc  5160
ccgccagttg ttgtgccacg cggttgggaa tgtaattcag ctccgccatc gccgcttcca  5220
ctttttcccg cgttttcgca gaaacgtggc tggcctggtt caccacgcgg gaaacggtct  5280
gataagagac accggcatac tctgcgacat cgtataacgt tactggtttc acattcacca  5340
ccctgaattg actctcttcc gggcgctatc atgccatacc gcgaaaggtt ttgcgccatt  5400
cgatggtgtc cgggatctcg acgctctccc ttatgcgact cctgcattag gaagcagccc  5460
agtagtaggt tgaggccgtt gagcaccgcc gccgcaagga atggtgcatg caaggagatg  5520
gcgcccaaca gtcccccggc cacggggagt caaaagcctc cggtcggagg cttttgactt  5580
ctagagagct gttgacactt tatgcttccg gctcgtataa tgtgtgtgga attgtgagcg  5640
gataacaagt ggaattgtga gcggataaca atttcacaca ggaaacagaa tcccatggag  5700
cggctatgca accgcattat gatctgattc tcgtgggggc tggactcgcg aatggcctta  5760
tcgccctgcg tctccagcag cagcaacctg atatgcgtat tttgcttatc gacgccgcac  5820
cccaggcggg cgggaatcat acgtggtcat ttcaccacga tgatttgact gagagccaac  5880
atcgttggat agctccgctg gtggttcatc actggcccga ctatcaggta cgctttccca  5940
cacgccgtcg taagctgaac agcggctact tttgtattac ttctcagcgt ttcgctgagg  6000
ttttacagcg acagtttggc ccgcacttgt ggatggatac cgcggtcgca gaggttaatg  6060
cggaatctgt tcggttgaaa aagggtcagg ttatcggtgc ccgcgcggtg attgacgggc  6120
ggggttatgc ggcaaattca gcactgagcg tgggcttcca ggcgtttatt ggccaggaat  6180
ggcgattgag ccacccgcat ggtttatcgt ctcccattat catggatgcc acggtcgatc  6240
agcaaaatgg ttatcgcttc gtgtacagcc tgccgctctc gccgaccaga ttgttaattg  6300
aagatacgca ctatattgat aatgcgacat tagatcctga atgcgcgcgg caaaatattt  6360
gcgactatgc cgcgcaacag ggttggcagc ttcagacact gctgcgagaa gaacagggcg  6420
ccttacccat tactctgtcg ggcaatgccg acgcattctg gcagcagcgc cccctggcct  6480
gtagtggatt acgtgccggt ctgttccatc ctaccaccgg ctattcactg ccgctggcgg  6540
ttgccgtggc cgaccgcctg agtgcacttg atgtctttac gtcggcctca attcaccatg  6600
ccattacgca ttttgcccgc gagcgctggc agcagcaggg ctttttccgc atgctgaatc  6660
gcatgctgtt tttagccgga cccgccgatt cacgctggcg ggttatgcag cgtttttatg  6720
gtttacctga agatttaatt gcccgttttt atgcgggaaa actcacgctg accgatcggc  6780
tacgtattct gagcggcaag ccgcctgttc cggtattagc agcattgcaa gccattatga  6840
cgactcatcg ttgactcgag                                              6860
```

```
SEQ ID NO: 74          moltype = DNA  length = 1749
FEATURE                Location/Qualifiers
source                 1..1749
                       mol_type = other DNA
                       organism = synthetic construct
SEQUENCE: 74
atggtggacg gtaattattc ggtagcgtcc aacgttatgg tgccgatgcg cgacggggtg  60
cgcttggctg tagatctgta ccgcccggac gcagatggcc ctgtaccggt cctgctggtc  120
cgcaacccct acgacaaatt cgacgtgttc gcttggagta cgcagagcac gaactggctg  180
gaatttgtgc gcgatgggta cgccgtcgtc atccaagaca cccggggcct ctttgcatcc  240
```

```
gaaggtgagt tcgttccaca tgttgatgac gaggcggatg cggaagacac gctgagctgg  300
atcttggaac aagcatggtg cgacggcaat gtgggtatgt tcggtgtaag ctacctgggc  360
gttacgcagt ggcaagctgc tgttagcggt gtgggtggtt tgaaggcaat cgccccgagc  420
atggcgagcg cggatctgta ccgtgccccc tggtacggtc ctggcggcgc cctgagcgtg  480
gaagcactcc tgggctggag cgcattgatc ggtacgggcc tgattaccag ccgtagcgat  540
gcccgcccgg aagacgcagc cgacttcgta cagctggcag ccatcctgaa cgatgtggcc  600
ggtgccgcaa gcgtgacccc tctggccgaa cagcccttgt tgggccgcct gatcccttgg  660
gtgatcgacc aggtggtgga ccatccagac aacgacgagt cgtggcagag catctcgctc  720
tttgaacgtt tgggtgggct cgctaccccg gccttgatta ccgccgggtg gtacgatggc  780
ttcgtgggcg agagcctccg taccttcgta gctgtgaagg acaacgcgga tgcgcgtctg  840
gtggtggggc cgtggagcca cagcaatctg accggccgta atgccgaccg taagtttggg  900
atcgccgcga cctaccccat ccaggaggcg acgaccatgc acaaggcttt tttcgaccgg  960
cacctccgtg gcgagaccga tgccctggca ggggtgccca aggtgcgcct cttcgtaatg  1020
ggtatcgatg agtggcgcga cgagaccgac tggccattgc cagataccgc ttacacgcct  1080
ttttacctcg gggggctccgg tgcggccaac acgagcacgg gtggtgggac cctgtcgacc  1140
tcgatcagcg gcacggagtc ggcggacacc tacctgtatg atcctgccga ccccgtgcca  1200
agtctgggcg gcaccctcct cttccataat ggggacaacg gtccagctga ccagcgcccg  1260
attcacgatc gcgacgacgt gctgtgctac tccaccgagg tgttgaccga ccccgtggaa  1320
gtaacgggga cggtttcggc tcgcctgttc gtgtcctcgt cggccgtgga taccgatttt  1380
accgccaagt tggtcgacgt gttccccgat ggtcgggcaa tcgctctctg cgacggcatc  1440
gtgcgtatgc gctaccggga gaccttggta aatcctacgc tcattgaggc cggtgagatt  1500
tacgaggtgg ctattgatat gctggccacc agcaacgtgt tttgccgggg ccaccgcatc  1560
atggtgcaag ttagcagctc gaacttcccg aagtacgacc gcaactccaa caccggcggc  1620
gtcatcgctc gcgagcaact ggaggaaatg tgcaccgccg taaaccgcat tcaccgcggc  1680
cccgaacacc cgtcccatat cgtgctgccg atcattaagc gcgactataa ggacgacgac  1740
gataagtga                                                         1749
```

```
SEQ ID NO: 75          moltype = AA  length = 582
FEATURE                Location/Qualifiers
source                 1..582
                       mol_type = protein
                       organism = synthetic construct
SEQUENCE: 75
MVDGNYSVAS NVMVPMRDGV RLAVDLYRPD ADGPVPVLLV RNPYDKFDVF AWSTQSTNWL  60
EFVRDGYAVV IQDTRGLFAS EGEFVPHVDD EADAEDTLSW ILEQAWCDGN VGMFGVSYLG  120
VTQWQAAVSG VGGLKAIAPS MASADLYRAP WYGPGGALSV EALLGWSALI GTGLITSRSD  180
ARPEDAADFV QLAAILNDVA GAASVTPLAE QPLLGRLIPW VIDQVVDHPD NDESWQSISL  240
FERLGGLATP ALITAGWYDG FVGESLRTFV AVKDNADARL VVGPWSHSNL TGRNADRKFG  300
IAATYPIQEA TTMHKAFFDR HLRGETDALA GVPKVRLFVM GIDEWRDETD WPLPDTAYTP  360
FYLGGSGAAN TSTGGGTLST SISGTESADT YLYDPADPVP SLGGTLLFHN GDNGPADQRP  420
IHDRDDVLCY STEVLTDPVE VTGTVSARLF VSSSAVDTDF TAKLVDVFPD GRAIALCDGI  480
VRMRYRETLV NPTLIEAGEI YEVAIDMLAT SNVFLPGHRI MVQVSSSNFP KYDRNSNTGG  540
VIAREQLEEM CTAVNRIHRG PEHPSHIVLP IIKRDYKDDD DK                    582
```

```
SEQ ID NO: 76          moltype = DNA  length = 936
FEATURE                Location/Qualifiers
source                 1..936
                       mol_type = other DNA
                       organism = synthetic construct
SEQUENCE: 76
atgtatccgt ttataaggac agcccgaatg acggtctgcg caaaaaaaca cgttcatctc  60
actcgcgatg ctgcggagca gttactggct gatattgatc gacgccttga tcagttattg  120
cccgtggagg gagaacggga tgttgtgggt gccgcgatgc gtgaaggtgc gctggcaccg  180
ggaaaacgta ttcgccccat gttgctgttg ctgaccgccc gcgatctggg ttgcgctgtc  240
agccatgacg gattactgga tttggcctgt gcggtggaaa tggtccacgc ggcttcgctg  300
atccttgacg atatgccctg catggacgat gcgaagctgc ggcgcggacg ccctaccatt  360
cattctcatt acggagagca tgtggcaata ctggcggcgg ttgccttgct gagtaaagcc  420
tttggcgtaa ttgccgatgc agatggcctc acgccgctgg caaaaaatcg ggcggtttct  480
gaactgtcaa acgccatcgg catgcaagga ttggttcagg gtcagttcaa ggatctgtct  540
gaaggggata agccgcgcag cgctgaagct attttgatga cgaatcactt taaaaccagc  600
acgctgtttt gtgcctccat gcagatggcc tcgattgttg cgaatgcctc cagcgaagcg  660
cgtgattgcc tgcatcgttt ttcacttgat cttggtcagg catttcaact gctggacgat  720
ttgaccgatg gcatgaccga caccggtaag gatagcaatc aggacgccgg taaatcgacg  780
ctggtcaatc tgttaggccc gagggcggtt gaagaacgtc tgagacaaca tcttcagctt  840
gccagtgagc atctctctgc ggcctgccaa cacgggcacg ccactcaaca ttttattcag  900
gcctggtttg acaaaaaact cgctgccgtc agttaa                           936
```

```
SEQ ID NO: 77          moltype = DNA  length = 930
FEATURE                Location/Qualifiers
source                 1..930
                       mol_type = other DNA
                       organism = synthetic construct
SEQUENCE: 77
atgaataatc cgtcgttact caatcatgcg gtcgaaacga tggcagttgg ctcgaaaagt  60
tttgcgacag cctcaaagtt atttgatgca aaaacccggc gcagcgtact gatgctctac  120
gcctggtgcc gccattgtga cgatgttatt gacgatcaga cgctgggctt tcaggcccgg  180
cagcctgcct tacaaacgcc cgaacaacgt ctgatgcaac ttgagatgaa aacgcgccag  240
gcctatgcag gatcgcagat gcacgaaccg gcgtttgcgg cttttcagga agtggctatg  300
gctcatgata tcgccccggc ttacgcgttt gatcatctgg aaggcttcgc catggatgta  360
```

-continued

```
cgcgaagcgc aatacagcca actggatgat acgctgcgct attgctatca cgttgcaggc  420
gttgtcggct tgatgatggc gcaaatcatg ggcgtgcggg ataacgccac gctggaccgc  480
gcctgtgacc ttgggctggc atttcagttg accaatattg ctcgcgatat tgtggacgat  540
gcgcatgcgg gccgctgtta tctgccggca agctggctgg agcatgaagg tctgaacaaa  600
gagaattatg cggcacctga aaaccgtcag gcgctgagcc gtatcgcccg tcgtttggtg  660
caggaagcag aaccttacta tttgtctgcc acagccggcc tggcagggtt gcccctgcgt  720
tccgcctggg caatcgctac ggcgaagcag gtttaccgga aaataggtgt caaagttgaa  780
caggccggtc agcaagcctg ggatcagcgg cagtcaacga ccacgcccga aaaattaacg  840
ctgctgctgg ccgcctctgg tcaggccctt acttcccgga tgcgggctca tcctccccgc  900
cctgcgcatc tctggcagcg cccgctctag                                  930

SEQ ID NO: 78          moltype = DNA  length = 1479
FEATURE                Location/Qualifiers
source                 1..1479
                       mol_type = other DNA
                       organism = synthetic construct
SEQUENCE: 78
atgaaaccaa ctacggtaat tggtgcaggc ttcggtggcc tggcactggc aattcgtcta  60
caagctgcgg ggattcccgt cttactgctt gaacaacgtg ataaacccgg cggtcgggct  120
tatgtctacg aggatcaggg gtttaccttt gatgcaggcc cgacggttat caccgatccc  180
agtgccattg aagaactgtt tgcactggca ggaaaacagt taaaagagta tgtcgaactg  240
ctgccggtta cgccgtttta ccgcctgtgt tgggagtcag ggaaggtctt taattacgat  300
aacgatcaaa cccggctcga agcgcagatt cagcagttta atccccgcga tgtcgaaggt  360
tatcgtcagt ttctggacta ttcacgcgcg gtgtttaaag aaggctatct aaagctcggt  420
actgtccctt ttttatcgtt cagagacatg cttcgcgccg cacctcaact ggcgaaactg  480
caggcatgga gaagcgttta cagtaaggtt gccagttaca tcgaagatga acatctgcgc  540
caggcgtttt ctttccactc gctgttggtg ggcggcaatc ccttcgccac ctcatccatt  600
tatacgttga tacacgcgct ggagcgtgag tggggcgtct ggtttccgcg tggcggcacc  660
ggcgcattag ttcaggggat gataaagctg tttcaggatc tgggtggcga agtcgtgtta  720
aacgccagag tcagccacat ggaaacgaca ggaaacaaga ttgaagccgt gcatttagag  780
gacggtcgca ggttcctgac gcaagccgtc gcgtcaaatg cagatgtggt tcatacctat  840
cgcgacctgt taagccagca ccctgccgcg gttaagcagt ccaacaaact gcagactaag  900
cgcatgagta actctctgtt tgtgctctat tttggtttga atcaccatca tgatcagctc  960
gcgcatcaca cggtttgttt cggcccgcgt taccgcgagc tgattgacga aatttttaat  1020
catgatggcc tcgcagagga cttctcactt tatctgcacg cgccctgtgt cacggattcg  1080
tcactggcgc ctgaaggttg cggcagttac tatgtgttgg cgccggtgcc gcatttaggc  1140
accgcgaacc tcgactggac ggttgagggg ccaaaactac gcgaccgtat ttttgcgtac  1200
cttgagcagc attacatgcc tggcttacgg agtcagctgg tcacgcaccg gatgtttacg  1260
ccgtttgatt ttcgcgacca gcttaatgcc tatcatggct cagccttttc tgtggagccc  1320
gttcttaccc agagcgcctg gtttcggccg cataaccgcg ataaaaccat tactaatctc  1380
tacctggtcg gcgcaggcac gcatcccggc gcaggcattc ctggcgtcat cggctcggca  1440
aaagcgacag caggtttgat gctggaggat ctgatttga                        1479

SEQ ID NO: 79          moltype = DNA  length = 1161
FEATURE                Location/Qualifiers
source                 1..1161
                       mol_type = other DNA
                       organism = synthetic construct
SEQUENCE: 79
atgggagcgg ctatgcaacc gcattatgat ctgattctcg tggggggctgg actcgcgaat  60
ggccttatcg ccctgcgtct ccagcagcag caacctgata tgcgtatttt gcttatcgac  120
gccgcacccc aggcgggcgg gaatcatacg tggtcatttc accacgatga tttgactgag  180
agccaacatc gttggatagc tccgctggtg gttcatcact ggcccgacta tcaggtacgc  240
tttcccacac gccgtcgtaa gctgaacagc ggctactttt gtattacttc tcagcgtttc  300
gctgaggttt tacagcgaca gtttggcccg cacttgtgga tggataccgc ggtcgcagag  360
gttaatgcgg aatctgttcg gttgaaaaag ggtcaggtta tcggtgcccg cgcggtgatt  420
gacgggcggg gttatgcggc aaattcagca ctgagcgtgg gcttccaggc gtttattggc  480
caggaatggc gattgagcca cccgcatggt ttatcgtctc ccattatcat ggatgccacg  540
gtcgatcagc aaaatggtta tcgcttcgtg tacagcctgc cgctctcgcc gaccagattg  600
ttaattgaag atacgcacta tattgataat gcgacattag atcctgaatg cgcgcggcaa  660
aatatttgcg actatgccgc gcaacagggt tggcagcttc agacactgct gcgagaagaa  720
cagggcgcct tacccattac tctgtcgggc aatgccgacg cattctggca gcagcgcccc  780
ctggcctgta gtggattacg tgccggtctg ttccatccta ccaccggcta ttcactgccg  840
ctggcggttg ccgtggccga ccgcctgagt gcacttgatg tctttacgtc ggcctcaatt  900
caccatgcca ttacgcattt tgcccgcgag cgctggcagc agcagggctt tttccgcatg  960
ctgaatcgca tgctgttttt agccggaccc gccgattcac gctggcgggt tatgcagcgt  1020
ttttatggtt tacctgaaga tttaattgcc cgtttttatg cgggaaaact cacgctgacc  1080
gatcggctac gtattctgag cggcaagccg cctgttccgg tattagcagc attgcaagcc  1140
attatgacga ctcatcgttg a                                           1161
```

INDUCIBLE PROMOTERS

CROSS REFERENCE TO RELATED APPLICATIONS

This application claims the benefit of, and priority to, U.S. Provisional Patent Application No. 63/332,507 filed Apr. 19, 2022, the entirety of which is incorporated herein by reference.

SEQUENCE LISTING

The instant application contains a Sequence Listing which has been submitted electronically in XML file format and is hereby incorporated by reference in its entirety. Said XML copy, created on Aug. 4, 2023, is named 110697-015901_US_SL.xml and is 133,847 bytes in size.

BACKGROUND

Inducible promoters are ubiquitous biotechnology tools for manufacturing proteins, providing molecular models of biosynthesis pathways, and as synthetic switches for a variety of environmental, physiological, and cellular tools. Inducible promoters have a consistent architecture including two key elements: the operator region recognized by transcriptional regulatory proteins and consensus sequences that recruit the sigma (σ) subunits of RNA polymerase to initiate transcription of the inducible gene. Despite their widespread use, leaky transcription in the "OFF" state remains a challenge for inducible promoters. Therefore, improved inducible promoters, cellular systems, and methods of generating proteins are needed to enable advances in protein production and various biotechnology applications.

BRIEF SUMMARY

Provided herein are nucleic acid constructs, wherein the nucleic acid constructs comprise: a modified inducible promoter, wherein the modified inducible promoter comprises: (a) a TXTXXTGT sequence at position −10, relative to a transcriptional start site of the promoter; (b) a TXGXCX-sequence at position −35, relative to a transcriptional start site of the promoter; and (c) a nucleic acid sequence that encodes a bacterial ribosome binding sequence, wherein X is any nucleobase. Further provided herein are nucleic acid constructs, wherein the nucleic acid constructs comprise: a modified inducible promoter, wherein the modified inducible promoter comprises: (a) a TATAAT sequence at position −10, relative to a transcriptional start site of the promoter; (b) a TTGACA sequence at position −35, relative to a transcriptional start site of the promoter; and (c) a nucleic acid sequence that encodes a bacterial ribosome binding sequence. In some embodiments, the nucleic acid construct further comprises a transgene. In some embodiments, the modified inducible promoter, when operatively linked to a transgene, facilitates expression of the transgene when the nucleic acid construct is inserted into a prokaryotic cell in the presence of an inducer; and wherein: (i) the expression of the transgene in the absence of the inducer is less than an amount of expression in the absence of the inducer of the transgene operatively coupled to a weak promoter in a comparable nucleic acid construct; and (ii) the expression of the transgene in the presence of the inducer is at least equal to an amount of expression in the presence of the inducer of the transgene operatively coupled to the strong promoter in the comparable nucleic acid construct. Further provided herein are nucleic acid constructs, wherein the nucleic acid constructs comprise: a modified inducible promoter, wherein the modified inducible promoter comprises: (a) a TATAATGT sequence at position −10, relative to a transcriptional start site of the promoter; (b) a TTGACA sequence at position −35, relative to a transcriptional start site of the promoter; and (c) a nucleic acid sequence that encodes a bacterial ribosome binding sequence. In some embodiments, the nucleic acid construct further comprises a transgene. In some embodiments, the modified inducible promoter, when operatively linked to a transgene, facilitates expression of the transgene when the nucleic acid construct is inserted into a prokaryotic cell in the presence of an inducer; and wherein: (i) the expression of the transgene in the absence of the inducer is less than an amount of expression in the absence of the inducer of the transgene operatively coupled to a weak promoter in a comparable nucleic acid construct; and (ii) the expression of the transgene in the presence of the inducer is at least equal to an amount of expression in the presence of the inducer of the transgene operatively coupled to the strong promoter in the comparable nucleic acid construct. In some embodiments, a strong promoter increases the amount of expression of a transgene provided herein relative to a comparable inducible promoter that does not comprise TATAAT, TTGACA, TATAATGT, TXTXXTGT, or TXGXCX. In some embodiments, the strong promoter increases the amount of expression of a transgene provided herein by at least 10% relative to the expression of a transgene expressed by a comparable inducible promoter that does not comprise TATAAT, TTGACA, TATAATGT, TXTXXTGT, or TXGXCX.

Provided herein are methods of expressing a transgene in a cell, the methods comprising: (a) transforming a nucleic acid construct into the cell, wherein the nucleic acid construct comprises a modified inducible promoter, wherein the modified inducible promoter comprises: (i) a TATAAT sequence or a TATAATGT sequence at position −10, relative to a transcriptional start site of the promoter; (ii) a TTGACA sequence at position −35, relative to a transcriptional start site of the promoter; (iii) a nucleic acid sequence encoding a bacterial ribosome binding sequence; and (iv) a transgene; and (b) contacting the cell with an inducer, thereby expressing the transgene. In some embodiments, when cloned into a comparable nucleic acid construct that comprises a strong promoter, the transgene inhibits growth of the cell prior to the contacting step (b) with the inducer, thereby preventing expression of the transgene via the comparable nucleic acid. In some embodiments, the cell is a prokaryotic cell. In some embodiments, the cell is a eukaryotic cell.

Provided herein are nucleic acid constructs, wherein the nucleic acid constructs comprise: (a) a first modified inducible promoter sequence, wherein the first modified inducible promoter comprises: (i) a TATAATGT sequence at position −10, relative to a transcriptional start site of the first modified inducible promoter sequence; (ii) a TTGACA sequence at position −35, relative to a transcriptional start site of the first modified inducible promoter sequence; and (iii) a nucleic acid sequence that encodes a first bacterial ribosome binding sequence; and (b) a second modified inducible promoter sequence, wherein the second modified inducible promoter sequence comprises: (i) a TATAATGT sequence at position −10, relative to a transcriptional start site of the second modified inducible promoter sequence; (ii) a TTGACA sequence at position −35, relative to a transcriptional start site of the second modified inducible promoter sequence; and (iii) a nucleic acid sequence that encodes a second bacterial ribosome binding sequence. In some embodiments, the nucleic acid constructs further comprise a transgene. In some embodiments, wherein the first modified inducible promoter sequence, when operatively linked to a transgene, facilitates expression of the transgene when the nucleic acid construct is in the presence of an inducer.

A composition comprising two or more of a nucleic acid construct provided herein.

Provided herein are isolated prokaryotic cells, wherein the isolated prokaryotic cells comprise a nucleic acid construct provided herein. Provided herein are isolated eukaryotic cells, wherein the isolated eukaryotic cells comprise a nucleic acid construct provided herein. Provided herein are cell-free systems, wherein the cell-free systems comprise a nucleic acid construct provided herein.

Provided herein are non-naturally occurring organisms, wherein the non-naturally occurring organisms comprise: a nucleic acid construct comprising: (a) a first inducible promotor sequence comprising: (i) a TATAATGT sequence at position −10, relative to a transcriptional start site of the promoter; (ii) a TTGACA sequence at position −35, relative to a transcriptional start site of the promoter; and (iii) a nucleic acid sequence that encodes a bacterial ribosome binding sequence; (b) one or more of a biosynthesis pathway transgene; and (c) a second modified inducible promotor sequence comprising: (i) a TATAATGT sequence at position −10, relative to a transcriptional start site of the second modified inducible promotor sequence; (ii) a TTGACA sequence at position −35, relative to a transcriptional start site of the second modified inducible promotor sequence; and (iii) a nucleic acid sequence that encodes a bacterial ribosome binding sequence. In some embodiments, the non-naturally occurring organisms comprise prokaryotic organisms. In some embodiments, the prokaryotic organisms comprise a population of bacteria. In some embodiments, the biosynthesis pathway transgene comprises a carotenoid synthesis gene.

Provided herein are compositions comprising a non-naturally occurring organism provided herein and an inducer.

Further provided herein are methods of expressing a transgene in a cell that does not comprise a T7 RNA polymerase, wherein the methods comprise: (a) transforming a nucleic acid construct into the cell, wherein the nucleic acid construct comprises a modified inducible promoter, wherein the modified inducible promoter comprises: (i) a TATAAT sequence or a TATAATGT-sequence at position −10, relative to a transcriptional start site of the promoter; (ii) a TTGACA-sequence at position −35, relative to a transcriptional start site of the promoter; and (iii) a bacterial ribosome binding sequence; and a transgene: and (b) contacting the cell with an inducer, thereby expressing a protein encoded by the transgene. In some embodiments, the expression of the protein in the absence of the inducer is less than an amount of expression of the protein in the absence of the inducer of the transgene operatively coupled to a T7 promoter in a comparable nucleic acid construct. In some embodiments, the expression of the protein encoded by the transgene in the presence of the inducer is greater than an amount of expression of the protein in the presence of the inducer of the transgene operatively coupled to the T7 promoter in the comparable nucleic acid construct. In some embodiments, the transgene is toxic to a prokaryotic cell that does not express a modified inducible promoter. In some embodiments, the cell is a prokaryotic cell. In some embodiments, the cell is a eukaryotic cell.

Further provided herein are methods of expressing a transgene in a cell-free system, wherein the methods comprise: (a) transforming a nucleic acid construct into the cell-free system, wherein the nucleic acid construct comprises a modified inducible promoter, wherein the modified inducible promoter comprises: (i) a TATAAT sequence or a TATAATGT sequence at position −10, relative to a transcriptional start site of the promoter; (ii) a TTGACA sequence at position −35, relative to a transcriptional start site of the promoter; and (iii) a bacterial ribosome binding sequence; and a transgene: and (b) contacting the cell-free system with an inducer, thereby expressing a protein encoded by the transgene. In some embodiments, the cell-free system further comprises: an RNA polymerase, ribonucleotides, and/or a buffer.

Provided herein are methods for producing a protein, the methods comprising: culturing the non-naturally occurring organism provided herein; and contacting the non-naturally occurring organism with an inducer, thereby producing the protein. Further provided herein are methods for producing a carotenoid, the methods comprising: culturing the non-naturally occurring organism provided herein; and contacting the non-naturally occurring organism with an inducer, thereby producing the protein. Provided herein are methods for producing an organic compound, the methods comprising: culturing the non-naturally occurring organism provided herein; and contacting the non-naturally occurring organism with an inducer, thereby producing the organic compound. Further provided herein are methods for producing a carotenoid, the methods comprising: culturing the non-naturally occurring organism provided herein; and contacting the non-naturally occurring organism with an inducer, thereby producing the carotenoid. In some embodiments, the organic compound or the protein comprises a polyketide, a terpene, a non-ribosomal peptide, or an enzyme protein. Provided herein are methods for producing benzoic acid, the methods comprising: culturing the non-naturally occurring organism provided herein; and contacting the non-naturally occurring organism with an inducer, thereby producing the benzoic acid. Further provided herein is a composition comprising benzoic acid made by a method provided herein. Further provided herein is a composition comprising a carotenoid made by a method provided herein.

Provided herein are kits, wherein the kits comprise a nucleic acid construct provided herein, a cell provided herein, a cell-free system provided herein, or a non-naturally occurring organism provided herein, packaging and materials, therefore.

BRIEF DESCRIPTION OF THE DRAWINGS

Novel features of exemplary embodiments are set forth with particularity in the appended claims. A better understanding of the features and advantages will be obtained by reference to the following detailed description that sets forth illustrative embodiments, in which the principles of the disclosed systems and methods are utilized, and the accompanying drawings of which:

FIG. 1A shows a schematic of a constitutive version of the synthetic lac and tet expression systems. FIG. 1B shows a schematic of inducible versions of the synthetic lac and tet expression systems in pColE1 backbone. Plasmids contain the Kanamycin selection marker and the attP sites specific fox Bxb1 integrase. # indicates the version of the promoter (e.g. V1Tc, V2lac, etc).

FIG. 2A shows the original lac (i) and synthetic lac (ii-vii) promoters. SEQ ID NOS: 3-9 are shown. FIG. 2B shows the original tet (i) and synthetic tet (ii-v) promoters. SEQ ID NOS: 10-14 are shown. FIG. 2C shows schematic representation of the function of synthetic lac and tet promoters. Each transcriptional unit is insulated by terminators. LacI/TetR regulators bind to the operators lacO/tetO. Addition of the inducers (yellow ovals) IPTG or anhydrotetracycline (aTc) remove the repressor allowing transcription from the promoters.

FIG. 3A shows absolute values of fluorescence measured in arbitrary units with far red wavelengths (excitation 604, emission 659, left panel), and green wavelengths (excitation 485, emission 510) *E. coli* DH10B, *P. putida* and *V. natriegens*. Note that these strains are wild type and do not contain any fluorescent protein genes. N=3. Error bars +/−SD. FIGS. 3B-3D show graphs of the fluorescence signal-to-background ratio of recombinant strains expressing sfGFP and mCardinal from the constitutive tacI promoter (these represent "signal") vs. wild type strains of (FIG. 3B) *E. coli* (FIG. 3C) *P. putida* & (FIG. 3D) *V. natriegens* (these wild type strains represent "background"). Signal-to-background measurement ratios are then plotted over time (left panels) The fluorescence values (in arbitrary units, AU) measured to create the signal-to-background ratios are shown in the middle (sfGFP) and right (mCardinal) panels. N=3. Error bars +/−SD.

FIGS. 4A-4C show graphs of the time course of mCardinal production in *E. coli* DH10B with synthetic lac and tet promoters. FIG. 4A shows the synthetic lac promoters, and FIG. 4B shows the synthetic tet promoters, with and without the transcriptional regulators tetR and lacI and induced after 3 hours with aTc or IPTG, respectively. FIG. 4C shows direct comparison of each promoter under evaluation against the strong constitutive promoter tacI. The recombinant DH10B carrying tacI-mCardinal was normalized to 100% mCardinal production and the wild type DH10B strain normalized to 0% mCardinal production. For all samples, the fluorescence mean of mCardinal signal (excitation 605, emission 659) was normalized by the cell density (OD600). N=4. Error bars +/−SD.

FIG. 5A shows gel electrophoresis of total crude extracts (top), the insoluble fraction analysis (middle panel), and the soluble fraction (bottom). The expected size of CocE is 63 kDa. *E. coli* expressing the pET and V2TcR expression systems, uninduced and induced (induced samples indicated with an asterisk). FIG. 5B shows a graph of benzoic acid production by CocE present in the soluble fraction, using cocaine as substrate. N=3. Error bars +/−SD. Key for X axis Groups: I: DH10B p$\sigma^{70}$ V2TcR-CocE; II: DH10B p$\sigma^{70}$ V2TcR-CocE aTc; III: DH10B p$\sigma^{70}$ V2TcR19-CocE; IV: DH10B p$\sigma^{70}$ V2TcR19-CocE aTc; V: BL21 pET21-cocE; VI: BL21 pET21-cocE IPTG.

FIGS. 6A-6C show graphs of the time course of mCardinal production in *P. putida*. Synthetic lac (FIG. 6A) and tet (FIG. 6B) promoters in their constitutive, repressed and induced states. All constructs were integrated in a single copy into the same genomic locus. FIG. 6C shows direct comparison of each promoter under evaluation against the constitutive promoter tacI in *P. putida*. *P. putida* with a single-copy integration of tacI-mCardinal was normalized to 100% mCardinal production and the wild type *P. putida* strain normalized to 0% mCardinal production. For all samples, the fluorescence mean of mCardinal signal (excitation 605, emission 659) was normalized by the cell density (OD600). N=4. Error bars +/−SD.

FIGS. 7A-7C show graphs of the time courses of mCardinal production in *V. natriegens*. Synthetic lac (FIG. 7A) and tet (FIG. 7B) promoters in their constitutive, repressed and induced states are represented. FIG. 7C shows direct comparison of each promoter under evaluation against the constitutive promoter tacI in *V. natriegens*. *V. natriegens* carrying tacI-mCardinal was normalized to 100% mCardinal production and the wild type *V. natriegens* strain normalized to 0% mCardinal production. For all samples, the fluorescence mean of mCardinal signal (excitation 605, emission 659) was normalized by the cell density (OD600). N=4. Error bars +/−SD.

FIG. 9A shows the design of the V2TcR-V2(3)LacI system. FIG. 9B shows a dual expression system controlling expression of mCardinal. FIG. 9C shows a dual expression system controlling expression of sfGFP and mCardinal. FIG. 9D shows a V2TcR expression system controlling the LYC operon. FIG. 9E shows a V2TcR expression system controlling expression of crtEBIY. FIG. 9F shows a dual expression system controlling expression of crtEBI and crtY. Exemplary sequences tested include SEQ ID NOS: 69-73 and 76-79.

FIG. 12A shows Lycopene levels that were extracted and measured by UHPLC. FIG. 12B shows B-carotene levels that were extracted and measured by UHPLC. N=3. Error bars +/−SD.

FIG. 13A shows lycopene levels that were extracted and measured by UHPLC. FIG. 13B shows β-carotene levels that were extracted and measured by UHPLC. N=3. Error bars +/−SD.

DETAILED DESCRIPTION

Overview

Figure 1A:
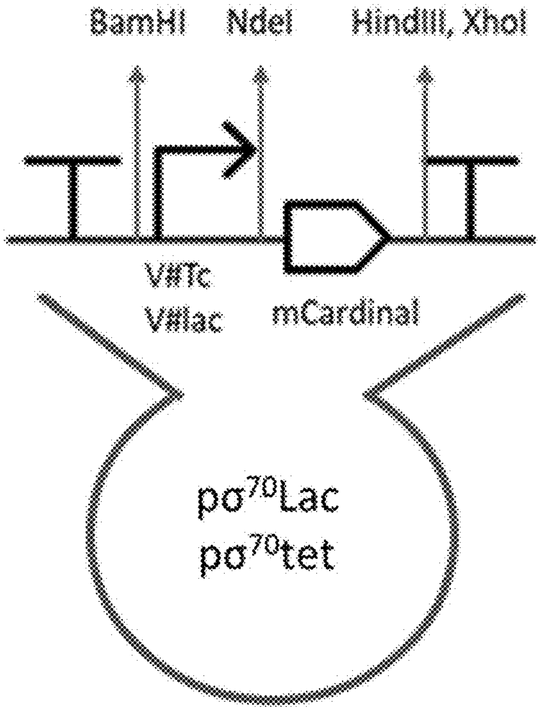
FIGS. 1A-1B show schematic diagrams of exemplary plasmids produced in accordance with the teachings of the present disclosure.

Disclosed herein are nucleic acid constructs that comprise a modified inducible promoter. Such constructs can be utilized to express a transgene operatively coupled to the promoter upon transformation into a cell or a cell-free system. As described herein, the modified inducible promoter does not substantially express the transgene in the absence of an inducer and in the presence of a specific transcriptional regulator. In some cases, a transgene is toxic to the cell when expressed utilizing the modified inducible promoter described herein. In some cases, a transgene is not toxic to the cell when expressed utilizing the modified inducible promoter described herein. Expression of toxic genes is one of many advantages to the modified inducible promoter systems provided herein. In addition, non-toxic gene product yields (e.g., proteins or organic compounds) are also higher as compared to inducible promoters that are not modified.

In contrast, many inducible promoters produce significant expression of the transgene even in the absence of an inducer. Such promoters, known as "leaky" promoters, cannot be used to express transgenes that are toxic to a cell, as the leaky expression of the transgene inhibits growth of the cell culture and thus prevents overexpression or avoids formation of inclusion bodies.

Further, nucleic acid constructs provided herein comprising a modified inducible promoter that generates the expression of a protein encoded by a transgene in the presence of an inducer that is comparable or to a greater extent than the expression of a protein encoded by the transgene when expressed using a different promoter (e.g., a T7 promoter such as a pET vector). In some embodiments, expression of the transgene can be carried out in various prokaryotic cells, eukaryotic cells, or cell-free systems without the need for T7 lysogenization.

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, such as plus or minus 10%. Where ranges and/or subranges of values are provided, the ranges and/or subranges include the endpoints of the ranges and/or subranges.

The term "substantially" as used herein refers to a value approaching 100% of a given value. For example, an expression system described herein that does not "substantially" express a transgene in the absence of an inducer can indicate that less than 10% of the transgene (e.g. less than 5%, less than 1%, less than 0.1%, or less than 0.01%) is expressed, relative to an amount of transgene expressed in the presence of the inducer.

As used herein, the term "operably linked" indicates that a promoter is in a correct functional location and/or orientation in relation to a nucleic acid sequence it regulates to control transcriptional initiation and/or expression of that sequence.

Modified Inducible Promoters

Inducible promoters often have a consistent architecture including two elements: (1) the operator region recognized by the transcriptional regulator proteins (e.g., lacI and tetR, and the −10) and −35 consensus sequences that recruits the sigma (σ) subunits of RNA polymerase to initiate transcription. Improvements to the lac promoter can be made to increase its strength and improve its regulation. For example, the −10 and −35 boxes of the original lac promoter (FIG. 1Ai) can be updated to generate improved variants such as the lacUV5 (FIG. 1Aii) and tacI (FIG. 1Aiii) promoters. In the lacUV5 promoter, the −10 box of the original lac promoter can be replaced by the Pribnow box (e.g., TATAAT) or any one of TATAATGT, TXTXXT, TATXXTGT, TATAXTGT, TATAATGT or TATAATGT. The lacUV5 and trp promoters shown in the working examples can be combined to create the tacI promoter, which increased transcription 11-fold compared to its predecessor with the incorporation of the −35 consensus box TTGACA. The tet promoter (FIG. 1Bi) shares the highly conserved −35 hexamer with tac promoter, but does not contain the Pribnow box.

Despite their ubiquitous use in biology, there remain problems with the current lac-based inducible expression systems. Leaky transcription in the OFF state remains a consistent challenge. Tight transcriptional control is indispensable to produce high yields of challenging recombinant proteins, including toxic genes and proteins that are impossible for a heterologous host to process or fold. For the pET system, target proteins are driven indirectly by controlling expression of the T7 polymerase under the lacUV5 promoter, and then driving the target gene transcription by the T7 promoter. Still, low level T7 transcription in the uninduced state leads to leaky transcription of the target gene. To combat this problem further, *E. coli* strains such as pLysS and pLysE with integration of the T7 lysozyme that inhibits low level T7 activity are used to obtain tighter transcriptional control. However, a host strain with T7 RNA polymerase under control of the lacUV5 promoter, and integration of T7 lysozyme, is required to tightly regulate target gene expression. Expression with the tet system has historically provided tighter transcriptional control than lac derived promoters, does not required specialized strains (such as the BL21), and fully induction is achieved by anhydrotetracycline (aTc) at concentrations that do not cause growth defect due the high affinity of aTc to TetR, and its imperceptible antibiotic activity. Remarkably, at the uninduced state just one mRNA molecule per three cells is produced, and up to 5000-fold induction has been reported, however, the yields of recombinant protein obtained by the tet expression system remains low compared to the pET expression system when using *E. coli* as heterologous host.

The repertoire of organisms used both in academic and industrial settings is rapidly expanding. To address challenges related to complex protein expression in *E. coli*, other chassis organisms such as *Pseudomonas putida* and *Vibrio natriegens* have been employed to produce challenging proteins (e.g., carotenoids) in a variety of biotechnological processes. Both lac and tet expressions systems can be adapted to *P. putida* and *V. natriegens*, though in some instances with lower total protein yield than achieved in pET. However, previous systems for inducible expression were not configured for use across various cell types (e.g., prokaryotic cells). Accordingly, disclosed herein are universal expression systems than can be directly ported between different gram-negative species, yield high quantities of recombinant protein comparable to expression via a pET in *E. coli*, and maintain tight transcriptional repression in the uninduced state. The expression system of the current disclosure is a significant improvement over the pET system in providing tight OFF state control while achieving similar yields of recombinant protein, and with the advantage of direct portability to alternative host species. Further, additional modifications can be performed to enable the expression of the transgene to be turned OFF after induction, thus allowing for reversible control of expression.

A modified, inducible promoter of the current disclosure comprises modified architecture of the lac and tet expression systems to improve their strength, control, and portability. In some embodiments, the genetic architecture of the lac and tet expression systems were modified in three ways: (1) addition of the consensus −10 and −35 sequence boxes to be strongly targeted by $\sigma^{70}$, (2) incorporation of a nucleic acid sequence that encodes a strong ribosome binding site recognized by a broad spectrum of gram-negative bacteria, and (3) independent control of the transcriptional regulators by appropriately-tuned constitutive promoters.

The nucleic acid constructs provided herein can comprise DNA, RNA, an artificial nucleic acid analog, or any combination thereof. In some embodiments, the nucleic acid constructs provided herein comprise, a nucleic acid modification (e.g., a chemical modification), a nucleobase substitution, or a nucleotide substitution. In some embodiments, the sequence at position −10, relative to the transcriptional start site of the promoter comprises one or more nucleobase substitutions. In some embodiments, the sequence at position −10, relative to the transcriptional start site of the promoter comprises a sequence of TXTXXT, where X is any nucleobase. In some embodiments, the sequence at position −10, relative to the transcriptional start site of the promoter comprises a sequence of TXTXXTGT, where X is any nucleobase. In some embodiments, the sequence at position −10, relative to the transcriptional start site of the promoter comprises a sequence of TATXXTGT, where X is any nucleobase. In some embodiments, the sequence at position −10, relative to the transcriptional start site of the promoter comprises a sequence of TATAXTGT, where X is any nucleobase. In some embodiments, the sequence at position −10, relative to the transcriptional start site of the promoter comprises a sequence of TATAATGT, where X is any nucleobase. In some embodiments, the sequence at position −10, relative to the transcriptional start site of the promoter comprises a sequence of TATAATGT, where X is any nucleobase.

In some embodiments, the sequence at position −35, relative to the transcriptional start site of the promoter comprises one or more nucleobase substitutions. In some embodiments, the sequence at position −35, relative to the transcriptional start site of the promoter comprises a sequence of TXGXCX, where X is any nucleobase. In some embodiments, the sequence at position −35, relative to the transcriptional start site of the promoter comprises a sequence of TTGXCX, where X is any nucleobase. In some embodiments, the sequence at position −35, relative to the transcriptional start site of the promoter comprises a sequence of TTGACX, where X is any nucleobase. In some embodiments, the sequence at position −35, relative to the transcriptional start site of the promoter comprises a sequence of TTGACA, where X is any nucleobase.

In some embodiments, a nucleic acid construct provided herein comprises a nucleotide analogue. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, $NH_2$, NHR, $NR_2$, or CN. shRNAs also can comprise non-natural elements such as non-natural bases, e.g., inosine and xanthine, sugars, e.g., 2'-methoxy ribose, or non-natural phosphodiester linkages, e.g., methylphosphonates, phosphorothioates and peptides.

The nucleic acid construct provided herein can comprise a sequence encoding a ribosome binding site. Ribosome binding sites (RBSs) are nucleic acid sequences that promote efficient and accurate translation of mRNAs for protein synthesis, and are also provided for use in the inducible promoters provided herein to permit modulation of the efficiency and rates of synthesis of the proteins encoded by the system. An RBS affects the translation rate of an open reading frame in two main ways—i) the rate at which ribosomes are recruited to the mRNA and initiate translation is dependent on the sequence of the RBS, and ii) the RBS can also affect the stability of the mRNA, thereby affecting the number of proteins made over the lifetime of the mRNA. Accordingly, one or more nucleic acid sequence encoding a ribosome binding site (RBS) or an RBS mRNA can be added to the nucleic acid constructs described herein to control expression of proteins.

In some embodiments, a nucleic acid construct provided herein further comprises a terminator sequence. Terminators are sequences that usually occur at the end of a gene or operon and cause transcription to stop, and are also provided for use in the modules and engineered systems described herein to regulate transcription and prevent transcription from occurring in an unregulated fashion, i.e., a terminator sequence prevents activation of downstream modules by upstream promoters. A terminator or termination signal can include the DNA sequences involved in specific termination of an RNA transcript by an RNA polymerase. Thus, in certain embodiments a terminator that ends the production of an RNA transcript is contemplated. A terminator can be necessary for use in vivo to achieve desirable message levels.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided. Such terminators will usually cause transcription to terminate on both the forward and reverse strand. Finally, in some embodiments, reverse transcriptional terminators can be used to terminate transcription on the reverse strand only.

In some embodiments, a nucleic acid construct provided herein comprises additional regulatory elements that increase or decrease transgene expression in a cell or cell-free system depending on the absence or presence of a particular inducer or set of inducers. In some embodiments, the regulatory element is an enhancer. Additional non-limiting examples of regulatory elements include: lasR activator (e.g., from *P. aeruginosa*), cinR activator, toxicity-gene activator (e.g., ToxR, from *Vibrio cholerae*), lacI (e.g., a wild-type, derivative, or variant thereof), lacI repressor, tetracycline repressor (e.g., TetR from transposon Tn10), mnt repressor, TP901, heat shock proteins, and any derivative or variant thereof.

Thus, in some embodiments, a nucleic acid construct provided herein can be part of a synthetic gene network. Synthetic gene networks can include an engineered composition that comprises at least one nucleic acid construct provided herein and can perform a function including, but not limited to, sensing the presence or absence of an analyte or inducer, a logic function, or a regulatory function. In some embodiments of a synthetic gene network comprising at least two nucleic acid constructs, the nucleic acid constructs can interact with each other directly or indirectly. A synthetic gene network can comprise a nucleic acid encoding a transgene operably linked to a modified inducible promoter provided herein.

The nucleic acid constructs provided herein can be used to visualize chemical, analyte, or protein production in the presence and absence of an inducer provided herein. In some embodiments, a nucleic acid construct provided herein further comprises a reporter gene. In some embodiments, the reporter gene is mCardinal or a green fluorescent protein (e.g., superfolder GFP or sfGFP). A reporter gene encoding any fluorescent protein can be applicable to the nucleic acid constructs and methods of use provided herein. Additional examples of genes encoding fluorescent proteins that can be used in accordance with the compositions and methods described herein include, without limitation, enhance yellow fluorescent protein (EYFP), engineered cyan fluorescent protein (ECFP), mOrange, mCherry, Venus YFP, Cerulean, mBanana, orange fluorescent protein (OFP), derivatives, or variants thereof.

In some embodiments, the reporter gene encodes for a colorimetric protein enzyme. Colorimetric enzymes can cleave a substrate (e.g., a chemical) to yield a color-changing product. In some embodiments, the protein tag is chitinase (which cleaves colorless 4-Nitrophenyl N,N'-diacetyl-beta-D-chitobioside substrate to yield a yellow p-nitrophenol product). In some embodiments, the reporter gene is LacZ (which encodes beta-galactosidase) or a fragment thereof. When LacZ is expressed, the enzyme cleaves the yellow chlorophenol Red-β-D-galactopyranoside (CPRG) substrate to produce the purple chlorophenol red product.

In some embodiments, the reporter gene comprises a catalytic nucleic acid. Examples of catalytic nucleic acids include, but are not limited to, a ribozyme, an RNA-cleaving deoxyribozyme, a group I ribozyme, RNase P, a Hepatitis delta ribozyme, and DNA-zymes.

In some embodiments, the reporter gene comprises an antigen for which a specific antibody or antibody fragment is available. In some embodiments, a reporter gene comprises an antibody, which when expressed, binds to a complementary antigen.

Methods of Expression

Provided herein are methods for expressing a transgene or a protein encoded by a transgene sequence using a nucleic acid construct provided herein having a modified inducible promoter as described herein. In some embodiments, a transgene can be expressed in a host cell that is toxic to the host cell or a non-naturally occurring organism (e.g., a bacterium). Such transgenes can be difficult to express utilizing a pET or other vector containing a leaky promoter, because the leaky expression upon transformation can inhibit growth of the host cell and thereby either prevent expression or express the transgene as an inclusion body. Indeed, tight OFF state control can allow the host cell to reach mid-log phase growth prior to induction, thus allowing for improved expression of the toxic transgene in the prokaryotic cell relative to expression via a vector having a leaky promoter.

The nucleic acid constructs provided herein can comprise a transgene encoding a protein or a fragment thereof. In some embodiments, the transgene or a protein encoded by the transgene is not toxic to the host cell. A protein and/or peptide or fragment thereof can be any protein of interest, for example, but not limited to: biological proteins; mutated proteins; therapeutic proteins; truncated proteins, and the like. Proteins can also be selected from a group comprising: mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. A transgene provided herein can comprise a gene that is, for example, part of a biosynthesis pathway for the production of a protein, an organic compound, or a molecule of interest. The cells, systems, and organisms provided herein provide for a facile method of manufacturing such proteins.

The modified inducible promoters provided herein can be introduced to any cell type or any system that can transcribe and translate the protein encoded by the transgene downstream of the promoter, In some embodiments, a cell provided herein is a prokaryotic cell or a eukaryotic cell. In some embodiments, the system is a cell-free system that can be used to produce the protein or organic compound of interest. A cell-free system is a composition comprising a set of reagents capable of providing for or supporting a biosynthetic reaction (e.g., transcription reaction, translation reaction, or both) in vitro in the absence of cells. For example, to provide for a transcription reaction, a cell-free system comprises promoter-containing DNA, RNA polymerase, ribonucleotides, and a buffer system. Cell-free systems can be prepared using enzymes, coenzymes, and other subcellular components either isolated or purified from eukaryotic or prokaryotic cells, including recombinant cells, or prepared as extracts or fractions of such cells. A cell-free system can be derived from a variety of sources, including, but not limited to, eukaryotic and prokaryotic cells, such as bacteria including, but not limited to, *E. coli, P. putida, V. natriegens*, thermophilic bacteria and the like, wheat germ, rabbit reticulocytes, mouse L cells, Ehrlich's ascitic cancer cells, HeLa cells, CHO cells, or budding yeast. In some embodiments, the cell-free system comprises an RNA polymerase. In some embodiments, the cell-free system comprises components sufficient for the translation reaction. In some embodiments, the cell-free system comprise ribosomes, aminoacyl transfer RNAs, translation factors, and a buffer system. The components can also comprise amino acids or amino acids and aminoacyl tRNA synthetases. Components of translation factors are disclosed, for example, in Shimizu and Ueda, "Pure Technology," Cell-Free Protein Production: Methods and Protocols, Methods in Molecular Biology, Endo et al. (Eds), Humana 2010, the contents of which is incorporated herein by reference in its entirety. Exemplary translation factors include, but are not limited to, factors responsible for protein biosynthesis are initiation factors (IF1, IF2, and IF3), elongation factors (EF-G, EF-Tu, and EF-Ts), and release factors (RF1, RF2, and RF3), as well as RRF for termination.

Prior to induction, the modified inducible promoter provided herein does not substantially express the transgene in the absence of an inducer (e.g. isopropyl β-d-1-thiogalactopyranoside (IPTG), anhydrotetracycline, and the like). In some embodiments, the amount of expressed transgene produced in the absence of inducer is less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, or less than 0.01% of an amount of expressed transgene produced in the presence of the inducer. In some embodiments, the amount of expressed transgene produced in the absence of inducer is less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, or less than 0.01% of an amount of expressed transgene produced by a comparable nucleic acid having a weak promoter (e.g. lacI) promoter in the absence of the inducer.

Expression of the transgene is performed by contacting the host cell or cell-free system provided herein with an inducer (e.g. isopropyl β-d-1-thiogalactopyranoside (IPTG), anhydrotetracycline, and the like). Non-limiting examples of inducers include: a chemical, a compound, and organic compound, a protein, an analyte, tetracycline and derivatives thereof, metallothionine, ecdysone, cocaine, hormones, steroids, and antibiotics (e.g., rapamycin, kanamycin). Exemplary environmental inducers include exposure to heat (i.e., thermal pulses or constant heat exposure), light (e.g., photoirradiation within the defined range of wavelengths), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

In some embodiments, the amount of expressed transgene produced in the presence of inducer is at least equal to the amount of expressed transgene produced by a comparable nucleic acid having a lacUV5 promoter and a T7 polymerase in the presence of the inducer. In some embodiments, the amount of protein expressed in the presence of the inducer is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 300%, at least 400%, at least 500%, at least 600%, at least 700%, at least 800%, at least 900%, or at least 1000% an amount of expressed transgene produced by a comparable nucleic acid having a strong (e.g., T7) promoter in the presence of the inducer.

Such expression can be carried in a variety of prokaryotic host cells. Indeed, while most expression is carried out in T7 lysogenized *E. coli* DE3 strains, the nucleic acid constructs of the present disclosure having a modified inducible promoter can be utilized in prokaryotic cells in the absence of T7 lysogenization.

The host cell for expression of a nucleic acid provided herein (e.g., a transgene) can comprise a prokaryotic cell or a eukaryotic cell. In some embodiments, the prokaryotic cell is a bacterial cell. In some embodiments, a prokaryotic cell can include any Gram-positive strain bacterial cell. In some embodiments, a prokaryotic cell can include any Gram-negative strain bacterial cell. Examples of bacterium that can be used include but are not limited to: non-T7 lysogenized *E. coli* strains such as DH5α, DH10β, or W3110, *P. putida, P. aeruginosa, H. influenzae, C. trachomatis, P. mirabilis, P. vulgaris, C. pneumoniaea, K. pneumoniaea, N. gonorrhoeae, H. pylori, A. cholera, S. aureus, S. enterica, C. jejuni, B. fragilis, L. pneumophila, V. parahaemolyticus*, and *V. natriegens*.

The host cell for expression can be a eukaryotic cells, e.g., a mammalian cell, an insect cell, a yeast cell, a fungal cell, and the like. A nucleic acid construct provided herein can be regulated in a cell-specific or tissue-specific manner such that it is only active in transcribing the associated coding region of a given transgene in a specific tissue type(s).

Exemplary Biosynthesis Pathways for Producing Gene Products

Provided herein are methods of producing a protein, an organic compound, or a molecule using the inducible promoters provided herein, a cell expressing an inducible promoter provided herein, a non-naturally occurring organism provided herein, or kits provided herein. In some embodiments, the non-naturally occurring organism provided herein comprises a nucleic acid construct comprising one or more inducible promoters provided herein and one or more sequence encoding a transgene. In some embodiments, the one or more transgene comprises a sequence encoding a protein in a biosynthesis pathway. In some embodiments, the nucleic acid construct provided herein comprise a biosynthesis pathway transgene. In some embodiments, the biosynthesis pathway is a polyketide synthesis pathway, a terpene synthesis pathway, a non-ribosomal peptide biosynthesis pathway, or a carotenoid biosynthesis pathway. In some embodiments, the cell expressing an inducible promoter provided herein or the a non-naturally occurring organism provided herein are cultured for a period of time. In some embodiments, the period of time is for at least 4 hours, 6 hours, 10 hours, 12 hours, or more. In some embodiments, the period of time is for at least 24 hours. In some embodiments, the period of time is for at least 96 hours.

In some embodiments, the biosynthesis pathway is a carotenoid synthesis pathway. Industrially useful carotenoids are generally produced by chemical synthesis processes for which possibility of undesired actions such as contamination of synthesis auxiliary materials is a major concern for the quality of the product. In addition, tastes of consumers tend to lean toward naturally-occurring carotenoids. However, there is a limit to extraction of carotenoids from plants and natural products, and an effective industrial process is not entirely established. As a production method of naturally-occurring carotenoids, microbial fermentation methods have been used. However, none of such cases enable production of carotenoids in an amount which is enough for economical industrial production. In many cases, through classical mutation and breeding, wild-type of carotenoid producing microorganisms do not generate enough carotenoid product for large-scale manufacturing. carotenoid biosynthesis pathway is made up of various enzymes, and genes encoding such enzymes have been analyzed by many researches. In a typical pathway, for example, carotenoid is synthesized in its early stage by an isoprenoid biosynthesis pathway which is shared by steroid and terpenoid, starting from mevalonic acid which is a basic metabolite. Farnesyl pyrophosphate having 15 carbons (C15) generating through the isoprenoid basic synthesis system is condensed with isopentenyl diphosphate (IPP) (C5), to give geranylgeranyl diphosphate (GGPP) (C20). Then through condensation of two molecules of GGPP, colorless phytoene which is the first carotenoid is synthesized. The phytoene is then converted into lycopene through a series of unsaturation reactions, and then the lycopene is converted into β-carotene through a cyclization reaction. Then, a hydroxyl group and a keto group are introduced into the (3-carotene, which leads synthesis of various xanthophylls represented by astaxanthin.

Provided herein are methods for producing a carotenoid, the method comprises culturing the non-naturally occurring organism provided herein or a plurality of non-naturally occurring organisms under conditions and for a sufficient period of time and contacting the non-naturally occurring organism with an inducer, thereby producing the carotenoid. In some embodiments, the cells or non-naturally occurring organisms provided herein are cultured in a cell culture medium (e.g., a lysogeny broth, also called LB broth or Luria Broth). In some embodiments, the cell or non-naturally occurring organisms are cultured in a bioreactor, a spinning flask, or a vessel suitable for cell growth and survival.

In some embodiments, the transgene encodes a polypeptide having such an enzymatic activity that converts a methylene group at 4 position in β-ionone ring into a keto group. In some embodiments the transgene comprises a crtW gene. In some embodiments, the transgene encodes a polypeptide having such an enzymatic activity that adds one hydroxyl group to a carbon at 3-position of 4-keto-β-ionone ring and/or at 3-position of β-ionone ring. In some embodiments, the transgene comprises a crtZ gene sequence. In some embodiments, the transgene encodes for a polypeptide having such an enzymatic activity that converts lycopene into β-carotene. In some embodiments, the transgene comprises a crtY gene sequence. In some embodiments, the transgene encodes for a polypeptide having such an enzymatic activity that converts phytoene into lycopene. In some embodiments, the transgene comprises a crtI gene sequence. In some embodiments, the transgene encodes for a polypeptide having prephytoene synthase activity. In some embodiments, the transgene comprises a crtB gene sequence. In some embodiments, the transgene encodes for a polypeptide having geranylgeranyl diphosphate synthase activity. In some embodiments, the transgene comprises a crtE gene sequence. In some embodiments, the transgene encodes for a polypeptide having a lycopene elongase/hydratase activity. In some embodiments, the transgene comprises a crtEB gene sequence. In some embodiments, the transgene comprises a crtEBI gene sequence. In some embodiments, the transgene comprises a crtEBIY gene sequence. In some embodiments, the transgene comprises a crtEBIYZ gene sequence. In some embodiments, the transgene comprises a crtEBI-YZW gene sequence. In some embodiments, the transgene comprises an ABA1 gene sequence. In some embodiments, the transgene comprises an ABA2 gene sequence. In some embodiments, the transgene comprises a sequence that is at least 85% identical to any one of SEQ ID NOS: 69-73, 76-79. In some embodiments, the comprises a sequence that is at least 90% identical to any one of SEQ ID NOS: 69-73, 76-79. In some embodiments, the comprises a sequence that is at least 95% identical to any one of SEQ ID NOS: 69-73, 76-79. In some embodiments, the comprises a sequence that is at least 99% identical to any one of SEQ ID NOS: 69-73, 76-79. In some embodiments, the comprises any one of SEQ ID NOS: 69-73, 76-79.

Further provided herein are methods of producing benzoic acid. In some embodiments, the biosynthetic pathway gene is a CocE gene. In some embodiments, the transgene comprises a sequence that is at least 85% identical to SEQ ID NO: 74. In some embodiments, the transgene comprises a sequence that is at least 90% identical to SEQ ID NO: 74. In some embodiments, the transgene comprises a sequence that is at least 95% identical to SEQ ID NO: 74. In some embodiments, the transgene comprises a sequence that is at least 99% identical to SEQ ID NO: 74. In some embodiments, the transgene comprises SEQ ID NO: 74.

Exemplary Embodiments:

Provided herein are nucleic acid constructs, wherein the nucleic acid constructs comprise: a modified inducible promoter, wherein the modified inducible promoter comprises: (a) a TXTXXTGT sequence at position −10, relative to a transcriptional start site of the promoter; (b) a TXGXCX sequence at position −35, relative to a transcriptional start site of the promoter; and (c) a nucleic acid sequence that encodes a bacterial ribosome binding sequence, wherein X is any nucleobase. Further provided herein are nucleic acid constructs, wherein the nucleic acid constructs comprise: a modified inducible promoter, wherein the modified inducible promoter comprises: (a) a TATAAT sequence at position −10, relative to a transcriptional start site of the promoter; (b) a TTGACA sequence at position −35, relative to a transcriptional start site of the promoter; and (c) a nucleic acid sequence that encodes a bacterial ribosome binding sequence. Further provide herein are nucleic acid constructs, wherein the nucleic acid constructs further comprises a transgene. Further provided herein are nucleic acid constructs, wherein the modified inducible promoter, when operatively linked to a transgene, facilitates expression of the transgene when the nucleic acid construct is inserted into a prokaryotic cell in the presence of an inducer; and wherein: (i) the expression of the transgene in the absence of the inducer is less than an amount of expression in the absence of the inducer of the transgene operatively coupled to a weak promoter in a comparable nucleic acid construct; and (ii) the expression of the transgene in the presence of the inducer is at least equal to an amount of expression in the presence of the inducer of the transgene operatively coupled to the strong promoter in the comparable nucleic acid construct. Further provided herein are nucleic acid constructs, wherein the nucleic acid constructs comprise: a modified inducible promoter, wherein the modified inducible promoter comprises: (a) a TATAATGT-sequence at position −10, relative to a transcriptional start site of the promoter; (b) a TTGACA-sequence at position −35, relative to a transcriptional start site of the promoter; and (c) a nucleic acid sequence that encodes a bacterial ribosome binding sequence. Further provided herein are nucleic acid constructs, wherein the nucleic acid constructs further comprise a transgene. Further provided herein are nucleic acid constructs, wherein the transgene is selected from the group consisting of: a crtW gene, a crtE gene, a crtY gene, a crtI gene, a crtZ gene, a crtEB gene, a crtEBI gene, a crtEBIY gene, a crtEBIYZ gene, a crtEBI-YZW gene, an ABA1 gene, an ABA2 gene, and a CocE gene. Further provided herein are nucleic acid constructs, wherein the modified inducible promoter, when operatively linked to a transgene, facilitates expression of the transgene when the nucleic acid construct is inserted into a cell in the presence of an inducer. Further provided herein are nucleic acid constructs, wherein the expression of the transgene in the absence of the inducer is less than an amount of expression in the absence of the inducer of the transgene operatively coupled to a weak promoter in a comparable nucleic acid construct. Further provided herein are nucleic acid constructs, wherein the expression of the transgene in the presence of the inducer is at least equal to an amount of expression in the presence of the inducer of the transgene operatively coupled to the strong promoter in the comparable nucleic acid construct. Further provided herein are nucleic acid constructs, wherein a strong promoter increases the amount of expression of a transgene provided herein relative to a comparable inducible promoter that does not comprise TATAAT, TTGACA, TATAATGT, TXTXXTGT, or TXGXCX. Further provided herein are nucleic acid constructs, wherein the strong promoter increases the amount of expression of a transgene provided herein by at least 10% relative to the expression of a transgene expressed by a comparable inducible promoter that does not comprise TATAAT, TTGACA, TATAATGT, TXTXXTGT, or TXGXCX. Further provided herein are nucleic acid constructs, wherein the nucleic acid constructs further comprise a sequence encoding a reporter gene. Further provided herein are nucleic acid constructs, wherein the nucleic acid constructs further comprise one or more regulatory element. Further provided herein are nucleic acid constructs, wherein the nucleic acid constructs further comprise a terminator sequence.

Provided herein are nucleic acid constructs comprising: a sequence that is at least 85% identical to a sequence comprising any one of: SEQ ID NOS: 1-14, 39-73. Further provided herein are nucleic acid constructs, wherein the nucleic acid constructs comprise a sequence that is at least 90% identical to a sequence comprising any one of: SEQ ID NOS: 1-14, 39-73. Further provided herein are nucleic acid constructs, wherein the nucleic acid constructs comprise a sequence that is at least 95% identical to a sequence comprising any one of: SEQ ID NOS: 1-14, 39-73. Further provided herein are nucleic acid constructs, wherein the nucleic acid constructs comprise a sequence that is at least 99% identical to a sequence comprising any one of: SEQ ID NOS: 1-14, 39-73. Further provided herein are nucleic acid constructs, wherein the nucleic acid constructs comprise a sequence comprising any one of: SEQ ID NOS: 1-14, 39-73.

Provided herein are nucleic acid constructs comprising: (a) a first modified inducible promoter sequence provided herein; and (b) a second modified inducible promoter sequence, wherein the second modified inducible promoter sequence comprises: (i) a TATAATGT sequence at position −10, relative to a transcriptional start site of the second modified inducible promoter sequence; (ii) a TTGACA sequence at position −35, relative to a transcriptional start site of the second modified inducible promoter sequence; and (iii) a nucleic acid sequence that encodes a second bacterial ribosome binding sequence. Further provided herein are nucleic acid constructs, wherein the nucleic acid construct further comprises a transgene. Further provided herein are nucleic acid constructs, wherein the modified inducible promoter, when operatively linked to a transgene, facilitates expression of the transgene when the nucleic acid construct is in the presence of an inducer. Further provided herein are nucleic acid constructs, wherein the expression of the transgene in the absence of the inducer is less than an amount of expression in the absence of the inducer of the transgene operatively coupled to a weak promoter in a comparable nucleic acid construct. Further provided herein are nucleic acid constructs, wherein the expression of the transgene in the presence of the inducer is at least equal to an amount of expression in the presence of the inducer of the transgene operatively coupled to the strong promoter in the comparable nucleic acid construct. Further provided herein are nucleic acid constructs, wherein the nucleic acid constructs further comprise a terminator sequence. Further provided herein are nucleic acid constructs, wherein the nucleic acid constructs further comprise one or more regulatory elements. Further provided herein are nucleic acid constructs, wherein the transgene comprises a carotenoid biosynthesis pathway gene. Further provided herein are nucleic acid constructs, wherein the transgene is selected from the group consisting of: a crtW gene, a crtE gene, a crtY gene, a crtI gene, a crtZ gene, a crtEB gene, a crtEBI gene, a crtEBIY gene, a crtEBIYZ gene, a crtEBI-YZW gene, an ABA1 gene, an ABA2 gene, and a CocE gene.

Provided herein are compositions, wherein the compositions comprise two or more nucleic acid constructs provided herein.

Provided herein are cells comprising a nucleic acid construct or a composition provided herein. Further provided herein are cells, wherein the cells are prokaryotic cells. Further provided herein are cells, wherein the cells are bacterial cells. Further provided herein are cells, wherein the cells are Gram-negative bacterial cells. Further provided herein are cells, wherein the cells are *P. putida* bacterial cells or *V. natriegens* bacterial cells. Further provided herein are cells, wherein the cells are eukaryotic cells. Further provided herein are cells, wherein the cells are mammalian cells.

Provided herein are cell-free systems comprising a nucleic acid construct provided herein, a composition provided herein and/or an RNA polymerase. Further provided herein are cell-free systems, wherein the cell-free systems further comprise ribosomes, aminoacyl transfer RNAs, translation factors, and a buffer.

Provided herein are methods of expressing a protein encoded by a transgene in a cell, the methods comprising: (a) transforming a cell with a nucleic acid construct, wherein the nucleic acid construct comprises a modified inducible promoter that comprises: (i) a TATAATGT sequence at position −10, relative to a transcriptional start site of the promoter; (ii) a TTGACA sequence at position −35, relative to a transcriptional start site of the promoter; (iii) a nucleic acid that encodes a bacterial ribosome binding sequence; and a transgene; and then (b) contacting the cell with an inducer, thereby expressing the protein encoded by the transgene. Further provided herein are methods, wherein the transgene when cloned into a comparable nucleic acid construct that comprises a strong promoter inhibits growth of the cell prior to the contacting with the inducer, thereby preventing expression of the transgene via the comparable nucleic acid. Further provided herein are methods, wherein the cell is a prokaryotic cell. Further provided herein are methods, wherein the prokaryotic cell is a bacterium. Further provided herein are methods, wherein the cell does not comprise a T7 promoter or a T7 polymerase. Further provided herein are methods, wherein when in the absence of the inducer, the expression of the protein encoded by the transgene is lower relative to the expression of the protein in a comparable cell comprising the transgene operably linked to a T7 promoter. Further provided herein are methods, wherein when in the presence of the inducer the expression of the protein encoded by the transgene is greater relative to the expression of the protein in a comparable cell comprising the transgene operably linked to a T7 promoter.

Provided herein are non-naturally occurring organisms comprising a nucleic acid construct comprising: (a) a first inducible promotor sequence comprising: (i) a TATAATGT sequence at position −10, relative to a transcriptional start site of the promoter; (ii) a TTGACA sequence at position −35, relative to a transcriptional start site of the promoter; and (iii) a nucleic acid sequence that encodes a bacterial ribosome binding sequence; (b) one or more of a biosynthesis pathway transgene; and (c) a second modified inducible promotor sequence comprising: (i) a TATAATGT consensus sequence at position −10, relative to a transcriptional start site of the promoter; (ii) a TTGACA sequence at position −35, relative to a transcriptional start site of the promoter; and (iii) a nucleic acid sequence that encodes a bacterial ribosome binding sequence. Further provided herein are non-naturally occurring organisms wherein the one or more biosynthesis pathway transgene is selected from the group consisting of: a crtW gene, a crtE gene, a crtY gene, a crtI gene, a crtZ gene, a crtEB gene, a crtEBI gene, a crtEBIY gene, a crtEBIYZ gene, a crtEBI-YZW gene, and a CocE gene. Further provided herein are non-naturally occurring organisms, wherein the non-naturally occurring organism comprises a bacterium. Further provided herein are non-naturally occurring organisms wherein the bacterium is a Gram-negative bacterium. Further provided herein are non-naturally occurring organisms, wherein the Gram-negative bacterium is a *P. putida* bacterium or a *V. natriegens* bacterium. Further provided herein are non-naturally occurring organisms, wherein the bacterium is a Gram-positive bacterium. Further provided herein are non-naturally occurring organisms, wherein the nucleic acid construct comprises a terminator sequence. Further provided herein are non-naturally occurring organisms, wherein the nucleic acid construct comprises one or more regulatory element. Further provided herein are non-naturally occurring organisms, wherein the nucleic acid construct comprises a reporter gene.

Provided herein are compositions, wherein the compositions comprise: the non-naturally occurring organism provided herein; and an inducer. Further provided herein are compositions, wherein the inducer comprises: anhydrotetracycline (aTc), isopropyl β-d-1-thiogalactopyranoside, cocaine, metallothionine, ecdysone, an antibiotic agent, galactose, a steroid, or a divalent cation.

Provided herein are methods for producing a carotenoid, the methods comprising: culturing the non-naturally occurring organism provided herein; and contacting the non-naturally occurring organism with an inducer, thereby producing the carotenoid. Further provided herein are methods, wherein the non-naturally occurring organism comprises a nucleic acid comprising a gene selected from the group consisting of: a crtW gene, a crtE gene, a crtY gene, a crtI gene, a crtZ gene, a crtEB gene, a crtEBI gene, a crtEBIY gene, a crtEBIYZ gene, and a crtEBI-YZW gene.

Provided herein is a carotenoid produced by the methods provided herein, wherein the carotenoid is lycopene, beta-carotene, zeaxanthin, canthaxanthin, or astaxanthine.

Provided herein are methods for producing benzoic acid, the methods comprising: culturing the cell provided herein; or the non-naturally occurring organism of provided herein; and contacting the cell or the non-naturally occurring organism with an inducer, thereby producing benzoic acid. Further provided herein are methods, wherein the cell or the non-naturally occurring organism comprises a nucleic acid comprising a CocE gene.

Provided herein are compositions comprising benzoic acid, wherein the benzoic acid is produced by the methods provided herein.

Provided herein are kits comprising the nucleic acid construct provided herein, packaging, buffers, and materials therefor.

Provided herein are kits comprising the cell provided herein, packaging, culture medium, buffers, and materials therefor.

Provided herein are kits comprising the non-naturally occurring organism provided herein, packaging, culture medium, buffers, and materials therefor.

Provided herein are nucleic acid constructs comprising a modified inducible promoter, wherein the modified inducible promoter comprises: a TATAAT consensus sequence at position −10, relative to a transcriptional start site of the promoter; a TTGACA sequence at the −35 position, relative to a transcriptional start site of the promoter; a bacterial ribosome binding sequence; wherein the modified inducible promoter, when operatively linked to a transgene, facilitates expression of the transgene when the nucleic acid construct is inserted into a cell in the presence of an inducer; and wherein: the expression of the transgene in the absence of the inducer is less than an amount of expression in the absence of the inducer of the transgene operatively coupled to a weak promoter in a comparable nucleic acid construct; and the expression of the transgene in the presence of the inducer is at least equal to an amount of expression in the presence of the inducer of the transgene operatively coupled to the strong promoter in the comparable nucleic acid construct.

Provided herein are isolated prokaryotic cells comprising a nucleic acid construct provided herein.

Provided herein are methods of expressing a transgene toxic to a prokaryotic cell, the methods comprising: transforming a nucleic acid construct into the prokaryotic cell, wherein the nucleic acid construct comprises a modified inducible promoter comprises: a TATAAT consensus sequence at position −10, relative to a transcriptional start site of the promoter; a TTGACA sequence at the −35 position, relative to a transcriptional start site of the promoter; a bacterial ribosome binding sequence; and contacting the prokaryotic cell with an inducer, thereby expressing the transgene; wherein the transgene when cloned into a comparable nucleic acid construct that comprises a strong promoter inhibits growth of the prokaryotic cell prior to the contacting with the inducer, thereby preventing expression of the transgene via the comparable nucleic acid.

Provided herein are methods of expressing a transgene in a prokaryotic cell that does not comprise a T7 RNA polymerase, the methods comprising: transforming a nucleic acid construct into the prokaryotic cell, wherein the nucleic acid construct comprises a modified inducible promoter comprises: a TATAAT consensus sequence at position −10, relative to a transcriptional start site of the promoter; a TTGACA sequence at the −35 position, relative to a transcriptional start site of the promoter; a bacterial ribosome binding sequence; and contacting the prokaryotic cell with an inducer, thereby expressing the transgene; wherein the expression of the transgene in the absence of the inducer is less than an amount of expression in the absence of the inducer of the transgene operatively coupled to a T7 promoter in a comparable nucleic acid construct; and the expression of the transgene in the presence of the inducer is greater than an amount of expression in the presence of the inducer of the transgene operatively coupled to the T7 promoter in the comparable nucleic acid construct.

Provided herein are nucleic acids, nucleic acid constructs, compositions, cells, non-naturally occurring organisms, cell-free systems, kit, or method provided herein.

For a better understanding of the present disclosure and of its many advantages, the following examples are given by way of illustration and without limiting the scope of this disclosure.

EXAMPLES

Example 1: Inducible Promotor Architecture

In exemplary embodiments, the −10 and −35 boxes of the original lac promoter (FIG. 1Ai), which are targeted by sigma 70 ($\sigma^{70}$), were modified to generate improved variants such as the lacUV5 (FIG. 1Aii) and tacI (FIG. 1Aiii) promoters. In the lacUV5 promoter, the −10 box of the original lac promoter was replaced by the Pribnow box (TATAAT). Later the lacUV5 and trp promoters were combined to create the tacI promoter, which increased transcription 11-fold compared to its predecessor with the incorporation of the −35 consensus box TTGACA. The tet promoter (FIG. 1Bi) shares the highly conserved −35 hexamer with tac promoter, however it does not contain the Pribnow box.

Provided herein are exemplary lac and tet expression systems with improved strength, control, and portability.

The genetic architecture of the lac and tet expression systems were modified in three ways:

(1) addition of the consensus −10 and −35 sequence boxes to be strongly targeted by σ70;

(2) incorporation of a strong ribosome binding site recognized by a broad spectrum of Gram-negative bacteria; and (3) independent control of the transcriptional regulators by appropriately-tuned constitutive promoters.

The results were validated with the reporter protein mCardinal, which significantly improves the dynamic range of promoter measurements over more commonly used green fluorescent proteins. The improvement seen in the mCardinal dynamic range is due to intrinsic fluorescence of many bacterial species that interferes with measurements in the green wavelengths, and the bacteria provided herein have reduced autofluorescence in the far red spectrum. Additionally, the inducible promoters provided herein were compared with the pET system with the production of the cocaine esterase CocE, a thermosensitive enzyme capable of metabolizing cocaine into benzoic acid. CocE, which is prone to form inclusion bodies in leaky *E. coli* expression systems, is expressed as an inducible and soluble protein using the promoters provided herein. The results and assays provided in Example 2 further support that the expression system provided herein is a significant improvement over available expression systems in providing tight OFF state control while achieving high yields of recombinant protein, and with the advantage of direct portability to alternative host species.

Example 2: Generation of Inducible Promotors in Gram Negative Bacteria

Bacterial Strains

*E. coli* DH10B, *P. putida* JE90 derivative of KT2440 with BxB1int-attB, and *V. natriegens* Vmax X2 (Codex DNA, Inc.) were used to evaluate the synthetic lac and tet promoters. The plasmid pET21a-mCardinal was evaluated in *E. coli* BL21 strain. Selective markers kanamycin (50 μg/mL for *E. coli* and *P. putida*, and 400 μg/mL for *V. natriegens*), ampicillin (100 μg/mL for *E. coli*) and spectinomycin (60 μg/mL for *E. coli* and *P. putida*, and 250 μg/mL for *V. natriegens*) were supplemented to LB medium when required. *E. coli* strains were transformed by electroporation and *V. natriegens* by chemical transformation. Integration of plasmids into *P. putida* chromosome was performed by electroporation following the protocol as described, for example, in Elmore et al. *Metab Eng Commun,* 5:1-8 (2017), the contents of which is incorporated herein by reference in its entirety.

Figure 2A:
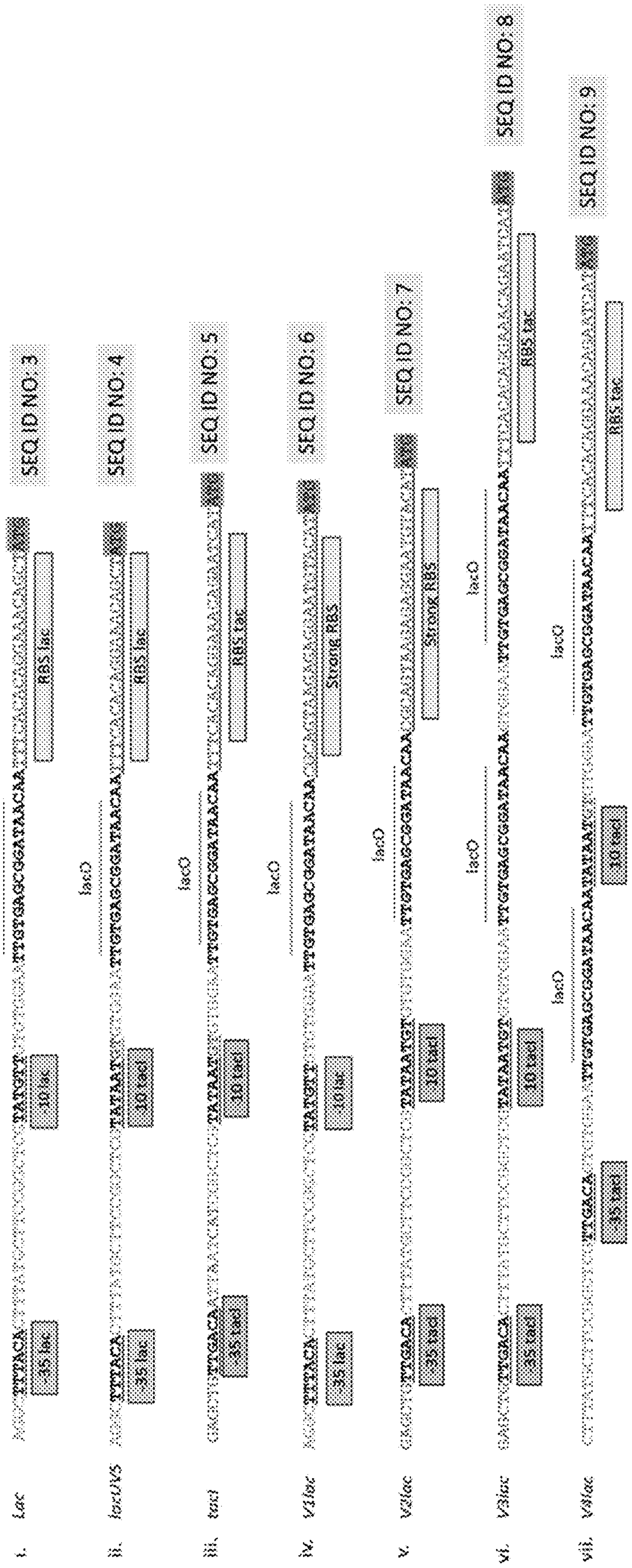
FIGS. 2A-2C show the architecture of exemplary synthetic lac and tet promoters. The sequences of the operators lacO and tetO are overlined, in bold text. The −35 and −10 sequences of the promoters are underlined. Boxes represent the native −35 and −10 sequences, and consensus σ70 −35 and −10 sequences. Conserved regions of the original lac promoter and the original tacI promoter are shown.
Figure 2B:
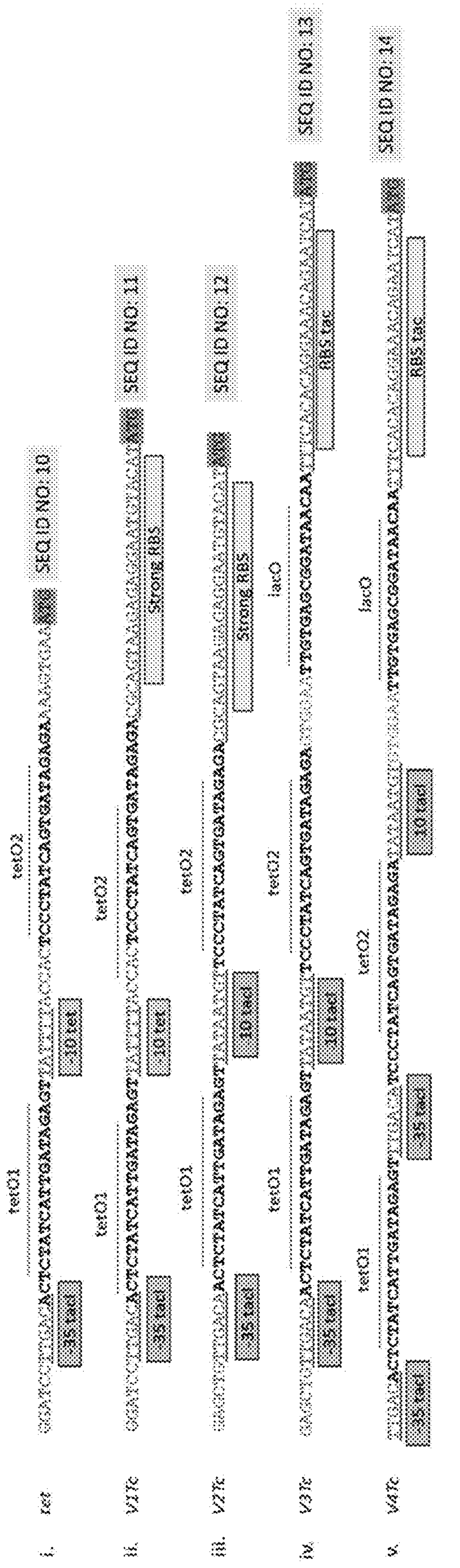

Plasmid information is listed in Table 1 below. Any plasmid containing any version of the $\sigma^{70}$-based promoters as shown in FIG. 2A and FIG. 2B has been labeled "p$\sigma^{70}$" followed by information about the construct and the specific promoter. "Lac" and "Tc" constructs are constitutive and do not express a repressor protein; "LacI" and "TcR" constructs are inducible and include expression of LacI or TetR, respectively. Numbers in parentheses indicate a vector backbone other than pJH0204 ((13) for pJH0228 with the pCloDF13 origin of replication, and (19) for pUC19).

TABLE 1

List of Plasmids and Vectors.

| Name | Backbone | Origin of replication | Selective marker | Construct |
|---|---|---|---|---|
| pJH0204 | pJH0204 | pColE1 | Kanamycin | |
| pJH0228 | pJH0228 | pCloDF13 | Spectinomycin/Streptomycin | |
| pJH0204F | pJH0204 | pColE1 | Kanamycin | |
| pFCtacI-GFP | pJH0204 | pColE1 | Kanamycin | tacI-sfGFP |
| pFCtacI-cardi | pJH0204 | pColE1 | Kanamycin | tacI-mCardinal |
| p$\sigma^{70}$ V1Lac-cardi | pJH0204 | pColE1 | Kanamycin | V1lac-mCardinal |
| p$\sigma^{70}$ V2Lac-cardi13 | pJH0228 | pCloDF13 | Spectinomycin/Streptomycin | V2lac-mCardinal |
| p$\sigma^{70}$ V3Lac-cardi | pJH0204 | pColE1 | Kanamycin | V3lac-mCardinal |
| p$\sigma^{70}$ V4Lac-cardi | pJH0204 | pColE1 | Kanamycin | V4lac-mCardinal |
| p$\sigma^{70}$ V1LacI-cardi | pJH0204 | pColE1 | Kanamycin | V1lac/lacI-mCardinal |
| p$\sigma^{70}$ V2LacI-cardi | pJH0204 | pColE1 | Kanamycin | V2lac/lacI-mCardinal |
| p$\sigma^{70}$ V2Lac-cardi13 | pJH0204 | pCloDF13 | Spectinomycin/Streptomycin | V2lac/lacI-mCardinal |
| p$\sigma^{70}$ V3LacI-cardi | pJH0204 | pColE1 | Kanamycin | V3lac/lacI-mCardinal |
| p$\sigma^{70}$ V4LacI-cardi | pJH0204 | pColE1 | Kanamycin | V4lac/lacI-mCardinal |
| p$\sigma^{70}$ V1Tc-cardi | pJH0204 | pColE1 | Kanamycin | V1Tc-mCardinal |
| p$\sigma^{70}$ V2Tc-cardi | pJH0204 | pColE1 | Kanamycin | V2Tc-mCardinal |
| p$\sigma^{70}$ V3Tc-cardi | pJH0204 | pColE1 | Kanamycin | V3Tc-mCardinal |
| p$\sigma^{70}$ V4Tc-cardi | pJH0204 | pColE1 | Kanamycin | V4Tc-mCardinal |
| p$\sigma^{70}$ V1TcR-cardi | pJH0204 | pColE1 | Kanamycin | V1Tc/tetR-mCardinal |
| p$\sigma^{70}$ V2TcR-cardi | pJH0204 | pColE1 | Kanamycin | V2Tc/tetR-mCardinal |

TABLE 1-continued

| List of Plasmids and Vectors. | | | | |
|---|---|---|---|---|
| Name | Backbone | Origin of replication | Selective marker | Construct |
| p$\sigma^{70}$ V3TcR-cardi | pJH0204 | pColE1 | Kanamycin | V3Tc/tetR-mCardinal |
| p$\sigma^{70}$ V4TcR-cardi | pJH0204 | pColE1 | Kanamycin | V4Tc/tetR-mCardinal |
| p$\sigma^{70}$ V1TcR-cardi19 | pUC19 | pMB1 | Ampicillin | V2Tc/tetR-mCardinal |
| pET21a-cardi | pET21a | pET | Ampicillin | pET |

Figure 1B:
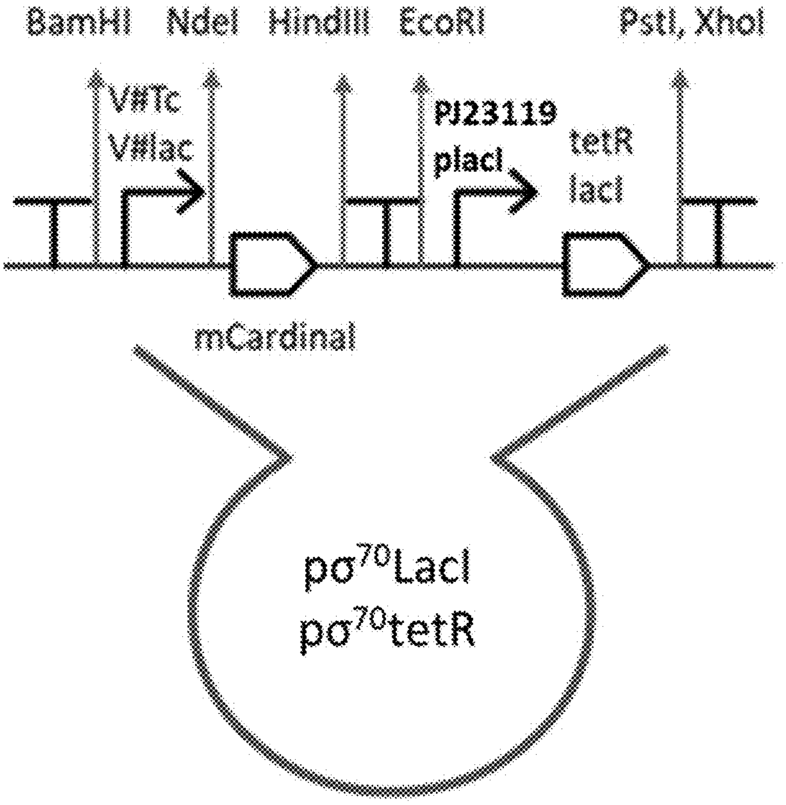

Molecular Cloning:

A schematic diagram of plasmid construction are shown in FIGS. 1A-1B. Polymerase chain reactions (PCR) were carried out with Phusion DNA polymerase (ThermoFisher Scientific, USA). Digestion of DNA was performed with fast digest restriction enzymes and DNA fragments were join by T4 DNA ligase or Gibson assembly kit (ThermoFisher Scientific, USA). Oligonucleotides and DNA synthesis were ordered to IDT (IDT, USA). DNA sequencing was performed (QuintaraBio, USA). Shuttle vectors pJH0204 and pJH0228 were used. The synthetic Vlac and VTc promoters were synthesized as gBLocks and incorporated into the MCS of pJH0204 using BamHI and XhoI. Further, sfGFP and mCardinal ORF were codon optimized for *P. putida* and inserted downstream the synthetic promoters using NdeI and HindIII. The transcriptional regulator tetR gene was synthesized with the PJ23119 promoter in a single gBlock and tetR was codon optimized for *P. putida* using the IDT DNA codon optimization tool (available on the world wide web at https://www.idtdna.com/pages/tools/codon-optimization-tool) and inserted after mCardinal with EcoRI and XhoI. The lacI gene was PCR amplified from pET21a vector and placed under the control of PJ23119 using NcoI and XhoI, but this combination resulted toxic for *E. coli*, therefore lacI was PCR amplified together with its native promoter and ligated after mCardinal using EcoRI and XhoI. pJH0228-V2lac-mCardinal and pJH0228-V2lac/lacI-mCardinal vectors were produced using the same cloning strategy. mCardinal was inserted into pET21a using NdeI and XhoI. The transcriptional unit V2Tc/tetR-mCardinal was inserted into the pUC19 vector by Gibson removing the NdeI RE nucleotide sequence in the plasmid and incorporating terminators insulating the transcriptional unit. DNA sequence of CocE was codon optimized for *P. putida* using the IDT DNA codon optimization tool and cloned into the pET21a and V2Tc-tetR expression system using NdeI and HindIII. A complete list of plasmids generated in this study is shown in Table 1. Primers used in this study are listed in Table 2.

TABLE 2

| List of Primers. | | |
|---|---|---|
| Primer name | SEQ ID NO: | Sequence 5' to 3' |
| pUC19 modified FW XhoI | 15 | attgcCTCGAGACTGATTTTTAAGGCGACTGATGAGTCGCCTTTTTTTTGTC TAGCTAACTCACATTAATTGCGTTGCGCT |
| pUC19 modified FW XhoI | 16 | gcaatGGATCCagtcaaaagcctccgaccggaggcttttgactAGTACAATC TGCTCTGATGCCGCATAGTT |
| 204F1_fwd | 17 | Ggcgcgtactccaaaaggatctaggtgaagatc |
| 204F1_rev | 18 | gagttcttctgattagacaaaaaaaaggcgac |
| 204F2_fwd | 19 | ttttttgtctaatcagaagaactcgtcaagaagg |
| 204F2_rev | 20 | gcccgacggcgaggatctcgtcgtgacgcatg |
| 204F3_fwd | 21 | cacgacgagatcctcgccgtcgggcatccgc |
| 204F3_rev | 22 | gtctagactgcaggaattcaagcttcatatgggatccggaccaaaacgAAA |
| 204F4_fwd | 23 | aagcttgaattcctgcagtctagaccatggctcgaggacgaacaataaggc |
| 204F4_rev | 24 | Cctagatccttttggagtacgcgcccgggga |
| placI upstream | 25 | TACTGGTTTCACATTCACCAC |
| lacI downstream | 26 | GTGGTGAATGTGAAACCAGTAA |
| lacI upstream | 27 | TTTCCAGTCGGGAAACCT |
| lacI downstream2 | 28 | AGGTTTCCCGACTGGAAA |
| tetR upstream | 29 | CCAATACAACGTGGGTTGCT |
| FwplacI | 30 | AACCGGAATTCccccgtggccggg |

TABLE 2-continued

| List of Primers. | | |
|---|---|---|
| Primer name | SEQ ID NO: | Sequence 5' to 3' |
| LXhoI RV | 31 | AACCGCTCGAGTCACTGCCCGCTTTCC |
| Fw PstI-lacI | 32 | attgcCTGCAGTCACTGCCCGCTTTCCAGTCG |
| Rv XbaI-lacI | 33 | gcaatTCTAGAagtcaaaagcctccgaccggaggcttttgactCCCCGTGGC CGGGGGACTG |
| XbaI-V3Lac-NcoI fwd | 34 | gcctccggtcggaggcttttgactt CTAGAGAGCTGTTGACACTTTATG |
| XbaI-V2Lac-NcoI rev | 35 | taatgagctcctcacccttactcacCATGGGTACATTCCTCTCTTACTGC |
| XbaI-V3Lac- | 36 | taatgagctcctcacccttactcac |
| NcoI_rev | 37 | CATGGGATTCTGTTTCCTGTGTG |
| Rv cardi XhoI | 38 | TCAGTCTCGAGTTACTTGTCGTCATCATCCTTAT |

Primers were used as sequencing primers (e.g., placI upstream, tetR upstream). 204F primers were used to incorporate BamHI, NdeI, HindIII, KpnI, EcorI, PstI, XbaI, NcoI, XhoI RE into the MCS of pJH0204 and remove NcoI from kanamycin cassette. The pUC19 modified FW XhoI primers were used to incorporate terminators into pUC19 vector and BamHI/XhoI sites.

Sequences of cocE, tetR, and mCardinal, codon optimized for *P. putida*, and the PJ23119 promoter sequence, are provided below.

DNA sequence of mCardinal codon optimized for *P. putida*:

(SEQ ID NO: 39)
ATGGTGAGTAAGGGTGAGGAGCTCATTAAGGAGAACATGCACATGAAGC

TGTATATGGAGGGCACCGTAAACAACCACCACTTCAAGTGTACCACCGA

GGGTGAAGGTAAACCCTACGAGGGGACGCAGACCCAACGCATCAAGGTC

GTGGAGGGCGGCCCGCTGCCTTTCGCATTCGACATTCTGGCGACCTGTT

TTATGTACGGCTCGAAGACCTTCATCAACCACACCCAAGGCATCCCGGA

CTTCTTCAAGCAGAGCTTCCCTGAGGGCTTCACCTGGGAGCGCGTCACC

ACGTATGAAGACGGTGGGGTGCTCACCGTGACCCAGGACACGAGCTTGC

AGGATGGCTGCTTGATTTACAACGTCAAGCTGCGCGGGGTGAACTTCCC

TAGCAACGGGCCAGTGATGCAGAAAAAGACGCTGGGTTGGGAGGCCACC

ACCGAGACCCTGTACCCGGCCGACGGGGGGCTGGAAGGGCGGTGCGATA

TGGCCCTGAAATTGGTCGGCGGCGGTCATTTGCACTGCAATCTCAAGAC

CACGTACCGCTCCAAGAAACCCGCCAAAAACCTGAAGATGCCTGGTGTT

TATTTTGTCGACCGGCGCCTGGAGCGCATCAAGGAAGCGGACAATGAGA

CGTACGTGGAACAGCACGAAGTGGCCGTGGCTCGTTATTGCGATCTGCC

GTCGAAGCTGGGTCACAAACTGAACGGCATGGATGAGCTGTACAAAGAT

TATAAGGATGATGACGACAAGTAA

DNA sequence of sfGFP codon optimized for *P. putida*:

(SEQ ID NO: 40)
ATGTCCAAAGGTGAAGAGCTGTTTACCGGCGTCGTGCCCATTCTGGTGG

AGCTGGATGGCGACGTCAACGGGCACAAGTTTAGCGTCCGTGGCGAAGG

TGAGGGCGACGCCACGAACGGTAAGCTGACGCTGAAATTCATTTGCACC

ACCGGCAAATTGCCTGTACCCTGGCCCACCCTGGTGACCACGCTCACCT

ACGGCGTACAGTGCTTCAGCCGTTACCCGGACCACATGAAGCGTCACGA

CTTCTTCAAAAGCGCCATGCCGGAGGGTTACGTGCAGGAGCGTACGATT

AGTTTCAAGGACGACGGCACCTATAAGACCCGTGCCGAAGTGAAGTTCG

AAGGCGATACGTTGGTGAACCGTATCGAGTTGAAGGGTATCGACTTTAA

GGAAGACGGCAACATCCTGGGCCATAAGCTGGAGTACAATTTCAACAGC

CATAACGTTTACATCACCGCCGATAAACAGAAGAACGGCATTAAAGCCA

ACTTTAAGATCCGCCACAACGTCGAAGACGGCTCGGTGCAGCTGGCCGA

CCATTATCAGCAAAACACCCCCATCGGTGATGGGCCCGTGCTGCTGCCG

GATAACCATTATCTGAGCACGCAGTCGGTGCTCAGCAAGGACCCTAACG

AAAAGCGCGATCACATGGTGCTGCTGGAGTTCGTCACGGCGGCGGGGAT

CACCCATGGGATGGACGAGCTCTACAAAGACTATAAAGATGACGATGAC

AAGTAAA

DNA sequence of tetR codon optimized for *P. putida*:

(SEQ ID NO: 41)
ATGTCCCGCCTGGATAAATCGAAAGTGATTAACTCGGCCCTCGAATTGC

TGAATGAAGTCGGTATCGAGGGGCTGACGACCCGTAAATTGGCACAAAA

GTTGGGGGTGGAGCAACCCACGTTGTATTGGCACGTCAAAAATAAGCGG

GCATTGCTGGATGCCCTCGCTATTGAAATGTTGGATCGCCACCATACCC

ATTTCTGTCCACTGGAGGGCGAGTCCTGGCAGGACTTTCTCCGCAACAA

CGCGAAATCCTTTCGCTGTGCACTCTTGTCCCATCGGGACGGTGCTAAG

GTGCACTTGGGCACCCGTCCCACCGAAAAACAATACGAAACCTTGGAAA

-continued

```
ATCAATTGGCGTTTTTGTGCCAGCAAGGGTTTAGCTTGGAGAATGCTCT

CTATGCGCTCTCGGCTGTCGGGCACTTTACGTTGGGGTGCGTGTTGGAG

GACCAGGAGCATCAAGTCGCAAAAGAGGAGCGTGAAACCCCAACCACGG

ACTCGATGCCACCTCTGCTCCGCCAAGCTATCGAACTCTTCGATCATCA

GGGCGCGGAGCCAGCCTTCCTCTTTGGGCTGGAGCTGATTATCTGCGGT

TTGGAAAAACAACTCAAGTGTGAAAGCGGGTCCTAA
```

DNA sequence of cocE codon optimized for *P. putida*:

```
                                                                (SEQ ID NO: 42)
CATATGGTGGACGGTAATTATTCGGTAGCGTCCAACGTTATGGTGCCGATGCGCGACGGGGTGCGCTTGGCTGTA

GATCTGTACCGCCCGGACGCAGATGGCCCTGTACCGGTCCTGCTGGTCCGCAACCCCTACGACAAATTCGACGTG

TTCGCTTGGAGTACGCAGAGCACGAACTGGCTGGAATTTGTGCGCGATGGGTACGCCGTCGTCATCCAAGACACC

CGGGGCCTCTTTGCATCCGAAGGTGAGTTCGTTCCACATGTTGATGACGAGGCGGATGCGGAAGACACGCTGAGC

TGGATCTTGGAACAAGCATGGTGCGACGGCAATGTGGGTATGTTCGGTGTAAGCTACCTGGGCGTTACGCAGTGG

CAAGCTGCTGTTAGCGGTGTGGGTGGTTTGAAGGCAATCGCCCCGAGCATGGCGAGCGCGGATCTGTACCGTGCC

CCCTGGTACGGTCCTGGCGGCGCCCTGAGCGTGGAAGCACTCCTGGGCTGGAGCGCATTGATCGGTACGGGCCTG

ATTACCAGCCGTAGCGATGCCCGCCCGGAAGACGCAGCCGACTTCGTACAGCTGGCAGCCATCCTGAACGATGTG

GCCGGTGCCGCAAGCGTGACCCCTCTGGCCGAACAGCCCTTGTTGGGCCGCCTGATCCCTTGGGTGATCGACCAG

GTGGTGGACCATCCAGACAACGACGAGTCGTGGCAGAGCATCTCGCTCTTTGAACGTTTGGGTGGGCTCGCTACC

CCGGCCTTGATTACCGCCGGGTGGTACGATGGCTTCGTGGGCGAGAGCCTCCGTACCTTCGTAGCTGTGAAGGAC

AACGCGGATGCGCGTCTGGTGGTGGGGCCGTGGAGCCACAGCAATCTGACCGGCCGTAATGCCGACCGTAAGTTT

GGGATCGCCGCGACCTACCCCATCCAGGAGGCGACGACCATGCACAAGGCTTTTTTCGACCGGCACCTCCGTGGC

GAGACCGATGCCCTGGCAGGGGTGCCCAAGGTGCGCCTCTTCGTAATGGGTATCGATGAGTGGCGCGACGAGACC

GACTGGCCATTGCCAGATACCGCTTACACGCCTTTTTACCTCGGGGGCTCCGGTGCGGCCAACACGAGCACGGGT

GGTGGGACCCTGTCGACCTCGATCAGCGGCACGGAGTCGGCGGACACCTACCTGTATGATCCTGCCGACCCCGTG

CCAAGTCTGGGCGGCACCCTCCTCTTCCATAATGGGGACAACGGTCCAGCTGACCAGCGCCCGATTCACGATCGC

GACGACGTGCTGTGCTACTCCACCGAGGTGTTGACCGACCCCGTGGAAGTAACGGGGACGGTTTCGGCTCGCCTG

TTCGTGTCCTCGTCGGCCGTGGATACCGATTTTACCGCCAAGTTGGTCGACGTGTTCCCCGATGGTCGGGCAATC

GCTCTCTGCGACGGCATCGTGCGTATGCGCTACCGGGAGACCTTGGTAAATCCTACGCTCATTGAGGCCGGTGAG

ATTTACGAGGTGGCTATTGATATGCTGGCCACCAGCAACGTGTTTTTGCCGGGCCACCGCATCATGGTGCAAGTT

AGCAGCTCGAACTTCCCGAAGTACGACCGCAACTCCAACACCGGCGGCGTCATCGCTCGCGAGCAACTGGAGGAA

ATGTGCACCGCCGTAAACCGCATTCACCGCGGCCCCGAACACCCGTCCCATATCGTGCTGCCGATCATTAAGCGC

GACTATAAGGACGACGACGATAAGTGAAAGCTT
```

DNA sequence of pJ23119 promoter:

```
                                              (SEQ ID NO: 43)
TTGACAGCTAGCTCAGTCCTAGGTATAATGCTAGCCGCAGTAAGAGAGG

AATGTACAC
```

SDS-PAGE

SDS-PAGE was carried out on a 4-12% Bis-tris Midi Protein Gel in an XCell4 SureLock Midi system (Invitrogen, USA). *E. coli, P. putida* and *V. natriegens* cell extracts were obtained from diluting an overnight culture 1:50 in 10 mL of fresh LB media and grown at 37° C. for *E. coli* and 30° C. for *P. putida* and *V. natriegens* at 220 rpm until the culture reached an optical density (OD) at 600 nm ($OD_{600}$) of 0.7 measured spectrophotometrically, then induced with 0.2 mM IPTG or 0.1 μg/mL aTc accordingly. Induced cultures were grown for 5 hours, and 2 mL culture were spun down at 14.000 rpm and 4° C. for 10 minutes and frozen at −20° C. for further analysis. Cells were lysed with Complete Bacterial Protein Extraction Reagent (ThermoFisher Scientific), and crude extracts were analyzed by SDS-PAGE. Total protein concentration was estimated with Thermo Scientific NanoDrop one and ~10 mg total protein of each cell extract was loaded into the SDS-gel.

Expression of CocE and Measurement of Benzoic Acid Production

Recombinant *E. coli* BL21 strain carrying the pET21a-cocE and DH10B containing either p$\sigma^{70}$ V2TcR-cocE or p$\sigma^{70}$ V2TcR-cocE19 plasmids were cultivated overnight at 30° C. at 220 rpm and fresh cultures were started with 5% of the ON culture and induced at ~$OD_{600}$ 0.7 with 0.2 mM IPTG or 0.1 μg/mL aTc accordingly. 1 mL samples were collected each hour for 6 hours by centrifugation at 4° C. and 14000 rpm and stored at −80° C. Cell pellets were disrupted using 150 μL of B-PE Complete Bacterial Protein Extraction Reagent (ThermoFisher Scientific) for 25 minutes at room temperature and soluble fractions were collected after centrifugation for 25 minutes at 4° C. and 14000 rpm. ~3 mg/mL of soluble fractions were incubated with 0.015 mg of cocaine for 20 minutes at 28° C. and benzoic acid production was estimated using the benzoic acid detection kit for feed (Attogene, EZ2013-03).

Example 3: Design of Synthetic lac and tet Promoters

Figure 2C:
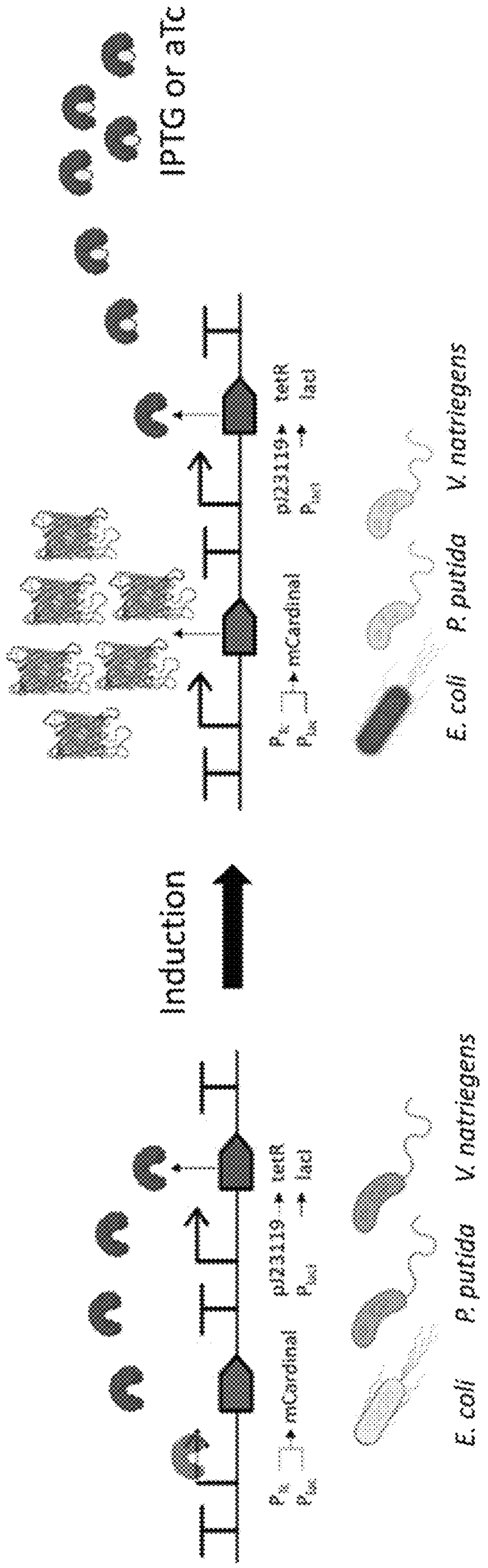

A schematic diagram of plasmid construction is shown in FIGS. 1A-1B. All plasmids used in the assay are listed in Table 1. The original lac promoter (FIG. 2Ai) lacks the −35 conserved box recognized by the $\sigma^{70}$ subunit of RNA polymerase. Original lac and tet (FIG. 2Bi) promoters lack the Pribnow (−10) box. Three synthetic variants of each promoter were constructed containing the highly conserved $\sigma^{70}$ consensus hexamers at positions −10 and −35. Version 1 (V1lac, FIG. 2Aiv, and V1Tc, FIG. 2Bii) of each promoter resembles the original lac and tet promoters, with the incorporation of a strong RBS from *P. putida*. The version 2 (V2lac, FIG. 2Av, and V2Tc, FIG. 2Biii) replaces the −35 and −10 boxes of Version 1 for the highly conserved $\sigma^{70}$ consensus hexamers TTGACA and TATAAT, respectively. Version 3 (V3lac, FIG. 2Avi, and V3Tc, FIG. 2Biv) incorporates an additional lacO operator and the RBS of the tacI promoter. Version 4 (V4lac, FIG. 2Avii, and V4Tc, FIG. 2Bv) displaces the location of the −10 and −35 boxes (V4lac) and incorporates an additional −35 box in V4Tc. The synthetic promoters were cloned into the MCS of the shuttle vector pJH0204 containing the origin of replication pColE1 with 25-30 copies per cell in *E. coli*. The design allowed the incorporation of the transcriptional regulators lacI and tetR after a terminator L3S2P21 and under the control of the constitutive promoter PJ23119 (FIG. 2C).

No aberrant phenotypes in the *E. coli* strains carrying the PJ23119-tetR construct were observed. However, *E. coli* failed to maintain the PJ23319-lacI construct. The plasmids containing the lacI repressor gene in this configuration produced slow-growing colonies and yielded plasmids with aberrant restriction patterns, indicating gross plasmid rearrangements. Therefore, the strong PJ23119 promoter was replace for the native lacI promoter and observed no further toxicity.

The reporter protein mCardinal was incorporated downstream of the synthetic promoters and the plasmids were transformed into *E. coli* DH10B, *P. putida* JE90 derivative KT2440, and *V. natriegens* Vmax X2 strains. The V2lac-mCardinal constructs could not be maintained in *E. coli*, likely due the high strength of the V2lac promoter. To avoid this abnormal phenotype, the genetic circuit V2lac-mCardinal was produced in the pJH0228 vector containing the CloDF13 origin of replication at about 10 copies per cell, allowing stable maintenance of the V2lac promoter.

Example 4: Selection of the Fluorescent Reporter System

GFP and other green fluorescent protein derivatives are widely used as reporters in bacterial expression systems. However, the intrinsic green fluorescence produced by endogenous molecules, such as proteins containing aromatic amino acids, negatively impact the interpretation of the exogenous green fluorescence generated by the reporter system. The autofluorescence is exacerbated in *P. putida*, a member of the fluorescent *Pseudomonas* species. Under iron limited conditions *P. putida* secretes the siderophore pyoverdine, a soluble fluorescent yellow green pigment. Far-red fluorescent proteins were explored, specifically mCardinal, a monomeric far red shifted derivative of mKate, as wavelengths between 600 and 900 nm are not absorbed by cells and organic molecules, thus reducing the noise of endogenous autofluorescence.

Figure 3A:
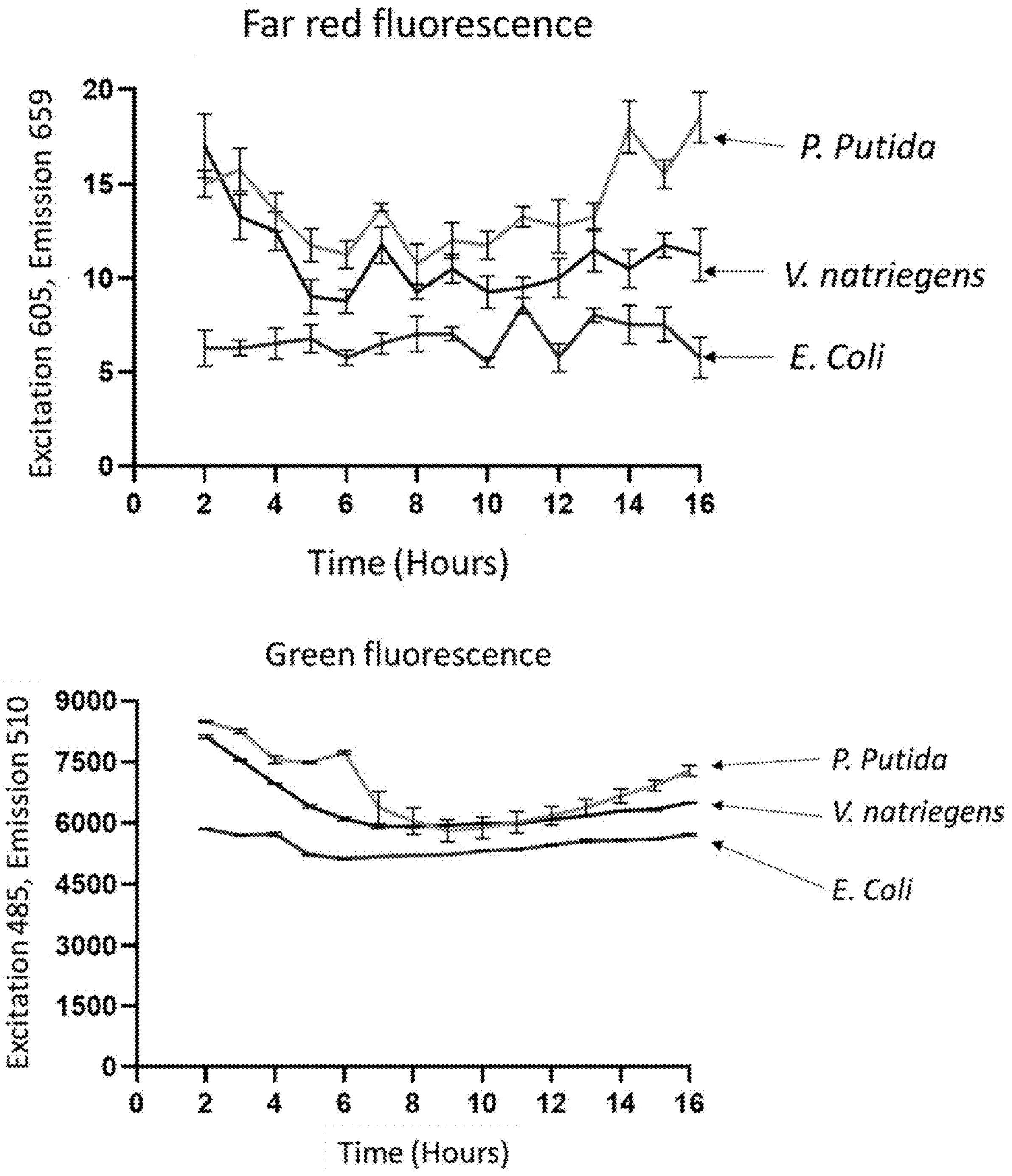
FIGS. 3A-3D show a graphical comparison of sfGFP and mCardinal emissions in Gram-negative bacteria.

To quantify the impact of autofluorescence on the selected Gram-negatives strains, the endogenous fluorescence of these strains cultivated in LB over time were measured. All three species emit fluorescence in the green spectrum, as expected (FIG. 3A, right panel). This fluorescence is more or less constant over time with *E. coli*, however *P. putida* and *V. natriegens* show variable production of molecules that absorb green light at different cell densities. In contrast, when measured in the far-red spectrum specific for mCardinal, there was approximately 400 times less detection of autofluorescence, in arbitrary units on the same instrument, in all strains as compared to the measurements in the green spectrum (FIG. 3A, left panel). Again, *E. coli* displayed rather consistent far red autofluorescence over time whereas *P. putida* and *V. natriegens* autofluorescence varies with cell density.

Figure 3B:
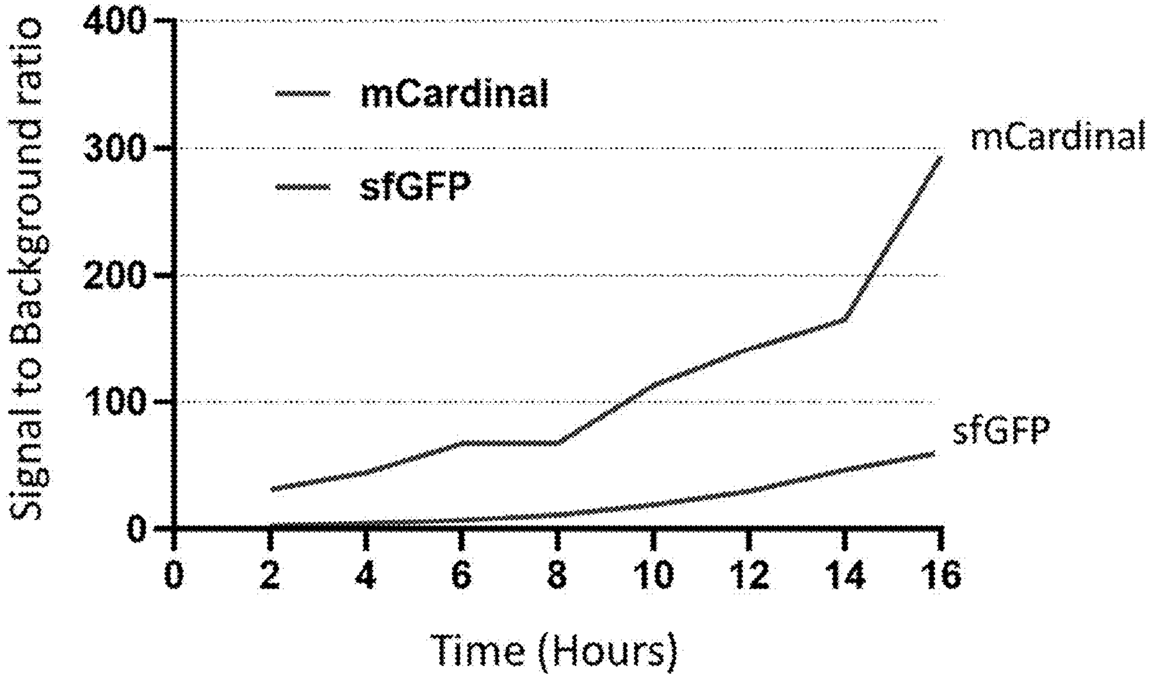
Figure 3B:
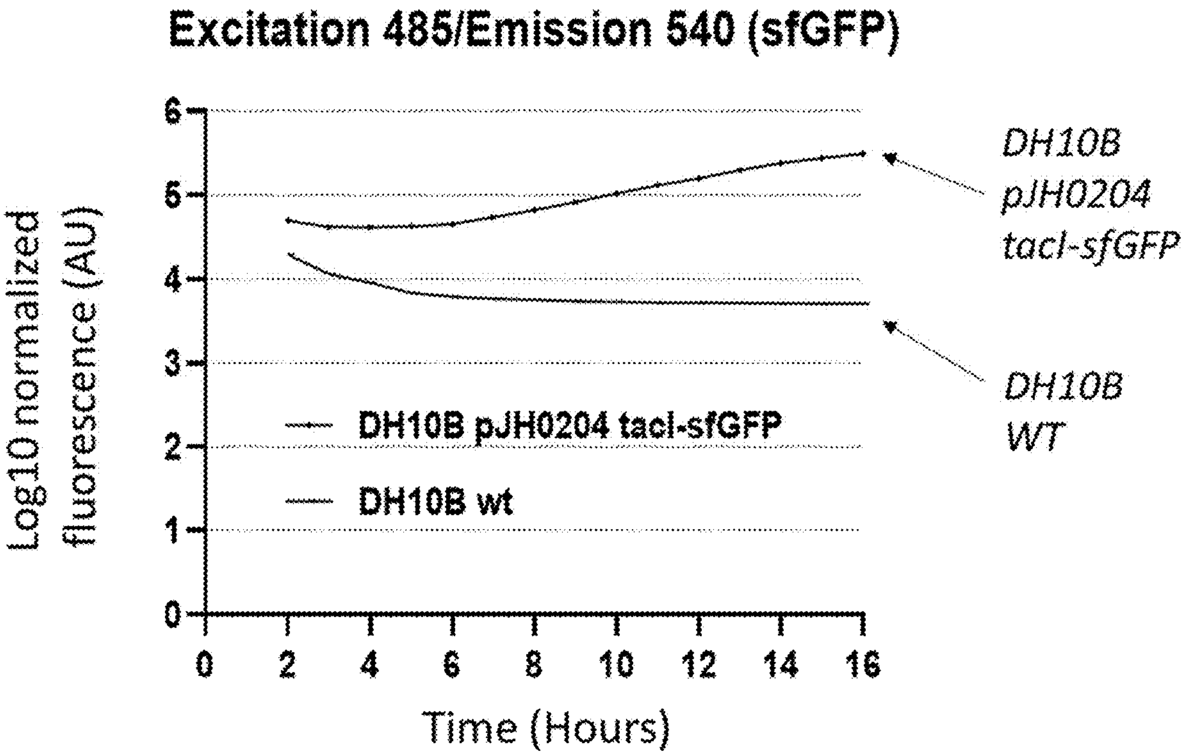
Figure 3B:
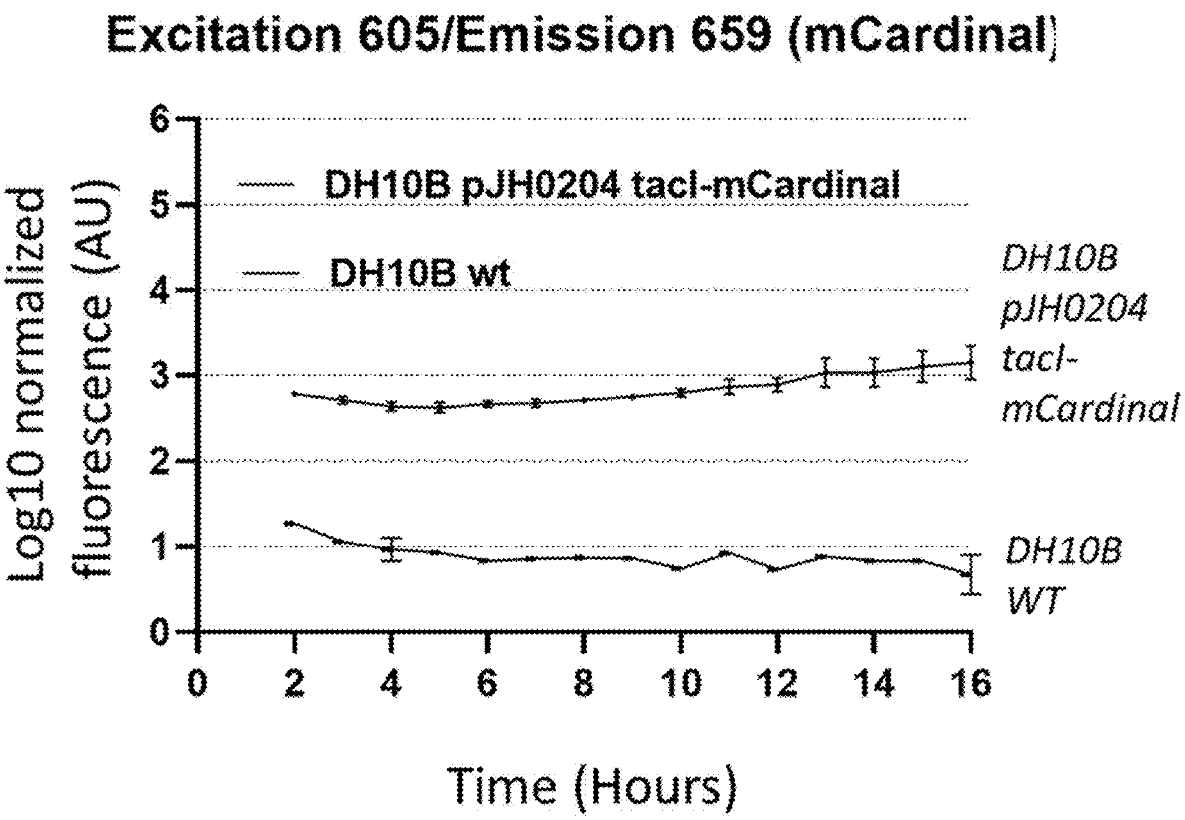
Figure 3C:
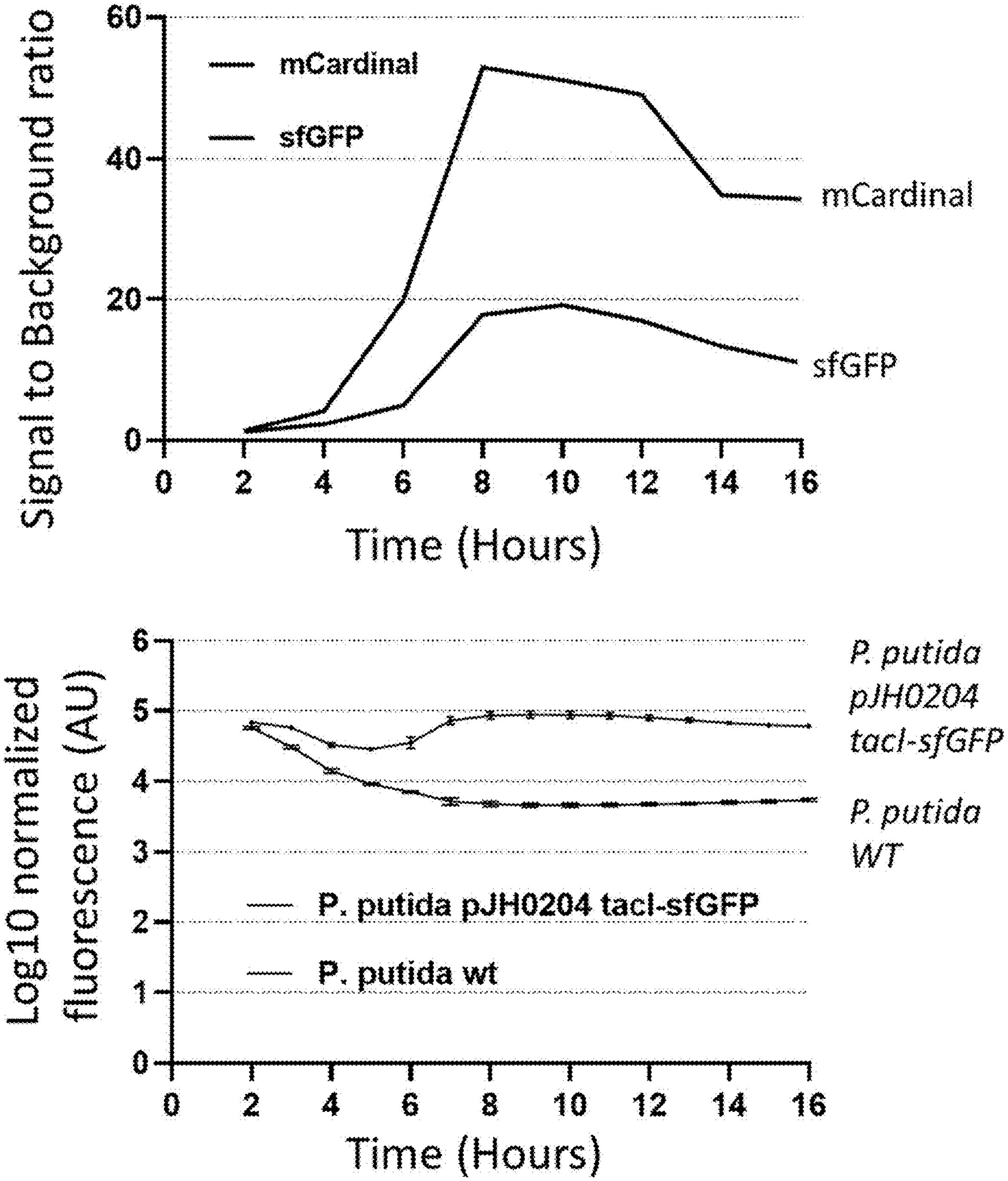
Figure 3C:
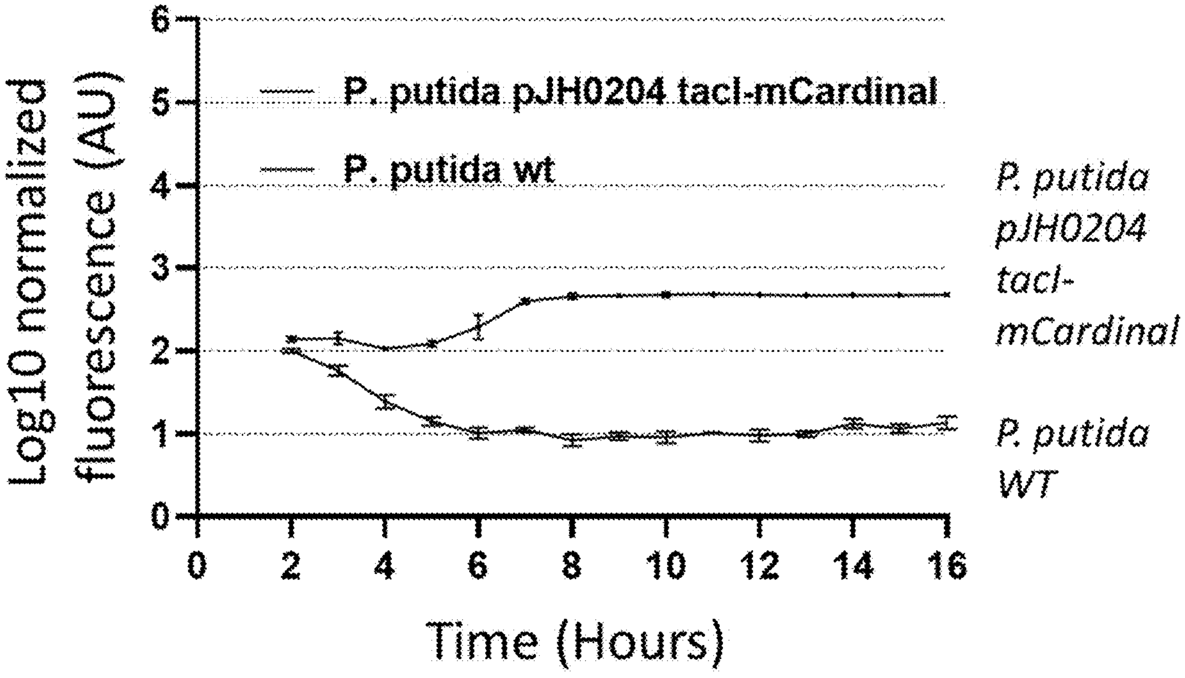
Figure 3D:
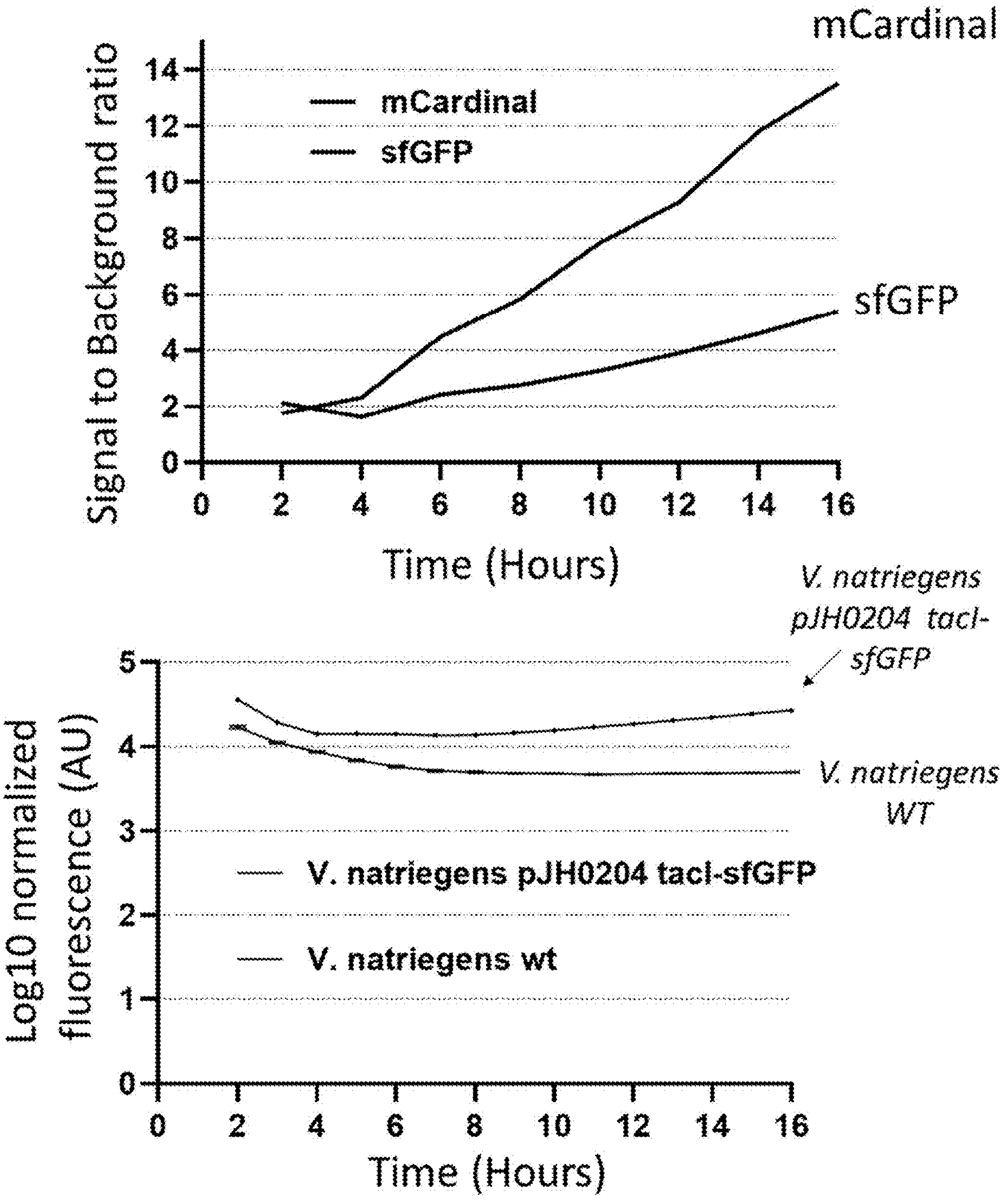
Figure 3D:
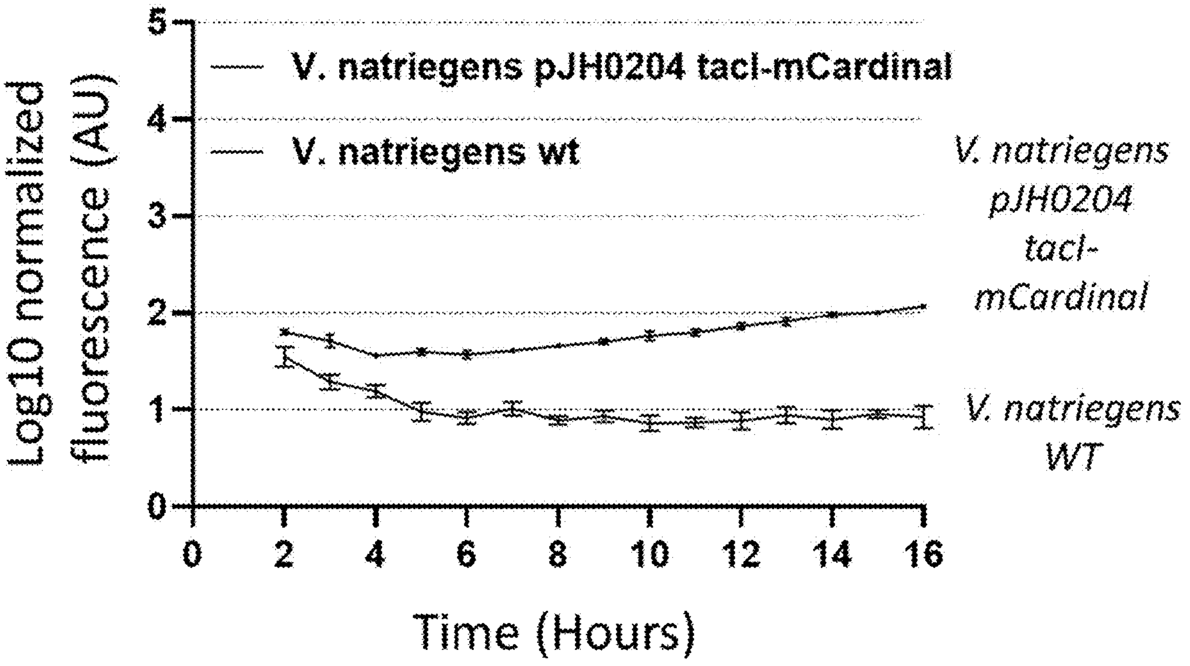

To further validate the benefit of using mCardinal instead of sfGFP, the inherent noise of each reporter system was quantified by measuring the fluorescence signal-to-background ratio of both reporter systems expressed under the control of the constitutive tacI promoter in the three species. After 16 hours of growth, the recombinant *E. coli, P. putida* and *V. natriegens* expressing sfGFP emitted 64, 11 and 5 times more green fluorescence than their respective wild type strains (not expressing a fluorescent protein). Meanwhile, mCardinal-expressing strains displayed 294, 34 and 13-fold higher red-light emission in *E. coli, P. putida* and *V. natriegens* compared to their wild type controls (FIGS. 3B-3D). Overall, the use of mCardinal rather than sfGFP significantly improves the dynamic range and facilitates measurement of promoter strength, as there is little endogenous autofluorescence in the far-red spectrum.

Example 5: Strength and Regulation of Synthetic lac Promoters in *Escherichia coli*

Figure 4A:
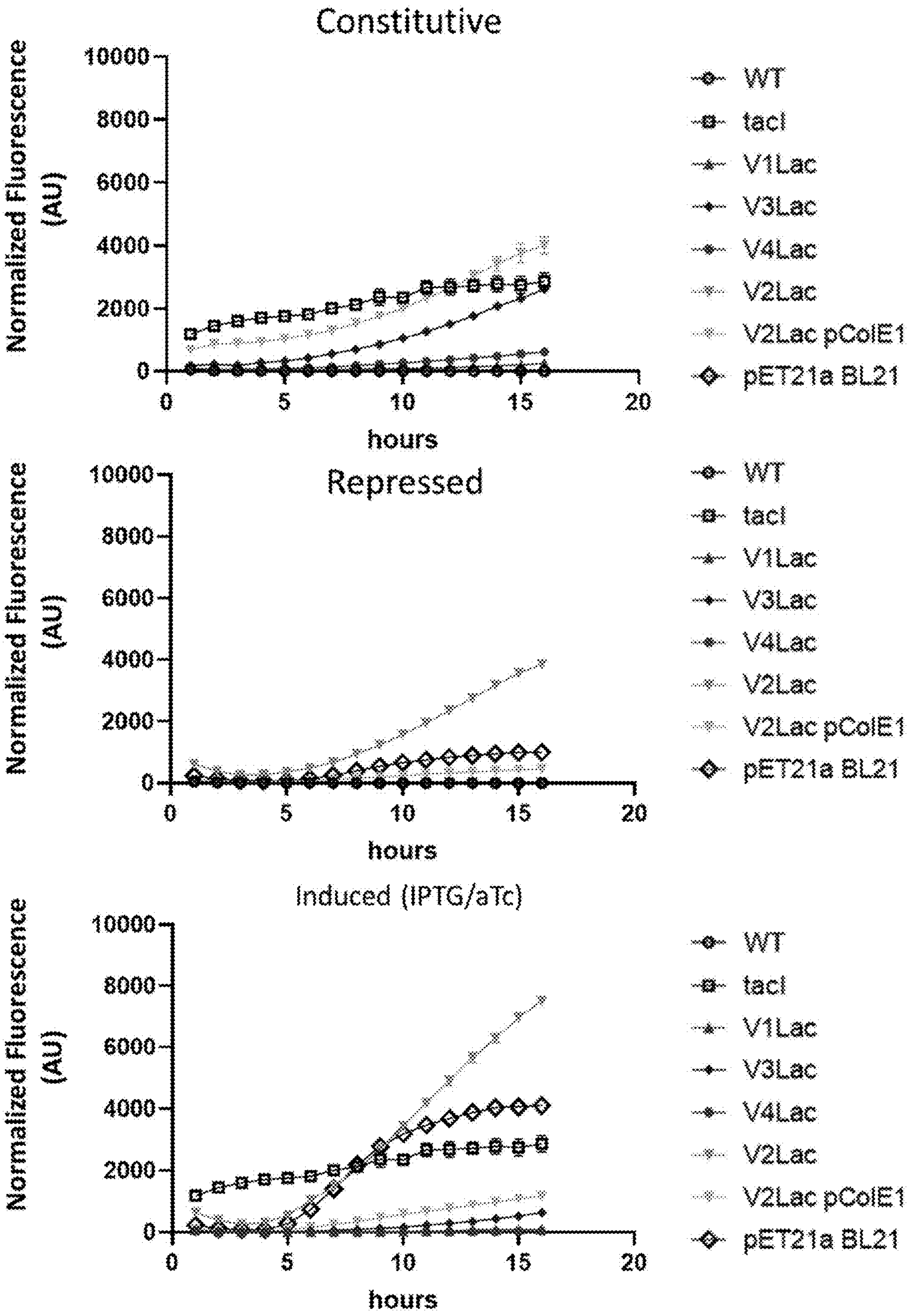

The lac promoter, and its derivates, are constitutively active in the absence of its transcriptional regulator lacI. The strength of the synthetic lac promoters were evaluated without lacI and compared these against the strong tacI promoter, which drives high levels of transcription and can result in recombinant protein production of up to 30% of total protein. The V1Lac promoter was 10-fold weaker than the tacI promoter (FIG. 4A), consistent with previous data observing an 11-fold difference between these two promoters. The V3lac promoter matched the tacI promoter strength, while the V4lac promoter showed 5 times less mCardinal than tacI (FIG. 4A). The V2lac promoter had to be tested in the low copy plasmid pCloDF13 because the medium copy pColE1 derived plasmid could not be maintained in *E. coli*. Even in the low copy configuration, the V2Lac promoter surpassed by ~1.4-fold the tacI promoter and was therefore the strongest constitutive promoter despite its expression in a low copy plasmid. The result suggests that maintenance of a promoter of this strength within in a medium copy plasmid exceeds the sustainable metabolic burden of *E. coli* (FIG. 4A). These results indicate that the incorporation of $\sigma^{70}$ consensus sequences at positions −35 and −10 efficiently increase the strength of the lac promoter.

Next, the transcriptional regulator lacI was incorporated into these circuits to quantify the efficiency of the OFF state. The V1Lac and V4lac constructs containing the lacI repressor produced a red fluorescence signal comparable to wild type *E. coli* (FIG. 4A), indicating tight transcriptional repression. The V3lac promoter could not be totally repressed by lacI, showing a slight tendency to leak, even with the presence of two lacO operators. The V2lac promoter with lacI was stably maintained by *E. coli* in both pColE1 and CloDF13-derived vectors. However, the repressed state of the V2lac promoter in the low and medium copy plasmids showed rather a constitutive behavior. LacI repressed ~9-fold the V2Lac promoter in the CloDF13 derived plasmid as compared to its constitutive construct (FIG. 4A), while the medium copy version of the V2lac-lacI system (which was not sustainable as a constitutive circuit) exhibited a strong constitutive expression ~1.3-fold higher than the tacI promoter, thus showing that one lacO operator region is not sufficient to block transcription of V2Lac containing both $\sigma^{70}$ consensus sequences by LacI, but incorporation of a second lacO reduces the leakage as observed in the V3Lac promoter (FIG. 4A).

To verify the inducibility of the synthetic lac promoters, *E. coli* was exposed to IPTG at the beginning of exponential phase. The V1lac and V4lac promoters showed minimal induction of mCardinal (FIG. 4A). The V3lac promoter, which mimics the V2lac promoter with an additional lacO operator, demonstrated a dynamic range of ~17-fold versus the uninduced state, but could only produce 24% of its full constitutive potential (FIG. 4A). The V2lac promoter in the low copy plasmid produced ~2-fold more mCardinal upon induction; similar behavior was observed in the medium copy version, where production of mCardinal reached the maximum values of all promoters tested at ~2.6-fold stronger than the tacI promoter (FIG. 4A). Overall, the results demonstrate that incorporation of $\sigma^{70}$ consensus sequences to the lac promoter improve its strength (V2Lac), producing more mCardinal than the strong tacI promoter in both, the constitutive LacI-less version in the low copy plasmid and the repressed and induced states in the medium copy plasmid. However, LacI could not repress the transcription of the synthetic V2Lac promoter. Thus, additional lacO operators are necessary to turn the lac promoter OFF containing the perfect $\sigma^{70}$ boxes, as observed in V3Lac, though full induction then becomes impossible in this architecture.

Example 6: Strength and Regulation of Synthetic tet Promoters in *Escherichia coli*

Figure 4B:
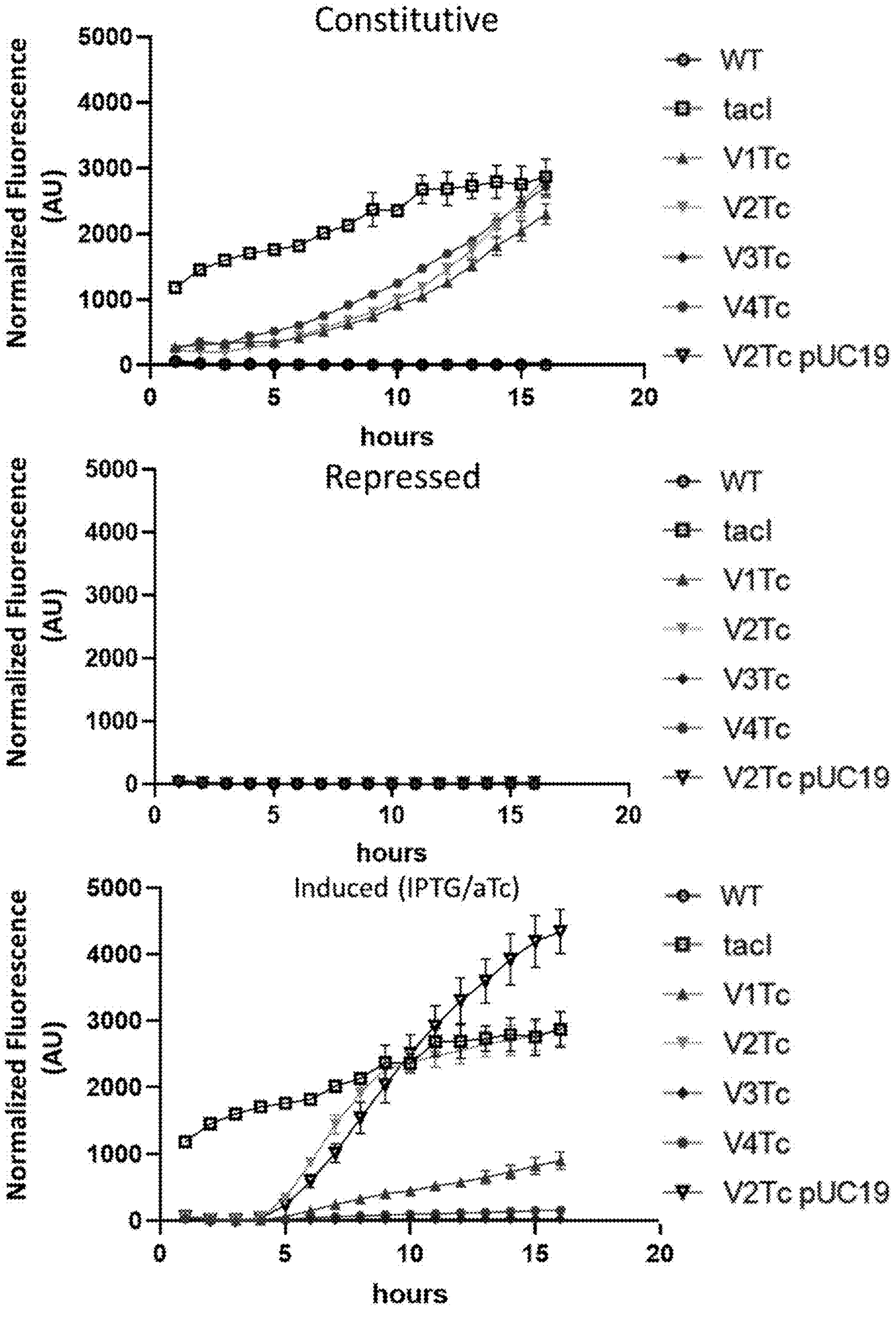

The tet promoter also drives transcription constitutively without TetR. The expression profile of the constitutive synthetic tet promoters were evaluated and compared against the tacI promoter. As observed for the lac promoter, replacement of the −10 and −35 sequences with the $\sigma^{70}$ consensus boxes in the tet promoter also increased the constitutive efficiency of the V2Tc promoter over the original V1Tc, in this case by 20%, and reached the yields obtained with tacI promoter (FIG. 4B). The V4Tc promoter showed similar results to the V2Tc, while the V3Tc lost any capability to initiate transcription (FIG. 4B). Further, incorporation of the tetR repressor to each of the four circuits under the control of the strong constitutive PJ23119 promoter completely silenced mCardinal production from all the synthetic tet promoters, even in the strong V2Tc promoter which harbors the optimal combination of consensus sequences recognized by the $\sigma^{70}$ (FIG. 4B).

To confirm the induction of each promoter and determine its functional dynamic range, each circuit was induced with anhydrotetracycline (aTc). The original tet promoter (V1Tc) only achieved ~37% of its full constitutive potential, reaching only 30% of mCardinal compared to tacI promoter confirming the middle level strength of the tet promoter (FIG. 4B). The V2Tc promoter achieved maximal induction reaching the full potential dynamic range and produced similar yields as the strong tacI promoter (FIG. 4B). Interestingly, the V4Tc promoter could not be de-repressed by aTc and showed a weak induction of only 5%, and as expected, the V3Tc promoter showed no activity (FIG. 4B). Together these results confirm that in *E. coli* the incorporation of the consensus boxes targeted by the $\sigma^{70}$ is key to boost the expression profile of promoters recognized by this transcription initiation factor and achieve the maximal transcriptional capacity of these promoters upon induction.

Example 7: Direct Comparison of Synthetic lac and tet Expression Systems to pET in *Escherichia coli*

In *E. coli*, the pET series of expression plasmids are the most popular systems for recombinant protein production. The efficiency of the synthetic lac and tet promoters were compared directly against pET21a. The pET expression system in the BL21 strain can produce more than 50% of the target gene as the total protein per cell, mCardinal production was measured in BL21. As expected, the pET system induced by IPTG produced ~1.5-fold more mCardinal than the strong constitutive tacI promoter, which is expected to accumulate up to 30% of total cell protein. Despite the massive production of mCardinal by the pET system, its OFF or uninduced state can be considered as a medium high constitutive expression system, yielding 30% of the constitutive tacI promoter as evidenced by mCardinal production (FIG. 4B, FIG. 4C). This transcriptional leakage in the pET system is well known in the scientific community.

Figure 8:
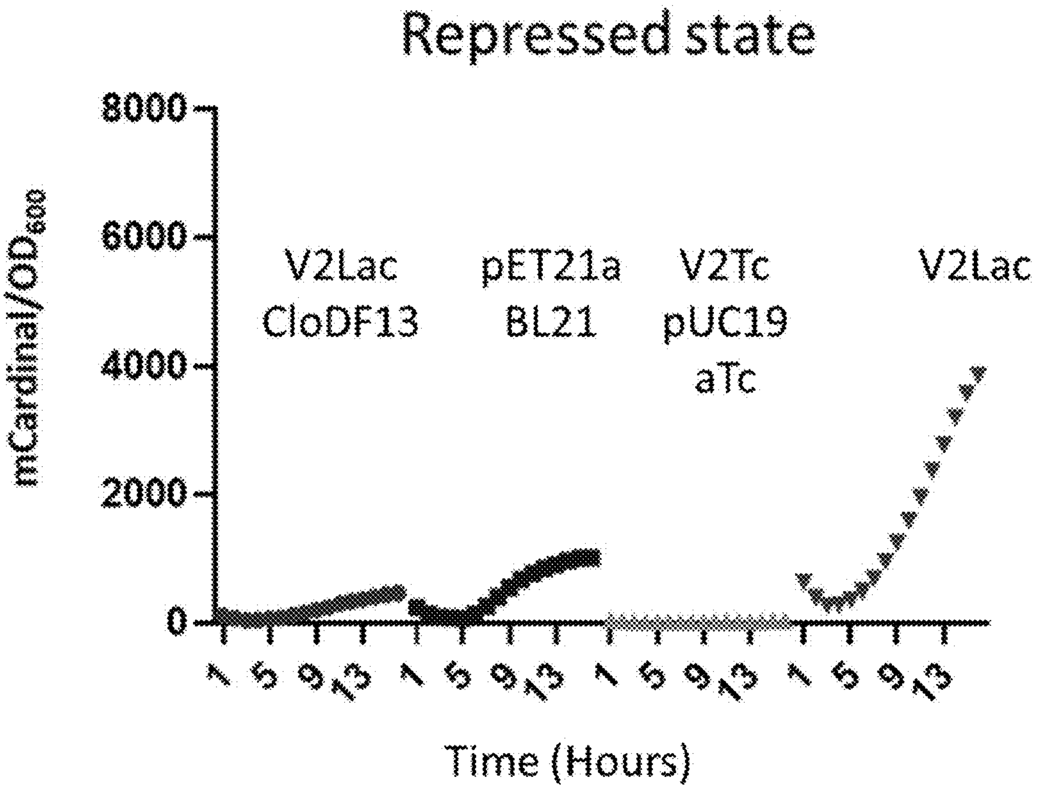
FIG. 8 shows a graphical comparison of the pET21a expression system in *E. coli* BL21 versus the synthetic V2Lac/lacI and V2Tc/tetR promoters in *E. coli* DH10B. Cultures were induced after 3 hours of cultivation and mCardinal mean was normalized by the cell density ($OD_{600}$). N=4. Error bars +/−SD.
Figure 8:
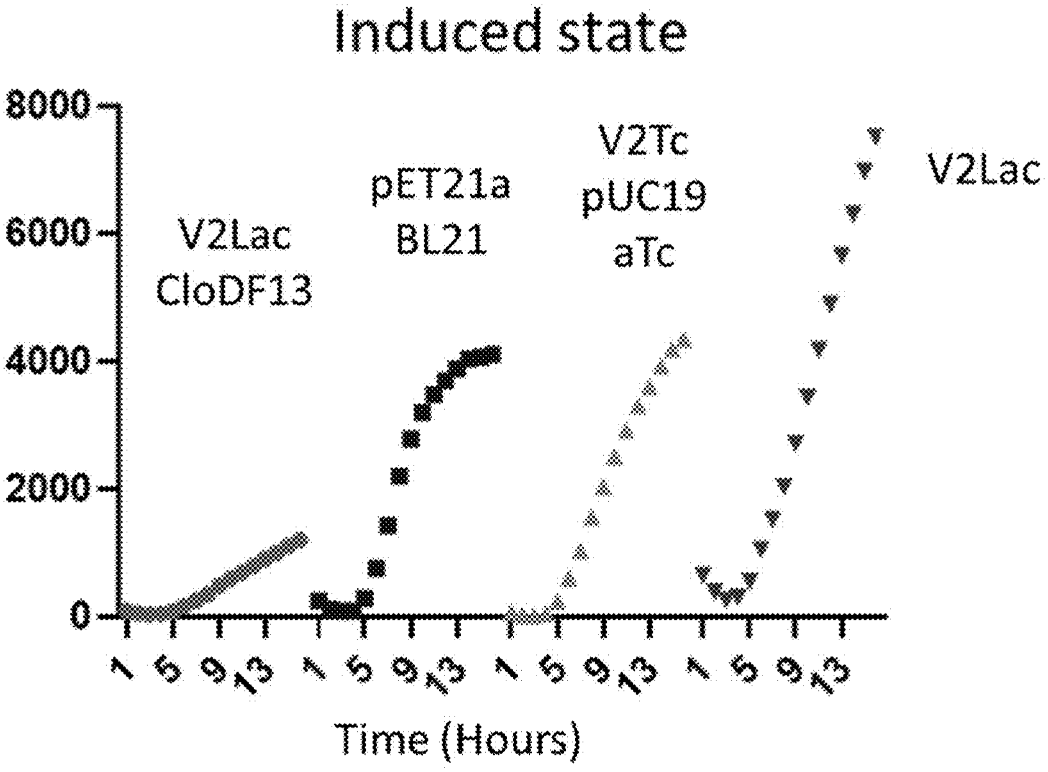

Among the synthetic lac and tet promoters, all tested in *E. coli* DH10B, only the V2Lac promoter surpassed the pET system in the medium copy plasmid pColE1. The IPTG induced V2Lac expression system produced ~1.8 times more recombinant protein than the pET system, however, the leakage of V2Lac promoter equals the induced state of the pET system (FIG. 4A and FIG. 8), therefore cancelling the advantages of an inducible expression system. The V3Lac expression system showed a tighter control of the OFF state, therefore, to increase its strength the V3Lac-lacI construct containing mCardinal was inserted into the pUC19 vector, thus increasing the copy number from 30 to 250 copies per cell. *E. coli* failed to maintain the V3lac-lacI construct in the pUC19 vector, likely due to the toxicity of LacI. The V2Tc-tetR expression system was evaluated in the pUC19 vector. *E. coli* stably maintained the V2Tc-tetR construct and no phenotypic or genotypic abnormalities were observed as in pUC19-V3Lac-lacI. mCardinal production by pUC19-V2Tc-tetR matched the pET21a expression system, with one exceptional difference, the pUC19-V2Tc-tetR maintained complete repression in the uninduced after 12 hours (FIG. 4B and FIG. 8). Thus, pUC19-V2Tc-tetR shows significant improvement in transcriptional control and dynamic range over pET21a (FIG. 4B, C). Further, equivalent protein production and tighter transcriptional control were achieved without the obligatory use of the BL21(DE3) strain, suggesting the system provided herein is readily portable to other strains and species.

Example 8: Expression of the Cocaine Esterase CocE and Production of Benzoic Acid To further validate the advantage of the expression system provided herein over the pET expression system, the production of a functional protein product, the cocaine esterase CocE, was assayed. This enzyme hydrolyses cocaine into benzoic acid and could expand the use of the narcotic compound as raw source in the production of the carboxylic acid widely used as precursor and preservative in the food and pharmaceutical industries. Expression of CocE has previously been shown to be a difficult and laborious task with the pET expression system, because CocE forms inclusion bodies; consequently, long incubation methods at low temperatures are required to isolate sufficient yields of functional CocE. *E. coli* could not support CocE expression in the repressor-less variants of the synthetic promoters, thus confirming this is a toxic protein for *E. coli*. Next, CocE in the V2Tc-tetR expression system was assessed in both the medium and high copy plasmid backbones, pJH0204 and pUC19 respectively (p$\sigma$70 V2TcR-cocE and p$\sigma$70 V2TcR-cocE, see Table 1), and compared against the pET expression system for the production of benzoic acid. Benzoic acid production is an indication that CocE was correctly folded and properly hydrolyzing cocaine.

Figure 5A:
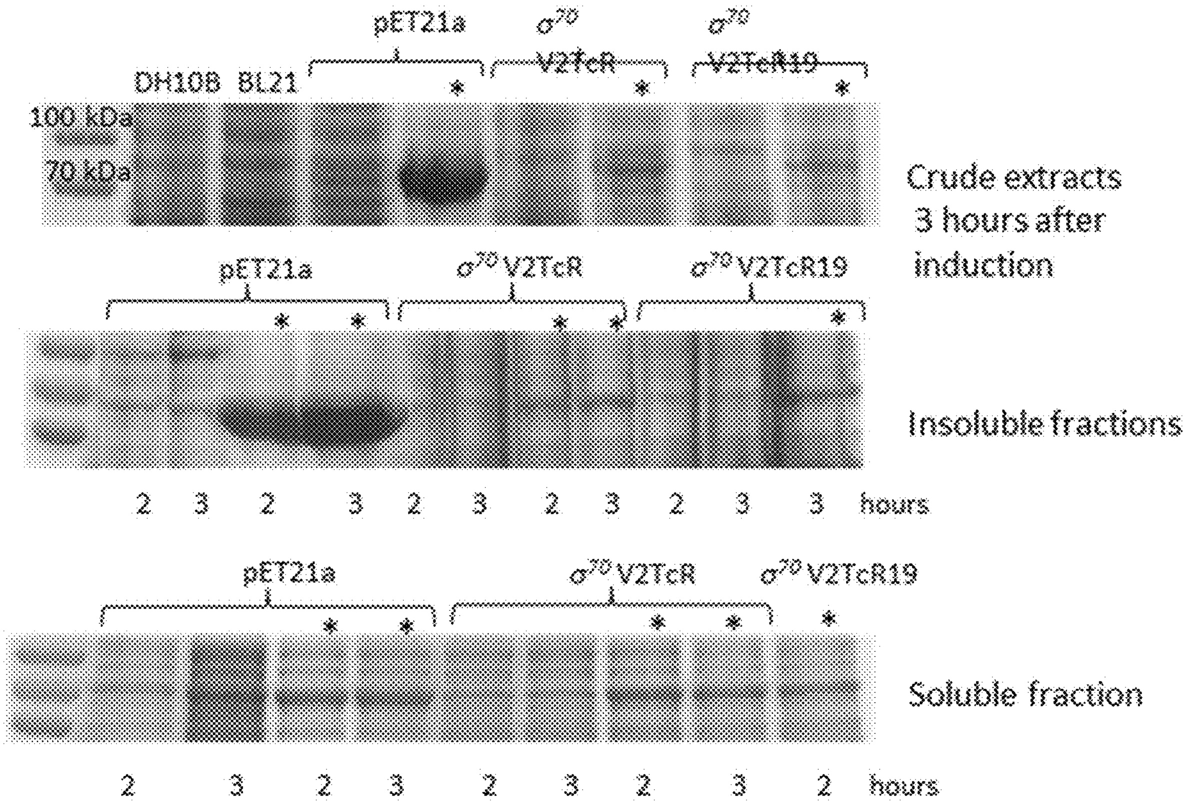
FIGS. 5A-5B show an SDS-Page gel and graph of the expression profile of CocE in *E. coli*.
Figure 5B:
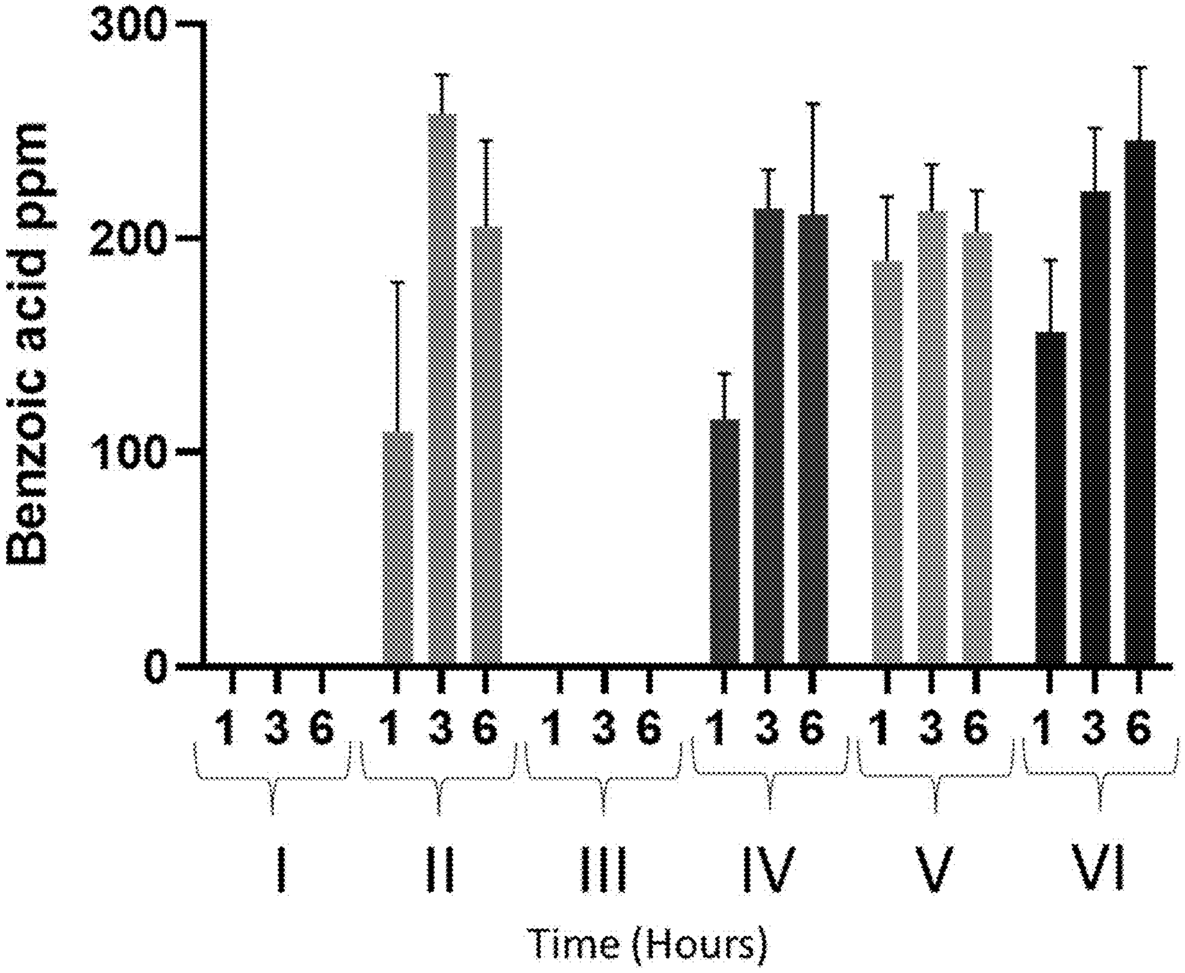

The soluble fraction recovered from the recombinant *E. coli* strain containing the pET21a-cocE expression system showed equivalent benzoic acid production in the presence of cocaine in both the uninduced and induced states (FIG. 5B), with a clear tendency to form inclusion bodies, as evidenced by the accumulation of protein in the insoluble fraction upon activation by IPTG (FIG. 5A). Thus, while induction of CocE by IPTG in the pET system does result in the additional production of protein, the additional protein made is insoluble and non-functional protein. Functionally speaking, the expression of CocE in pET21 a is not inducible, but instead behaves constitutively, as there is no difference in cocaine hydrolysis in the uninduced and induced states (FIG. 5B).

The soluble fractions from the recombinant *E. coli* V2Tc-tetR-cocE expression system, in both the pJH0204 and pUC19 plasmids, showed no benzoic acid production in the absence of the inducer. The addition of aTc triggered production of CocE with protein production and function roughly equivalent to the soluble pET21a-cocE plasmid (FIG. 5A, FIG. 5B). In both plasmids, benzoic acid production was observed after only one hour of aTc induction, and reached maximal production by 3 hours (FIG. 5B). These results confirmed the advantage of the incorporation of the $\sigma^{70}$ boxes to the tetracycline promoter, keeping the toxic enzyme CocE OFF in the uninduced state and producing sufficient amounts of mature CocE after 3 hours of induction. This is significantly shorter than induction of 16 hours previously recorded (data not shown). Further, the expression system provided herein produced soluble and functional protein without evidence of massive toxicity or inclusion body formation. This method facilitates the scalability of this bioprocess which has potential as an alternative, environmentally friendly method to obtain benzoic by replacing petroleum-based starting materials.

Example 9: Strength and Regulation of Synthetic lac and tet Promoters in *Pseudomonas putida*

Figure 6A:
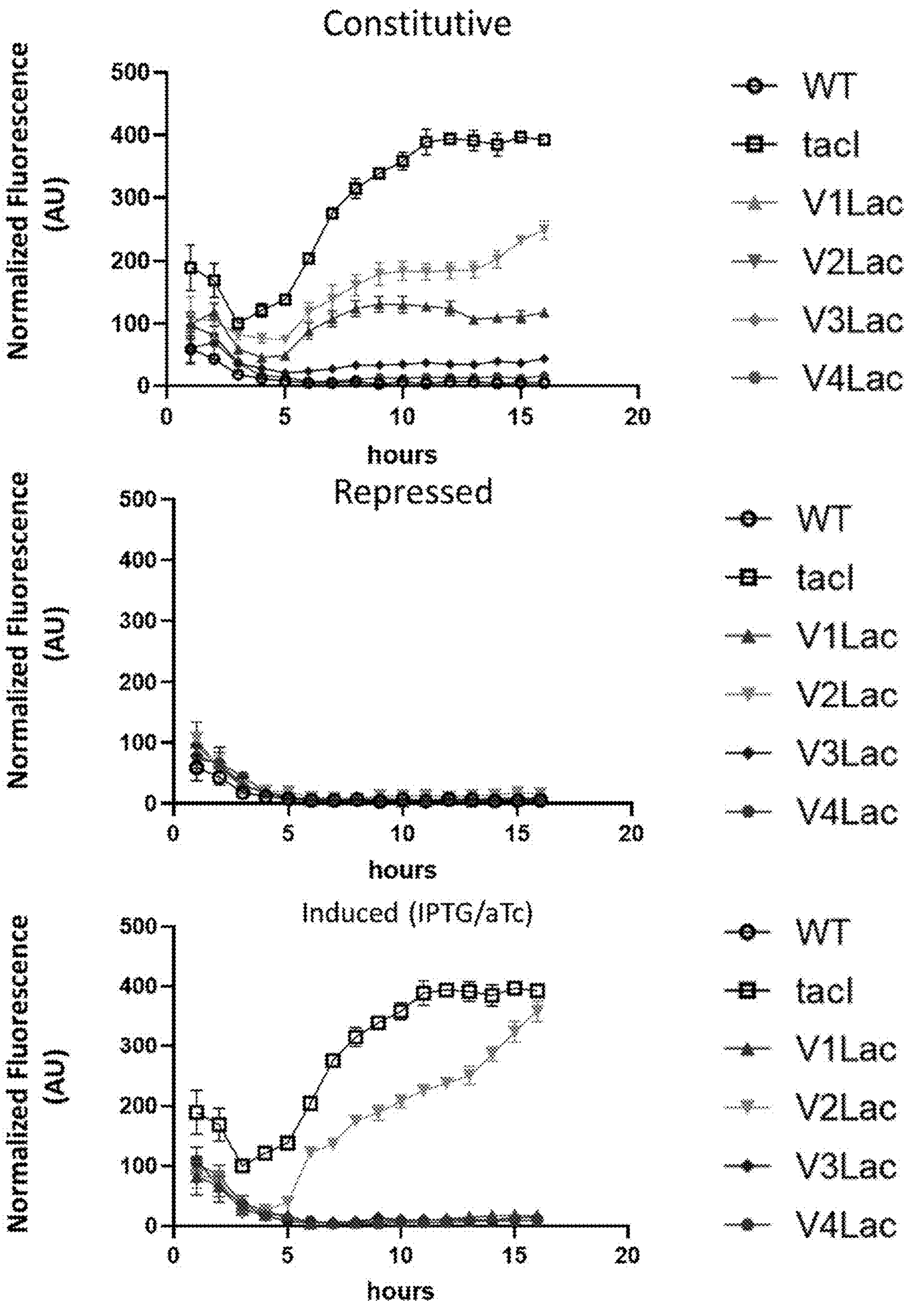

Genetic control in the soil-dwelling species *P. putida* is of great interest for biotechnological applications due to the ability of this microorganism to synthesize complex natural products and metabolize a variety of xenobiotic compounds. The constitutive strength, repression, and inducibility of synthetic promoters in *P. putida* were assayed. The lac-based promoter systems (which include the tacI promoter) are reported to have poor dynamic range and instability in high-copy plasmids when harbored in *P. putida* as replicative plasmids. To address this problem, the genetic circuits were integrated into the *P. putida* chromosome. The constitutive strength of V1lac, V2lac, V3lac and V4lac promoters were measured using mCardinal, and found out that tacI is stronger than all the synthetic lac variants by ~3, 1.5, 10 and 33-fold respectively (FIG. 6A, FIG. 6C). The incorporation of the transcriptional regulator lad efficiently repressed the V1lac, V3lac and V4lac promoters, but as seen in *E. coli*, the V2lac showed a tendency to leak, though not as egregiously as in *E. coli* (FIG. 6A, FIG. 6C). Induction by IPTG was barely detected in the V1lac, V3lac and V4Lac promoters, thus indicating the weakness of the original lac promoter in *P. putida* (FIG. 6A, FIG. 6C). Interestingly and analogously to *E. coli*, the V2lac promoter showed ~27-fold increase in mCardinal production against the uninduced state and surpassed its theoretical dynamic range as compared to the constitutive version, ultimately achieving similar yields as the strong tacI promoter (FIG. 6A, FIG. 6C). These results confirm that the incorporation of the $\sigma$70 consensus sequences to the lac promoter (V2Lac) significantly improve the strength of this promoter in the *P. putida* host.

Figure 6B:
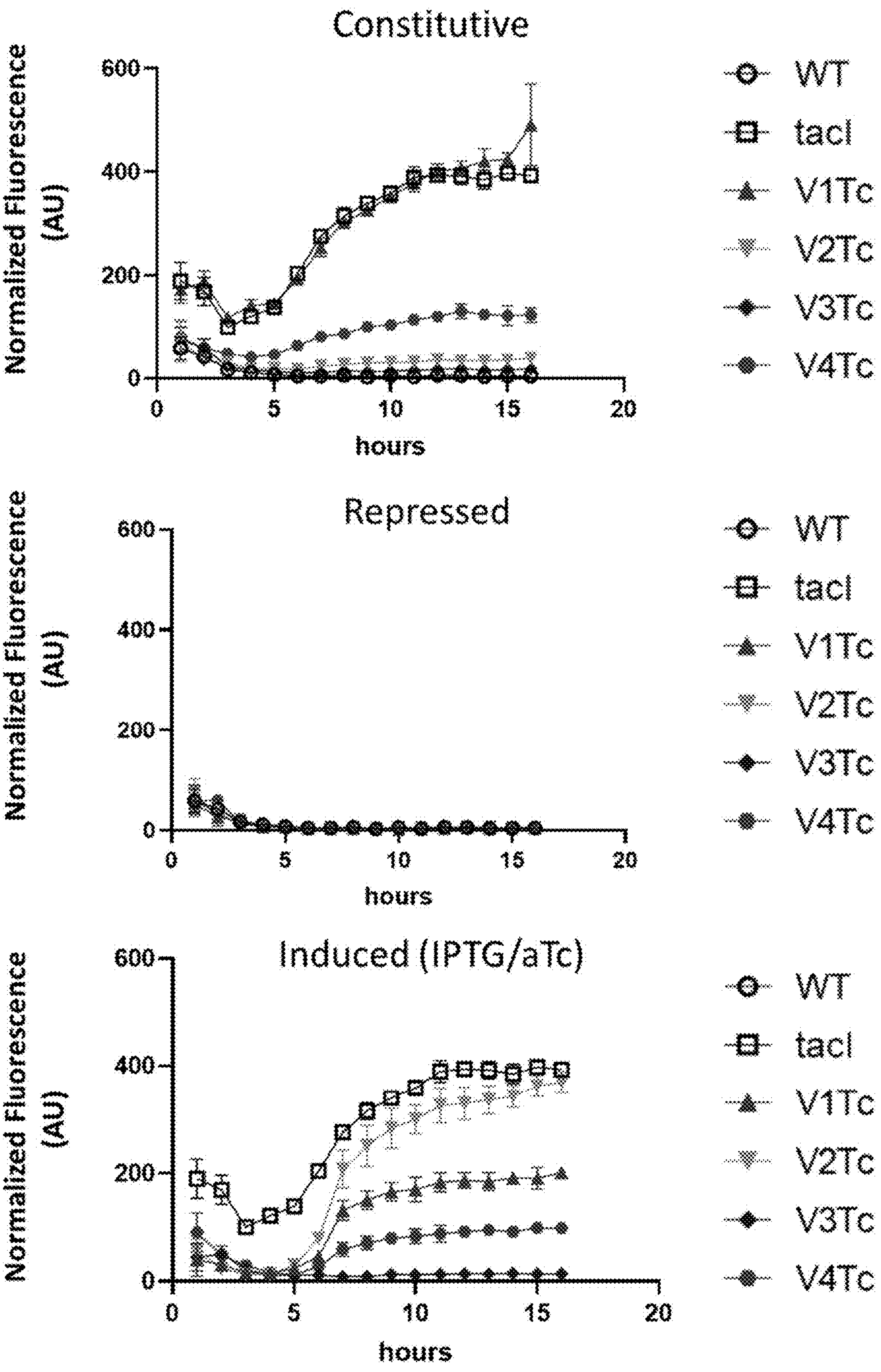

The tet promoters in *P. putida* were also evaluated. The original tet promoter with a strong RBS (V1Tc) was the strongest among all synthetic tet promoters in the absence of tetR, followed by V4Tc, V2Tc and V3Tc (FIG. 6B, FIG. 6C). Incorporation of the tetR repressor under the control of the PJ23119 promoter silenced all the synthetic tet promoters, as in *E. coli* (FIG. 6B, 6C). Addition of aTc activated the four tet promoters and remarkably, the induced V2Tc promoter showed the highest mCardinal induction exceeding its constitutive expression by ~10-fold and matching the tacI promoter. The V2Tc promoter was revealed to be ~2 and 3-fold more efficient than the V1Tc and V4Tc promoters after induction respectively, while the V3Tc proved to be inefficient in *P. putida* (FIG. 6B, FIG. 6C). These results highlight the importance of the consensus sequences targeted by $\sigma$70 to amplify the strength of inducible promoters also in *P. putida*.

Example 10: Strength and Regulation of Synthetic lac and tet Promoters in *Vibrio natriegens*

Figure 7A:
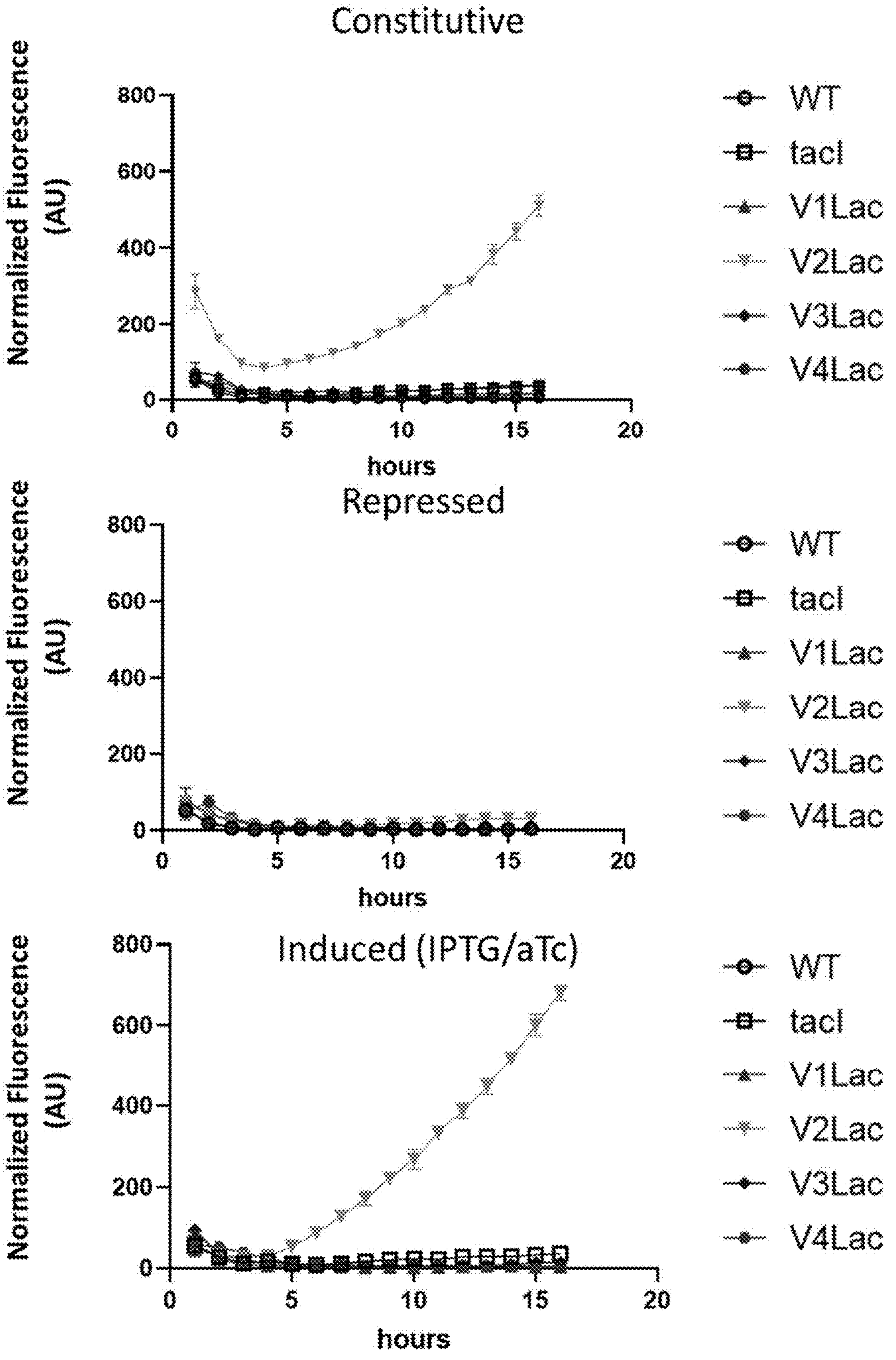
Figure 7B:
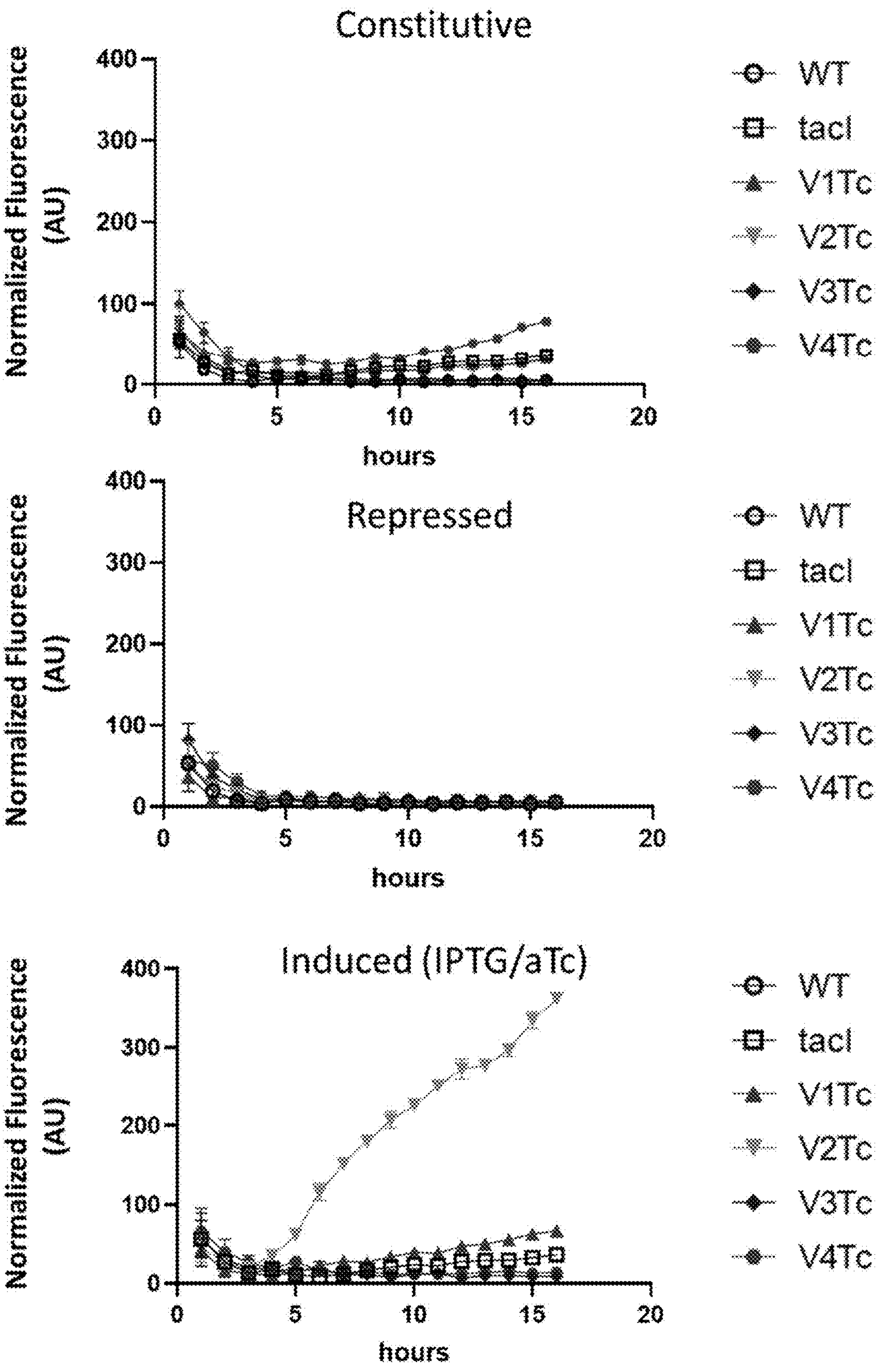

The circuits were next evaluated in the marine bacterium *V. natriegens* which has gained popularity for routine molecular biology applications due its ability to double in<10 min. In this host, previous studies indicated that the tacI promoter produced GFP upon activation with IPTG, while induction of the tet promoter resulted in low GFP yields. The constitutive and inducible versions of the synthetic lac and tet promoters were evaluated in the pColE1 derived plasmid with ~300 copies per cell, except for the constitutive V2Lac, which was evaluated in pCloDF13 derived vector with ~64 copies per cell in this strain. The constitutive V2Lac and V4Tc promoters outperformed tacI by ~16 and ~2-fold respectively, while V3Lac, V1Tc and V2Tc produced similar levels as tacI (FIGS. 7A-7C). V1Lac and V3Lac underperformed tacI by ~2.7-fold, and V3Tc showed no activity (FIGS. 7A-7C). Incorporation of the transcriptional regulators lacI and tetR turned OFF all the synthetic promoters except for V2Lac, which continued to show leakage, as in *E. coli* and *P. putida* (FIG. 7A). Induction of the synthetic lac promoters by IPTG revealed that only the V2Lac promoter was fully activated, surpassing its constitutive version by ~1.3-fold and showed a potential dynamic range of ~25-fold (FIG. 7A). The V3Lac reached 30% of its full potential, and the V1Lac and V4Lac showed no induction (FIG. 7A). While addition of aTc activated all four synthetic tet promoters, the V3Tc and V4Tc promoters rather showed weak mCardinal production, and V1Tc produced 2-fold more mCardinal than its constitutive variant (FIG. 7B). The V2Tc promoter, which harbors the 2 consensus $\sigma^{70}$ boxes, demonstrated strong inducibility producing 11-fold more mCardinal than the tacI promoter and displaying full potential of its dynamic range producing 100-fold more mCardinal than its OFF version (FIG. 7B, C). These results confirmed that the adaptation of the two consensus boxes recognized by the $\sigma^{70}$ in the V2lac and V2Tc promoters improved the performance of the inducible lac and tet promoters in *V. natriegens.*

Example 11: Additional Considerations for Inducible Promoter Design

Production of recombinant proteins is and will continue to be one of the main tools scientists use to understand biological processes and transfer academic results to industrial applications. The pET system is well known to induce the formation of inclusion bodies, a major drawback in the production of soluble proteins. pET requires specific strains that carry the T7 RNA polymerase, it lacks real tuneability, and fails to keep the target gene OFF. Leakiness in the OFF state negates the main advantage of an inducible system, which is intended to permit time- or context-specific control of gene expression.

In contrast to pET, the results provided in Examples 2-9 show that inclusion of the $\sigma^{70}$ consensus sequences into the lac and tet inducible promoters improve both repression and induction. The tight transcriptional control does not require any particular strain background, and permits rapid expression of soluble proteins, including toxic proteins such as CocE. The inducible promoters provided herein can be easily optimized to be used in a variety of Gram-negative hosts, including *P. putida* and *V. natriegens*, thus widening the applicability of these tools to a broad spectrum of bacteria. The inducible promoters provided herein offer a significant advance to the biotechnology industry in offering additional platforms for exogenous protein expression and purification.

The V2lac promoter expressed very highly across three Gram-negative species. Indeed, in *V. natriegens* the V2lac promoter is the strongest promoter yet described, as it surpasses the widely used tacI promoter by 16-20-fold (FIG. 7). Additional factors can affect promoter performance, for instance, the length and sequence of the spacer between the −10 and −35 elements can have dramatic effects on promoter strength.

The results in FIG. 5 suggest that complete OFF state control is key to avoiding common problems with protein expression of challenging proteins, such as the formation of inclusion bodies. Future promoter configurations could be aided by the combination of additional mechanisms to achieve complete OFF state control, such as the additional of small RNA transcriptional and translational regulators. These approaches have increased appeal over the pET system with pLysE, for example, as they permit facile portability among strains and species. OFF state control of the lac promoters was less of an issue in *P. putida* and *V. natriegens*, where better repression of the strong V2lac promoter was achieved (FIGS. 6A-7C). Without being bound by a particular theory, it is likely that species-specific differences in RNA polymerase binding and promoter clearance may affect the behavior of inducible promoters.

The challenges of leakiness were entirely eliminated by the use of tet-based promoters in the system provided herein. An often-cited drawback of tet promoters for protein expression was the limitation of protein production as compared to /ac-based systems. Incorporation of the $\sigma^{70}$ consensus sequence into the tet promoter (V2Tc) significantly increased expression above that of the original tet promoter (V1Tc) to the point where the promoter output equaled (and in the case of *V. natriegens*, exceeded) that of the tacI promoter. As a complementary approach to inducible promoter manufacturing and design, the sigma factor can be replaced with $\sigma^{70}$ sequences to assess promoter performance. Promoter performance was quantified herein by using far-red reporters, which significantly decreased background fluorescence and increased dynamic range in the bacterial species assayed.

Different yields of recombinant protein can be achieved based on promoter and host selection. Overall, the incorporation of the consensus −35 sequence and Pribnow (−10) box unlocks the strength of the lac and tet promoters in Gram-negative bacteria, facilitating the production of any given target gene in different host with the same set of plasmids.

The V2Tc promoter provided herein offers an improvement over the pET-based protein expression systems that remain very widely used. V2Tc is tightly regulated, robustly inducible, and drives protein production comparable to or better than the tacI promoter in all three species that were examined. No specific strain backgrounds were necessary, as it does not rely on the presence of the T7 polymerase.

Example 12: Development of the Dual Expression System V2TcR/V2(3)LacI

The $\sigma^{70}$ adapted expression systems V2TcR and V3LacI have tight regulation and strong induction in *E. coli* in the presence of anhydrotetracycline (aTc) and IPTG respectively, while in *P. putida* and *V. natriegens* the V2TcR and V2LacI showed the best performance as inducible promoters in these host bacteria. A dual expression system was developed using as backbone the pJH0204 vector containing the origin of replication pColE1 and the attB sites specific for bxb1 recombinase. Each transcriptional unit of the dual expression system was insolated by terminators and the transcriptional regulators tetR and lacI were located in-between and in opposite direction of the inducible promoters V2Tc and V2/3Lac to block undesired transcription of the open reading frames (ORF). Further, 2 different multicloning sites were located after the inducible promoters V2Tc and V2/3Lac to facilitate the incorporation of target genes (FIGS. 9A-9F, and FIG. 14).

Figure 9A:
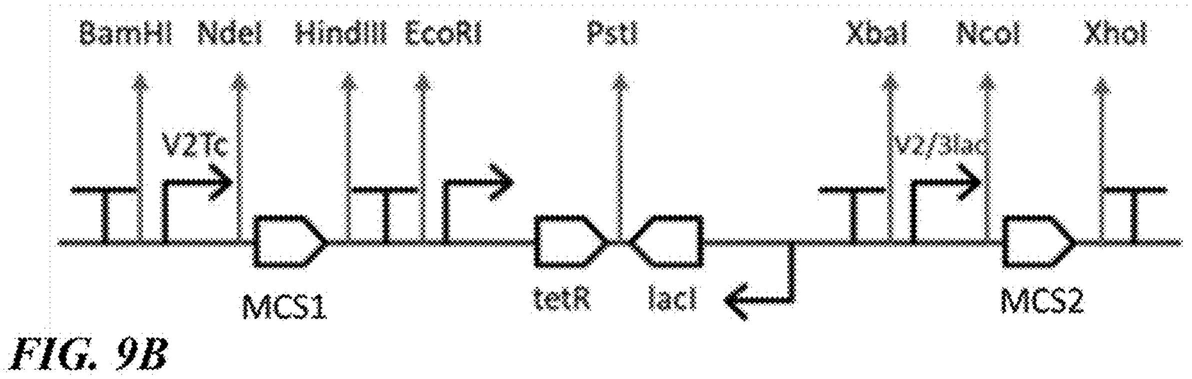
FIGS. 9A-9F shows a schematic representation of an exemplary dual expression system.
Figure 9B:
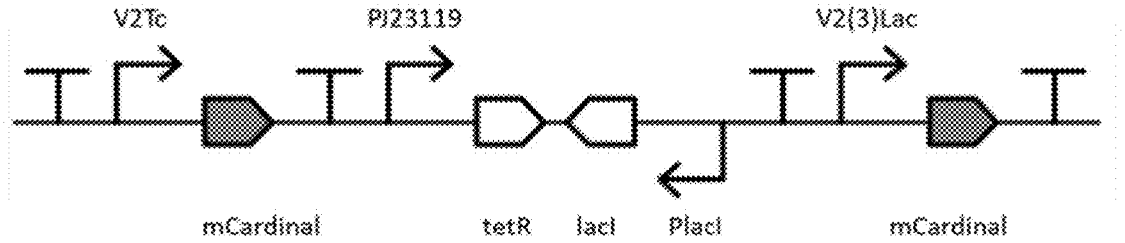
Figure 9C:
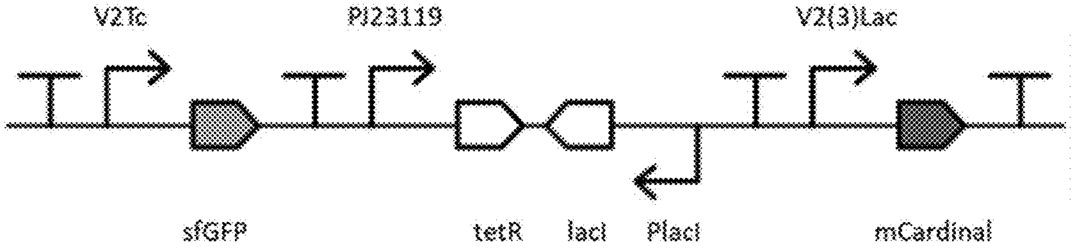
Figure 9D:
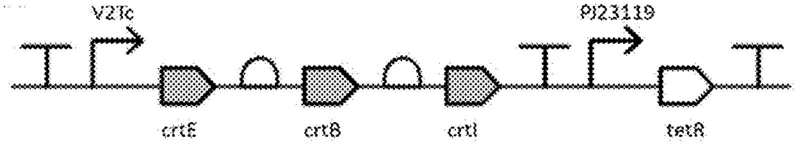
Figure 9E:
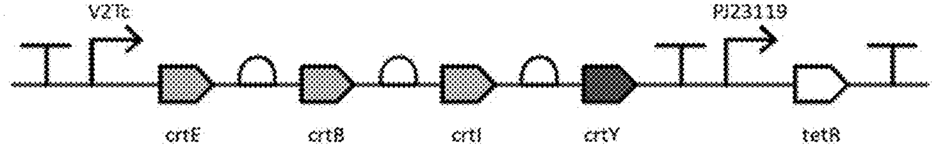
Figure 9F:
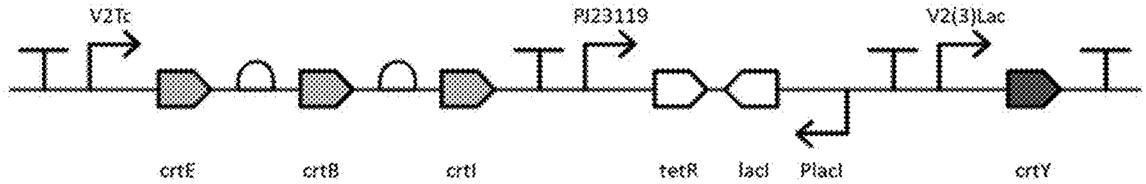

The dual expression systems were tested in *E. coli, P. putida* and *V. natriegens* to evaluate i) synergy ii) expression of different recombinant proteins and iii) production of the biosynthetic gene cluster (BGC) leading to the biosynthesis of lycopene and B-carotene. Synergy was evaluated with the reporter system mCardinal which was accommodated in both inducible promoters of the dual expression system (FIG. 9B). Expression of different recombinant proteins was performed by adapting the sfGFP under the control of V2TcR and mCardinal controlled by V2/3LacI (FIG. 9C). Finally, production of the terpenoids lycopene and B-carotene by the dual expression system was achieved by the assembly of the crtEBIY genes from *Pantoea ananatis*. The crtEBIY genes were synthesized with the codon usage for *E. coli*. The crtEBI operon was assembled in the pUC19 vector via Gibson adapting the ribosome binding site (RBS) of J23119 9 to crtB and the RBS pJL1 to crtI, further the synthetic construct was transferred to the V2TcR expression system to evaluate lycopene production (FIG. 9D). B-carotene production was evaluated with the incorporation of the crtY gene with the J23119 RBS to V2TcR-crtEBI yielding V2TcR-crtEBIY (FIG. 9E). The dual control of the crtEBI operon together with the crtY gene to produce B-carotene was achieved by adapting the crtEBI to the V2TcR expression system and the crtY gene to V2(3)LacI expression system present in the dual vector (FIG. 9F). All measurements were performed using LB as growth medium as the scope of this work is not to optimize the production of terpenoids. After transforming the plasmids listed in Table 3 in the three bacterial species no difference in the wild type strains was observed, thereby confirming the stability of the dual expression systems.

TABLE 3

List of Plasmids.

| Name | Expression system 1 | ORF1 | Expression system 2 | ORF2 |
|---|---|---|---|---|
| p$\sigma^{70}$ V2TcR-mCardinal | V2TcR | mCardinal | | |
| p$\sigma^{70}$ V2lacI-mCardinal | V2lacI | mCardinal | | |
| p$\sigma^{70}$ V3LacI-mCardinal | V3LacI | mCardinal | | |
| p$\sigma^{70}$ V2TcR-sfGFP | V2TcR | sfGFP | | |
| p$\sigma^{70}$ V2lacI-sfGFP | V2LacI | sfGFP | | |
| p$\sigma^{70}$ V3LacI-sfGFP | V3LacI | sfGFP | | |
| pJH0204F | | | | |
| p$\sigma^{70}$ V2TcR-mCardinal/ V2LacI-mCardinal | V2TcR | mCardinal | V2LacI | mCardinal |
| p$\sigma^{70}$ V2TcR-mCardinal/ V3LacI-mCardinal | V2TcR | mCardinal | V3LacI | mCardinal |
| p$\sigma^{70}$ V2TcR-sfGFP/ V2LacI-mCardinal | V2TcR | mCardinal | V2LacI | sfGFP |
| p$\sigma^{70}$ V2TcR- sfGFP/ V3LacI- mCardinal | V2TcR | mCardinal | V3LacI | sfGFP |
| pUC19-crtEBI | — | crtEBI | | |
| p$\sigma^{70}$ V2TcR-crtEBI | V2TcR | crtEBI | | |
| p$\sigma^{70}$ V2TcR-crtEBIY | V2TcR | crtEBIY | | |
| p$\sigma^{70}$ V2TcR-crtEBI/ V2LacI-crtY | V2TcR | crtEBI | V2LacI | crtY |
| p$\sigma^{70}$ V2TcR-crtEBI/ V3LacI-crtY | V2TcR | crtEBI | V3LacI | crtY |

Note:
SEQ ID NOS: are listed in the SEQUENCES section of this paper.

Example 13: Synergy of the Dual Expression System V2TcR/V2(3)LacI

Figure 10A:
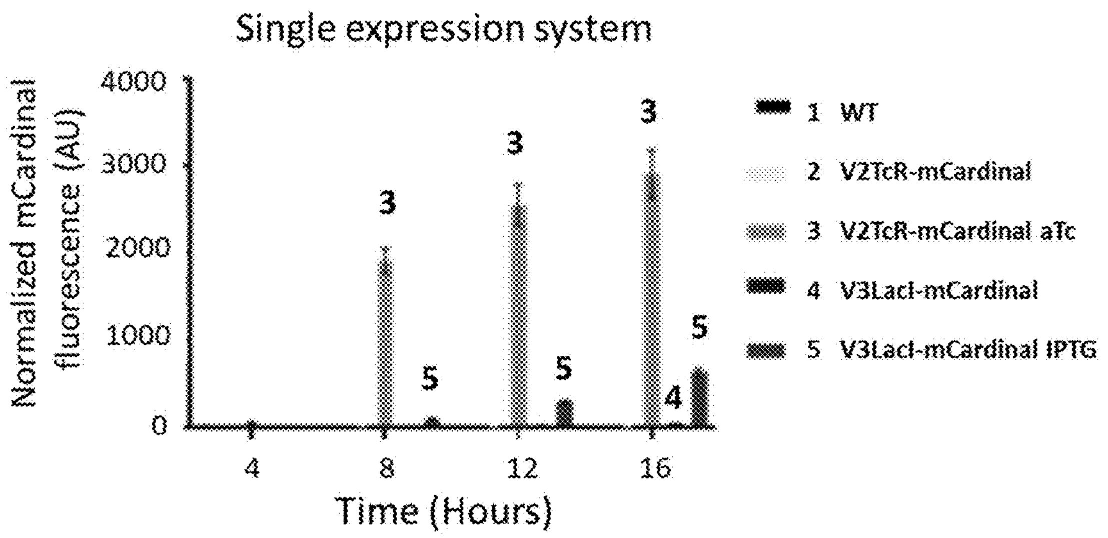
FIGS. 10A-10C show graphs of the time course of mCardinal production in *E. coli* (FIG. 10A), *P. putida* (FIG. 10B) & *V. natriegens* (FIG. 10C). Left graphs show the recombinant strains containing the V2TcR-mCardinal (SEQ ID NO: 56) and V2(3)LacI-mCardinal expression systems and the right graphs show the recombinant strains containing the dual V2TcR-mCardinal/V2(3)LacI-mCardinal expression system. For all samples, the fluorescence mean of mCardinal signal (excitation 605, emission 659) was normalized by the cell density (OD600). N=3. Error bars +/−SD.
Figure 10A:
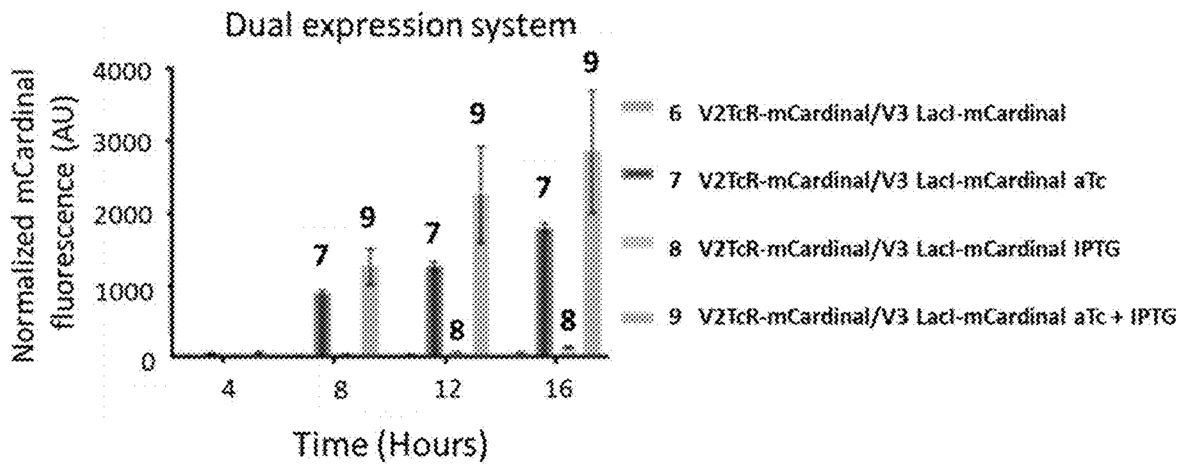

Increasing the copy number in *E. coli* efficiently boosted production of mCardinal by the p$\sigma$70V2TcR expression system but had a negative impact in the p$\sigma$70 V3LacI expression system due the toxicity of the transcriptional regulator LacI. Therefore, the synergistic effect of the duet expression system p$\sigma$70V2TcR/V3LacI both controlling mCardinal as different studies demonstrated that combined promoters enhance production of the target protein. The *E. coli* strain containing the duet expression system V2TcR/V3LacI produced 2-fold and 4-fold less red fluorescence than the strains containing the V2TcR and V3LacI when induced with aTc and IPGT respectively (FIG. 10A). Synergy was observed by the addition of IPTG and aTc to the V2TcR/V3LacI strain improving mCardinal production by 1.5-fold against the induction obtained with aTc alone (FIG. 10A). However, the synergy in mCardinal production in the duet system reached equal amounts of mCardinal as the V2TcR expression system (FIG. 10A). These results indicate that the tandem version of the synthetic promoters V2TcR/V3LacI offer an alternative to co-express different genes at high levels using different inducers.

Figure 10B:
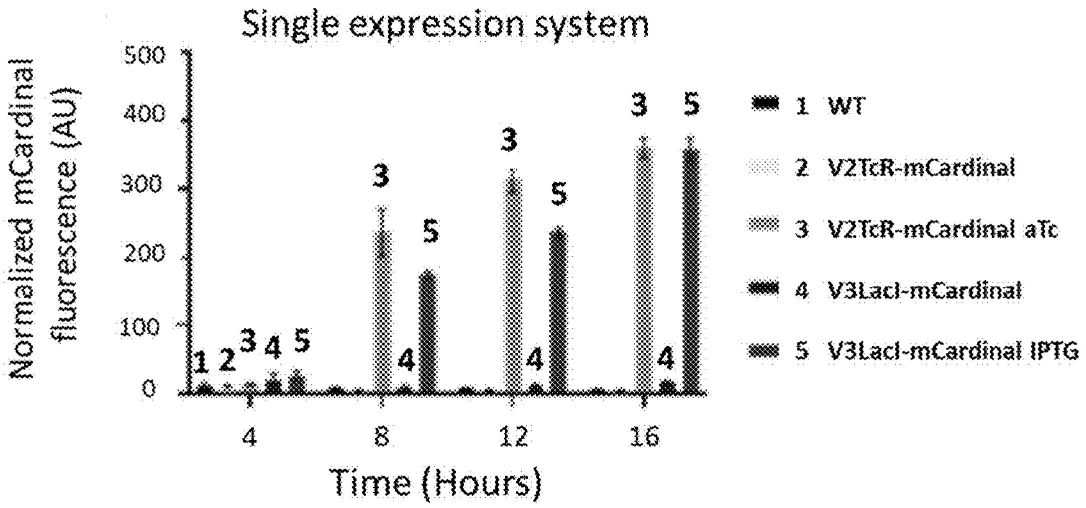
Figure 10B:
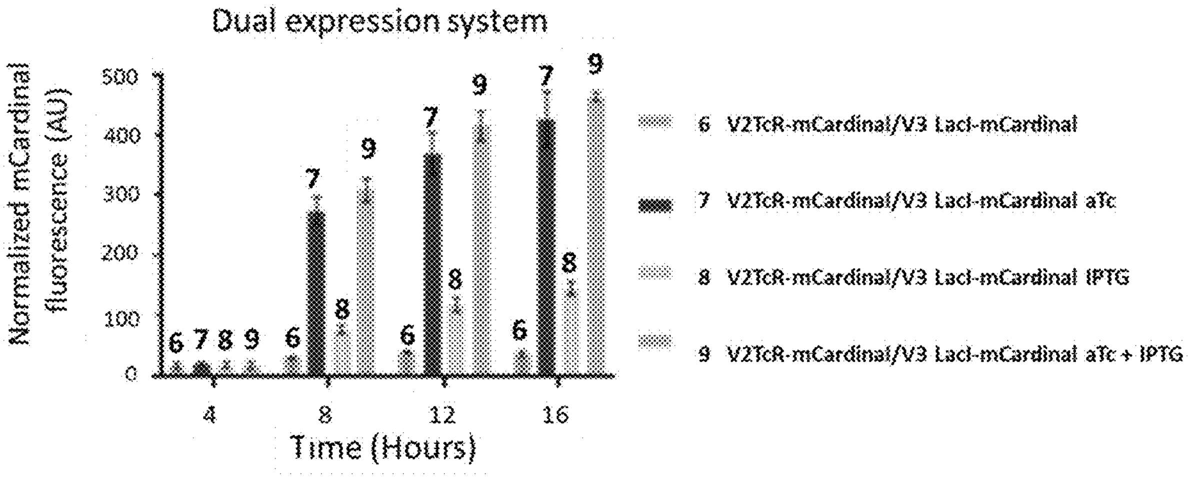

In *P. putida* the V2TcR and V2lacI expression systems showed the best performance activating transcription of heterologous proteins. Consequently, we integrated both promoters controlling expression of mCardinal into the chromosome of this host. Single induction of the dual system by aTc resulted in induction of mCardinal equivalent to V2TcR system; single induction of the dual system with IPTG resulted in a 3-fold decrease relative to V2lacI alone (FIG. 10B). However, the addition of both inducers (aTc+IPTG) increased mCardinal by 1.1-fold over the V2TcR and V2lacI expression system, thus showing a minimal synergistic effect of the dual promoters in *P. putida* (FIG. 10B).

Figure 10C:
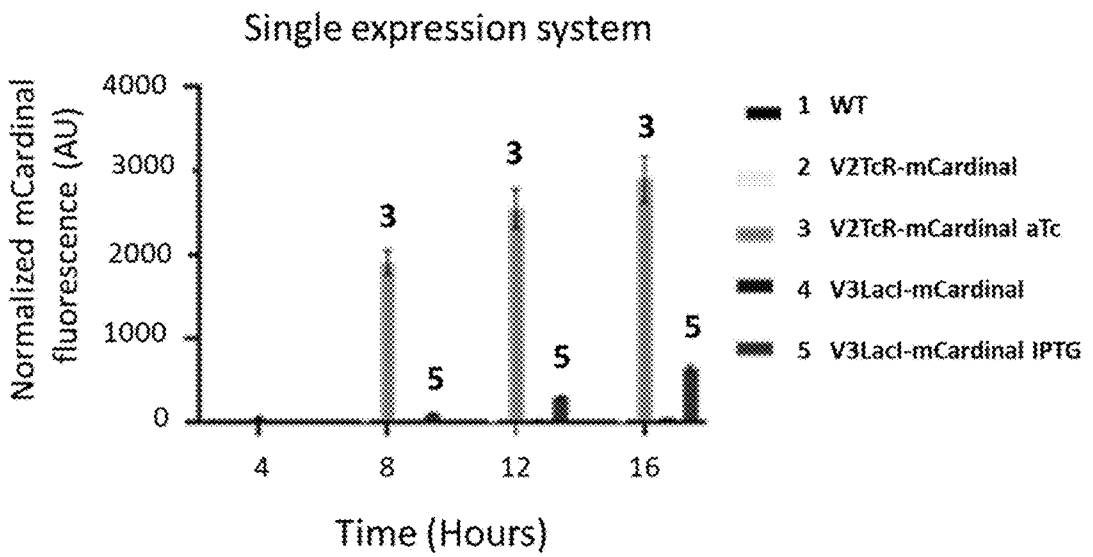
Figure 10C:
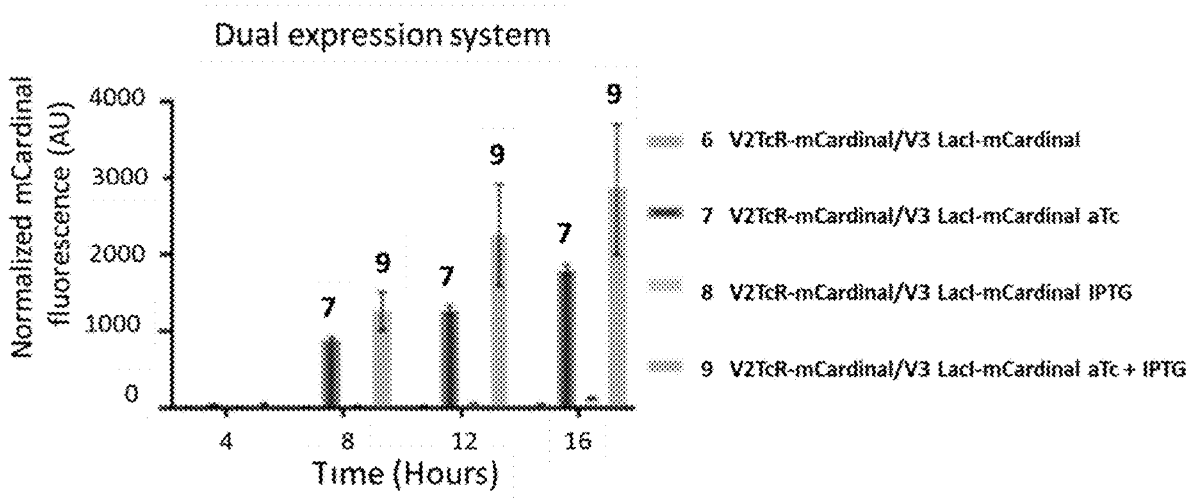

The duet expression system V2TcR/V2LacI decreased substantially the efficiency of the synthetic promoters in *V. natriegens* compared to the single expression system counterparts by 12 and 2-fold for V2LacI and V2TcR after induction with IPTG and aTc, respectively (FIG. 10C). Co-induction with IPTG+aTc did not have a synergistic effect in mCardinal production, but reached similar yields as obtained by induction with aTc alone (FIG. 10C). Together, this information demonstrates that synergy cannot be achieved with the dual expression system V2TcR/V2(3)LacI in medium copy plasmids as is the case for *E. coli* and *V. natriegens*. On the contrary, the duet expression system diminishes the activity of each promoter probably due the constitutive expression of the transcriptional regulators TetR and LacI, and competition of the $\sigma^{70}$ for both promoters. In *P. putida* the duet expression system was directly integrated into the chromosome and reduced the quantities of the transcriptional regulators TetR and LacI. Surprisingly, in this host the V2TcR expression system gained strength in the dual version, the V2lacI expression system lost efficiency, and synergy was observed, thus indicating that duet expression system gain performance as single copies in the chromosome of the host bacterium.

Example 14: Expression of Different Recombinant Proteins with the Dual Expression System V2TcR/V2(3)LacI Prior to the expression systems provided herein there was not a universal dual expression system that allows differential expression of distinct set of genes via two independent inducible promoters that is portable among different Gram-negative species. The V2TcR/V2(3)LacI dual expression system demonstrated that it can control the co-expression of mCardinal, although synergy was only observed in *P. putida*. Two different reporter proteins were expressed to evaluate their production in *E. coli, P. putida* and *V. natriegens* using the V2TcR/V2(3)LacI expression system. The transcriptional unit V2TcR controlling the expression of sfGFP while the V2(3)LacI unit controlling mCardinal production.

Figure 11A:
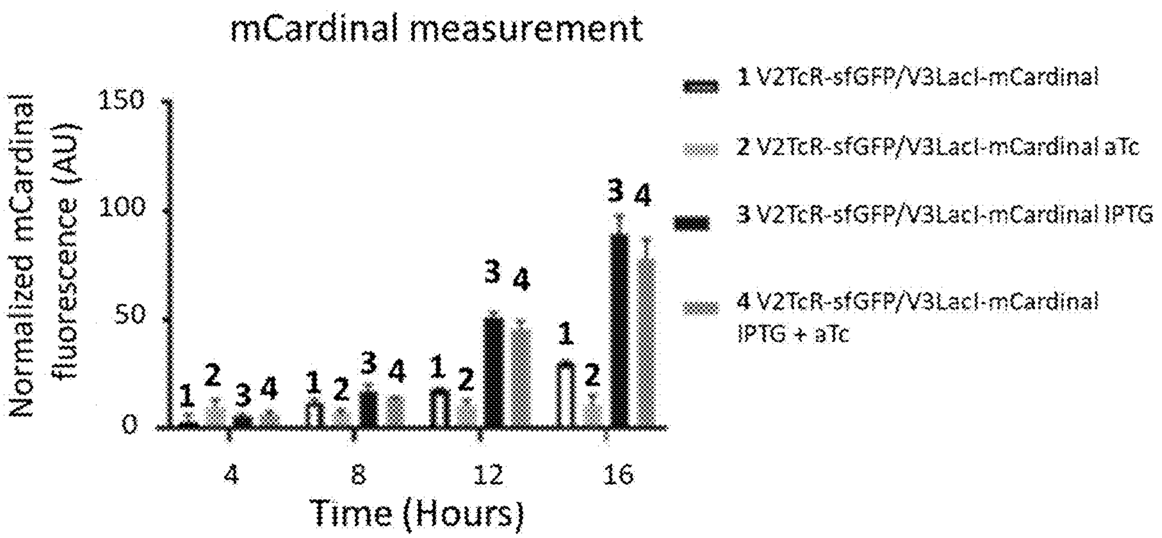
FIGS. 11A-11C shows graphs of the time course of the reporter systems mCardinal and sfGFP in *E. coli* (FIG. 11A), *P. putida* (FIG. 11B), and *V. natriegens* (FIG. 11C) containing the dual expression system V2TcR-sfGFP/V2(3)LacI-mCardinal. Left graphs measure mCardinal production and right graphs measure sfGFP. For all samples, the fluorescence mean of mCardinal signal (excitation 605, emission 659) and sfGFP signal (excitation 485, emission 510) was normalized by the cell density (OD600). N=3. Error bars +/−SD.
Figure 11A:
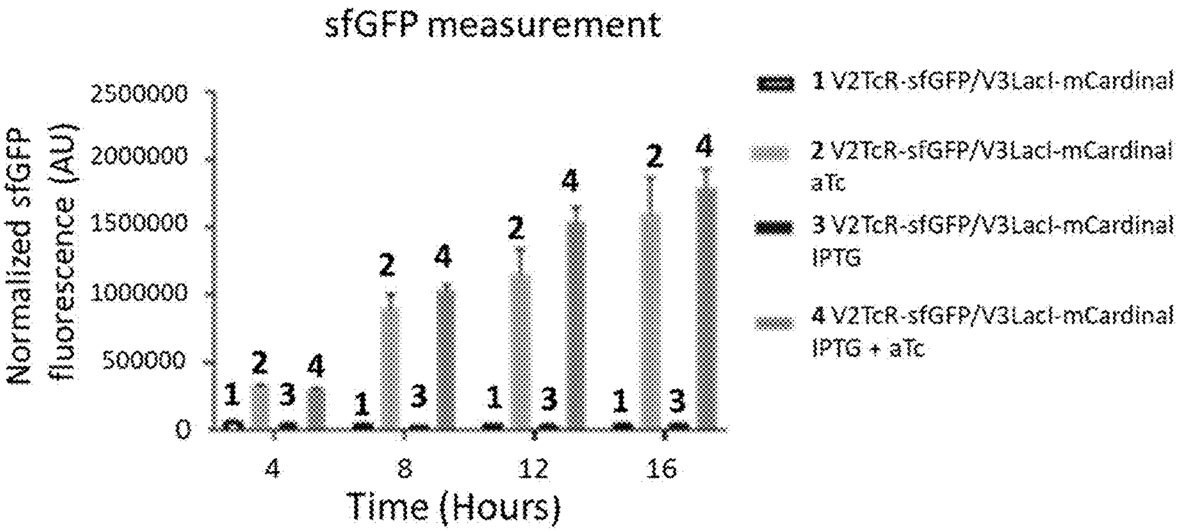
Figure 11B:
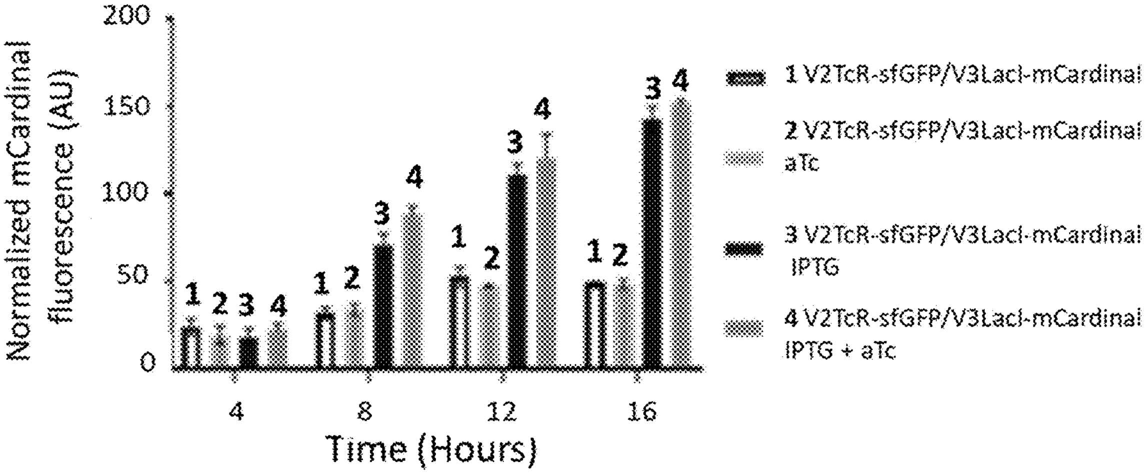
Figure 11B:
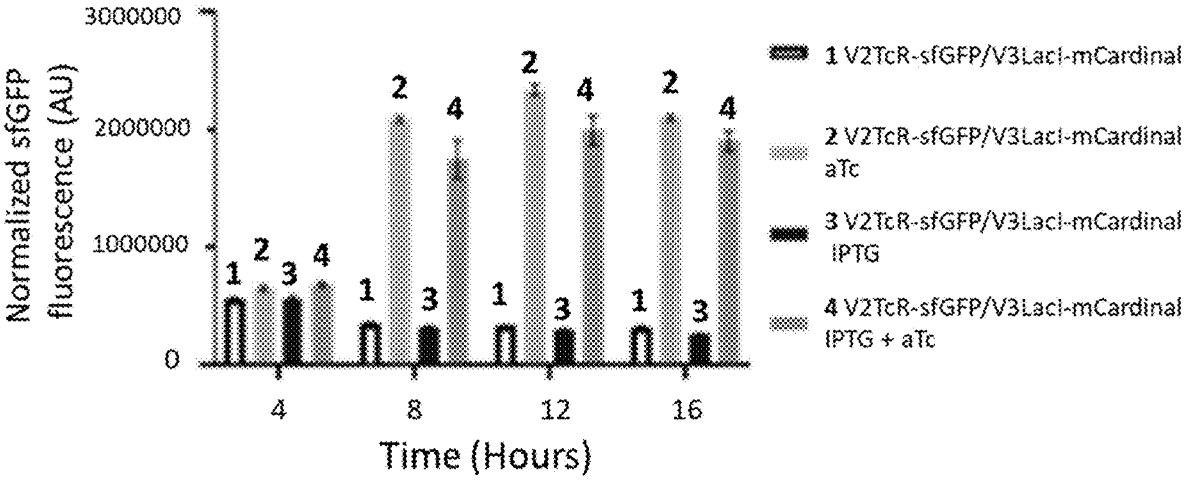
Figure 11C:
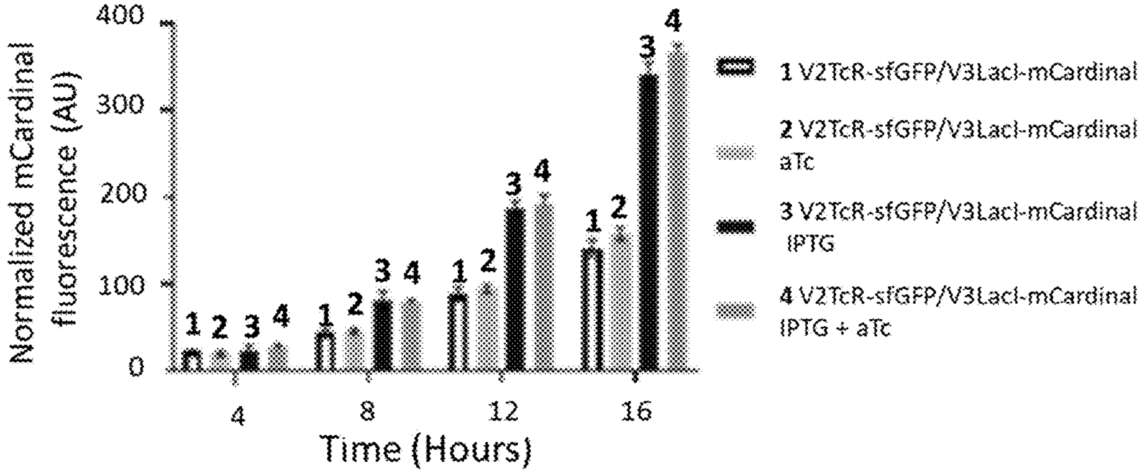
Figure 11C:
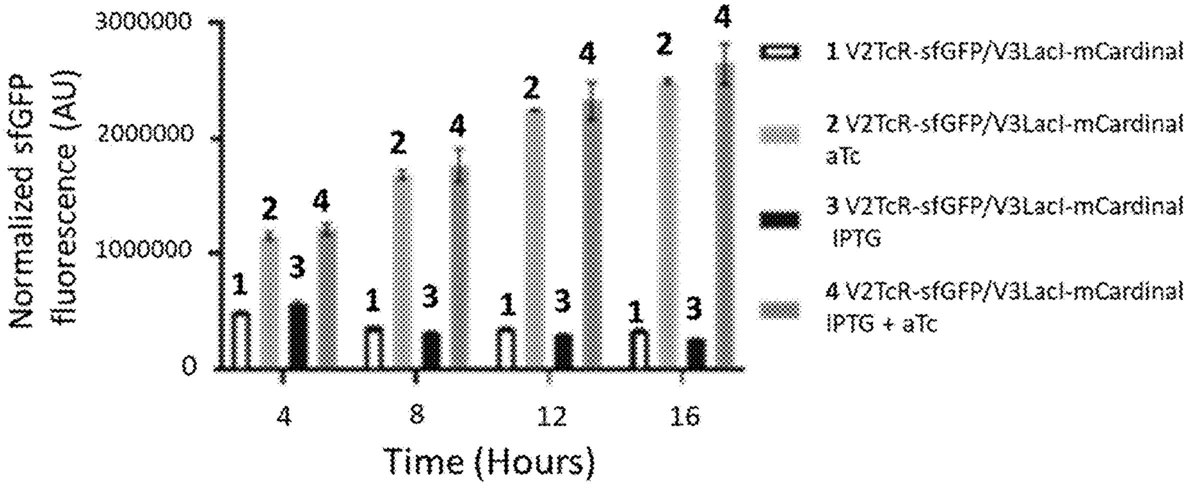

The three bacterial species under study containing V2TcR-sfGFP/V2(3)LacI-mCardinal expression system showed no green fluorescence in the uninduced state, thus confirming the tight regulation of the V2TcR expression system, however, the V2(3)LacI-mCardinal is prone to leak and red fluorescence was observed in the absence of IPTG (FIGS. 11A-11C). Addition of aTc induced the production of sfGFP, and similar result was observed with the addition of IPTG which triggered production of mCardinal. Interestingly, when the cultures were co-induced with aTc+IPTG the green and red fluorescence reached similar levels compared with the cultures induced with only one inducer, thus indicating that both promoters (V2TcR/V2(3)LacI) are unaffected by the activation of each other reaching their maximum activity either in their sole activation or their independent combined activation (FIGS. 11A-11C).

Figure 12A:
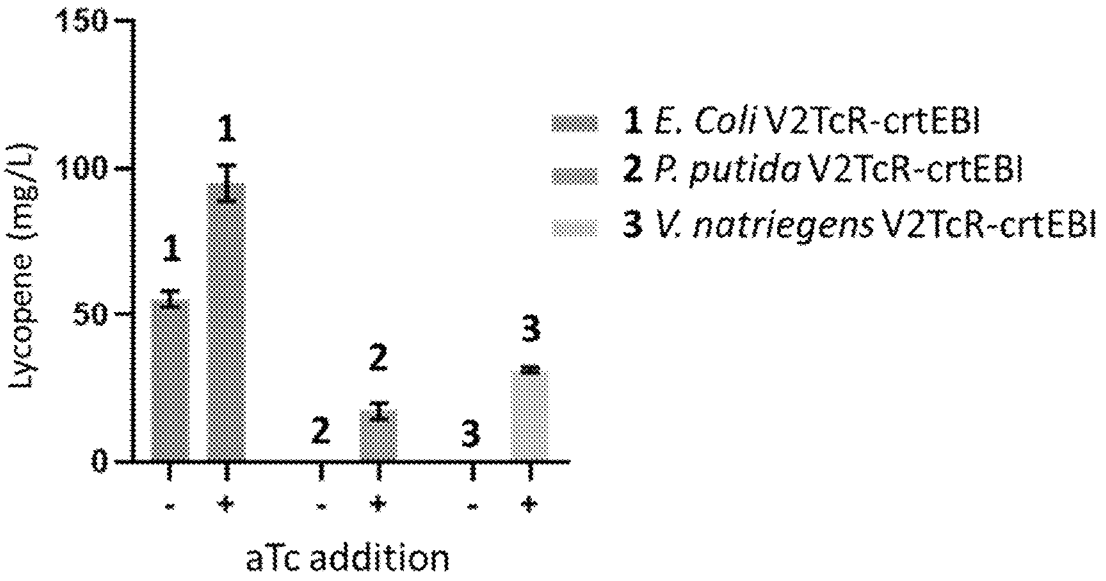
FIGS. 12A-12B shows graphs of the production of lycopene and β-carotene with the V2TcR expression system in *E. coli, P. putida*, and *V. natriegens*. Cultures were induced with aTc at OD600. 0.7 and cultured for 4 hours.
Figure 12B:
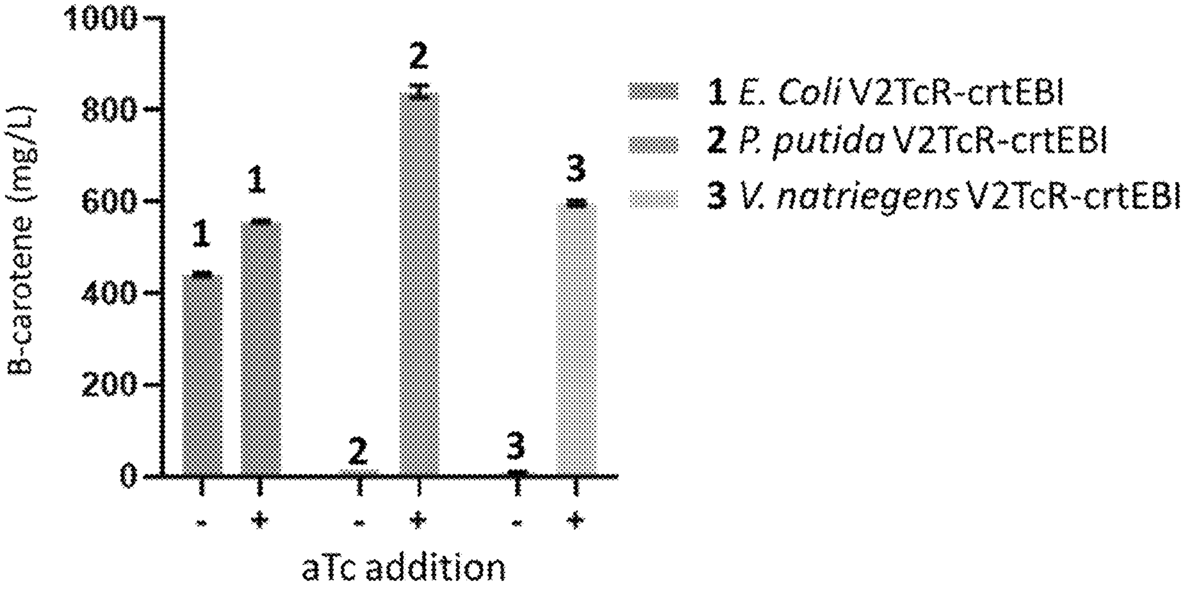

Example 15: Production of Lycopene and B-Carotene in *E. coli, P. putida* And *V. natriegens* with the Expression System V2TcR To decipher the capability of the dual-expression system V2TcR/V2(3)LacI to produce natural products we first had to test the ability of the V2TcR expression system to control the expression of multiple genes, we therefore decided to evaluate the production of lycopene and B-carotene in *E. coli, P. putida* and *V. natriegens*. Lycopene production has already been demonstrated in *E. coli* and *P. putida* via heterologous expression of the lycopene-producing operon (LYC) containing the crtEBI genes from *Pantoea ananatis*. Lycopene is the biosynthetic precursor of B-carotene, thus expression of the LYC operon together with crtY yields B-carotene production, which also has been demonstrated in *E. coli* and *V. natriegens*. The LYC and the crtEBIY operons were accommodated in the V2TcR expression system and lycopene and B-carotene production were measured by UHPLC after 4 hours of induction with aTc. In *E. coli* production of both, lycopene and B-carotene, was achieved but the induced culture produced only 1.7 and 1.2-fold more lycopene and B-carotene respectively than the uninduced culture, thus demonstrating that the tight control of the V2TcR can't totally repress the expression of the crtEBI and crtEBIY genes (FIGS. 12A-12B). Lycopene biosynthesis in *E. coli* using the pET expression system also demonstrated abundant leakage and production of 170 mg/L lycopene after 40 hours of induction, 1.1-fold more than the uninduced culture. Despite the V2TcR expression system produced 94 mg/L, this was achieved after 4 hours of induction, against the 40 hours reported with the pET expression system. This result confirms the advantage of the V2TcR expression system over the pET expression system as described in Examples 2-10. In *P. putida* and *V. natriegens* containing the V2TcR-crtEBI (SEQ ID NO: 70) and V2TcR-crtEBIY (SEQ ID NO: 71) transcriptional units no lycopene or B-carotene production was observed in the uninduced state, and activation of by aTc yielded production of the terpenoids (FIGS. 12A-12B). *P. putida* was reported to produce 1.22 ng/mL of lycopene after 24 hours of growth with the pSEVA421 vector, with the V2TcR expression system lycopene production reached 17 mg/L after 4 hours of cultivation, which is a substantial increment (13.000×), and B-carotene production by *P. putida* reached 840 mg/L, the highest among the three species under study (FIG. 12). *V. natriegens* was reported to produce 2.93 mg/L of B-carotene, while the V2TcR expression system achieved 597 mg/L of B-carotene and 31 mg/L of lycopene. These results demonstrate that the V2TcR can be efficiently programmed for production of biosynthetic gene clusters in Gram-negative bacteria.

Figure 13A:
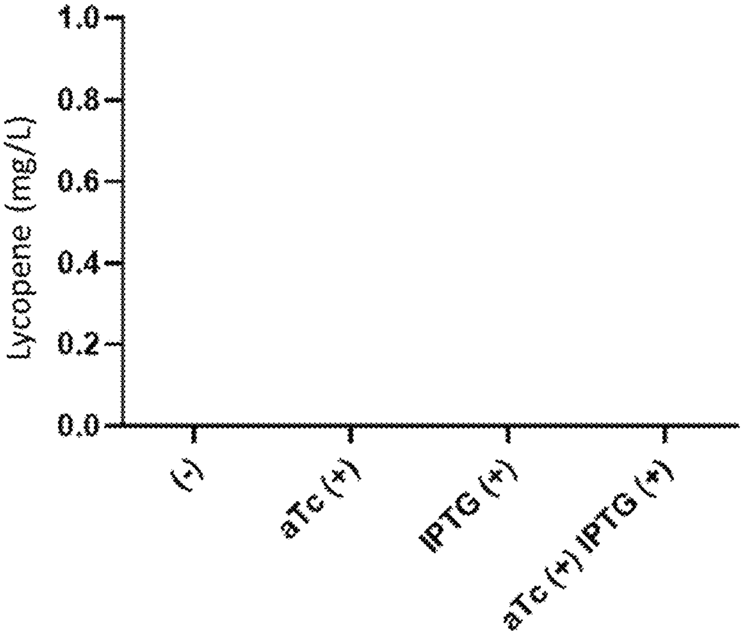
FIGS. 13A-13B shows graphs of the production of lycopene and beta (β)-carotene by the dual expression system in *E. coli, P. putida*, and *V. natriegens*. Cultures were induced with aTc, IPTG or both inducers at OD600. 0.7 and cultured for 4 hours.

Example 16: Coordinated Expression of the Lycopene and B-Carotene Biosynthetic Gene Clusters (BGC) with the Dual Expression System V2TcR/V2(3)LacI Natural products are encoded by BGC and ability to activate each gene at a different time point with a different inducer represent an advantage when the genes are toxic, or the metabolites produce by the BGC affect the cell growth of the heterologous host. As provided herein, the V2TcR expression system can activate the production of lycopene and B-carotene. In order to control the production of B-carotene with two different inducers, aTc and IPTG were used. The LYC operon was incorporated to the V2TcR expression system and the crtY gene was controlled by the V2(3)LacI expression system. The plasmid p$\sigma^{70}$ V2TcR-crtEBI/V3LacI-crtY (SEQ ID NO: 73) was transformed into *E. coli* and the plasmid p$\sigma^{70}$ V2TcR-crtEBI/V2lacI-crtY (SEQ ID NO: 72) was transformed into *P. putida* and *V. natriegens*. In the three bacteria species no lycopene production was observed despite the V2TcR expression system was controlling the crtEBI genes and activation by aTc should trigger production of lycopene (FIG. 13A). This result is explained in *E. coli* by the leakage of the crtEBIY genes under the control of the synthetic promoters V2TcR and V3LacI, demonstrating the high processivity of the B-carotene BGC to metabolize the endogenous IPP isopentenyl diphosphate directly into B-carotene. However, the V2TcR-crtEBI showed no leakage in *P. putida* and *V. natriegens*, but the V2lacI expression system was reported to leak, consequently, the lycopene produced after addition of aTc is directly transformed into B-carotene by the CrtY present in the cells due its minimal expression and high processivity.

Figure 13B:
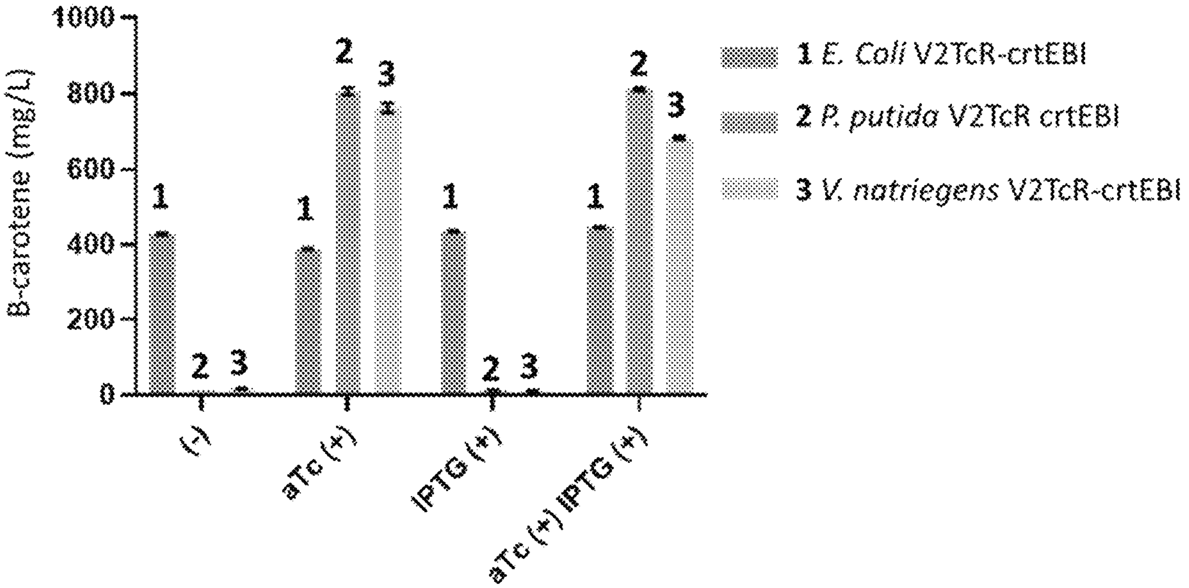

B-carotene production in *E. coli* was observed no matter the absence or presence of the inducers aTc and IPTG (FIG. 13B), thus demonstrating that the V2TcR/V3LacI expression system failed to keep downregulated the B-carotene BGC in in this host. In *P. putida* and *V. natriegens* B-carotene production was only achieved when the cultures were induced with aTc or with aTc+IPTG (FIG. 13A). IPTG induction alone did not conduce to B-carotene production because the crtEBI genes were not transcribed by the V2TcR expression system. Addition of aTc resulted in B-carotene levels similar to induction with aTc+IPTG (FIG. 13A), thus indicating that the minimal leakage of the V2lacI-crtY is sufficient to metabolize the lycopene produced by the V2TcR-crtEBI into B-carotene.

Importantly, the yields of B-carotene reached by *E. coli* were always lower than the production achieved by *P. putida* and *V. natriegens*. Thus, *P. putida* can be used to produce complex biosynthetic gene clusters. Therefore, a dual expression system developed in this study expands the genetic tool kit of *P. putida* to produce complex proteins. Also, *V. natriegens* outperformed *E. coli*, and the dual expression system allowed higher production of B-carotene compared with the V2TcR by 1.2-fold. Together these results demonstrate the potential of the dual expression system presented here to fully capitalize the potential of heterologous host in industrial applications.

SEQUENCES

FIG. 2A Sequences:

Lac (SEQ ID NO: 3)

AGGCTTTACACTTTATGCTTCCGGCTCGTATGTTGTGTGGAATTGTGAGCGGATAACAATTTCACACAGGAAACA
GCTATG

-continued

| SEQUENCES |
|---|

lacUV5 (SEQ ID NO: 4)
AGGCTTTACACTTTATGCTTCCGGCTCGTATAATGTGTGGAATTGTGAGCGGATAACAATTTCACACAGGAAACA
GCTATG tacI (SEQ ID NO: 5)
GAGCTGTTGACAATTAATCATCGGCTCGTATAATGTGTGGAATTGTGAGCGGATAACAATTTCACACAGGAAACA
GAATCATATG V1lac (SEQ ID NO: 6)
AGGCTTTACACTTTATGCTTCCGGCTCGTATGTTGTGTGGAATTGTGAGCGGATAACAACGCAGTAAGAGAGGAA
TGTACATATG V2lac (SEQ ID NO: 7)
GAGCTGTTGACACTTTATGCTTCCGGCTCGTATAATGTGTGTGGAATTGTGAGCGGATAACAACGCAGTAAGAGA
GGAATGTACATATG V3lac (SEQ ID NO: 8)
GAGCTGTTGACACTTTATGCTTCCGGCTCGTATAATGTGTGTGGAATTGTGAGCGGATAACAAGTGGAATTGTGA
GCGGATAACAATTTCACACAGGAAACAGAATCATATG V4lac (SEQ ID NO: 9)
CTTTATGCTTCCGGCTCGTTGACAGTGTGGAATTGTGAGCGGATAACAATATAATGTGTGGAATTGTGAGCGGAT
AACAATTTCACACAGGAAACAGAATCATATG FIG. 2B Sequences:
Tet (SEQ ID NO: 10)
GGATCCTTGACACTCTATCATTGATAGAGTTATTTTACCACTCCCTATCAGTGATAGAGAAAAGTGAAATG V1Tc (SEQ ID NO: 11)
GGATCCTTGACACTCTATCATTGATAGAGTTATTTTACCACTCCCTATCAGTGATAGAGACGCAGTAAGAGAGGA
ATGTACATATG V2Tc (SEQ ID NO: 12)
GAGCTGTTGACAACTCTATCATTGATAGAGTTATAATGTTCCCTATCAGTGATAGAGACGCAGTAAGAGAGGAAT
GTACATATG V3Tc (SEQ ID NO: 13)
GAGCTGTTGACAACTCTATCATTGATAGAGTTATAATGTTCCCTATCAGTGATAGAGAGTGGAATTGTGAGCGGA
TAACAATTTCACACAGGAAACAGAATCATATG V4Tc (SEQ ID NO: 14)
TTGACACTCTATCATTGATAGAGTTTGACATCCCTATCAGTGATAGAGATATAATGTGTGGAATTGTGAGCGGAT
AACAATTTCACACAGGAAACAGAATCATATG SEQ ID NOS: 15-38 are provided in Table 2.

SEQ ID NOS: 39-43 are provided in Example 2.

SEQ ID NOS: 44-53 are provided in the Detailed Description.

Figure 14:
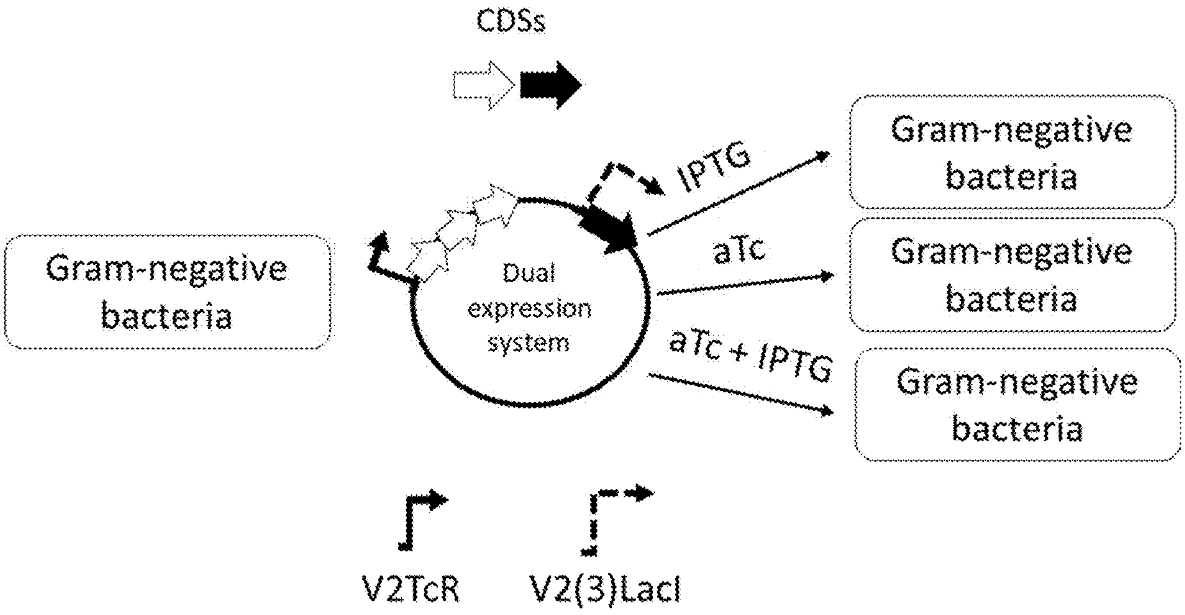
FIG. 14 shows a schematic of an exemplary dual expression system. Exemplary sequences include SEQ ID NO: 54 and SEQ ID NO: 55.

FIG. 14 Full-length Sequence:
V2Tc/tetR-V2lac/lacI (SEQ ID NO: 54)
GAGCTGTTGACAACTCTATCATTGATAGAGTTATAATGTTCCCTATCAGTGATAGAGACGCAGTAAGAGAGGAAT
GTACATATGAAGCTTCTCGGTACCAAATTCCAGAAAAGAGGCCTCCCGAAAGGGGGGCCTTTTTTCGTTTTGGTC
CGAATTCTTGACAGCTAGCTCAGTCCTAGGTATAATGCTAGCCGCAGTAAGAGAGGAATGTACACATGTCCCGCC
TGGATAAATCGAAAGTGATTAACTCGGCCCTCGAATTGCTGAATGAAGTCGGTATCGAGGGGCTGACGACCCGTA
AATTGGCACAAAAGTTGGGGGTGGAGCAACCCACGTTGTATTGGCACGTCAAAAATAAGCGGGCATTGCTGGATG
CCCTCGCTATTGAAATGTTGGATCGCCACCATACCCATTTCTGTCCACTGGAGGGCGAGTCCTGGCAGGACTTTC
TCCGCAACAACGCGAAATCCTTTCGCTGTGCACTCTTGTCCCATCGGGACGGTGCTAAGGTGCACTTGGGCACCC
GTCCCACCGAAAAACAATACGAAACCTTGGAAAATCAATTGGCGTTTTTGTGCCAGCAAGGGTTTAGCTTGGAGA
ATGCTCTCTATGCGCTCTCGGCTGTCGGGCACTTTACGTTGGGGTGCGTGTTGGAGGACCAGGAGCATCAAGTCG
CAAAAGAGGAGCGTGAAACCCCAACCACGGACTCGATGCCACCTCTGCTCCGCCAAGCTATCGAACTCTTCGATC
ATCAGGGCGCGGAGCCAGCCTTCCTCTTTGGGCTGGAGCTGATTATCTGCGGTTTGGAAAAACAACTCAAGTGTG
AAAGCGGGTCCTAACTGCAGTCACTGCCCGCTTTCCAGTCGGGAAACCTGTCGTGCCAGCTGCATTAATGAATCG
GCCAACGCGCGGGGAGAGGCGGTTTGCGTATTGGGCGCCAGGGTGGTTTTTCTTTTCACCAGTGAGACGGGCAAC
AGCTGATTGCCCTTCACCGCCTGGCCCTGAGAGAGTTGCAGCAAGCGGTCCACGCTGGTTTGCCCCAGCAGGCGA
AAATCCTGTTTGATGGTGGTTAACGGCGGGATATAACATGAGCTGTCTTCGGTATCGTCGTATCCCACTACCGAG
ATATCCGCACCAACGCGCAGCCCGGACTCGGTAATGGCGCGCATTGCGCCCAGCGCCATCTGATCGTTGGCAACC
AGCATCGCAGTGGGAACGATGCCCTCATTCAGCATTTGCATGGTTTGTTGAAAACCGGACATGGCACTCCAGTCG
CCTTCCCGTTCCGCTATCGGCTGAATTTGATTGCGAGTGAGATATTTATGCCAGCCAGCCAGACGCAGACGCGCC
GAGACAGAACTTAATGGGCCCGCTAACAGCGCGATTTGCTGGTGACCCAATGCGACCAGATGCTCCACGCCCAGT
CGCGTACCGTCTTCATGGGAGAAAATAATACTGTTGATGGGTGTCTGGTCAGAGACATCAAGAAATAACGCCGGA
ACATTAGTGCAGGCAGCTTCCACAGCAATGGCATCCTGGTCATCCAGCGGATAGTTAATGATCAGCCCACTGACG
CGTTGCGCGAGAAGATTGTGCACCGCCGCTTTACAGGCTTCGACGCCGCTTCGTTCTACCATCGACACCACCACG
CTGGCACCCAGTTGATCGGCGCGAGATTTAATCGCCGCGACAATTTGCGACGGCGCGTGCAGGGCCAGACTGGAG
GTGGCAACGCCAATCAGCAACGACTGTTTGCCCGCCAGTTGTTGTGCCACGCGGTTGGGAATGTAATTCAGCTCC
GCCATCGCCGCTTCCACTTTTTCCCGCGTTTTCGCAGAAACGTGGCTGGCCTGGTTCACCACGCGGGAAACGGTC -continued

| SEQUENCES |
|---|
| TGATAAGAGACACCGGCATACTCTGCGACATCGTATAACGTTACTGGTTTCACATTCACCACCCTGAATTGACTC |
| TCTTCCGGGCGCTATCATGCCATACCGCGAAAGGTTTTGCGCCATTCGATGGTGTCCGGGATCTCGACGCTCTCC |
| CTTATGCGACTCCTGCATTAGGAAGCAGCCCAGTAGTAGGTTGAGGCCGTTGAGCACCGCCGCCGCAAGGAATGG |
| TGCATGCAAGGAGATGGCGCCCAACAGTCCCCCGGCCACGGGGagtcaaaagcctccggtcggaggcttttgact |
| TCTAGAGAGCTGTTGACACTTTATGCTTCCGGCTCGTATAATGTGTGTGGAATTGTGAGCGGATAACAACGCAGT |
| AAGAGAGGAATGTACCCATGGCCATGGCTCGAGgacgaacaataaggcctccctaacggggggcctttttttattg |
| ataacaaaa |
| |
| Additional sequences: |
| V2Tc/tetR-V3lac/lacI (SEQ ID NO: 55) |
| GAGCTGTTGACAACTCTATCATTGATAGAGTTATAATGTTCCCTATCAGTGATAGAGACGCAGTAAGAGAGGAAT |
| GTACATATGAAGCTTCTCGGTACCAAATTCCAGAAAAGAGGCCTCCCGAAAGGGGGGCCTTTTTTCGTTTTGGTC |
| CGAATTCTTGACAGCTAGCTCAGTCCTAGGTATAATGCTAGCCGCAGTAAGAGAGGAATGTACACATGTCCCGCC |
| TGGATAAATCGAAAGTGATTAACTCGGCCCTCGAATTGCTGAATGAAGTCGGTATCGAGGGGCTGACGACCCGTA |
| AATTGGCACAAAAGTTGGGGGTGGAGCAACCCACGTTGTATTGGCACGTCAAAAATAAGCGGGCATTGCTGGATG |
| CCCTCGCTATTGAAATGTTGGATCGCCACCATACCCATTTCTGTCCACTGGAGGGCGAGTCCTGGCAGGACTTTC |
| TCCGCAACAACGCGAAATCCTTTCGCTGTGCACTCTTGTCCCATCGGGACGGTGCTAAGGTGCACTTGGGCACCC |
| GTCCCACCGAAAAACAATACGAAACCTTGGAAAATCAATTGGCGTTTTTGTGCCAGCAAGGGTTTAGCTTGGAGA |
| ATGCTCTCTATGCGCTCTCGGCTGTCGGGCACTTTACGTTGGGGTGCGTGTTGGAGGACCAGGAGCATCAAGTCG |
| CAAAAGAGGAGCGTGAAACCCCAACCACGGACTCGATGCCACCTCTGCTCCGCCAAGCTATCGAACTCTTCGATC |
| ATCAGGGCGCGGAGCCAGCCTTCCTCTTTGGGCTGGAGCTGATTATCTGCGGTTTGGAAAAACAACTCAAGTGTG |
| AAAGCGGGTCCTAACTGCAGTCACTGCCCGCTTTCCAGTCGGGAAACCTGTCGTGCCAGCTGCATTAATGAATCG |
| GCCAACGCGCGGGGAGAGGCGGTTTGCGTATTGGGCGCCAGGGTGGTTTTTCTTTTCACCAGTGAGACGGGCAAC |
| AGCTGATTGCCCTTCACCGCCTGGCCCTGAGAGAGTTGCAGCAAGCGGTCCACGCTGGTTTGCCCCAGCAGGCGA |
| AAATCCTGTTTGATGGTGGTTAACGGCGGGATATAACATGAGCTGTCTTCGGTATCGTCGTATCCCACTACCGAG |
| ATATCCGCACCAACGCGCAGCCCGGACTCGGTAATGGCGCGCATTGCGCCCAGCGCCATCTGATCGTTGGCAACC |
| AGCATCGCAGTGGGAACGATGCCCTCATTCAGCATTTGCATGGTTTGTTGAAAACCGGACATGGCACTCCAGTCG |
| CCTTCCCGTTCCGCTATCGGCTGAATTTGATTGCGAGTGAGATATTTATGCCAGCCAGCCAGACGCAGACGCGCC |
| GAGACAGAACTTAATGGGCCCGCTAACAGCGCGATTTGCTGGTGACCCAATGCGACCAGATGCTCCACGCCCAGT |
| CGCGTACCGTCTTCATGGGAGAAAATAATACTGTTGATGGGTGTCTGGTCAGAGACATCAAGAAATAACGCCGGA |
| ACATTAGTGCAGGCAGCTTCCACAGCAATGGCATCCTGGTCATCCAGCGGATAGTTAATGATCAGCCCACTGACG |
| CGTTGCGCGAGAAGATTGTGCACCGCCGCTTTACAGGCTTCGACGCCGCTTCGTTCTACCATCGACACCACCACG |
| CTGGCACCCAGTTGATCGGCGCGAGATTTAATCGCCGCGACAATTTGCGACGGCGCGTGCAGGGCCAGACTGGAG |
| GTGGCAACGCCAATCAGCAACGACTGTTTGCCCGCCAGTTGTTGTGCCACGCGGTTGGGAATGTAATTCAGCTCC |
| GCCATCGCCGCTTCCACTTTTTCCCGCGTTTTCGCAGAAACGTGGCTGGCCTGGTTCACCACGCGGGAAACGGTC |
| TGATAAGAGACACCGGCATACTCTGCGACATCGTATAACGTTACTGGTTTCACATTCACCACCCTGAATTGACTC |
| TCTTCCGGGCGCTATCATGCCATACCGCGAAAGGTTTTGCGCCATTCGATGGTGTCCGGGATCTCGACGCTCTCC |
| CTTATGCGACTCCTGCATTAGGAAGCAGCCCAGTAGTAGGTTGAGGCCGTTGAGCACCGCCGCCGCAAGGAATGG |
| TGCATGCAAGGAGATGGCGCCCAACAGTCCCCCGGCCACGGGGagtcaaaagcctccggtcggaggcttttgact |
| TCTAGAGAGCTGTTGACACTTTATGCTTCCGGCTCGTATAATGTGTGTGGAATTGTGAGCGGATAACAAGTGGAA |
| TTGTGAGCGGATAACAATTTCACACAGGAAACAGAATCCCATGGCTCGAGgacgaacaataaggcctccctaacg |
| gggggcctttttttattgataacaaaa |

TABLE 3

| List of Plasmids |
|---|
| pσ[70] V2TcR-mCardinal (SEQ ID NO: 56) |
| ggatccGAGCTGTTGACAACTCTATCATTGATAGAGTTATAATGTTCCCTATCAGTGATAGAGACGCAGTAAGAG |
| AGGAATGTACATATGGTGAGTAAGGGTGAGGAGCTCATTAAGGAGAACATGCACATGAAGCTGTATATGGAGGGC |
| ACCGTAAACAACCACCACTTCAAGTGTACCACCGAGGGTGAAGGTAAACCCTACGAGGGGACGCAGACCCAACGC |
| ATCAAGGTCGTGGAGGGCGGCCCGCTGCCTTTCGCATTCGACATTCTGGCGACCTGTTTTATGTACGGCTCGAAG |
| ACCTTCATCAACCACACCCAAGGCATCCCGGACTTCTTCAAGCAGAGCTTCCCTGAGGGCTTCACCTGGGAGCGC |
| GTCACCACGTATGAAGACGGTGGGGTGCTCACCGTGACCCAGGACACGAGCTTGCAGGATGGCTGCTTGATTTAC |
| AACGTCAAGCTGCGCGGGGTGAACTTCCCTAGCAACGGGCCAGTGATGCAGAAAAAGACGCTGGGTTGGGAGGCC |
| ACCACCGAGACCCTGTACCCGGCCGACGGGGGGCTGGAAGGGCGGTGCGATATGGCCCTGAAATTGGTCGGCGGC |
| GGTCATTTGCACTGCAATCTCAAGACCACGTACCGCTCCAAGAAACCCGCCAAAAACCTGAAGATGCCTGGTGTT |
| TATTTTGTCGACCGGCGCCTGGAGCGCATCAAGGAAGCGGACAATGAGACGTACGTGGAACAGCACGAAGTGGCC |
| GTGGCTCGTTATTGCGATCTGCCGTCGAAGCTGGGTCACAAACTGAACGGCATGGATGAGCTGTACAAAGATTAT |
| AAGGATGATGACGACAAGTAAAAGCTTCTCGGTACCAAATTCCAGAAAAGAGGCCTCCCGAAAGGGGGGCCTTTT |
| TTCGTTTTGGTCCGAATTCTTGACAGCTAGCTCAGTCCTAGGTATAATGCTAGCCGCAGTAAGAGAGGAATGTAC |
| ACATGTCCCGCCTGGATAAATCGAAAGTGATTAACTCGGCCCTCGAATTGCTGAATGAAGTCGGTATCGAGGGGC |
| TGACGACCCGTAAATTGGCACAAAAGTTGGGGGTGGAGCAACCCACGTTGTATTGGCACGTCAAAAATAAGCGGG |
| CATTGCTGGATGCCCTCGCTATTGAAATGTTGGATCGCCACCATACCCATTTCTGTCCACTGGAGGGCGAGTCCT |
| GGCAGGACTTTCTCCGCAACAACGCGAAATCCTTTCGCTGTGCACTCTTGTCCCATCGGGACGGTGCTAAGGTGC |
| ACTTGGGCACCCGTCCCACCGAAAAACAATACGAAACCTTGGAAAATCAATTGGCGTTTTTGTGCCAGCAAGGGT |
| TTAGCTTGGAGAATGCTCTCTATGCGCTCTCGGCTGTCGGGCACTTTACGTTGGGGTGCGTGTTGGAGGACCAGG |
| AGCATCAAGTCGCAAAAGAGGAGCGTGAAACCCCAACCACGGACTCGATGCCACCTCTGCTCCGCCAAGCTATCG |
| AACTCTTCGATCATCAGGGCGCGGAGCCAGCCTTCCTCTTTGGGCTGGAGCTGATTATCTGCGGTTTGGAAAAAC |
| AACTCAAGTGTGAAAGCGGGTCCTAACTGCAGTCTAGACCATGGctcgag |
| |
| V2lacI-mCardinal (SEQ ID NO: 57) |
| GGATCCGAGCTGTTGACACTTTATGCTTCCGGCTCGTATAATGTGTGTGGAATTGTGAGCGGATAACAACGCAGT |
| AAGAGAGGAATGTACATATGGTGAGTAAGGGTGAGGAGCTCATTAAGGAGAACATGCACATGAAGCTGTATATGG |
| AGGGCACCGTAAACAACCACCACTTCAAGTGTACCACCGAGGGTGAAGGTAAACCCTACGAGGGGACGCAGACCC |

TABLE 3-continued

List of Plasmids

AACGCATCAAGGTCGTGGAGGGCGGCCCGCTGCCTTTCGCATTCGACATTCTGGCGACCTGTTTTATGTACGGCT
CGAAGACCTTCATCAACCACACCCAAGGCATCCCGGACTTCTTCAAGCAGAGCTTCCCTGAGGGCTTCACCTGGG
AGCGCGTCACCACGTATGAAGACGGTGGGGTGCTCACCGTGACCCAGGACACGAGCTTGCAGGATGGCTGCTTGA
TTTACAACGTCAAGCTGCGCGGGGTGAACTTCCCTAGCAACGGGCCAGTGATGCAGAAAAAGACGCTGGGTTGGG
AGGCCACCACCGAGACCCTGTACCCGGCCGACGGGGGGCTGGAAGGGCGGTGCGATATGGCCCTGAAATTGGTCG
GCGGCGGTCATTTGCACTGCAATCTCAAGACCACGTACCGCTCCAAGAAACCCGCCAAAAACCTGAAGATGCCTG
GTGTTTATTTTGTCGACCGGCGCCTGGAGCGCATCAAGGAAGCGGACAATGAGACGTACGTGGAACAGCACGAAG
TGGCCGTGGCTCGTTATTGCGATCTGCCGTCGAAGCTGGGTCACAAACTGAACGGCATGGATGAGCTGTACAAAG
ATTATAAGGATGATGACGACAAGTAAAAGCTTCTCGGTACCAAATTCCAGAAAAGAGGCCTCCCGAAAGGGGGGC
CTTTTTTCGTTTTGGTCCGAATTCCCCCGTGGCCGGGGGACTGTTGGGCGCCATCTCCTTGCATGCACCATTCCT
TGCGGCGGCGGTGCTCAACGGCCTCAACCTACTACTGGGCTGCTTCCTAATGCAGGAGTCGCATAAGGGAGAGCG
TCGAGATCCCGGACACCATCGAATGGCGCAAAACCTTTCGCGGTATGGCATGATAGCGCCCGGAAGAGAGTCAAT
TCAGGGTGGTGAATGTGAAACCAGTAACGTTATACGATGTCGCAGAGTATGCCGGTGTCTCTTATCAGACCGTTT
CCCGCGTGGTGAACCAGGCCAGCCACGTTTCTGCGAAAACGCGGGAAAAAGTGGAAGCGGCGATGGCGGAGCTGA
ATTACATTCCCAACCGCGTGGCACAACAACTGGCGGGCAAACAGTCGTTGCTGATTGGCGTTGCCACCTCCAGTC
TGGCCCTGCACGCGCCGTCGCAAATTGTCGCGGCGATTAAATCTCGCGCCGATCAACTGGGTGCCAGCGTGGTGG
TGTCGATGGTAGAACGAAGCGGCGTCGAAGCCTGTAAAGCGGCGGTGCACAATCTTCTCGCGCAACGCGTCAGTG
GGCTGATCATTAACTATCCGCTGGATGACCAGGATGCCATTGCTGTGGAAGCTGCCTGCACTAATGTTCCGGCGT
TATTTCTTGATGTCTCTGACCAGACACCCATCAACAGTATTATTTTCTCCCATGAAGACGGTACGCGACTGGGCG
TGGAGCATCTGGTCGCATTGGGTCACCAGCAAATCGCGCTGTTAGCGGGCCCATTAAGTTCTGTCTCGGCGCGTC
TGCGTCTGGCTGGCTGGCATAAATATCTCACTCGCAATCAAATTCAGCCGATAGCGGAACGGGAAGGCGACTGGA
GTGCCATGTCCGGTTTTCAACAAACCATGCAAATGCTGAATGAGGGCATCGTTCCCACTGCGATGCTGGTTGCCA
ACGATCAGATGGCGCTGGGCGCAATGCGCGCCATTACCGAGTCCGGGCTGCGCGTTGGTGCGGATATCTCGGTAG
TGGGATACGACGATACCGAAGACAGCTCATGTTATATCCCGCCGTTAACCACCATCAAACAGGATTTTCGCCTGC
TGGGGCAAACCAGCGTGGACCGCTTGCTGCAACTCTCTCAGGGCCAGGCGGTGAAGGGCAATCAGCTGTTGCCCG
TCTCACTGGTGAAAAGAAAAACCACCCTGGCGCCCAATACGCAAACCGCCTCTCCCCGCGCGTTGGCCGATTCAT
TAATGCAGCTGGCACGACAGGTTTCCCGACTGGAAAGCGGGCAGTGACTGCAGCTCGAG p$\sigma^{70}$ V3LacI-mCardinal (SEQ ID NO: 60)
GGATCCGAGCTGTTGACACTTTATGCTTCCGGCTCGTATAATGTGTGTGGAATTGTGAGCGGATAACAAGTGGAA
TTGTGAGCGGATAACAATTTCACACAGGAAACAGAATCATATGGTGAGTAAGGGTGAGGAGCTCATTAAGGAGAA
CATGCACATGAAGCTGTATATGGAGGGCACCGTAAACAACCACCACTTCAAGTGTACCACCGAGGGTGAAGGTAA
ACCCTACGAGGGGACGCAGACCCAACGCATCAAGGTCGTGGAGGGCGGCCCGCTGCCTTTCGCATTCGACATTCT
GGCGACCTGTTTTATGTACGGCTCGAAGACCTTCATCAACCACACCCAAGGCATCCCGGACTTCTTCAAGCAGAG
CTTCCCTGAGGGCTTCACCTGGGAGCGCGTCACCACGTATGAAGACGGTGGGGTGCTCACCGTGACCCAGGACAC
GAGCTTGCAGGATGGCTGCTTGATTTACAACGTCAAGCTGCGCGGGGTGAACTTCCCTAGCAACGGGCCAGTGAT
GCAGAAAAAGACGCTGGGTTGGGAGGCCACCACCGAGACCCTGTACCCGGCCGACGGGGGGCTGGAAGGGCGGTG
CGATATGGCCCTGAAATTGGTCGGCGGCGGTCATTTGCACTGCAATCTCAAGACCACGTACCGCTCCAAGAAACC
CGCCAAAAACCTGAAGATGCCTGGTGTTTATTTTGTCGACCGGCGCCTGGAGCGCATCAAGGAAGCGGACAATGA
GACGTACGTGGAACAGCACGAAGTGGCCGTGGCTCGTTATTGCGATCTGCCGTCGAAGCTGGGTCACAAACTGAA
CGGCATGGATGAGCTGTACAAAGATTATAAGGATGATGACGACAAGTAAAAGCTTCTCGGTACCAAATTCCAGAA
AAGAGGCCTCCCGAAAGGGGGGCCTTTTTTCGTTTTGGTCCGAATTCCCCCGTGGCCGGGGGACTGTTGGGCGCC
ATCTCCTTGCATGCACCATTCCTTGCGGCGGCGGTGCTCAACGGCCTCAACCTACTACTGGGCTGCTTCCTAATG
CAGGAGTCGCATAAGGGAGAGCGTCGAGATCCCGGACACCATCGAATGGCGCAAAACCTTTCGCGGTATGGCATG
ATAGCGCCCGGAAGAGAGTCAATTCAGGGTGGTGAATGTGAAACCAGTAACGTTATACGATGTCGCAGAGTATGC
CGGTGTCTCTTATCAGACCGTTTCCCGCGTGGTGAACCAGGCCAGCCACGTTTCTGCGAAAACGCGGGAAAAAGT
GGAAGCGGCGATGGCGGAGCTGAATTACATTCCCAACCGCGTGGCACAACAACTGGcGGGCAAACAGTCGTTGCT
GATTGGCGTTGCCACCTCCAGTCTGGCCCTGCACGCGCCGTCGCAAATTGTCGCGGCGATTAAATCTCGCGCCGA
TCAACTGGGTGCCAGCGTGGTGGTGTCGATGGTAGAACGAAGCGGCGTCGAAGCCTGTAAAGCGGCGGTGCACAA
TCTTCTCGCGCAACGCGTCAGTGGGCTGATCATTAACTATCCGCTGGATGACCAGGATGCCATTGCTGTGGAAGC
TGCCTGCACTAATGTTCCGGCGTTATTTCTTGATGTCTCTGACCAGACACCCATCAACAGTATTATTTTCTCCCA
TGAAGACGGTACGCGACTGGGCGTGGAGCATCTGGTCGCATTGGGTCACCAGCAAATCGCGCTGTTAGCGGGCCC
ATTAAGTTCTGTCTCGGCGCGTCTGCGTCTGGCTGGCTGGCATAAATATCTCACTCGCAATCAAATTCAGCCGAT
AGCGGAACGGGAAGGCGACTGGAGTGCCATGTCCGGTTTTCAACAAACCATGCAAATGCTGAATGAGGGCATCGT
TCCCACTGCGATGCTGGTTGCCAACGATCAGATGGCGCTGGGCGCAATGCGCGCCATTACCGAGTCCGGGCTGCG
CGTTGGTGCGGATATCTCGGTAGTGGGATACGACGATACCGAAGACAGCTCATGTTATATCCCGCCGTTAACCAC
CATCAAACAGGATTTTCGCCTGCTGGGGCAAACCAGCGTGGACCGCTTGCTGCAACTCTCTCAGGGCCAGGCGGT
GAAGGGCAATCAGCTGTTGCCCGTCTCACTGGTGAAAAGAAAAACCACCCTGGCGCCCAATACGCAAACCGCCTC
TCCCCGCGCGTTGGCCGATTCATTAATGCAGCTGGCACGACAGGTTTCCCGACTGGAAAGCGGGCAGTGACTGCA
GCTCGAG p$\sigma^{70}$ V2TcR-sfGFP (SEQ ID NO: 61)
GGATCCGAGCTGTTGACAACTCTATCATTGATAGAGTTATAATGTTCCCTATCAGTGATAGAGACGCAGTAAGAG
AGGAATGTACATATGTCCAAAGGTGAAGAGCTGTTTACCGGCGTCGTGCCCATTCTGGTGGAGCTGGATGGCGAC
GTCAACGGGCACAAGTTTAGCGTCCGTGGCGAAGGTGAGGGCGACGCCACGAACGGTAAGCTGACGCTGAAATTC
ATTTGCACCACCGGCAAATTGCCTGTACCCTGGCCCACCCTGGTGACCACGCTCACCTACGGCGTACAGTGCTTC
AGCCGTTACCCGGACCACATGAAGCGTCACGACTTCTTCAAAAGCGCCATGCCGGAGGGTTACGTGCAGGAGCGT
ACGATTAGTTTCAAGGACGACGGCACCTATAAGACCCGTGCCGAAGTGAAGTTCGAAGGCGATACGTTGGTGAAC
CGTATCGAGTTGAAGGGTATCGACTTTAAGGAAGACGGCAACATCCTGGGCCATAAGCTGGAGTACAATTTCAAC
AGCCATAACGTTTACATCACCGCCGATAAACAGAAGAACGGCATTAAAGCCAACTTTAAGATCCGCCACAACGTC
GAAGACGGCTCGGTGCAGCTGGCCGACCATTATCAGCAAAACACCCCCATCGGTGATGGGCCCGTGCTGCTGCCG
GATAACCATTATCTGAGCACGCAGTCGGTGCTCAGCAAGGACCCTAACGAAAAGCGCGATCACATGGTGCTGCTG
GAGTTCGTCACGGCGGCGGGGATCACCCATGGGATGGACGAGCTCTACAAAGACTATAAAGATGACGATGACAAG
TAAAAGCTTCTCGGTACCAAATTCCAGAAAAGAGGCCTCCCGAAAGGGGGGCCTTTTTTCGTTTTGGTCCGAATT
CTTGACAGCTAGCTCAGTCCTAGGTATAATGCTAGCCGCAGTAAGAGAGGAATGTACACATGTCCCGCCTGGATA
AATCGAAAGTGATTAACTCGGCCCTCGAATTGCTGAATGAAGTCGGTATCGAGGGGCTGACGACCCGTAAATTGG
CACAAAAGTTGGGGGTGGAGCAACCCACGTTGTATTGGCACGTCAAAAATAAGCGGGCATTGCTGGATGCCCTCG
CTATTGAAATGTTGGATCGCCACCATACCCATTTCTGTCCACTGGAGGGCGAGTCCTGGCAGGACTTTCTCCGCA TABLE 3-continued

| List of Plasmids |
| --- |
| ACAACGCGAAATCCTTTCGCTGTGCACTCTTGTCCCATCGGGACGGTGCTAAGGTGCACTTGGCACCCGTCCCA<br>CCGAAAAACAATACGAAACCTTGGAAAATCAATTGGCGTTTTTGTGCCAGCAAGGGTTTAGCTTGGAGAATGCTC<br>TCTATGCGCTCTCGGCTGTCGGGCACTTTACGTTGGGGTGCGTGTTGGAGGACCAGGAGCATCAAGTCGCAAAAG<br>AGGAGCGTGAAACCCCAACCACGGACTCGATGCCACCTCTGCTCCGCCAAGCTATCGAACTCTTCGATCATCAGG<br>GCGCGGAGCCAGCCTTCCTCTTTGGGCTGGAGCTGATTATCTGCGGTTTGGAAAAACAACTCAAGTGTGAAAGCG<br>GGTCCTAACTGCAGCTCGAG |
| p$\sigma^{70}$ V2lacI-sfGFP (SEQ ID NO: 62)<br>GGATCCGAGCTGTTGACACTTTATGCTTCCGGCTCGTATAATGTGTGTGGAATTGTGAGCGGATAACAACGCAGT<br>AAGAGAGGAATGTACATATGTCCAAAGGTGAAGAGCTGTTTACCGGCGTCGTGCCCATTCTGGTGGAGCTGGATG<br>GCGACGTCAACGGGCACAAGTTTAGCGTCCGTGGCGAAGGTGAGGGCGACGCCACGAACGGTAAGCTGACGCTGA<br>AATTCATTTGCACCACCGGCAAATTGCCTGTACCCTGGCCCACCCTGGTGACCACGCTCACCTACGGCGTACAGT<br>GCTTCAGCCGTTACCCGGACCACATGAAGCGTCACGACTTCTTCAAAAGCGCCATGCCGGAGGGTTACGTGCAGG<br>AGCGTACGATTAGTTTCAAGGACGACGGCACCTATAAGACCCGTGCCGAAGTGAAGTTCGAAGGCGATACGTTGG<br>TGAACCGTATCGAGTTGAAGGGTATCGACTTTAAGGAAGACGGCAACATCCTGGGCCATAAGCTGGAGTACAATT<br>TCAACAGCCATAACGTTTACATCACCGCCGATAAACAGAAGAACGGCATTAAAGCCAACTTTAAGATCCGCCACA<br>ACGTCGAAGACGGCTCGGTGCAGCTGGCCGACCATTATCAGCAAAACACCCCCATCGGTGATGGGCCCGTGCTGC<br>TGCCGGATAACCATTATCTGAGCACGCAGTCGGTGCTCAGCAAGGACCCTAACGAAAAGCGCGATCACATGGTGC<br>TGCTGGAGTTCGTCACGGCGGCGGGGATCACCCATGGGATGGACGAGCTCTACAAAGACTATAAAGATGACGATG<br>ACAAGTAAAAGCTTCTCGGTACCAAATTCCAGAAAAGAGGCCTCCCGAAAGGGGGGCCTTTTTTCGTTTTGGTCC<br>GAATTCCCCCGTGGCCGGGGGACTGTTGGGCGCCATCTCCTTGCATGCACCATTCCTTGCGGCGGCGGTGCTCAA<br>CGGCCTCAACCTACTACTGGGCTGCTTCCTAATGCAGGAGTCGCATAAGGGAGAGCGTCGAGATCCCGGACACCA<br>TCGAATGGCGCAAAACCTTTCGCGGTATGGCATGATAGCGCCCGGAAGAGAGTCAATTCAGGGTGGTGAATGTGA<br>AACCAGTAACGTTATACGATGTCGCAGAGTATGCCGGTGTCTCTTATCAGACCGTTTCCCGCGTGGTGAACCAGG<br>CCAGCCACGTTTCTGCGAAAACGCGGGAAAAAGTGGAAGCGGCGATGGCGGAGCTGAATTACATTCCCAACCGCG<br>TGGCACAACAACTGGCGGGCAAACAGTCGTTGCTGATTGGCGTTGCCACCTCCAGTCTGGCCCTGCACGCGCCGT<br>CGCAAATTGTCGCGGCGATTAAATCTCGCGCCGATCAACTGGGTGCCAGCGTGGTGGTGTCGATGGTAGAACGAA<br>GCGGCGTCGAAGCCTGTAAAGCGGCGGTGCACAATCTTCTCGCGCAACGCGTCAGTGGGCTGATCATTAACTATC<br>CGCTGGATGACCAGGATGCCATTGCTGTGGAAGCTGCCTGCACTAATGTTCCGGCGTTATTTCTTGATGTCTCTG<br>ACCAGACACCCATCAACAGTATTATTTTCTCCCATGAAGACGGTACGCGACTGGGCGTGGAGCATCTGGTCGCAT<br>TGGGTCACCAGCAAATCGCGCTGTTAGCGGGCCCATTAAGTTCTGTCTCGGCGCGTCTGCGTCTGGCTGGCTGGC<br>ATAAATATCTCACTCGCAATCAAATTCAGCCGATAGCGGAACGGGAAGGCGACTGGAGTGCCATGTCCGGTTTTC<br>AACAAACCATGCAAATGCTGAATGAGGGCATCGTTCCCACTGCGATGCTGGTTGCCAACGATCAGATGGCGCTGG<br>GCGCAATGCGCGCCATTACCGAGTCCGGGCTGCGCGTTGGTGCGGATATCTCGGTAGTGGGATACGACGATACCG<br>AAGACAGCTCATGTTATATCCCGCCGTTAACCACCATCAAACAGGATTTTCGCCTGCTGGGGCAAACCAGCGTGG<br>ACCGCTTGCTGCAACTCTCTCAGGGCCAGGCGGTGAAGGGCAATCAGCTGTTGCCCGTCTCACTGGTGAAAAGAA<br>AAACCACCCTGGCGCCCAATACGCAAACCGCCTCTCCCCGCGCGTTGGCCGATTCATTAATGCAGCTGGCACGAC<br>AGGTTTCCCGACTGGAAAGCGGGCAGTGACTGCAGCTCGAG |
| p$\sigma^{70}$ V3LacI-sfGFP (SEQ ID NO: 63)<br>GGATCCGAGCTGTTGACACTTTATGCTTCCGGCTCGTATAATGTGTGTGGAATTGTGAGCGGATAACAAGTGGAA<br>TTGTGAGCGGATAACAATTTCACACAGGAAACAGAATCATATGTCCAAAGGTGAAGAGCTGTTTACCGGCGTCGT<br>GCCCATTCTGGTGGAGCTGGATGGCGACGTCAACGGGCACAAGTTTAGCGTCCGTGGCGAAGGTGAGGGCGACGC<br>CACGAACGGTAAGCTGACGCTGAAATTCATTTGCACCACCGGCAAATTGCCTGTACCCTGGCCCACCCTGGTGAC<br>CACGCTCACCTACGGCGTACAGTGCTTCAGCCGTTACCCGGACCACATGAAGCGTCACGACTTCTTCAAAAGCGC<br>CATGCCGGAGGGTTACGTGCAGGAGCGTACGATTAGTTTCAAGGACGACGGCACCTATAAGACCCGTGCCGAAGT<br>GAAGTTCGAAGGCGATACGTTGGTGAACCGTATCGAGTTGAAGGGTATCGACTTTAAGGAAGACGGCAACATCCT<br>GGGCCATAAGCTGGAGTACAATTTCAACAGCCATAACGTTTACATCACCGCCGATAAACAGAAGAACGGCATTAA<br>AGCCAACTTTAAGATCCGCCACAACGTCGAAGACGGCTCGGTGCAGCTGGCCGACCATTATCAGCAAAACACCCC<br>CATCGGTGATGGGCCCGTGCTGCTGCCGGATAACCATTATCTGAGCACGCAGTCGGTGCTCAGCAAGGACCCTAA<br>CGAAAAGCGCGATCACATGGTGCTGCTGGAGTTCGTCACGGCGGCGGGGATCACCCATGGGATGGACGAGCTCTA<br>CAAAGACTATAAAGATGACGATGACAAGTAAAAGCTTCTCGGTACCAAATTCCAGAAAAGAGGCCTCCCGAAAGG<br>GGGGCCTTTTTTCGTTTTGGTCCGAATTCCCCCGTGGCCGGGGGACTGTTGGGCGCCATCTCCTTGCATGCACCA<br>TTCCTTGCGGCGGCGGTGCTCAACGGCCTCAACCTACTACTGGGCTGCTTCCTAATGCAGGAGTCGCATAAGGGA<br>GAGCGTCGAGATCCCGGACACCATCGAATGGCGCAAAACCTTTCGCGGTATGGCATGATAGCGCCCGGAAGAGAG<br>TCAATTCAGGGTGGTGAATGTGAAACCAGTAACGTTATACGATGTCGCAGAGTATGCCGGTGTCTCTTATCAGAC<br>CGTTTCCCGCGTGGTGAACCAGGCCAGCCACGTTTCTGCGAAAACGCGGGAAAAAGTGGAAGCGGCGATGGCGGA<br>GCTGAATTACATTCCCAACCGCGTGGCACAACAACTGGCGGGCAAACAGTCGTTGCTGATTGGCGTTGCCACCTC<br>CAGTCTGGCCCTGCACGCGCCGTCGCAAATTGTCGCGGCGATTAAATCTCGCGCCGATCAACTGGGTGCCAGCGT<br>GGTGGTGTCGATGGTAGAACGAAGCGGCGTCGAAGCCTGTAAAGCGGCGGTGCACAATCTTCTCGCGCAACGCGT<br>CAGTGGGCTGATCATTAACTATCCGCTGGATGACCAGGATGCCATTGCTGTGGAAGCTGCCTGCACTAATGTTCC<br>GGCGTTATTTCTTGATGTCTCTGACCAGACACCCATCAACAGTATTATTTTCTCCCATGAAGACGGTACGCGACT<br>GGGCGTGGAGCATCTGGTCGCATTGGGTCACCAGCAAATCGCGCTGTTAGCGGGCCCATTAAGTTCTGTCTCGGC<br>GCGTCTGCGTCTGGCTGGCTGGCATAAATATCTCACTCGCAATCAAATTCAGCCGATAGCGGAACGGGAAGGCGA<br>CTGGAGTGCCATGTCCGGTTTTCAACAAACCATGCAAATGCTGAATGAGGGCATCGTTCCCACTGCGATGCTGGT<br>TGCCAACGATCAGATGGCGCTGGGCGCAATGCGCGCCATTACCGAGTCCGGGCTGCGCGTTGGTGCGGATATCTC<br>GGTAGTGGGATACGACGATACCGAAGACAGCTCATGTTATATCCCGCCGTTAACCACCATCAAACAGGATTTTCG<br>CCTGCTGGGGCAAACCAGCGTGGACCGCTTGCTGCAACTCTCTCAGGGCCAGGCGGTGAAGGGCAATCAGCTGTT<br>GCCCGTCTCACTGGTGAAAAGAAAAACCACCCTGGCGCCCAATACGCAAACCGCCTCTCCCCGCGCGTTGGCCGA<br>TTCATTAATGCAGCTGGCACGACAGGTTTCCCGACTGGAAAGCGGGCAGTGACTGCAGCTCGAG |
| pJH0204F (SEQ ID NO: 64)<br>aaaaggatctaggtgaagatcctttttgataatctcatgaccaaaatcccttaacgtgagttttcgttccactga<br>gcgtcagaccccgtagaaaagatcaaaggatcttcttgagatcctttttttctgcgcgtaatctgctgcttgcaa<br>acaaaaaaaccaccgctaccagcggtggtttgtttgccggatcaagagctaccaactctttttccgaaggtaact<br>ggcttcagcagagcgcagataccaaatactgttcttctagtgtagccgtagttaggccaccacttcaagaactct<br>gtagcaccgcctacatacctcgctctgctaatcctgttaccagtggctgctgccagtggcgataagtcgtgtctt<br>accgggttggactcaagacgatagttaccggataaggcgcagcggtcgggctgaacggggggttcgtgcacacag |

TABLE 3-continued

| List of Plasmids |
| --- |
| cccagcttggagcgaacgacctacaccgaactgagatacctacagcgtgagctatgagaaagcgccacgcttccc<br>gaagggagaaaggcggacaggtatccggtaagcggcagggtcggaacaggagagcgcacgagggagcttccaggg<br>ggaaacgcctggtatctttatagtcctgtcgggtttcgccacctctgacttgagcgtcgatttttgtgatgctcg<br>tcaggggggcggagcctatggaaaaacgccagcaacgcggcctttttacggttcctggccttttgctggcctttt<br>gctcacatgttctttcctgcgttatcccctgattctgtggataaccgtattaccgcctttgagtgagctgatacc<br>gctcgccgcagccgaacgaccgagcgcagcgagtcagtgagcgaggaagcggaagagcgcccaatacgcaaaccg<br>cctctgggagaccagaaacaaaaaaaggccgcgttagcggccttcaataattggacctggctcctaactgatttt<br>taaggcgactgatgagtcgccttttttttgtctaatcagaagaactcgtcaagaaggcgatagaaggcgatgcgc<br>tgcgaatcgggagcggcgataccgtaaagcacgaggaagcggtcagcccattcgccgccaagctcttcagcaata<br>tcacgggtagccaacgctatgtcctgatagcggtccgccacacccagccggccacagtcgatgaatccagaaaag<br>cggccattttccaccatgatattcggcaagcaggcatcgccatgCgtcacgacgagatcctcgccgtcgggcatc<br>cgcgccttgagcctggcgaacagttcggctggcgcgagcccctgatgctcttcgtccagatcatcctgatcgaca<br>agaccggcttccatccgagtacgtgctcgctcgatgcgatgtttcgcttggtggtcgaatgggcaggtagccgga<br>tcaagcgtatgcagccgccgcattgcatcagccatgatggatactttctcggcaggagcaaggtgagatgacagg<br>agatcctgccccggcacttcgcccaatagcagccagtcccttcccgcttcagtgacaacgtcgagcacagctgcg<br>caaggaacgcccgtcgtggccagccacgatagccgcgctgcctcgtcttggagttcattcagggcaccggacagg<br>tcggtcttgacaaaaagaaccgggcgcccctgcgctgacagccggaacacggcggcatcagagcagccgattgtc<br>tgttgtgcccagtcatagccgaatagcctctccacccaagcggccggagaacctgcgtgcaatccatcttgttca<br>atcatgcgaaacgatcctcatcctgtctcttgatcagatcttgatcccctgcgccatcagatccttggcggcaag<br>aaagccatccagtttactttgcagggcttcccaaccttaccagagggcgccccagctggcaattccggttcgctt<br>gctgtccataaaaccgcccagtctagctatcgccatgtaagcccactgcaagctacctgctttctctttgcgctt<br>gcgttttcccttgtccagatagcccagtagctgacattcatccgggacgtcgtgccccaactggggtaacctttg<br>agttctctcagttgggggatcgatagtcaaaagcctccggtcggaggcttttgactagcacctcggtaccaaatt<br>ccagaaaagaggcctcccgaaaggggggccttttttcgttttggtccggatccCATATGAAGCTTGAATTCCTGC<br>AGTCTAGACCATGGctcgaggacgaacaataaggcctccctaacgggggggcctttttattgataacaaaaatcc<br>acaaggaaaaattaaaggggagataaaatccccccttttggttaactgcggccgcgtcgtggtttgtctggtca<br>accaccgcggtctcagtggtgtacggtacaaaccccgacgctagcaacgcatgagaaagcccccggaagatcacc<br>ttccgggggctttttattgcgctgcgggtgccagggcgtgcccttgggctccccgggcgcgtactcc |
| $p\sigma^{70}$ V2TcR-mCardinal/V2LacI-mCardinal (SEQ ID NO: 65)<br>ggatccGAGCTGTTGACAACTCTATCATTGATAGAGTTATAATGTTCCCTATCAGTGATAGAGACGCAGTAAGAG<br>AGGAATGTACATATGGTGAGTAAGGGTGAGGAGCTCATTAAGGAGAACATGCACATGAAGCTGTATATGGAGGGC<br>ACCGTAAACAACCACCACTTCAAGTGTACCACCGAGGGTGAAGGTAAACCCTACGAGGGGACGCAGACCCAACGC<br>ATCAAGGTCGTGGAGGGCGGCCCGCTGCCTTTCGCATTCGACATTCTGGCGACCTGTTTTATGTACGGCTCGAAG<br>ACCTTCATCAACCACACCCAAGGCATCCCGGACTTCTTCAAGCAGAGCTTCCCTGAGGGCTTCACCTGGGAGCGC<br>GTCACCACGTATGAAGACGGTGGGGTGCTCACCGTGACCCAGGACACGAGCTTGCAGGATGGCTGCTTGATTTAC<br>AACGTCAAGCTGCGCGGGGTGAACTTCCCTAGCAACGGGCCAGTGATGCAGAAAAAGACGCTGGGTTGGGAGGCC<br>ACCACCGAGACCCTGTACCCGGCCGACGGGGGGCTGGAAGGGCGGTGCGATATGGCCCTGAAATTGGTCGGCGGC<br>GGTCATTTGCACTGCAATCTCAAGACCACGTACCGCTCCAAGAAACCCGCCAAAAACCTGAAGATGCCTGGTGTT<br>TATTTTGTCGACCGGCGCCTGGAGCGCATCAAGGAAGCGGACAATGAGACGTACGTGGAACAGCACGAAGTGGCC<br>GTGGCTCGTTATTGCGATCTGCCGTCGAAGCTGGGTCACAAACTGAACGGCATGGATGAGCTGTACAAAGATTAT<br>AAGGATGATGACGACAAGTAAAAGCTTCTCGGTACCAAATTCCAGAAAAGAGGCCTCCCGAAAGGGGGGCCTTTT<br>TTCGTTTTGGTCCGAATTCTTGACAGCTAGCTCAGTCCTAGGTATAATGCTAGCCGCAGTAAGAGAGGAATGTAC<br>ACATGTCCCGCCTGGATAAATCGAAAGTGATTAACTCGGCCCTCGAATTGCTGAATGAAGTCGGTATCGAGGGGC<br>TGACGACCCGTAAATTGGCACAAAAGTTGGGGGTGGAGCAACCCACGTTGTATTGGCACGTCAAAAATAAGCGGG<br>CATTGCTGGATGCCCTCGCTATTGAAATGTTGGATCGCCACCATACCCATTTCTGTCCACTGGAGGGCGAGTCCT<br>GGCAGGACTTTCTCCGCAACAACGCGAAATCCTTTCGCTGTGCACTCTTGTCCCATCGGGACGGTGCTAAGGTGC<br>ACTTGGGCACCCGTCCCACCGAAAAACAATACGAAACCTTGGAAAATCAATTGGCGTTTTTGTGCCAGCAAGGGT<br>TTAGCTTGGAGAATGCTCTCTATGCGCTCTCGGCTGTCGGGCACTTTACGTTGGGGTGCGTGTTGGAGGACCAGG<br>AGCATCAAGTCGCAAAAGAGGAGCGTGAAACCCCAACCACGGACTCGATGCCACCTCTGCTCCGCCAAGCTATCG<br>AACTCTTCGATCATCAGGGCGCGGAGCCAGCCTTCCTCTTTGGGCTGGAGCTGATTATCTGCGGTTTGGAAAAAC<br>AACTCAAGTGTGAAAGCGGGTCCTAACTGCAGTCACTGCCCGCTTTCCAGTCGGGAAACCTGTCGTGCCAGCTGC<br>ATTAATGAATCGGCCAACGCGCGGGGAGAGGCGGTTTGCGTATTGGGCGCCAGGGTGGTTTTTCTTTTCACCAGT<br>GAGACGGGCAACAGCTGATTGCCCTTCACCGCCTGGCCCTGAGAGAGTTGCAGCAAGCGGTCCACGCTGGTTTGC<br>CCCAGCAGGCGAAAATCCTGTTTGATGGTGGTTAACGGCGGGATATAACATGAGCTGTCTTCGGTATCGTCGTAT<br>CCCACTACCGAGATATCCGCACCAACGCGCAGCCCGGACTCGGTAATGGCGCGCATTGCGCCCAGCGCCATCTGA<br>TCGTTGGCAACCAGCATCGCAGTGGGAACGATGCCCTCATTCAGCATTTGCATGGTTTGTTGAAAACCGGACATG<br>GCACTCCAGTCGCCTTCCCGTTCCGCTATCGGCTGAATTTGATTGCGAGTGAGATATTTATGCCAGCCAGCCAGA<br>CGCAGACGCGCCGAGACAGAACTTAATGGGCCCGCTAACAGCGCGATTTGCTGGTGACCCAATGCGACCAGATGC<br>TCCACGCCCAGTCGCGTACCGTCTTCATGGGAGAAAATAATACTGTTGATGGGTGTCTGGTCAGAGACATCAAGA<br>AATAACGCCGGAACATTAGTGCAGGCAGCTTCCACAGCAATGGCATCCTGGTCATCCAGCGGATAGTTAATGATC<br>AGCCCACTGACGCGTTGCGCGAGAAGATTGTGCACCGCCGCTTTACAGGCTTCGACGCCGCTTCGTTCTACCATC<br>GACACCACCACGCTGGCACCCAGTTGATCGGCGCGAGATTTAATCGCCGCGACAATTTGCGACGGCGCGTGCAGG<br>GCCAGACTGGAGGTGGCAACGCCAATCAGCAACGACTGTTTGCCCGCCAGTTGTTGTGCCACGCGGTTGGGAATG<br>TAATTCAGCTCCGCCATCGCCGCTTCCACTTTTTCCCGCGTTTTCGCAGAAACGTGGCTGGCCTGGTTCACCACG<br>CGGGAAACGGTCTGATAAGAGACACCGGCATACTCTGCGACATCGTATAACGTTACTGGTTTCACATTCACCACC<br>CTGAATTGACTCTCTTCCGGGCGCTATCATGCCATACCGCGAAAGGTTTTGCGCCATTCGATGGTGTCCGGGATC<br>TCGACGCTCTCCCTTATGCGACTCCTGCATTAGGAAGCAGCCCAGTAGTAGGTTGAGGCCGTTGAGCACCGCCGC<br>CGCAAGGAATGGTGCATGCAAGGAGATGGCGCCCAACAGTCCCCCGGCCACGGGGagtcaaaagcctccggtcgg<br>aggcttttgactTCTAGAGAGCTGTTGACACTTTATGCTTCCGGCTCGTATAATGTGTGTGGAATTGTGAGCGGA<br>TAACAACGCAGTAAGAGAGGAATGTACCCATGGTGAGTAAGGGTGAGGAGCTCATTAAGGAGAACATGCACATGA<br>AGCTGTATATGGAGGGCACCGTAAACAACCACCACTTCAAGTGTACCACCGAGGGTGAAGGTAAACCCTACGAGG<br>GGACGCAGACCCAACGCATCAAGGTCGTGGAGGGCGGCCCGCTGCCTTTCGCATTCGACATTCTGGCGACCTGTT<br>TTATGTACGGCTCGAAGACCTTCATCAACCACACCCAAGGCATCCCGGACTTCTTCAAGCAGAGCTTCCCTGAGG<br>GCTTCACCTGGGAGCGCGTCACCACGTATGAAGACGGTGGGGTGCTCACCGTGACCCAGGACACGAGCTTGCAGG<br>ATGGCTGCTTGATTTACAACGTCAAGCTGCGCGGGGTGAACTTCCCTAGCAACGGGCCAGTGATGCAGAAAAAGA<br>CGCTGGGTTGGGAGGCCACCACCGAGACCCTGTACCCGGCCGACGGGGGGCTGGAAGGGCGGTGCGATATGGCCC<br>TGAAATTGGTCGGCGGCGGTCATTTGCACTGCAATCTCAAGACCACGTACCGCTCCAAGAAACCCGCCAAAAACC |

TABLE 3-continued

List of Plasmids

TGAAGATGCCTGGTGTTTATTTTGTCGACCGGCGCCTGGAGCGCATCAAGGAAGCGGACAATGAGACGTACGTGG
AACAGCACGAAGTGGCCGTGGCTCGTTATTGCGATCTGCCGTCGAAGCTGGGTCACAAACTGAACGGCATGGATG
AGCTGTACAAAGATTATAAGGATGATGACGACAAGTAACTCGAG p$\sigma^{70}$ V2TcR-mCardinal/V3LacI-mCardinal (SEQ ID NO: 66)
ggatccGAGCTGTTGACAACTCTATCATTGATAGAGTTATAATGTTCCCTATCAGTGATAGAGACGCAGTAAGAG
AGGAATGTACATATGGTGAGTAAGGGTGAGGAGCTCATTAAGGAGAACATGCACATGAAGCTGTATATGGAGGGC
ACCGTAAACAACCACCACTTCAAGTGTACCACCGAGGGTGAAGGTAAACCCTACGAGGGGACGCAGACCCAACGC
ATCAAGGTCGTGGAGGGCGGCCCGCTGCCTTTCGCATTCGACATTCTGGCGACCTGTTTTATGTACGGCTCGAAG
ACCTTCATCAACCACACCCAAGGCATCCCGGACTTCTTCAAGCAGAGCTTCCCTGAGGGCTTCACCTGGGAGCGC
GTCACCACGTATGAAGACGGTGGGGTGCTCACCGTGACCCAGGACACGAGCTTGCAGGATGGCTGCTTGATTTAC
AACGTCAAGCTGCGCGGGGTGAACTTCCCTAGCAACGGGCCAGTGATGCAGAAAAAGACGCTGGGTTGGGAGGCC
ACCACCGAGACCCTGTACCCGGCCGACGGGGGGCTGGAAGGGCGGTGCGATATGGCCCTGAAATTGGTCGGCGGC
GGTCATTTGCACTGCAATCTCAAGACCACGTACCGCTCCAAGAAACCCGCCAAAAACCTGAAGATGCCTGGTGTT
TATTTTGTCGACCGGCGCCTGGAGCGCATCAAGGAAGCGGACAATGAGACGTACGTGGAACAGCACGAAGTGGCC
GTGGCTCGTTATTGCGATCTGCCGTCGAAGCTGGGTCACAAACTGAACGGCATGGATGAGCTGTACAAAGATTAT
AAGGATGATGACGACAAGTAAAAGCTTCTCGGTACCAAATTCCAGAAAAGAGGCCTCCCGAAAGGGGGGCCTTTT
TTCGTTTTGGTCCGAATTCTTGACAGCTAGCTCAGTCCTAGGTATAATGCTAGCCGCAGTAAGAGAGGAATGTAC
ACATGTCCCGCCTGGATAAATCGAAAGTGATTAACTCGGCCCTCGAATTGCTGAATGAAGTCGGTATCGAGGGGC
TGACGACCCGTAAATTGGCACAAAAGTTGGGGGTGGAGCAACCCACGTTGTATTGGCACGTCAAAAATAAGCGGG
CATTGCTGGATGCCCTCGCTATTGAAATGTTGGATCGCCACCATACCCATTTCTGTCCACTGGAGGGCGAGTCCT
GGCAGGACTTTCTCCGCAACAACGCGAAATCCTTTCGCTGTGCACTCTTGTCCCATCGGGACGGTGCTAAGGTGC
ACTTGGGCACCCGTCCCACCGAAAAACAATACGAAACCTTGGAAAATCAATTGGCGTTTTTGTGCCAGCAAGGGT
TTAGCTTGGAGAATGCTCTCTATGCGCTCTCGGCTGTCGGGCACTTTACGTTGGGGTGCGTGTTGGAGGACCAGG
AGCATCAAGTCGCAAAAGAGGAGCGTGAAACCCCAACCACGGACTCGATGCCACCTCTGCTCCGCCAAGCTATCG
AACTCTTCGATCATCAGGGCGCGGAGCCAGCCTTCCTCTTTGGGCTGGAGCTGATTATCTGCGGTTTGGAAAAAC
AACTCAAGTGTGAAAGCGGGTCCTAACTGCAGTCACTGCCCGCTTTCCAGTCGGGAAACCTGTCGTGCCAGCTGC
ATTAATGAATCGGCCAACGCGCGGGGAGAGGCGGTTTGCGTATTGGGCGCCAGGGTGGTTTTTCTTTTCACCAGT
GAGACGGGCAACAGCTGATTGCCCTTCACCGCCTGGCCCTGAGAGAGTTGCAGCAAGCGGTCCACGCTGGTTTGC
CCCAGCAGGCGAAAATCCTGTTTGATGGTGGTTAACGGCGGGATATAACATGAGCTGTCTTCGGTATCGTCGTAT
CCCACTACCGAGATATCCGCACCAACGCGCAGCCCGGACTCGGTAATGGCGCGCATTGCGCCCAGCGCCATCTGA
TCGTTGGCAACCAGCATCGCAGTGGGAACGATGCCCTCATTCAGCATTTGCATGGTTTGTTGAAAACCGGACATG
GCACTCCAGTCGCCTTCCCGTTCCGCTATCGGCTGAATTTGATTGCGAGTGAGATATTTATGCCAGCCAGCCAGA
CGCAGACGCGCCGAGACAGAACTTAATGGGCCCGCTAACAGCGCGATTTGCTGGTGACCCAATGCGACCAGATGC
TCCACGCCCAGTCGCGTACCGTCTTCATGGGAGAAAATAATACTGTTGATGGGTGTCTGGTCAGAGACATCAAGA
AATAACGCCGGAACATTAGTGCAGGCAGCTTCCACAGCAATGGCATCCTGGTCATCCAGCGGATAGTTAATGATC
AGCCCACTGACGCGTTGCGCGAGAAGATTGTGCACCGCCGCTTTACAGGCTTCGACGCCGCTTCGTTCTACCATC
GACACCACCACGCTGGCACCCAGTTGATCGGCGCGAGATTTAATCGCCGCGACAATTTGCGACGGCGCGTGCAGG
GCCAGACTGGAGGTGGCAACGCCAATCAGCAACGACTGTTTGCCCGCCAGTTGTTGTGCCACGCGGTTGGGAATG
TAATTCAGCTCCGCCATCGCCGCTTCCACTTTTTCCCGCGTTTTCGCAGAAACGTGGCTGGCCTGGTTCACCACG
CGGGAAACGGTCTGATAAGAGACACCGGCATACTCTGCGACATCGTATAACGTTACTGGTTTCACATTCACCACC
CTGAATTGACTCTCTTCCGGGCGCTATCATGCCATACCGCGAAAGGTTTTGCGCCATTCGATGGTGTCCGGGATC
TCGACGCTCTCCCTTATGCGACTCCTGCATTAGGAAGCAGCCCAGTAGTAGGTTGAGGCCGTTGAGCACCGCCGC
CGCAAGGAATGGTGCATGCAAGGAGATGGCGCCCAACAGTCCCCCGGCCACGGGGagtcaaaagcctccggtcgg
aggcttttgactTCTAGAGAGCTGTTGACACTTTATGCTTCCGGCTCGTATAATGTGTGGAATTGTGAGCGGA
TAACAAGTGGAATTGTGAGCGGATAACAATTTCACACAGGAAACAGAATCCCATGGTGAGTAAGGGTGAGGAGCT
CATTAAGGAGAACATGCACATGAAGCTGTATATGGAGGGCACCGTAAACAACCACCACTTCAAGTGTACCACCGA
GGGTGAAGGTAAACCCTACGAGGGGACGCAGACCCAACGCATCAAGGTCGTGGAGGGCGGCCCGCTGCCTTTCGC
ATTCGACATTCTGGCGACCTGTTTTATGTACGGCTCGAAGACCTTCATCAACCACACCCAAGGCATCCCGGACTT
CTTCAAGCAGAGCTTCCCTGAGGGCTTCACCTGGGAGCGCGTCACCACGTATGAAGACGGTGGGGTGCTCACCGT
GACCCAGGACACGAGCTTGCAGGATGGCTGCTTGATTTACAACGTCAAGCTGCGCGGGGTGAACTTCCCTAGCAA
CGGGCCAGTGATGCAGAAAAAGACGCTGGGTTGGGAGGCCACCACCGAGACCCTGTACCCGGCCGACGGGGGGCT
GGAAGGGCGGTGCGATATGGCCCTGAAATTGGTCGGCGGCGGTCATTTGCACTGCAATCTCAAGACCACGTACCG
CTCCAAGAAACCCGCCAAAAACCTGAAGATGCCTGGTGTTTATTTTGTCGACCGGCGCCTGGAGCGCATCAAGGA
AGCGGACAATGAGACGTACGTGGAACAGCACGAAGTGGCCGTGGCTCGTTATTGCGATCTGCCGTCGAAGCTGGG
TCACAAACTGAACGGCATGGATGAGCTGTACAAAGATTATAAGGATGATGACGACAAGTAACTCGAG p$\sigma^{70}$ V2TcR-sfGFP/V2LacI-mCardinal (SEQ ID NO: 67)
ggatccGAGCTGTTGACAACTCTATCATTGATAGAGTTATAATGTTCCCTATCAGTGATAGAGACGCAGTAAGAG
AGGAATGTACATATGTCCAAAGGTGAAGAGCTGTTTACCGGCGTCGTGCCCATTCTGGTGGAGCTGGATGGCGAC
GTCAACGGGCACAAGTTTAGCGTCCGTGGCGAAGGTGAGGGCGACGCCACGAACGGTAAGCTGACGCTGAAATTC
ATTTGCACCACCGGCAAATTGCCTGTACCCTGGCCCACCCTGGTGACCACGCTCACCTACGGCGTACAGTGCTTC
AGCCGTTACCCGGACCACATGAAGCGTCACGACTTCTTCAAAAGCGCCATGCCGGAGGGTTACGTGCAGGAGCGT
ACGATTAGTTTCAAGGACGACGGCACCTATAAGACCCGTGCCGAAGTGAAGTTCGAAGGCGATACGTTGGTGAAC
CGTATCGAGTTGAAGGGTATCGACTTTAAGGAAGACGGCAACATCCTGGGCCATAAGCTGGAGTACAATTTCAAC
AGCCATAACGTTTACATCACCGCCGATAAACAGAAGAACGGCATTAAAGCCAACTTTAAGATCCGCCACAACGTC
GAAGACGGCTCGGTGCAGCTGGCCGACCATTATCAGCAAAACACCCCCATCGGTGATGGCCCGTGCTGCTGCCG
GATAACCATTATCTGAGCACGCAGTCGGTGCTCAGCAAGGACCCTAACGAAAAGCGCGATCACATGGTGCTGCTG
GAGTTCGTCACGGCGGCGGGGATCACCCATGGGATGGACGAGCTCTACAAAGACTATAAAGATGACGATGACAAG
TAAAAGCTTCTCGGTACCAAATTCCAGAAAAGAGGCCTCCCGAAAGGGGGGCCTTTTTTCGTTTTGGTCCGAATT
CTTGACAGCTAGCTCAGTCCTAGGTATAATGCTAGCCGCAGTAAGAGAGGAATGTACACATGTCCCGCCTGGATA
AATCGAAAGTGATTAACTCGGCCCTCGAATTGCTGAATGAAGTCGGTATCGAGGGGCTGACGACCCGTAAATTGG
CACAAAAGTTGGGGGTGGAGCAACCCACGTTGTATTGGCACGTCAAAAATAAGCGGGCATTGCTGGATGCCCTCG
CTATTGAAATGTTGGATCGCCACCATACCCATTTCTGTCCACTGGAGGGCGAGTCCTGGCAGGACTTTCTCCGCA
ACAACGCGAAATCCTTTCGCTGTGCACTCTTGTCCCATCGGGACGGTGCTAAGGTGCACTTGGGCACCCGTCCCA
CCGAAAAACAATACGAAACCTTGGAAAATCAATTGGCGTTTTTGTGCCAGCAAGGGTTTAGCTTGGAGAATGCTC
TCTATGCGCTCTCGGCTGTCGGGCACTTTACGTTGGGGTGCGTGTTGGAGGACCAGGAGCATCAAGTCGCAAAAG
AGGAGCGTGAAACCCCAACCACGGACTCGATGCCACCTCTGCTCCGCCAAGCTATCGAACTCTTCGATCATCAGG TABLE 3-continued List of Plasmids GCGCGGAGCCAGCCTTCCTCTTTGGGCTGGAGCTGATTATCTGCGGTTTGGAAAAACAACTCAAGTGTGAAAGCG
GGTCCTAACTGCAGTCACTGCCCGCTTTCCAGTCGGGAAACCTGTCGTGCCAGCTGCATTAATGAATCGGCCAAC
GCGCGGGGAGAGGCGGTTTGCGTATTGGGCGCCAGGGTGGTTTTTCTTTTCACCAGTGAGACGGGCAACAGCTGA
TTGCCCTTCACCGCCTGGCCCTGAGAGAGTTGCAGCAAGCGGTCCACGCTGGTTTGCCCCAGCAGGCGAAAATCC
TGTTTGATGGTGGTTAACGGCGGGATATAACATGAGCTGTCTTCGGTATCGTCGTATCCCACTACCGAGATATCC
GCACCAACGCGCAGCCCGGACTCGGTAATGGCGCGCATTGCGCCCAGCGCCATCTGATCGTTGGCAACCAGCATC
GCAGTGGGAACGATGCCCTCATTCAGCATTTGCATGGTTTGTTGAAAACCGGACATGGCACTCCAGTCGCCTTCC
CGTTCCGCTATCGGCTGAATTTGATTGCGAGTGAGATATTTATGCCAGCCAGCCAGACGCAGACGCGCCGAGACA
GAACTTAATGGGCCCGCTAACAGCGCGATTTGCTGGTGACCCAATGCGACCAGATGCTCCACGCCCAGTCGCGTA
CCGTCTTCATGGGAGAAAATAATACTGTTGATGGGTGTCTGGTCAGAGACATCAAGAAATAACGCCGGAACATTA
GTGCAGGCAGCTTCCACAGCAATGGCATCCTGGTCATCCAGCGGATAGTTAATGATCAGCCCACTGACGCGTTGC
GCGAGAAGATTGTGCACCGCCGCTTTACAGGCTTCGACGCCGCTTCGTTCTACCATCGACACCACCACGCTGGCA
CCCAGTTGATCGGCGCGAGATTTAATCGCCGCGACAATTTGCGACGGCGCGTGCAGGGCCAGACTGGAGGTGGCA
ACGCCAATCAGCAACGACTGTTTGCCCGCCAGTTGTTGTGCCACGCGGTTGGGAATGTAATTCAGCTCCGCCATC
GCCGCTTCCACTTTTTCCCGCGTTTTCGCAGAAACGTGGCTGGCCTGGTTCACCACGCGGGAAACGGTCTGATAA
GAGACACCGGCATACTCTGCGACATCGTATAACGTTACTGGTTTCACATTCACCACCCTGAATTGACTCTCTTCC
GGGCGCTATCATGCCATACCGCGAAAGGTTTTGCGCCATTCGATGGTGTCCGGGATCTCGACGCTCTCCCTTATG
CGACTCCTGCATTAGGAAGCAGCCCAGTAGTAGGTTGAGGCCGTTGAGCACCGCCGCCGCAAGGAATGGTGCATG
CAAGGAGATGGCGCCCAACAGTCCCCCGGCCACGGGGagtcaaaagcctccggtcggaggcttttgactTCTAGA
GAGCTGTTGACACTTTATGCTTCCGGCTCGTATAATGTGTGTGGAATTGTGAGCGGATAACAACGCAGTAAGAGA
GGAATGTACCCATGGTGAGTAAGGGTGAGGAGCTCATTAAGGAGAACATGCACATGAAGCTGTATATGGAGGGCA
CCGTAAACAACCACCACTTCAAGTGTACCACCGAGGGTGAAGGTAAACCCTACGAGGGGACGCAGACCCAACGCA
TCAAGGTCGTGGAGGGCGGCCCGCTGCCTTTCGCATTCGACATTCTGGCGACCTGTTTTATGTACGGCTCGAAGA
CCTTCATCAACCACACCCAAGGCATCCCGGACTTCTTCAAGCAGAGCTTCCCTGAGGGCTTCACCTGGGAGCGCG
TCACCACGTATGAAGACGGTGGGGTGCTCACCGTGACCCAGGACACGAGCTTGCAGGATGGCTGCTTGATTTACA
ACGTCAAGCTGCGCGGGGTGAACTTCCCTAGCAACGGGCCAGTGATGCAGAAAAAGACGCTGGGTTGGGAGGCCA
CCACCGAGACCCTGTACCCGGCCGACGGGGGGCTGGAAGGGCGGTGCGATATGGCCCTGAAATTGGTCGGCGGCG
GTCATTTGCACTGCAATCTCAAGACCACGTACCGCTCCAAGAAACCCGCCAAAAACCTGAAGATGCCTGGTGTTT
ATTTTGTCGACCGGCGCCTGGAGCGCATCAAGGAAGCGGACAATGAGACGTACGTGGAACAGCACGAAGTGGCCG
TGGCTCGTTATTGCGATCTGCCGTCGAAGCTGGGTCACAAACTGAACGGCATGGATGAGCTGTACAAAGATTATA
AGGATGATGACGACAAGTAACTCGAG p$\sigma^{70}$ V2TcR-sfGFP/V3LacI-mCardinal (SEQ ID NO: 68)
ggatccGAGCTGTTGACAACTCTATCATTGATAGAGTTATAATGTTCCCTATCAGTGATAGAGACGCAGTAAGAG
AGGAATGTACATATGTCCAAAGGTGAAGAGCTGTTTACCGGCGTCGTGCCCATTCTGGTGGAGCTGGATGGCGAC
GTCAACGGGCACAAGTTTAGCGTCCGTGGCGAAGGTGAGGGCGACGCCACGAACGGTAAGCTGACGCTGAAATTC
ATTTGCACCACCGGCAAATTGCCTGTACCCTGGCCCACCCTGGTGACCACGCTCACCTACGGCGTACAGTGCTTC
AGCCGTTACCCGGACCACATGAAGCGTCACGACTTCTTCAAAAGCGCCATGCCGGAGGGTTACGTGCAGGAGCGT
ACGATTAGTTTCAAGGACGACGGCACCTATAAGACCCGTGCCGAAGTGAAGTTCGAAGGCGATACGTTGGTGAAC
CGTATCGAGTTGAAGGGTATCGACTTTAAGGAAGACGGCAACATCCTGGGCCATAAGCTGGAGTACAATTTCAAC
AGCCATAACGTTTACATCACCGCCGATAAACAGAAGAACGGCATTAAAGCCAACTTTAAGATCCGCCACAACGTC
GAAGACGGCTCGGTGCAGCTGGCCGACCATTATCAGCAAAACACCCCCATCGGTGATGGGCCCGTGCTGCTGCCG
GATAACCATTATCTGAGCACGCAGTCGGTGCTCAGCAAGGACCCTAACGAAAAGCGCGATCACATGGTGCTGCTG
GAGTTCGTCACGGCGGCGGGGATCACCCATGGGATGGACGAGCTCTACAAAGACTATAAAGATGACGATGACAAG
TAAAAGCTTCTCGGTACCAAATTCCAGAAAAGAGGCCTCCCGAAAGGGGGGCCTTTTTTCGTTTTGGTCCGAATT
CTTGACAGCTAGCTCAGTCCTAGGTATAATGCTAGCCGCAGTAAGAGAGGAATGTACACATGTCCCGCCTGGATA
AATCGAAAGTGATTAACTCGGCCCTCGAATTGCTGAATGAAGTCGGTATCGAGGGGCTGACGACCCGTAAATTGG
CACAAAAGTTGGGGGTGGAGCAACCCACGTTGTATTGGCACGTCAAAAATAAGCGGGCATTGCTGGATGCCCTCG
CTATTGAAATGTTGGATCGCCACCATACCCATTTCTGTCCACTGGAGGGCGAGTCCTGGCAGGACTTTCTCCGCA
ACAACGCGAAATCCTTTCGCTGTGCACTCTTGTCCCATCGGGACGGTGCTAAGGTGCACTTGGGCACCCGTCCCA
CCGAAAAACAATACGAAACCTTGGAAAATCAATTGGCGTTTTTGTGCCAGCAAGGGTTTAGCTTGGAGAATGCTC
TCTATGCGCTCTCGGCTGTCGGGCACTTTACGTTGGGGTGCGTGTTGGAGGACCAGGAGCATCAAGTCGCAAAAG
AGGAGCGTGAAACCCCAACCACGGACTCGATGCCACCTCTGCTCCGCCAAGCTATCGAACTCTTCGATCATCAGG
GCGCGGAGCCAGCCTTCCTCTTTGGGCTGGAGCTGATTATCTGCGGTTTGGAAAAACAACTCAAGTGTGAAAGCG
GGTCCTAACTGCAGTCACTGCCCGCTTTCCAGTCGGGAAACCTGTCGTGCCAGCTGCATTAATGAATCGGCCAAC
GCGCGGGGAGAGGCGGTTTGCGTATTGGGCGCCAGGGTGGTTTTTCTTTTCACCAGTGAGACGGGCAACAGCTGA
TTGCCCTTCACCGCCTGGCCCTGAGAGAGTTGCAGCAAGCGGTCCACGCTGGTTTGCCCCAGCAGGCGAAAATCC
TGTTTGATGGTGGTTAACGGCGGGATATAACATGAGCTGTCTTCGGTATCGTCGTATCCCACTACCGAGATATCC
GCACCAACGCGCAGCCCGGACTCGGTAATGGCGCGCATTGCGCCCAGCGCCATCTGATCGTTGGCAACCAGCATC
GCAGTGGGAACGATGCCCTCATTCAGCATTTGCATGGTTTGTTGAAAACCGGACATGGCACTCCAGTCGCCTTCC
CGTTCCGCTATCGGCTGAATTTGATTGCGAGTGAGATATTTATGCCAGCCAGCCAGACGCAGACGCGCCGAGACA
GAACTTAATGGGCCCGCTAACAGCGCGATTTGCTGGTGACCCAATGCGACCAGATGCTCCACGCCCAGTCGCGTA
CCGTCTTCATGGGAGAAAATAATACTGTTGATGGGTGTCTGGTCAGAGACATCAAGAAATAACGCCGGAACATTA
GTGCAGGCAGCTTCCACAGCAATGGCATCCTGGTCATCCAGCGGATAGTTAATGATCAGCCCACTGACGCGTTGC
GCGAGAAGATTGTGCACCGCCGCTTTACAGGCTTCGACGCCGCTTCGTTCTACCATCGACACCACCACGCTGGCA
CCCAGTTGATCGGCGCGAGATTTAATCGCCGCGACAATTTGCGACGGCGCGTGCAGGGCCAGACTGGAGGTGGCA
ACGCCAATCAGCAACGACTGTTTGCCCGCCAGTTGTTGTGCCACGCGGTTGGGAATGTAATTCAGCTCCGCCATC
GCCGCTTCCACTTTTTCCCGCGTTTTCGCAGAAACGTGGCTGGCCTGGTTCACCACGCGGGAAACGGTCTGATAA
GAGACACCGGCATACTCTGCGACATCGTATAACGTTACTGGTTTCACATTCACCACCCTGAATTGACTCTCTTCC
GGGCGCTATCATGCCATACCGCGAAAGGTTTTGCGCCATTCGATGGTGTCCGGGATCTCGACGCTCTCCCTTATG
CGACTCCTGCATTAGGAAGCAGCCCAGTAGTAGGTTGAGGCCGTTGAGCACCGCCGCCGCAAGGAATGGTGCATG
CAAGGAGATGGCGCCCAACAGTCCCCCGGCCACGGGGagtcaaaagcctccggtcggaggcttttgactTCTAGA
GAGCTGTTGACACTTTATGCTTCCGGCTCGTATAATGTGTGTGGAATTGTGAGCGGATAACAAGTGGAATTGTGA
GCGGATAACAATTTCACACAGGAAACAGAATCCCATGGTGAGTAAGGGTGAGGAGCTCATTAAGGAGAACATGCA
CATGAAGCTGTATATGGAGGGCACCGTAAACAACCACCACTTCAAGTGTACCACCGAGGGTGAAGGTAAACCCTA
CGAGGGGACGCAGACCCAACGCATCAAGGTCGTGGAGGGCGGCCCGCTGCCTTTCGCATTCGACATTCTGGCGAC
CTGTTTTATGTACGGCTCGAAGACCTTCATCAACCACACCCAAGGCATCCCGGACTTCTTCAAGCAGAGCTTCCC
TGAGGGCTTCACCTGGGAGCGCGTCACCACGTATGAAGACGGTGGGGTGCTCACCGTGACCCAGGACACGAGCTT TABLE 3-continued List of Plasmids GCAGGATGGCTGCTTGATTTACAACGTCAAGCTGCGCGGGGTGAACTTCCCTAGCAACGGGCCAGTGATGCAGAA
AAAGACGCTGGGTTGGGAGGCCACCACCGAGACCCTGTACCCGGCCGACGGGGGGCTGGAAGGGCGGTGCGATAT
GGCCCTGAAATTGGTCGGCGGCGGTCATTTGCACTGCAATCTCAAGACCACGTACCGCTCCAAGAAACCCGCCAA
AAACCTGAAGATGCCTGGTGTTTATTTTGTCGACCGGCGCCTGGAGCGCATCAAGGAAGCGGACAATGAGACGTA
CGTGGAACAGCACGAAGTGGCCGTGGCTCGTTATTGCGATCTGCCGTCGAAGCTGGGTCACAAACTGAACGGCAT
GGATGAGCTGTACAAAGATTATAAGGATGATGACGACAAGTAACTCGAG pUC19-crtEBI (SEQ ID NO: 69)
CATATGTATCCGTTTATAAGGACAGCCCGAATGACGGTCTGCGCAAAAAAACACGTTCATCTCACTCGCGATGCT
GCGGAGCAGTTACTGGCTGATATTGATCGACGCCTTGATCAGTTATTGCCCGTGGAGGGAGAACGGGATGTTGTG
GGTGCCGCGATGCGTGAAGGTGCGCTGGCACCGGGAAAACGTATTCGCCCCATGTTGCTGTTGCTGACCGCCCGC
GATCTGGGTTGCGCTGTCAGCCATGACGGATTACTGGATTTGGCCTGTGCGGTGGAAATGGTCCACGCGGCTTCG
CTGATCCTTGACGATATGCCCTGCATGGACGATGCGAAGCTGCGGCGCGGACGCCCTACCATTCATTCTCATTAC
GGAGAGCATGTGGCAATACTGGCGGCGGTTGCCTTGCTGAGTAAAGCCTTTGGCGTAATTGCCGATGCAGATGGC
CTCACGCCGCTGGCAAAAAATCGGGCGGTTTCTGAACTGTCAAACGCCATCGGCATGCAAGGATTGGTTCAGGGT
CAGTTCAAGGATCTGTCTGAAGGGGATAAGCCGCGCAGCGCTGAAGCTATTTTGATGACGAATCACTTTAAAACC
AGCACGCTGTTTTGTGCCTCCATGCAGATGGCCTCGATTGTTGCGAATGCCTCCAGCGAAGCGCGTGATTGCCTG
CATCGTTTTTCACTTGATCTTGGTCAGGCATTTCAACTGCTGGACGATTTGACCGATGGCATGACCGACACCGGT
AAGGATAGCAATCAGGACGCCGGTAAATCGACGCTGGTCAATCTGTTAGGCCCGAGGGCGGTTGAAGAACGTCTG
AGACAACATCTTCAGCTTGCCAGTGAGCATCTCTCTGCGGCCTGCCAACACGGGCACGCCACTCAACATTTTATT
CAGGCCTGGTTTGACAAAAAACTCGCTGCCGTCAGTTAACGCAGTAAGAGAGGAATGTAGATATGAATAATCCGT
CGTTACTCAATCATGCGGTCGAAACGATGGCAGTTGGCTCGAAAAGTTTTGCGACAGCCTCAAAGTTATTTGATG
CAAAAACCCGGCGCAGCGTACTGATGCTCTACGCCTGGTGCCGCCATTGTGACGATGTTATTGACGATCAGACGC
TGGGCTTTCAGGCCCGGCAGCCTGCCTTACAAACGCCCGAACAACGTCTGATGCAACTTGAGATGAAAACGCGCC
AGGCCTATGCAGGATCGCAGATGCACGAACCGGCGTTTGCGGCTTTTCAGGAAGTGGCTATGGCTCATGATATCG
CCCCGGCTTACGCGTTTGATCATCTGGAAGGCTTCGCCATGGATGTACGCGAAGCGCAATACAGCCAACTGGATG
ATACGCTGCGCTATTGCTATCACGTTGCAGGCGTTGTCGGCTTGATGATGGCGCAAATCATGGGCGTGCGGGATA
ACGCCACGCTGGACCGCGCCTGTGACCTTGGGCTGGCATTTCAGTTGACCAATATTGCTCGCGATATTGTGGACG
ATGCGCATGCGGGCCGCTGTTATCTGCCGGCAAGCTGGCTGGAGCATGAAGGTCTGAACAAAGAGAATTATGCGG
CACCTGAAAACCGTCAGGCGCTGAGCCGTATCGCCCGTCGTTTGGTGCAGGAAGCAGAACCTTACTATTTGTCTG
CCACAGCCGGCCTGGCAGGGTTGCCCCTGCGTTCCGCCTGGGCAATCGCTACGGCGAAGCAGGTTTACCGGAAAA
TAGGTGTCAAAGTTGAACAGGCCGGTCAGCAAGCCTGGGATCAGCGGCAGTCAACGACCACGCCCGAAAAATTAA
CGCTGCTGCTGGCCGCCTCTGGTCAGGCCCTTACTTCCCGGATGCGGGCTCATCCTCCCCGCCCTGCGCATCTCT
GGCAGCGCCCGCTCTGAAATAATTTTGTTTAACTTTAAGAAGGAGATATAATGAAACCAACTACGGTAATTGGTG
CAGGCTTCGGTGGCCTGGCACTGGCAATTCGTCTACAAGCTGCGGGGATTCCCGTCTTACTGCTTGAACAACGTG
ATAAACCCGGCGGTCGGGCTTATGTCTACGAGGATCAGGGGTTTACCTTTGATGCAGGCCCGACGGTTATCACCG
ATCCCAGTGCCATTGAAGAACTGTTTGCACTGGCAGGAAAACAGTTAAAAGAGTATGTCGAACTGCTGCCGGTTA
CGCCGTTTTACCGCCTGTGTTGGGAGTCAGGGAAGGTCTTTAATTACGATAACGATCAAACCCGGCTCGAAGCGC
AGATTCAGCAGTTTAATCCCCGCGATGTCGAAGGTTATCGTCAGTTTCTGGACTATTCACGCGCGGTGTTTAAAG
AAGGCTATCTAAAGCTCGGTACTGTCCCTTTTTTATCGTTCAGAGACATGCTTCGCGCCGCACCTCAACTGGCGA
AACTGCAGGCATGGAGAAGCGTTTACAGTAAGGTTGCCAGTTACATCGAAGATGAACATCTGCGCCAGGCGTTTT
CTTTCCACTCGCTGTTGGTGGGCGGCAATCCCTTCGCCACCTCATCCATTTATACGTTGATACACGCGCTGGAGC
GTGAGTGGGGCGTCTGGTTTCCGCGTGGCGGCACCGGCGCATTAGTTCAGGGGATGATAAAGCTGTTTCAGGATC
TGGGTGGCGAAGTCGTGTTAAACGCCAGAGTCAGCCACATGGAAACGACAGGAAACAAGATTGAAGCCGTGCATT
TAGAGGACGGTCGCAGGTTCCTGACGCAAGCCGTCGCGTCAAATGCAGATGTGGTTCATACCTATCGCGACCTGT
TAAGCCAGCACCCTGCCGCGGTTAAGCAGTCCAACAAACTGCAGACTAAGCGCATGAGTAACTCTCTGTTTGTGC
TCTATTTTGGTTTGAATCACCATCATGATCAGCTCGCGCATCACACGGTTTGTTTCGGCCCGCGTTACCGCGAGC
TGATTGACGAAATTTTTAATCATGATGGCCTCGCAGAGGACTTCTCACTTTATCTGCACGCGCCCTGTGTCACGG
ATTCGTCACTGGCGCCTGAAGGTTGCGGCAGTTACTATGTGTTGGCGCCGGTGCCGCATTTAGGCACCGCGAACC
TCGACTGGACGGTTGAGGGGCCAAAACTACGCGACCGTATTTTTGCGTACCTTGAGCAGCATTACATGCCTGGCT
TACGGAGTCAGCTGGTCACGCACCGGATGTTTACGCCGTTTGATTTTCGCGACCAGCTTAATGCCTATCATGGCT
CAGCCTTTTCTGTGGAGCCCGTTCTTACCCAGAGCGCCTGGTTTCGGCCGCATAACCGCGATAAAACCATTACTA
ATCTCTACCTGGTCGGCGCAGGCACGCATCCCGGCGCAGGCATTCCTGGCGTCATCGGCTCGGCAAAAGCGACAG
CAGGTTTGATGCTGGAGGATCTGATTTGA p$\sigma^{70}$ V2TcR-crtEBI (SEQ ID NO: 70)
GGATCCGAGCTGTTGACAACTCTATCATTGATAGAGTTATAATGTTCCCTATCAGTGATAGAGACGCAGTAAGAG
AGGAATGTACATATGTATCCGTTTATAAGGACAGCCCGAATGACGGTCTGCGCAAAAAAACACGTTCATCTCACT
CGCGATGCTGCGGAGCAGTTACTGGCTGATATTGATCGACGCCTTGATCAGTTATTGCCCGTGGAGGGAGAACGG
GATGTTGTGGGTGCCGCGATGCGTGAAGGTGCGCTGGCACCGGGAAAACGTATTCGCCCCATGTTGCTGTTGCTG
ACCGCCCGCGATCTGGGTTGCGCTGTCAGCCATGACGGATTACTGGATTTGGCCTGTGCGGTGGAAATGGTCCAC
GCGGCTTCGCTGATCCTTGACGATATGCCCTGCATGGACGATGCGAAGCTGCGGCGCGGACGCCCTACCATTCAT
TCTCATTACGGAGAGCATGTGGCAATACTGGCGGCGGTTGCCTTGCTGAGTAAAGCCTTTGGCGTAATTGCCGAT
GCAGATGGCCTCACGCCGCTGGCAAAAAATCGGGCGGTTTCTGAACTGTCAAACGCCATCGGCATGCAAGGATTG
GTTCAGGGTCAGTTCAAGGATCTGTCTGAAGGGGATAAGCCGCGCAGCGCTGAAGCTATTTTGATGACGAATCAC
TTTAAAACCAGCACGCTGTTTTGTGCCTCCATGCAGATGGCCTCGATTGTTGCGAATGCCTCCAGCGAAGCGCGT
GATTGCCTGCATCGTTTTTCACTTGATCTTGGTCAGGCATTTCAACTGCTGGACGATTTGACCGATGGCATGACC
GACACCGGTAAGGATAGCAATCAGGACGCCGGTAAATCGACGCTGGTCAATCTGTTAGGCCCGAGGGCGGTTGAA
GAACGTCTGAGACAACATCTTCAGCTTGCCAGTGAGCATCTCTCTGCGGCCTGCCAACACGGGCACGCCACTCAA
CATTTTATTCAGGCCTGGTTTGACAAAAAACTCGCTGCCGTCAGTTAACGCAGTAAGAGAGGAATGTAGATATGA
ATAATCCGTCGTTACTCAATCATGCGGTCGAAACGATGGCAGTTGGCTCGAAAAGTTTTGCGACAGCCTCAAAGT
TATTTGATGCAAAAACCCGGCGCAGCGTACTGATGCTCTACGCCTGGTGCCGCCATTGTGACGATGTTATTGACG
ATCAGACGCTGGGCTTTCAGGCCCGGCAGCCTGCCTTACAAACGCCCGAACAACGTCTGATGCAACTTGAGATGA
AAACGCGCCAGGCCTATGCAGGATCGCAGATGCACGAACCGGCGTTTGCGGCTTTTCAGGAAGTGGCTATGGCTC
ATGATATCGCCCCGGCTTACGCGTTTGATCATCTGGAAGGCTTCGCCATGGATGTACGCGAAGCGCAATACAGCC
AACTGGATGATACGCTGCGCTATTGCTATCACGTTGCAGGCGTTGTCGGCTTGATGATGGCGCAAATCATGGGCG
TGCGGGATAACGCCACGCTGGACCGCGCCTGTGACCTTGGGCTGGCATTTCAGTTGACCAATATTGCTCGCGATA
TTGTGGACGATGCGCATGCGGGCCGCTGTTATCTGCCGGCAAGCTGGCTGGAGCATGAAGGTCTGAACAAAGAGA TABLE 3-continued

| List of Plasmids |
|---|
| ATTATGCGGCACCTGAAAACCGTCAGGCGCTGAGCCGTATCGCCCGTCGTTTGGTGCAGGAAGCAGAACCTTACT<br>ATTTGTCTGCCACAGCCGGCCTGGCAGGGTTGCCCCTGCGTTCCGCCTGGGCAATCGCTACGGCGAAGCAGGTTT<br>ACCGGAAAATAGGTGTCAAAGTTGAACAGGCCGGTCAGCAAGCCTGGGATCAGCGGCAGTCAACGACCACGCCCG<br>AAAAATTAACGCTGCTGCTGGCCGCCTCTGGTCAGGCCCTTACTTCCCGGATGCGGGCTCATCCTCCCCGCCCTG<br>CGCATCTCTGGCAGCGCCCGCTCTGAAATAATTTTGTTTAACTTTAAGAAGGAGATATAATGAAACCAACTACGG<br>TAATTGGTGCAGGCTTCGGTGGCCTGGCACTGGCAATTCGTCTACAAGCTGCGGGGATTCCCGTCTTACTGCTTG<br>AACAACGTGATAAACCCGGCGGTCGGGCTTATGTCTACGAGGATCAGGGGTTTACCTTTGATGCAGGCCCGACGG<br>TTATCACCGATCCCAGTGCCATTGAAGAACTGTTTGCACTGGCAGGAAAACAGTTAAAAGAGTATGTCGAACTGC<br>TGCCGGTTACGCCGTTTTACCGCCTGTGTTGGGAGTCAGGGAAGGTCTTTAATTACGATAACGATCAAACCCGGC<br>TCGAAGCGCAGATTCAGCAGTTTAATCCCCGCGATGTCGAAGGTTATCGTCAGTTTCTGGACTATTCACGCGCGG<br>TGTTTAAAGAAGGCTATCTAAAGCTCGGTACTGTCCCTTTTTTATCGTTCAGAGACATGCTTCGCGCCGCACCTC<br>AACTGGCGAAACTGCAGGCATGGAGAAGCGTTTACAGTAAGGTTGCCAGTTACATCGAAGATGAACATCTGCGCC<br>AGGCGTTTTCTTTCCACTCGCTGTTGGTGGGCGGCAATCCCTTCGCCACCTCATCCATTTATACGTTGATACACG<br>CGCTGGAGCGTGAGTGGGGCGTCTGGTTTCCGCGTGGCGGCACCGGCGCATTAGTTCAGGGGATGATAAAGCTGT<br>TTCAGGATCTGGGTGGCGAAGTCGTGTTAAACGCCAGAGTCAGCCACATGGAAACGACAGGAAACAAGATTGAAG<br>CCGTGCATTTAGAGGACGGTCGCAGGTTCCTGACGCAAGCCGTCGCGTCAAATGCAGATGTGGTTCATACCTATC<br>GCGACCTGTTAAGCCAGCACCCTGCCGCGGTTAAGCAGTCCAACAAACTGCAGACTAAGCGCATGAGTAACTCTC<br>TGTTTGTGCTCTATTTTGGTTTGAATCACCATCATGATCAGCTCGCGCATCACACGGTTTGTTTCGGCCCGCGTT<br>ACCGCGAGCTGATTGACGAAATTTTTAATCATGATGGCCTCGCAGAGGACTTCTCACTTTATCTGCACGCGCCCT<br>GTGTCACGGATTCGTCACTGGCGCCTGAAGGTTGCGGCAGTTACTATGTGTTGGCGCCGGTGCCGCATTTAGGCA<br>CCGCGAACCTCGACTGGACGGTTGAGGGGCCAAAACTACGCGACCGTATTTTTGCGTACCTTGAGCAGCATTACA<br>TGCCTGGCTTACGGAGTCAGCTGGTCACGCACCGGATGTTTACGCCGTTTGATTTTCGCGACCAGCTTAATGCCT<br>ATCATGGCTCAGCCTTTTCTGTGGAGCCCGTTCTTACCCAGAGCGCCTGGTTTCGGCCGCATAACCGCGATAAAA<br>CCATTACTAATCTCTACCTGGTCGGCGCAGGCACGCATCCCGGCGCAGGCATTCCTGGCGTCATCGGCTCGGCAA<br>AAGCGACAGCAGGTTTGATGCTGGAGGATCTGATTTGAAAGCTTCTCGGTACCAAATTCCAGAAAAGAGGCCTCC<br>CGAAAGGGGGGCCTTTTTTCGTTTTGGTCCGAATTCTTGACAGCTAGCTCAGTCCTAGGTATAATGCTAGCCGCA<br>GTAAGAGAGGAATGTACACATGTCCCGCCTGGATAAATCGAAAGTGATTAACTCGGCCCTCGAATTGCTGAATGA<br>AGTCGGTATCGAGGGGCTGACGACCCGTAAATTGGCACAAAAGTTGGGGGTGGAGCAACCCACGTTGTATTGGCA<br>CGTCAAAAATAAGCGGGCATTGCTGGATGCCCTCGCTATTGAAATGTTGGATCGCCACCATACCCATTTCTGTCC<br>ACTGGAGGGCGAGTCCTGGCAGGACTTTCTCCGCAACAACGCGAAATCCTTTCGCTGTGCACTCTTGTCCCATCG<br>GGACGGTGCTAAGGTGCACTTGGGCACCCGTCCCACCGAAAAACAATACGAAACCTTGGAAAATCAATTGGCGTT<br>TTTGTGCCAGCAAGGGTTTAGCTTGGAGAATGCTCTCTATGCGCTCTCGGCTGTCGGGCACTTTACGTTGGGGTG<br>CGTGTTGGAGGACCAGGAGCATCAAGTCGCAAAAGAGGAGCGTGAAACCCCAACCACGGACTCGATGCCACCTCT<br>GCTCCGCCAAGCTATCGAACTCTTCGATCATCAGGGCGCGGAGCCAGCCTTCCTCTTTGGGCTGGAGCTGATTAT<br>CTGCGGTTTGGAAAAACAACTCAAGTGTGAAAGCGGGTCCTAACTGCAGCTCGAG |
| $p\sigma^{70}$ V2TcR-crtEBIY (SEQ ID NO: 71)<br>GGATCCGAGCTGTTGACAACTCTATCATTGATAGAGTTATAATGTTCCCTATCAGTGATAGAGACGCAGTAAGAG<br>AGGAATGTACATATGTATCCGTTTATAAGGACAGCCCGAATGACGGTCTGCGCAAAAAAACACGTTCATCTCACT<br>CGCGATGCTGCGGAGCAGTTACTGGCTGATATTGATCGACGCCTTGATCAGTTATTGCCCGTGGAGGGAGAACGG<br>GATGTTGTGGGTGCCGCGATGCGTGAAGGTGCGCTGGCACCGGGAAAACGTATTCGCCCCATGTTGCTGTTGCTG<br>ACCGCCCGCGATCTGGGTTGCGCTGTCAGCCATGACGGATTACTGGATTTGGCCTGTGCGGTGGAAATGGTCCAC<br>GCGGCTTCGCTGATCCTTGACGATATGCCCTGCATGGACGATGCGAAGCTGCGGCGCGGACGCCCTACCATTCAT<br>TCTCATTACGGAGAGCATGTGGCAATACTGGCGGCGGTTGCCTTGCTGAGTAAAGCCTTTGGCGTAATTGCCGAT<br>GCAGATGGCCTCACGCCGCTGGCAAAAAATCGGGCGGTTTCTGAACTGTCAAACGCCATCGGCATGCAAGGATTG<br>GTTCAGGGTCAGTTCAAGGATCTGTCTGAAGGGGATAAGCCGCGCAGCGCTGAAGCTATTTTGATGACGAATCAC<br>TTTAAAACCAGCACGCTGTTTTGTGCCTCCATGCAGATGGCCTCGATTGTTGCGAATGCCTCCAGCGAAGCGCGT<br>GATTGCCTGCATCGTTTTTCACTTGATCTTGGTCAGGCATTTCAACTGCTGGACGATTTGACCGATGGCATGACC<br>GACACCGGTAAGGATAGCAATCAGGACGCCGGTAAATCGACGCTGGTCAATCTGTTAGGCCCGAGGGCGGTTGAA<br>GAACGTCTGAGACAACATCTTCAGCTTGCCAGTGAGCATCTCTCTGCGGCCTGCCAACACGGGCACGCCACTCAA<br>CATTTTATTCAGGCCTGGTTTGACAAAAAACTCGCTGCCGTCAGTTAACGCAGTAAGAGAGGAATGTAGATATGA<br>ATAATCCGTCGTTACTCAATCATGCGGTCGAAACGATGGCAGTTGGCTCGAAAAGTTTTGCGACAGCCTCAAAGT<br>TATTTGATGCAAAAACCCGGCGCAGCGTACTGATGCTCTACGCCTGGTGCCGCCATTGTGACGATGTTATTGACG<br>ATCAGACGCTGGGCTTTCAGGCCCGGCAGCCTGCCTTACAAACGCCCGAACAACGTCTGATGCAACTTGAGATGA<br>AAACGCGCCAGGCCTATGCAGGATCGCAGATGCACGAACCGGCGTTTGCGGCTTTTCAGGAAGTGGCTATGGCTC<br>ATGATATCGCCCCGGCTTACGCGTTTGATCATCTGGAAGGCTTCGCCATGGATGTACGCGAAGCGCAATACAGCC<br>AACTGGATGATACGCTGCGCTATTGCTATCACGTTGCAGGCGTTGTCGGCTTGATGATGGCGCAAATCATGGGCG<br>TGCGGGATAACGCCACGCTGGACCGCGCCTGTGACCTTGGGCTGGCATTTCAGTTGACCAATATTGCTCGCGATA<br>TTGTGGACGATGCGCATGCGGGCCGCTGTTATCTGCCGGCAAGCTGGCTGGAGCATGAAGGTCTGAACAAAGAGA<br>ATTATGCGGCACCTGAAAACCGTCAGGCGCTGAGCCGTATCGCCCGTCGTTTGGTGCAGGAAGCAGAACCTTACT<br>ATTTGTCTGCCACAGCCGGCCTGGCAGGGTTGCCCCTGCGTTCCGCCTGGGCAATCGCTACGGCGAAGCAGGTTT<br>ACCGGAAAATAGGTGTCAAAGTTGAACAGGCCGGTCAGCAAGCCTGGGATCAGCGGCAGTCAACGACCACGCCCG<br>AAAAATTAACGCTGCTGCTGGCCGCCTCTGGTCAGGCCCTTACTTCCCGGATGCGGGCTCATCCTCCCCGCCCTG<br>CGCATCTCTGGCAGCGCCCGCTCTGAAATAATTTTGTTTAACTTTAAGAAGGAGATATAATGAAACCAACTACGG<br>TAATTGGTGCAGGCTTCGGTGGCCTGGCACTGGCAATTCGTCTACAAGCTGCGGGGATTCCCGTCTTACTGCTTG<br>AACAACGTGATAAACCCGGCGGTCGGGCTTATGTCTACGAGGATCAGGGGTTTACCTTTGATGCAGGCCCGACGG<br>TTATCACCGATCCCAGTGCCATTGAAGAACTGTTTGCACTGGCAGGAAAACAGTTAAAAGAGTATGTCGAACTGC<br>TGCCGGTTACGCCGTTTTACCGCCTGTGTTGGGAGTCAGGGAAGGTCTTTAATTACGATAACGATCAAACCCGGC<br>TCGAAGCGCAGATTCAGCAGTTTAATCCCCGCGATGTCGAAGGTTATCGTCAGTTTCTGGACTATTCACGCGCGG<br>TGTTTAAAGAAGGCTATCTAAAGCTCGGTACTGTCCCTTTTTTATCGTTCAGAGACATGCTTCGCGCCGCACCTC<br>AACTGGCGAAACTGCAGGCATGGAGAAGCGTTTACAGTAAGGTTGCCAGTTACATCGAAGATGAACATCTGCGCC<br>AGGCGTTTTCTTTCCACTCGCTGTTGGTGGGCGGCAATCCCTTCGCCACCTCATCCATTTATACGTTGATACACG<br>CGCTGGAGCGTGAGTGGGGCGTCTGGTTTCCGCGTGGCGGCACCGGCGCATTAGTTCAGGGGATGATAAAGCTGT<br>TTCAGGATCTGGGTGGCGAAGTCGTGTTAAACGCCAGAGTCAGCCACATGGAAACGACAGGAAACAAGATTGAAG<br>CCGTGCATTTAGAGGACGGTCGCAGGTTCCTGACGCAAGCCGTCGCGTCAAATGCAGATGTGGTTCATACCTATC<br>GCGACCTGTTAAGCCAGCACCCTGCCGCGGTTAAGCAGTCCAACAAACTGCAGACTAAGCGCATGAGTAACTCTC<br>TGTTTGTGCTCTATTTTGGTTTGAATCACCATCATGATCAGCTCGCGCATCACACGGTTTGTTTCGGCCCGCGTT<br>ACCGCGAGCTGATTGACGAAATTTTTAATCATGATGGCCTCGCAGAGGACTTCTCACTTTATCTGCACGCGCCCT |

TABLE 3-continued

| List of Plasmids |
|---|
| GTGTCACGGATTCGTCACTGGCGCCTGAAGGTTGCGGCAGTTACTATGTGTTGGCGCCGGTGCCGCATTTAGGCA<br>CCGCGAACCTCGACTGGACGGTTGAGGGGCCAAAACTACGCGACCGTATTTTTGCGTACCTTGAGCAGCATTACA<br>TGCCTGGCTTACGGAGTCAGCTGGTCACGCACCGGATGTTTACGCCGTTTGATTTTCGCGACCAGCTTAATGCCT<br>ATCATGGCTCAGCCTTTTCTGTGGAGCCCGTTCTTACCCAGAGCGCCTGGTTTCGGCCGCATAACCGCGATAAAA<br>CCATTACTAATCTCTACCTGGTCGGCGCAGGCACGCATCCCGGCGCAGGCATTCCTGGCGTCATCGGCTCGGCAA<br>AAGCGACAGCAGGTTTGATGCTGGAGGATCTGATTTGACGCAGTAAGAGAGGAATGTAGATATGGGAGCGGCTAT<br>GCAACCGCATTATGATCTGATTCTCGTGGGGGCTGGACTCGCGAATGGCCTTATCGCCCTGCGTCTCCAGCAGCA<br>GCAACCTGATATGCGTATTTTGCTTATCGACGCCGCACCCCAGGCGGGCGGGAATCATACGTGGTCATTTCACCA<br>CGATGATTTGACTGAGAGCCAACATCGTTGGATAGCTCCGCTGGTGGTTCATCACTGGCCCGACTATCAGGTACG<br>CTTTCCCACACGCCGTCGTAAGCTGAACAGCGGCTACTTTTGTATTACTTCTCAGCGTTTCGCTGAGGTTTTACA<br>GCGACAGTTTGGCCCGCACTTGTGGATGGATACCGCGGTCGCAGAGGTTAATGCGGAATCTGTTCGGTTGAAAAA<br>GGGTCAGGTTATCGGTGCCCGCGCGGTGATTGACGGGGGGGTTATGCGGCAAATTCAGCACTGAGCGTGGGCTT<br>CCAGGCGTTTATTGGCCAGGAATGGCGATTGAGCCACCCGCATGGTTTATCGTCTCCCATTATCATGGATGCCAC<br>GGTCGATCAGCAAAATGGTTATCGCTTCGTGTACAGCCTGCCGCTCTCGCCGACCAGATTGTTAATTGAAGATAC<br>GCACTATATTGATAATGCGACATTAGATCCTGAATGCGCGCGGCAAAATATTTGCGACTATGCCGCGCAACAGGG<br>TTGGCAGCTTCAGACACTGCTGCGAGAAGAACAGGGCGCCTTACCCATTACTCTGTCGGGCAATGCCGACGCATT<br>CTGGCAGCAGCGCCCCCTGGCCTGTAGTGGATTACGTGCCGGTCTGTTCCATCCTACCACCGGCTATTCACTGCC<br>GCTGGCGGTTGCCGTGGCCGACCGCCTGAGTGCACTTGATGTCTTTACGTCGGCCTCAATTCACCATGCCATTAC<br>GCATTTTGCCCGCGAGCGCTGGCAGCAGCAGGGCTTTTTCCGCATGCTGAATCGCATGCTGTTTTTAGCCGGACC<br>CGCCGATTCACGCTGGCGGGTTATGCAGCGTTTTTATGGTTTACCTGAAGATTTAATTGCCCGTTTTTATGCGGG<br>AAAACTCACGCTGACCGATCGGCTACGTATTCTGAGCGGCAAGCCGCCTGTTCCGGTATTAGCAGCATTGCAAGC<br>CATTATGACGACTCATCGTTGAAAGCTTCTCGGTACCAAATTCCAGAAAAGAGGCCTCCCGAAAGGGGGGCCTTT<br>TTTCGTTTTGGTCCGAATTCTTGACAGCTAGCTCAGTCCTAGGTATAATGCTAGCCGCAGTAAGAGAGGAATGTA<br>CACATGTCCCGCCTGGATAAATCGAAAGTGATTAACTCGGCCCTCGAATTGCTGAATGAAGTCGGTATCGAGGGG<br>CTGACGACCCGTAAATTGGCACAAAAGTTGGGGGTGGAGCAACCCACGTTGTATTGGCACGTCAAAAATAAGCGG<br>GCATTGCTGGATGCCCTCGCTATTGAAATGTTGGATCGCCACCATACCCATTTCTGTCCACTGGAGGGCGAGTCC<br>TGGCAGGACTTTCTCCGCAACAACGCGAAATCCTTTCGCTGTGCACTCTTGTCCCATCGGGACGGTGCTAAGGTG<br>CACTTGGGCACCCGTCCCACCGAAAAACAATACGAAACCTTGGAAAATCAATTGGCGTTTTTGTGCCAGCAAGGG<br>TTTAGCTTGGAGAATGCTCTCTATGCGCTCTCGGCTGTCGGGCACTTTACGTTGGGGTGCGTGTTGGAGGACCAG<br>GAGCATCAAGTCGCAAAAGAGGAGCGTGAAACCCCAACCACGGACTCGATGCCACCTCTGCTCCGCCAAGCTATC<br>GAACTCTTCGATCATCAGGGCGCGGAGCCAGCCTTCCTCTTTGGGCTGGAGCTGATTATCTGCGGTTTGGAAAAA<br>CAACTCAAGTGTGAAAGCGGGTCCTAACTGCAGCTCGAG |
| p$\sigma^{70}$ V2TcR-crtEBI/V2LacI-crtY (SEQ ID NO: 72)<br>ggatccGAGCTGTTGACAACTCTATCATTGATAGAGTTATAATGTTCCCTATCAGTGATAGAGACGCAGTAAGAG<br>AGGAATGTACATATGTATCCGTTTATAAGGACAGCCCGAATGACGGTCTGCGCAAAAAAACACGTTCATCTCACT<br>CGCGATGCTGCGGAGCAGTTACTGGCTGATATTGATCGACGCCTTGATCAGTTATTGCCCGTGGAGGGAGAACGG<br>GATGTTGTGGGTGCCGCGATGCGTGAAGGTGCGCTGGCACCGGGAAAACGTATTCGCCCCATGTTGCTGTTGCTG<br>ACCGCCCGCGATCTGGGTTGCGCTGTCAGCCATGACGGATTACTGGATTTGGCCTGTGCGGTGGAAATGGTCCAC<br>GCGGCTTCGCTGATCCTTGACGATATGCCCTGCATGGACGATGCGAAGCTGCGGCGCGGACGCCCTACCATTCAT<br>TCTCATTACGGAGAGCATGTGGCAATACTGGCGGCGGTTGCCTTGCTGAGTAAAGCCTTTGGCGTAATTGCCGAT<br>GCAGATGGCCTCACGCCGCTGGCAAAAAATCGGGCGGTTTCTGAACTGTCAAACGCCATCGGCATGCAAGGATTG<br>GTTCAGGGTCAGTTCAAGGATCTGTCTGAAGGGGATAAGCCGCGCAGCGCTGAAGCTATTTTGATGACGAATCAC<br>TTTAAAACCAGCACGCTGTTTTGTGCCTCCATGCAGATGGCCTCGATTGTTGCGAATGCCTCCAGCGAAGCGCGT<br>GATTGCCTGCATCGTTTTTCACTTGATCTTGGTCAGGCATTTCAACTGCTGGACGATTTGACCGATGGCATGACC<br>GACACCGGTAAGGATAGCAATCAGGACGCCGGTAAATCGACGCTGGTCAATCTGTTAGGCCCGAGGGCGGTTGAA<br>GAACGTCTGAGACAACATCTTCAGCTTGCCAGTGAGCATCTCTCTGCGGCCTGCCAACACGGGCACGCCACTCAA<br>CATTTTATTCAGGCCTGGTTTGACAAAAAACTCGCTGCCGTCAGTTAACGCAGTAAGAGAGGAATGTAGATATGA<br>ATAATCCGTCGTTACTCAATCATGCGGTCGAAACGATGGCAGTTGGCTCGAAAAGTTTTGCGACAGCCTCAAAGT<br>TATTTGATGCAAAAACCCGGCGCAGCGTACTGATGCTCTACGCCTGGTGCCGCCATTGTGACGATGTTATTGACG<br>ATCAGACGCTGGGCTTTCAGGCCCGGCAGCCTGCCTTACAAACGCCCGAACAACGTCTGATGCAACTTGAGATGA<br>AAACGCGCCAGGCCTATGCAGGATCGCAGATGCACGAACCGGCGTTTGCGGCTTTTCAGGAAGTGGCTATGGCTC<br>ATGATATCGCCCCGGCTTACGCGTTTGATCATCTGGAAGGCTTCGCCATGGATGTACGCGAAGCGCAATACAGCC<br>AACTGGATGATACGCTGCGCTATTGCTATCACGTTGCAGGCGTTGTCGGCTTGATGATGGCGCAAATCATGGGCG<br>TGCGGGATAACGCCACGCTGGACCGCGCCTGTGACCTTGGGCTGGCATTTCAGTTGACCAATATTGCTCGCGATA<br>TTGTGGACGATGCGCATGCGGGCCGCTGTTATCTGCCGGCAAGCTGGCTGGAGCATGAAGGTCTGAACAAAGAGA<br>ATTATGCGGCACCTGAAAACCGTCAGGCGCTGAGCCGTATCGCCCGTCGTTTGGTGCAGGAAGCAGAACCTTACT<br>ATTTGTCTGCCACAGCCGGCCTGGCAGGGTTGCCCCTGCGTTCCGCCTGGGCAATCGCTACGGCGAAGCAGGTTT<br>ACCGGAAAATAGGTGTCAAAGTTGAACAGGCCGGTCAGCAAGCCTGGGATCAGCGGCAGTCAACGACCACGCCCG<br>AAAAATTAACGCTGCTGCTGGCCGCCTCTGGTCAGGCCCTTACTTCCCGGATGCGGGCTCATCCTCCCCGCCCTG<br>CGCATCTCTGGCAGCGCCCGCTCTGAAATAATTTTGTTTAACTTTAAGAAGGAGATATAATGAAACCAACTACGG<br>TAATTGGTGCAGGCTTCGGTGGCCTGGCACTGGCAATTCGTCTACAAGCTGCGGGGATTCCCGTCTTACTGCTTG<br>AACAACGTGATAAACCCGGCGGTCGGGCTTATGTCTACGAGGATCAGGGGTTTACCTTTGATGCAGGCCCGACGG<br>TTATCACCGATCCCAGTGCCATTGAAGAACTGTTTGCACTGGCAGGAAAACAGTTAAAAGAGTATGTCGAACTGC<br>TGCCGGTTACGCCGTTTTACCGCCTGTGTTGGGAGTCAGGGAAGGTCTTTAATTACGATAACGATCAAACCCGGC<br>TCGAAGCGCAGATTCAGCAGTTTAATCCCCGCGATGTCGAAGGTTATCGTCAGTTTCTGGACTATTCACGCGCGG<br>TGTTTAAAGAAGGCTATCTAAAGCTCGGTACTGTCCCTTTTTTATCGTTCAGAGACATGCTTCGCGCCGCACCTC<br>AACTGGCGAAACTGCAGGCATGGAGAAGCGTTTACAGTAAGGTTGCCAGTTACATCGAAGATGAACATCTGCGCC<br>AGGCGTTTTCTTTCCACTCGCTGTTGGTGGGCGGCAATCCCTTCGCCACCTCATCCATTTATACGTTGATACACG<br>CGCTGGAGCGTGAGTGGGGCGTCTGGTTTCCGCGTGGCGGCACCGGCGCATTAGTTCAGGGGATGATAAAGCTGT<br>TTCAGGATCTGGGTGGCGAAGTCGTGTTAAACGCCAGAGTCAGCCACATGGAAACGACAGGAAACAAGATTGAAG<br>CCGTGCATTTAGAGGACGGTCGCAGGTTCCTGACGCAAGCCGTCGCGTCAAATGCAGATGTGGTTCATACCTATC<br>GCGACCTGTTAAGCCAGCACCCTGCCGCGGTTAAGCAGTCCAACAAACTGCAGACTAAGCGCATGAGTAACTCTC<br>TGTTTGTGCTCTATTTTGGTTTGAATCACCATCATGATCAGCTCGCGCATCACACGGTTTGTTTCGGCCCGCGTT<br>ACCGCGAGCTGATTGACGAAATTTTTAATCATGATGGCCTCGCAGAGGACTTCTCACTTTATCTGCACGCGCCCT<br>GTGTCACGGATTCGTCACTGGCGCCTGAAGGTTGCGGCAGTTACTATGTGTTGGCGCCGGTGCCGCATTTAGGCA<br>CCGCGAACCTCGACTGGACGGTTGAGGGGCCAAAACTACGCGACCGTATTTTTGCGTACCTTGAGCAGCATTACA<br>TGCCTGGCTTACGGAGTCAGCTGGTCACGCACCGGATGTTTACGCCGTTTGATTTTCGCGACCAGCTTAATGCCT |

TABLE 3-continued

List of Plasmids

ATCATGGCTCAGCCTTTTCTGTGGAGCCCGTTCTTACCCAGAGCGCCTGGTTTCGGCCGCATAACCGCGATAAAA
CCATTACTAATCTCTACCTGGTCGGCGCAGGCACGCATCCCGGCGCAGGCATTCCTGGCGTCATCGGCTCGGCAA
AAGCGACAGCAGGTTTGATGCTGGAGGATCTGATTTGAAAGCTTCTCGGTACCAAATTCCAGAAAAGAGGCCTCC
CGAAAGGGGGGCCTTTTTTCGTTTTGGTCCGAATTCTTGACAGCTAGCTCAGTCCTAGGTATAATGCTAGCCGCA
GTAAGAGAGGAATGTACACATGTCCCGCCTGGATAAATCGAAAGTGATTAACTCGGCCCTCGAATTGCTGAATGA
AGTCGGTATCGAGGGGCTGACGACCCGTAAATTGGCACAAAAGTTGGGGGTGGAGCAACCCACGTTGTATTGGCA
CGTCAAAAATAAGCGGGCATTGCTGGATGCCCTCGCTATTGAAATGTTGGATCGCCACCATACCCATTTCTGTCC
ACTGGAGGGCGAGTCCTGGCAGGACTTTCTCCGCAACAACGCGAAATCCTTTCGCTGTGCACTCTTGTCCCATCG
GGACGGTGCTAAGGTGCACTTGGGCACCCGTCCCACCGAAAAACAATACGAAACCTTGGAAAATCAATTGGCGTT
TTTGTGCCAGCAAGGGTTTAGCTTGGAGAATGCTCTCTATGCGCTCTCGGCTGTCGGGCACTTTACGTTGGGGTG
CGTGTTGGAGGACCAGGAGCATCAAGTCGCAAAAGAGGAGCGTGAAACCCCAACCACGGACTCGATGCCACCTCT
GCTCCGCCAAGCTATCGAACTCTTCGATCATCAGGGCGCGGAGCCAGCCTTCCTCTTTGGGCTGGAGCTGATTAT
CTGCGGTTTGGAAAAACAACTCAAGTGTGAAAGCGGGTCCTAACTGCAGTCACTGCCCGCTTTCCAGTCGGGAAA
CCTGTCGTGCCAGCTGCATTAATGAATCGGCCAACGCGCGGGGAGAGGCGGTTTGCGTATTGGGCGCCAGGGTGG
TTTTTCTTTTCACCAGTGAGACGGGCAACAGCTGATTGCCCTTCACCGCCTGGCCCTGAGAGAGTTGCAGCAAGC
GGTCCACGCTGGTTTGCCCCAGCAGGCGAAAATCCTGTTTGATGGTGGTTAACGGCGGGATATAACATGAGCTGT
CTTCGGTATCGTCGTATCCCACTACCGAGATATCCGCACCAACGCGCAGCCCGGACTCGGTAATGGCGCGCATTG
CGCCCAGCGCCATCTGATCGTTGGCAACCAGCATCGCAGTGGGAACGATGCCCTCATTCAGCATTTGCATGGTTT
GTTGAAAACCGGACATGGCACTCCAGTCGCCTTCCCGTTCCGCTATCGGCTGAATTTGATTGCGAGTGAGATATT
TATGCCAGCCAGCCAGACGCAGACGCGCCGAGACAGAACTTAATGGGCCCGCTAACAGCGCGATTTGCTGGTGAC
CCAATGCGACCAGATGCTCCACGCCCAGTCGCGTACCGTCTTCATGGGAGAAAATAATACTGTTGATGGGTGTCT
GGTCAGAGACATCAAGAAATAACGCCGGAACATTAGTGCAGGCAGCTTCCACAGCAATGGCATCCTGGTCATCCA
GCGGATAGTTAATGATCAGCCCACTGACGCGTTGCGCGAGAAGATTGTGCACCGCCGCTTTACAGGCTTCGACGC
CGCTTCGTTCTACCATCGACACCACCACGCTGGCACCCAGTTGATCGGCGCGAGATTTAATCGCCGCGACAATTT
GCGACGGCGCGTGCAGGGCCAGACTGGAGGTGGCAACGCCAATCAGCAACGACTGTTTGCCCGCCAGTTGTTGTG
CCACGCGGTTGGGAATGTAATTCAGCTCCGCCATCGCCGCTTCCACTTTTTCCCGCGTTTTCGCAGAAACGTGGC
TGGCCTGGTTCACCACGCGGGAAACGGTCTGATAAGAGACACCGGCATACTCTGCGACATCGTATAACGTTACTG
GTTTCACATTCACCACCCTGAATTGACTCTCTTCCGGGCGCTATCATGCCATACCGCGAAAGGTTTTGCGCCATT
CGATGGTGTCCGGGATCTCGACGCTCTCCCTTATGCGACTCCTGCATTAGGAAGCAGCCCAGTAGTAGGTTGAGG
CCGTTGAGCACCGCCGCCGCAAGGAATGGTGCATGCAAGGAGATGGCGCCCAACAGTCCCCCGGCCACGGGGagt
caaaagcctccggtcggaggcttttgactTCTAGAGAGCTGTTGACACTTTATGCTTCCGGCTCGTATAATGTGT
GTGGAATTGTGAGCGGATAACAACGCAGTAAGAGAGGAATGTACCCATGGAGCGGCTATGCAACCGCATTATGAT
CTGATTCTCGTGGGGGCTGGACTCGCGAATGGCCTTATCGCCCTGCGTCTCCAGCAGCAGCAACCTGATATGCGT
ATTTTGCTTATCGACGCCGCACCCCAGGCGGGCGGGAATCATACGTGGTCATTTCACCACGATGATTTGACTGAG
AGCCAACATCGTTGGATAGCTCCGCTGGTGGTTCATCACTGGCCCGACTATCAGGTACGCTTTCCCACACGCCGT
CGTAAGCTGAACAGCGGCTACTTTTGTATTACTTCTCAGCGTTTCGCTGAGGTTTTACAGCGACAGTTTGGCCCG
CACTTGTGGATGGATACCGCGGTCGCAGAGGTTAATGCGGAATCTGTTCGGTTGAAAAAGGGTCAGGTTATCGGT
GCCCGCGCGGTGATTGACGGGCGGGGTTATGCGGCAAATTCAGCACTGAGCGTGGGCTTCCAGGCGTTTATTGGC
CAGGAATGGCGATTGAGCCACCCGCATGGTTTATCGTCTCCCATTATCATGGATGCCACGGTCGATCAGCAAAAT
GGTTATCGCTTCGTGTACAGCCTGCCGCTCTCGCCGACCAGATTGTTAATTGAAGATACGCACTATATTGATAAT
GCGACATTAGATCCTGAATGCGCGCGGCAAAATATTTGCGACTATGCCGCGCAACAGGGTTGGCAGCTTCAGACA
CTGCTGCGAGAAGAACAGGGCGCCTTACCCATTACTCTGTCGGGCAATGCCGACGCATTCTGGCAGCAGCGCCCC
CTGGCCTGTAGTGGATTACGTGCCGGTCTGTTCCATCCTACCACCGGCTATTCACTGCCGCTGGCGGTTGCCGTG
GCCGACCGCCTGAGTGCACTTGATGTCTTTACGTCGGCCTCAATTCACCATGCCATTACGCATTTTGCCCGCGAG
CGCTGGCAGCAGCAGGGCTTTTTCCGCATGCTGAATCGCATGCTGTTTTTAGCCGGACCCGCCGATTCACGCTGG
CGGGTTATGCAGCGTTTTTATGGTTTACCTGAAGATTTAATTGCCCGTTTTTATGCGGGAAAACTCACGCTGACC
GATCGGCTACGTATTCTGAGCGGCAAGCCGCCTGTTCCGGTATTAGCAGCATTGCAAGCCATTATGACGACTCAT
CGTTGACTCGAG p$\sigma^{70}$ V2TcR-crtEBI/V3LacI-crtY (SEQ ID NO: 73)
ggatccGAGCTGTTGACAACTCTATCATTGATAGAGTTATAATGTTCCCTATCAGTGATAGAGACGCAGTAAGAG
AGGAATGTACATATGTATCCGTTTATAAGGACAGCCCGAATGACGGTCTGCGCAAAAAAACACGTTCATCTCACT
CGCGATGCTGCGGAGCAGTTACTGGCTGATATTGATCGACGCCTTGATCAGTTATTGCCCGTGGAGGGAGAACGG
GATGTTGTGGGTGCCGCGATGCGTGAAGGTGCGCTGGCACCGGGAAAACGTATTCGCCCCATGTTGCTGTTGCTG
ACCGCCCGCGATCTGGGTTGCGCTGTCAGCCATGACGGATTACTGGATTTGGCCTGTGCGGTGGAAATGGTCCAC
GCGGCTTCGCTGATCCTTGACGATATGCCCTGCATGGACGATGCGAAGCTGCGGCGCGGACGCCCTACCATTCAT
TCTCATTACGGAGAGCATGTGGCAATACTGGCGGCGGTTGCCTTGCTGAGTAAAGCCTTTGGCGTAATTGCCGAT
GCAGATGGCCTCACGCCGCTGGCAAAAAATCGGGCGGTTTCTGAACTGTCAAACGCCATCGGCATGCAAGGATTG
GTTCAGGGTCAGTTCAAGGATCTGTCTGAAGGGGATAAGCCGCGCAGCGCTGAAGCTATTTTGATGACGAATCAC
TTTAAAACCAGCACGCTGTTTTGTGCCTCCATGCAGATGGCCTCGATTGTTGCGAATGCCTCCAGCGAAGCGCGT
GATTGCCTGCATCGTTTTTCACTTGATCTTGGTCAGGCATTTCAACTGCTGGACGATTTGACCGATGGCATGACC
GACACCGGTAAGGATAGCAATCAGGACGCCGGTAAATCGACGCTGGTCAATCTGTTAGGCCCGAGGGCGGTTGAA
GAACGTCTGAGACAACATCTTCAGCTTGCCAGTGAGCATCTCTCTGCGGCCTGCCAACACGGGCACGCCACTCAA
CATTTTATTCAGGCCTGGTTTGACAAAAAACTCGCTGCCGTCAGTTAACGCAGTAAGAGAGGAATGTAGATATGA
ATAATCCGTCGTTACTCAATCATGCGGTCGAAACGATGGCAGTTGGCTCGAAAAGTTTTGCGACAGCCTCAAAGT
TATTTGATGCAAAAACCCGGCGCAGCGTACTGATGCTCTACGCCTGGTGCCGCCATTGTGACGATGTTATTGACG
ATCAGACGCTGGGCTTTCAGGCCCGGCAGCCTGCCTTACAAACGCCCGAACAACGTCTGATGCAACTTGAGATGA
AAACGCGCCAGGCCTATGCAGGATCGCAGATGCACGAACCGGCGTTTGCGGCTTTTCAGGAAGTGGCTATGGCTC
ATGATATCGCCCCGGCTTACGCGTTTGATCATCTGGAAGGCTTCGCCATGGATGTACGCGAAGCGCAATACAGCC
AACTGGATGATACGCTGCGCTATTGCTATCACGTTGCAGGCGTTGTCGGCTTGATGATGGCGCAAATCATGGGCG
TGCGGGATAACGCCACGCTGGACCGCGCCTGTGACCTTGGGCTGGCATTTCAGTTGACCAATATTGCTCGCGATA
TTGTGGACGATGCGCATGCGGGCCGCTGTTATCTGCCGGCAAGCTGGCTGGAGCATGAAGGTCTGAACAAAGAGA
ATTATGCGGCACCTGAAAACCGTCAGGCGCTGAGCCGTATCGCCCGTCGTTTGGTGCAGGAAGCAGAACCTTACT
ATTTGTCTGCCACAGCCGGCCTGGCAGGGTTGCCCCTGCGTTCCGCCTGGGCAATCGCTACGGCGAAGCAGGTTT
ACCGGAAAATAGGTGTCAAAGTTGAACAGGCCGGTCAGCAAGCCTGGGATCAGCGGCAGTCAACGACCACGCCCG
AAAAATTAACGCTGCTGCTGGCCGCCTCTGGTCAGGCCCTTACTTCCCGGATGCGGGCTCATCCTCCCCGCCCTG
CGCATCTCTGGCAGCGCCCGCTCTGAAATAATTTGTTTAACTTTAAGAAGGAGATATAATGAAACCAACTACGG
TAATTGGTGCAGGCTTCGGTGGCCTGGCACTGGCAATTCGTCTACAAGCTGCGGGGATTCCCGTCTTACTGCTTG TABLE 3-continued List of Plasmids AACAACGTGATAAACCCGGCGGTCGGGCTTATGTCTACGAGGATCAGGGGTTTACCTTTGATGCAGGCCCGACGG
TTATCACCGATCCCAGTGCCATTGAAGAACTGTTTGCACTGGCAGGAAAACAGTTAAAAGAGTATGTCGAACTGC
TGCCGGTTACGCCGTTTTACCGCCTGTGTTGGGAGTCAGGGAAGGTCTTTAATTACGATAACGATCAAACCCGGC
TCGAAGCGCAGATTCAGCAGTTTAATCCCCGCGATGTCGAAGGTTATCGTCAGTTTCTGGACTATTCACGCGCGG
TGTTTAAAGAAGGCTATCTAAAGCTCGGTACTGTCCCTTTTTTATCGTTCAGAGACATGCTTCGCGCCGCACCTC
AACTGGCGAAACTGCAGGCATGGAGAAGCGTTTACAGTAAGGTTGCCAGTTACATCGAAGATGAACATCTGCGCC
AGGCGTTTTCTTTCCACTCGCTGTTGGTGGGCGGCAATCCCTTCGCCACCTCATCCATTTATACGTTGATACACG
CGCTGGAGCGTGAGTGGGGCGTCTGGTTTCCGCGTGGCGGCACCGGCGCATTAGTTCAGGGGATGATAAAGCTGT
TTCAGGATCTGGGTGGCGAAGTCGTGTTAAACGCCAGAGTCAGCCACATGGAAACGACAGGAAACAAGATTGAAG
CCGTGCATTTAGAGGACGGTCGCAGGTTCCTGACGCAAGCCGTCGCGTCAAATGCAGATGTGGTTCATACCTATC
GCGACCTGTTAAGCCAGCACCCTGCCGCGGTTAAGCAGTCCAACAAACTGCAGACTAAGCGCATGAGTAACTCTC
TGTTTGTGCTCTATTTTGGTTTGAATCACCATCATGATCAGCTCGCGCATCACACGGTTTGTTTCGGCCCGCGTT
ACCGCGAGCTGATTGACGAAATTTTTAATCATGATGGCCTCGCAGAGGACTTCTCACTTTATCTGCACGCGCCCT
GTGTCACGGATTCGTCACTGGCGCCTGAAGGTTGCGGCAGTTACTATGTGTTGGCGCCGGTGCCGCATTTAGGCA
CCGCGAACCTCGACTGGACGGTTGAGGGGCCAAAACTACGCGACCGTATTTTTGCGTACCTTGAGCAGCATTACA
TGCCTGGCTTACGGAGTCAGCTGGTCACGCACCGGATGTTTACGCCGTTTGATTTTCGCGACCAGCTTAATGCCT
ATCATGGCTCAGCCTTTTCTGTGGAGCCCGTTCTTACCCAGAGCGCCTGGTTTCGGCCGCATAACCGCGATAAAA
CCATTACTAATCTCTACCTGGTCGGCGCAGGCACGCATCCCGGCGCAGGCATTCCTGGCGTCATCGGCTCGGCAA
AAGCGACAGCAGGTTTGATGCTGGAGGATCTGATTTGAAAGCTTCTCGGTACCAAATTCCAGAAAAGAGGCCTCC
CGAAAGGGGGGCCTTTTTTCGTTTTGGTCCGAATTCTTGACAGCTAGCTCAGTCCTAGGTATAATGCTAGCCGCA
GTAAGAGAGGAATGTACACATGTCCCGCCTGGATAAATCGAAAGTGATTAACTCGGCCCTCGAATTGCTGAATGA
AGTCGGTATCGAGGGGCTGACGACCCGTAAATTGGCACAAAAGTTGGGGGTGGAGCAACCCACGTTGTATTGGCA
CGTCAAAAATAAGCGGGCATTGCTGGATGCCCTCGCTATTGAAATGTTGGATCGCCACCATACCCATTTCTGTCC
ACTGGAGGGCGAGTCCTGGCAGGACTTTCTCCGCAACAACGCGAAATCCTTTCGCTGTGCACTCTTGTCCCATCG
GGACGGTGCTAAGGTGCACTTGGGCACCCGTCCCACCGAAAAACAATACGAAACCTTGGAAAATCAATTGGCGTT
TTTGTGCCAGCAAGGGTTTAGCTTGGAGAATGCTCTCTATGCGCTCTCGGCTGTCGGGCACTTTACGTTGGGGTG
CGTGTTGGAGGACCAGGAGCATCAAGTCGCAAAAGAGGAGCGTGAAACCCCAACCACGGACTCGATGCCACCTCT
GCTCCGCCAAGCTATCGAACTCTTCGATCATCAGGGCGCGGAGCCAGCCTTCCTCTTTGGGCTGGAGCTGATTAT
CTGCGGTTTGGAAAAACAACTCAAGTGTGAAAGCGGGTCCTAACTGCAGTCACTGCCCGCTTTCCAGTCGGGAAA
CCTGTCGTGCCAGCTGCATTAATGAATCGGCCAACGCGCGGGGAGAGGCGGTTTGCGTATTGGGCGCCAGGGTGG
TTTTTCTTTTCACCAGTGAGACGGGCAACAGCTGATTGCCCTTCACCGCCTGGCCCTGAGAGAGTTGCAGCAAGC
GGTCCACGCTGGTTTGCCCCAGCAGGCGAAAATCCTGTTTGATGGTGGTTAACGGCGGGATATAACATGAGCTGT
CTTCGGTATCGTCGTATCCCACTACCGAGATATCCGCACCAACGCGCAGCCCGGACTCGGTAATGGCGCGCATTG
CGCCCAGCGCCATCTGATCGTTGGCAACCAGCATCGCAGTGGGAACGATGCCCTCATTCAGCATTTGCATGGTTT
GTTGAAAACCGGACATGGCACTCCAGTCGCCTTCCCGTTCCGCTATCGGCTGAATTTGATTGCGAGTGAGATATT
TATGCCAGCCAGCCAGACGCAGACGCGCCGAGACAGAACTTAATGGGCCCGCTAACAGCGCGATTTGCTGGTGAC
CCAATGCGACCAGATGCTCCACGCCCAGTCGCGTACCGTCTTCATGGGAGAAAATAATACTGTTGATGGGTGTCT
GGTCAGAGACATCAAGAAATAACGCCGGAACATTAGTGCAGGCAGCTTCCACAGCAATGGCATCCTGGTCATCCA
GCGGATAGTTAATGATCAGCCCACTGACGCGTTGCGCGAGAAGATTGTGCACCGCCGCTTTACAGGCTTCGACGC
CGCTTCGTTCTACCATCGACACCACCACGCTGGCACCCAGTTGATCGGCGCGAGATTTAATCGCCGCGACAATTT
GCGACGGCGCGTGCAGGGCCAGACTGGAGGTGGCAACGCCAATCAGCAACGACTGTTTGCCCGCCAGTTGTTGTG
CCACGCGGTTGGGAATGTAATTCAGCTCCGCCATCGCCGCTTCCACTTTTTCCCGCGTTTTCGCAGAAACGTGGC
TGGCCTGGTTCACCACGCGGGAAACGGTCTGATAAGAGACACCGGCATACTCTGCGACATCGTATAACGTTACTG
GTTTCACATTCACCACCCTGAATTGACTCTCTTCCGGGCGCTATCATGCCATACCGCGAAAGGTTTTGCGCCATT
CGATGGTGTCCGGGATCTCGACGCTCTCCCTTATGCGACTCCTGCATTAGGAAGCAGCCCAGTAGTAGGTTGAGG
CCGTTGAGCACCGCCGCCGCAAGGAATGGTGCATGCAAGGAGATGGCGCCCAACAGTCCCCCGGCCACGGGGagt
caaaagcctccggtcggaggcttttgactTCTAGAGAGCTGTTGACACTTTATGCTTCCGGCTCGTATAATGTGT
GTGGAATTGTGAGCGGATAACAAGTGGAATTGTGAGCGGATAACAATTTCACACAGGAAACAGAATCCCATGGAG
CGGCTATGCAACCGCATTATGATCTGATTCTCGTGGGGGCTGGACTCGCGAATGGCCTTATCGCCCTGCGTCTCC
AGCAGCAGCAACCTGATATGCGTATTTTGCTTATCGACGCCGCACCCCAGGCGGGCGGGAATCATACGTGGTCAT
TTCACCACGATGATTTGACTGAGAGCCAACATCGTTGGATAGCTCCGCTGGTGGTTCATCACTGGCCCGACTATC
AGGTACGCTTTCCCACACGCCGTCGTAAGCTGAACAGCGGCTACTTTTGTATTACTTCTCAGCGTTTCGCTGAGG
TTTTACAGCGACAGTTTGGCCCGCACTTGTGGATGGATACCGCGGTCGCAGAGGTTAATGCGGAATCTGTTCGGT
TGAAAAAGGGTCAGGTTATCGGTGCCCGCGCGGTGATTGACGGGGGGGTTATGCGGCAAATTCAGCACTGAGCG
TGGGCTTCCAGGCGTTTATTGGCCAGGAATGGCGATTGAGCCACCCGCATGGTTTATCGTCTCCCATTATCATGG
ATGCCACGGTCGATCAGCAAAATGGTTATCGCTTCGTGTACAGCCTGCCGCTCTCGCCGACCAGATTGTTAATTG
AAGATACGCACTATATTGATAATGCGACATTAGATCCTGAATGCGCGCGGCAAAATATTTGCGACTATGCCGCGC
AACAGGGTTGGCAGCTTCAGACACTGCTGCGAGAAGAACAGGGCGCCTTACCCATTACTCTGTCGGGCAATGCCG
ACGCATTCTGGCAGCAGCGCCCCCTGGCCTGTAGTGGATTACGTGCCGGTCTGTTCCATCCTACCACCGGCTATT
CACTGCCGCTGGCGGTTGCCGTGGCCGACCGCCTGAGTGCACTTGATGTCTTTACGTCGGCCTCAATTCACCATG
CCATTACGCATTTTGCCCGCGAGCGCTGGCAGCAGCAGGGCTTTTTCCGCATGCTGAATCGCATGCTGTTTTTAG
CCGGACCCGCCGATTCACGCTGGCGGGTTATGCAGCGTTTTTATGGTTTACCTGAAGATTTAATTGCCCGTTTTT
ATGCGGGAAAACTCACGCTGACCGATCGGCTACGTATTCTGAGCGGCAAGCCGCCTGTTCCGGTATTAGCAGCAT
TGCAAGCCATTATGACGACTCATCGTTGACTCGAG cocE DNA sequence (SEQ ID NO: 74)
ATGGTGGACGGTAATTATTCGGTAGCGTCCAACGTTATGGTGCCGATGCGCGACGGGGTGCGCTTGGCTGTAGAT
CTGTACCGCCCGGACGCAGATGGCCCTGTACCGGTCCTGCTGGTCCGCAACCCCTACGACAAATTCGACGTGTTC
GCTTGGAGTACGCAGAGCACGAACTGGCTGGAATTTGTGCGCGATGGGTACGCCGTCGTCATCCAAGACACCCGG
GGCCTCTTTGCATCCGAAGGTGAGTTCGTTCCACATGTTGATGACGAGGCGGATGCGGAAGACACGCTGAGCTGG
ATCTTGGAACAAGCATGGTGCGACGGCAATGTGGGTATGTTCGGTGTAAGCTACCTGGGCGTTACGCAGTGGCAA
GCTGCTGTTAGCGGTGTGGGTGGTTTGAAGGCAATCGCCCCGAGCATGGCGAGCGCGGATCTGTACCGTGCCCCC
TGGTACGGTCCTGGCGGCGCCCTGAGCGTGGAAGCACTCCTGGGCTGGAGCGCATTGATCGGTACGGGCCTGATT
ACCAGCCGTAGCGATGCCCGCCCGGAAGACGCAGCCGACTTCGTACAGCTGGCAGCCATCCTGAACGATGTGGCC
GGTGCCGCAAGCGTGACCCCTCTGGCCGAACAGCCCTTGTTGGGCCGCCTGATCCCTTGGGTGATCGACCAGGTG
GTGGACCATCCAGACAACGACGAGTCGTGGCAGAGCATCTCGCTCTTTGAACGTTTGGGTGGGCTCGCTACCCCG
GCCTTGATTACCGCCGGGTGGTACGATGGCTTCGTGGGCGAGAGCCTCCGTACCTTCGTAGCTGTGAAGGACAAC
GCGGATGCGCGTCTGGTGGTGGGGCCGTGGAGCCACAGCAATCTGACCGGCCGTAATGCCGACCGTAAGTTTGGG TABLE 3-continued

| List of Plasmids |
| --- |
| ATCGCCGCGACCTACCCCATCCAGGAGGCGACGACCATGCACAAGGCTTTTTTCGACCGGCACCTCCGTGGCGAG<br>ACCGATGCCCTGGCAGGGGTGCCCAAGGTGCGCCTCTTCGTAATGGGTATCGATGAGTGGCGCGACGAGACCGAC<br>TGGCCATTGCCAGATACCGCTTACACGCCTTTTTACCTCGGGGGCTCCGGTGCGGCCAACACGAGCACGGGTGGT<br>GGGACCCTGTCGACCTCGATCAGCGGCACGGAGTCGGCGGACACCTACCTGTATGATCCTGCCGACCCCGTGCCA<br>AGTCTGGGCGGCACCCTCCTCTTCCATAATGGGGACAACGGTCCAGCTGACCAGCGCCCGATTCACGATCGCGAC<br>GACGTGCTGTGCTACTCCACCGAGGTGTTGACCGACCCCGTGGAAGTAACGGGGACGGTTTCGGCTCGCCTGTTC<br>GTGTCCTCGTCGGCCGTGGATACCGATTTTACCGCCAAGTTGGTCGACGTGTTCCCCGATGGTCGGGCAATCGCT<br>CTCTGCGACGGCATCGTGCGTATGCGCTACCGGGAGACCTTGGTAAATCCTACGCTCATTGAGGCCGGTGAGATT<br>TACGAGGTGGCTATTGATATGCTGGCCACCAGCAACGTGTTTTTGCCGGGCCACCGCATCATGGTGCAAGTTAGC<br>AGCTCGAACTTCCCGAAGTACGACCGCAACTCCAACACCGGCGGCGTCATCGCTCGCGAGCAACTGGAGGAAATG<br>TGCACCGCCGTAAACCGCATTCACCGCGGCCCCGAACACCCGTCCCATATCGTGCTGCCGATCATTAAGCGCGAC<br>TATAAGGACGACGACGATAAGTGA |
| cocE Amino acid sequence (SEQ ID NO: 75)<br>MVDGNYSVASNVMVPMRDGVRLAVDLYRPDADGPVPVLLVRNPYDKEDVFAWSTQSTNWLEFVRDGYAVVIQDTR<br>GLFASEGEFVPHVDDEADAEDTLSWILEQAWCDGNVGMFGVSYLGVTQWQAAVSGVGGLKAIAPSMASADLYRAP<br>WYGPGGALSVEALLGWSALIGTGLITSRSDARPEDAADFVQLAAILNDVAGAASVTPLAEQPLLGRLIPWVIDQV<br>VDHPDNDESWQSISLFERLGGLATPALITAGWYDGFVGESLRTFVAVKDNADARLVVGPWSHSNLTGRNADRKFG<br>IAATYPIQEATTMHKAFFDRHLRGETDALAGVPKVRLFVMGIDEWRDETDWPLPDTAYTPFYLGGSGAANTSTGG<br>GTLSTSISGTESADTYLYDPADPVPSLGGTLLFHNGDNGPADQRPIHDRDDVLCYSTEVLTDPVEVTGTVSARLF<br>VSSSAVDTDFTAKLVDVFPDGRAIALCDGIVRMRYRETLVNPTLIEAGEIYEVAIDMLATSNVELPGHRIMVQVS<br>SSNFPKYDRNSNTGGVIAREQLEEMCTAVNRIHRGPEHPSHIVLPIIKRDYKDDDDK- |
| crtE (SEQ ID NO: 76)<br>ATGTATCCGTTTATAAGGACAGCCCGAATGACGGTCTGCGCAAAAAAACACGTTCATCTCACTCGCGATGCTGCG<br>GAGCAGTTACTGGCTGATATTGATCGACGCCTTGATCAGTTATTGCCCGTGGAGGGAGAACGGGATGTTGTGGGT<br>GCCGCGATGCGTGAAGGTGCGCTGGCACCGGGAAAACGTATTCGCCCCATGTTGCTGTTGCTGACCGCCCGCGAT<br>CTGGGTTGCGCTGTCAGCCATGACGGATTACTGGATTTGGCCTGTGCGGTGGAAATGGTCCACGCGGCTTCGCTG<br>ATCCTTGACGATATGCCCTGCATGGACGATGCGAAGCTGCGGCGCGGACGCCCTACCATTCATTCTCATTACGGA<br>GAGCATGTGGCAATACTGGCGGCGGTTGCCTTGCTGAGTAAAGCCTTTGGCGTAATTGCCGATGCAGATGGCCTC<br>ACGCCGCTGGCAAAAAATCGGGCGGTTTCTGAACTGTCAAACGCCATCGGCATGCAAGGATTGGTTCAGGGTCAG<br>TTCAAGGATCTGTCTGAAGGGGATAAGCCGCGCAGCGCTGAAGCTATTTTGATGACGAATCACTTTAAAACCAGC<br>ACGCTGTTTTGTGCCTCCATGCAGATGGCCTCGATTGTTGCGAATGCCTCCAGCGAAGCGCGTGATTGCCTGCAT<br>CGTTTTTCACTTGATCTTGGTCAGGCATTTCAACTGCTGGACGATTTGACCGATGGCATGACCGACACCGGTAAG<br>GATAGCAATCAGGACGCCGGTAAATCGACGCTGGTCAATCTGTTAGGCCCGAGGGCGGTTGAAGAACGTCTGAGA<br>CAACATCTTCAGCTTGCCAGTGAGCATCTCTCTGCGGCCTGCCAACACGGGCACGCCACTCAACATTTTATTCAG<br>GCCTGGTTTGACAAAAAACTCGCTGCCGTCAGTTAA |
| crtB (SEQ ID NO: 77)<br>ATGAATAATCCGTCGTTACTCAATCATGCGGTCGAAACGATGGCAGTTGGCTCGAAAAGTTTTGCGACAGCCTCA<br>AAGTTATTTGATGCAAAAACCCGGCGCAGCGTACTGATGCTCTACGCCTGGTGCCGCCATTGTGACGATGTTATT<br>GACGATCAGACGCTGGGCTTTCAGGCCCGGCAGCCTGCCTTACAAACGCCCGAACAACGTCTGATGCAACTTGAG<br>ATGAAAACGCGCCAGGCCTATGCAGGATCGCAGATGCACGAACCGGCGTTTGCGGCTTTTCAGGAAGTGGCTATG<br>GCTCATGATATCGCCCCGGCTTACGCGTTTGATCATCTGGAAGGCTTCGCCATGGATGTACGCGAAGCGCAATAC<br>AGCCAACTGGATGATACGCTGCGCTATTGCTATCACGTTGCAGGCGTTGTCGGCTTGATGATGGCGCAAATCATG<br>GGCGTGCGGGATAACGCCACGCTGGACCGCGCCTGTGACCTTGGGCTGGCATTTCAGTTGACCAATATTGCTCGC<br>GATATTGTGGACGATGCGCATGCGGGCCGCTGTTATCTGCCGGCAAGCTGGCTGGAGCATGAAGGTCTGAACAAA<br>GAGAATTATGCGGCACCTGAAAACCGTCAGGCGCTGAGCCGTATCGCCCGTCGTTTGGTGCAGGAAGCAGAACCT<br>TACTATTTGTCTGCCACAGCCGGCCTGGCAGGGTTGCCCCTGCGTTCCGCCTGGGCAATCGCTACGGCGAAGCAG<br>GTTTACCGGAAAATAGGTGTCAAAGTTGAACAGGCCGGTCAGCAAGCCTGGGATCAGCGGCAGTCAACGACCACG<br>CCCGAAAAATTAACGCTGCTGCTGGCCGCCTCTGGTCAGGCCCTTACTTCCCGGATGCGGGCTCATCCTCCCCGC<br>CCTGCGCATCTCTGGCAGCGCCCGCTCTAG |
| crtI (SEQ ID NO: 78)<br>ATGAAACCAACTACGGTAATTGGTGCAGGCTTCGGTGGCCTGGCACTGGCAATTCGTCTACAAGCTGCGGGGATT<br>CCCGTCTTACTGCTTGAACAACGTGATAAACCCGGCGGTCGGGCTTATGTCTACGAGGATCAGGGGTTTACCTTT<br>GATGCAGGCCCGACGGTTATCACCGATCCCAGTGCCATTGAAGAACTGTTTGCACTGGCAGGAAAACAGTTAAAA<br>GAGTATGTCGAACTGCTGCCGGTTACGCCGTTTTACCGCCTGTGTTGGGAGTCAGGGAAGGTCTTTAATTACGAT<br>AACGATCAAACCCGGCTCGAAGCGCAGATTCAGCAGTTTAATCCCCGCGATGTCGAAGGTTATCGTCAGTTTCTG<br>GACTATTCACGCGCGGTGTTTAAAGAAGGCTATCTAAAGCTCGGTACTGTCCCTTTTTTATCGTTCAGAGACATG<br>CTTCGCGCCGCACCTCAACTGGCGAAACTGCAGGCATGGAGAAGCGTTTACAGTAAGGTTGCCAGTTACATCGAA<br>GATGAACATCTGCGCCAGGCGTTTTCTTTCCACTCGCTGTTGGTGGGCGGCAATCCCTTCGCCACCTCATCCATT<br>TATACGTTGATACACGCGCTGGAGCGTGAGTGGGGCGTCTGGTTTCCGCGTGGCGGCACCGGCGCATTAGTTCAG<br>GGGATGATAAAGCTGTTTCAGGATCTGGGTGGCGAAGTCGTGTTAAACGCCAGAGTCAGCCACATGGAAACGACA<br>GGAAACAAGATTGAAGCCGTGCATTTAGAGGACGGTCGCAGGTTCCTGACGCAAGCCGTCGCGTCAAATGCAGAT<br>GTGGTTCATACCTATCGCGACCTGTTAAGCCAGCACCCTGCCGCGGTTAAGCAGTCCAACAAACTGCAGACTAAG<br>CGCATGAGTAACTCTCTGTTTGTGCTCTATTTTGGTTTGAATCACCATCATGATCAGCTCGCGCATCACACGGTT<br>TGTTTCGGCCCGCGTTACCGCGAGCTGATTGACGAAATTTTTAATCATGATGGCCTCGCAGAGGACTTCTCACTT<br>TATCTGCACGCGCCCTGTGTCACGGATTCGTCACTGGCGCCTGAAGGTTGCGGCAGTTACTATGTGTTGGCGCCG<br>GTGCCGCATTTAGGCACCGCGAACCTCGACTGGACGGTTGAGGGGCCAAAACTACGCGACCGTATTTTTGCGTAC<br>CTTGAGCAGCATTACATGCCTGGCTTACGGAGTCAGCTGGTCACGCACCGGATGTTTACGCCGTTTGATTTTCGC<br>GACCAGCTTAATGCCTATCATGGCTCAGCCTTTTCTGTGGAGCCCGTTCTTACCCAGAGCGCCTGGTTTCGGCCG<br>CATAACCGCGATAAAACCATTACTAATCTCTACCTGGTCGGCGCAGGCACGCATCCCGGCGCAGGCATTCCTGGC<br>GTCATCGGCTCGGCAAAAGCGACAGCAGGTTTGATGCTGGAGGATCTGATTTGA |
| crtY (SEQ ID NO: 79)<br>ATGGGAGCGGCTATGCAACCGCATTATGATCTGATTCTCGTGGGGGCTGGACTCGCGAATGGCCTTATCGCCCTG<br>CGTCTCCAGCAGCAGCAACCTGATATGCGTATTTTGCTTATCGACGCCGCACCCCAGGCGGGCGGGAATCATACG |

TABLE 3-continued

| List of Plasmids |
|---|
| TGGTCATTTCACCACGATGATTTGACTGAGAGCCAACATCGTTGGATAGCTCCGCTGGTGGTTCATCACTGGCCC GACTATCAGGTACGCTTTCCCACACGCCGTCGTAAGCTGAACAGCGGCTACTTTTGTATTACTTCTCAGCGTTTC GCTGAGGTTTTACAGCGACAGTTTGGCCCGCACTTGTGGATGGATACCGCGGTCGCAGAGGTTAATGCGGAATCT GTTCGGTTGAAAAAGGGTCAGGTTATCGGTGCCCGCGCGGTGATTGACGGGCGGGGTTATGCGGCAAATTCAGCA CTGAGCGTGGGCTTCCAGGCGTTTATTGGCCAGGAATGGCGATTGAGCCACCCGCATGGTTTATCGTCTCCCATT ATCATGGATGCCACGGTCGATCAGCAAAATGGTTATCGCTTCGTGTACAGCCTGCCGCTCTCGCCGACCAGATTG TTAATTGAAGATACGCACTATATTGATAATGCGACATTAGATCCTGAATGCGCGCGGCAAAATATTTGCGACTAT GCCGCGCAACAGGGTTGGCAGCTTCAGACACTGCTGCGAGAAGAACAGGGCGCCTTACCCATTACTCTGTCGGGC AATGCCGACGCATTCTGGCAGCAGCGCCCCCTGGCCTGTAGTGGATTACGTGCCGGTCTGTTCCATCCTACCACC GGCTATTCACTGCCGCTGGCGGTTGCCGTGGCCGACCGCCTGAGTGCACTTGATGTCTTTACGTCGGCCTCAATT CACCATGCCATTACGCATTTTGCCCGCGAGCGCTGGCAGCAGCAGGGCTTTTTCCGCATGCTGAATCGCATGCTG TTTTTAGCCGGACCCGCCGATTCACGCTGGCGGGTTATGCAGCGTTTTTATGGTTTACCTGAAGATTTAATTGCC CGTTTTTATGCGGGAAAACTCACGCTGACCGATCGGCTACGTATTCTGAGCGGCAAGCCGCCTGTTCCGGTATTA GCAGCATTGCAAGCCATTATGACGACTCATCGTTGA |

While exemplary embodiments have been shown and described herein, it will be obvious to those skilled in the art that such embodiments are provided by way of example only. Numerous variations, changes, and substitutions will occur to those skilled in the art. It should be understood that various alternatives to the embodiments described herein may be employed. It is intended that the following claims define the scope of the disclosure and that methods and structures within the scope of these claims and their equivalents be covered thereby.

What is claimed is:

1. A nucleic acid construct comprising a modified inducible promoter, wherein the modified inducible promoter comprises:
   a. a TATAATGT sequence at position −10, relative to a transcriptional start site of the promoter;
   b. a TTGACA sequence at position −35, relative to the transcriptional start site of the promoter; and
   c. a nucleic acid sequence that encodes a bacterial ribosome binding sequence.

2. The nucleic acid construct of claim 1, wherein the nucleic acid construct further comprises a transgene.

3. The nucleic acid construct of claim 2, wherein the transgene is selected from the group consisting of: a crtW gene, a crtE gene, a crtY gene, a crtI gene, a crtZ gene, a crtEB gene, a crtEBI gene, a crtEBIY gene, a crtEBIYZ gene, a crtEBI-YZW gene, an ABA1 gene, an ABA2 gene, and a CocE gene.

4. The nucleic acid construct of claim 1, wherein the nucleic acid construct further comprises a sequence encoding a reporter gene.

5. The nucleic acid construct of claim 1, wherein the nucleic acid construct further comprises a regulatory element.

6. The nucleic acid construct of claim 1, wherein the nucleic acid construct further comprises a terminator sequence.

7. The nucleic acid construct of claim 1, wherein the nucleic acid construct further comprises:
   a transgene; and
   a second modified inducible promoter sequence, wherein the second modified inducible promoter sequence comprises:
   (i) a TATAATGT sequence at position −10, relative to a transcriptional start site of the second modified inducible promoter sequence;
   (ii) a TTGACA sequence at position −35, relative to the transcriptional start site of the second modified inducible promoter sequence; and
   (iii) a nucleic acid sequence that encodes a second bacterial ribosome binding sequence.

8. The nucleic acid construct of claim 1, wherein promoter nucleic acid sequence integrity downstream of the TATAATGT sequence at position −10 is maintained.

9. The nucleic acid construct of claim 7, wherein promoter nucleic acid sequence integrity downstream of the TATAATGT sequence at position −10 is maintained.

10. A composition comprising the nucleic acid construct of claim 1; and an inducer.

11. A kit comprising the nucleic acid construct of claim 1, packaging, buffers, and, optionally, instructions for use.

12. A method of expressing a protein encoded by a transgene in a cell, the method comprising:
   a. transforming a cell with a nucleic acid construct, wherein the nucleic acid construct comprises a modified inducible promoter that comprises:
      i. a TATAATGT sequence at position −10, relative to a transcriptional start site of the promoter;
      ii. a TTGACA sequence at −35 position, relative to the transcriptional start site of the promoter;
      iii. a nucleic acid that encodes a bacterial ribosome binding sequence; and
      iv. a transgene; and
   b. contacting the cell with an inducer, thereby expressing the protein encoded by the transgene.

13. The method of claim 12, wherein the cell is a prokaryotic cell.

14. The method of claim 13, wherein the prokaryotic cell is a bacterium.

15. The method of claim 12, wherein the cell does not comprise a T7 promoter or a T7 polymerase.

16. The method of claim 12, wherein, when contacting the cell with the inducer, the protein expression is greater than the protein expression in a comparable cell that comprises the transgene operably linked to a T7 promoter.

* * * * *